(12) United States Patent
Bentley et al.

(10) Patent No.: US 8,454,697 B2
(45) Date of Patent: *Jun. 4, 2013

(54) METHOD AND APPARATUS FOR THE TREATMENT OF TISSUE

(75) Inventors: Ishmael Bentley, Eagan, MN (US); Matthew M. Burns, Orono, MN (US); Joseph C. Cauthen, III, Gainesville, FL (US); Brian L. Dukart, Brooklyn Park, MN (US); Rodney L. Houfburg, Prior Lake, MN (US); Lawrence W. Wales, Maplewood, MN (US); Bradley J. Wessman, Wilmington, NC (US)

(73) Assignee: Anulex Technologies, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/440,838

(22) Filed: Apr. 5, 2012

(65) Prior Publication Data

US 2012/0253392 A1 Oct. 4, 2012

Related U.S. Application Data

(63) Continuation of application No. 12/553,583, filed on Sep. 3, 2009, now Pat. No. 8,163,022, which is a continuation-in-part of application No. 12/251,295, filed on Oct. 14, 2008, now Pat. No. 8,128,698.

(51) Int. Cl.
*A61F 2/44* (2006.01)
(52) U.S. Cl.
USPC ........... 623/17.11; 606/99; 606/139; 128/898

(58) Field of Classification Search
USPC ................ 623/17.11–17.16; 606/60, 246, 99, 606/279, 139, 151; 128/898
See application file for complete search history.

(56) References Cited

U.S. PATENT DOCUMENTS

| | | | |
|---|---|---|---|
| 1,995,970 A | 3/1935 | Dorough |
| 2,609,347 A | 9/1952 | Wilson |
| 2,653,917 A | 9/1953 | Hammon |
| 2,659,935 A | 11/1953 | Hammon |
| 2,664,366 A | 12/1953 | Wilson |
| 2,664,367 A | 12/1953 | Wilson |
| 2,676,945 A | 4/1954 | Higgins |
| 2,683,136 A | 7/1954 | Higgins |
| 2,703,316 A | 3/1955 | Schneider |
| 2,758,987 A | 8/1956 | Satzberg |

(Continued)

FOREIGN PATENT DOCUMENTS

| | | |
|---|---|---|
| DE | 43 23 959501 | 7/1994 |
| EP | 0 020 021 | 12/1980 |

(Continued)

OTHER PUBLICATIONS

US 6,447,535, Sep. 2002, Jacobs et al. (withdrawn).

(Continued)

*Primary Examiner* — Ellen C Hammond
(74) *Attorney, Agent, or Firm* — Faegre Baker Daniels LLP

(57) ABSTRACT

This disclosure presents methods and devices for treating a defect in soft tissue of a patient. The methods and devices can employ fixation delivery apparatuses and fixation apparatuses positioned, at least in part, in or on the soft tissue to be repaired. In some aspects, these techniques include the use of this includes a fixation apparatus that includes at least one bone anchor connected to at least one tissue anchor by a shortenable elongate member.

13 Claims, 69 Drawing Sheets

U.S. PATENT DOCUMENTS

| | | |
|---|---|---|
| 2,846,407 A | 8/1958 | Wilson |
| 2,951,828 A | 9/1960 | Zeile |
| 3,531,561 A | 9/1970 | Trehu |
| 3,580,256 A | 5/1971 | Wilkinson |
| 3,867,728 A | 2/1975 | Stubstad et al. |
| 3,874,388 A | 4/1975 | King et al. |
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Field |
| 4,059,115 A | 11/1977 | Jumashev |
| 4,224,413 A | 9/1980 | Burbidge |
| 4,349,921 A | 9/1982 | Kuntz |
| 4,369,788 A | 1/1983 | Goald |
| 4,413,359 A | 11/1983 | Akiyama et al. |
| 4,502,161 A | 3/1985 | Wall |
| 4,512,338 A | 4/1985 | Balko et al. |
| 4,532,926 A | 8/1985 | O'Holla |
| 4,545,374 A | 10/1985 | Jacobson |
| 4,602,635 A | 7/1986 | Mulhollan et al. |
| 4,632,100 A | 12/1986 | Somers et al. |
| 4,663,358 A | 5/1987 | Hyon et al. |
| 4,669,473 A | 6/1987 | Richards et al. |
| 4,678,459 A | 7/1987 | Onik et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,863,477 A | 9/1989 | Monson |
| 4,873,976 A | 10/1989 | Schreiber |
| 4,884,572 A | 12/1989 | Bays et al. |
| 4,890,612 A | 1/1990 | Kensey |
| 4,895,148 A | 1/1990 | Bays et al. |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,378 A | 8/1990 | Hirayama et al. |
| 4,955,908 A | 9/1990 | Frey et al. |
| 4,976,715 A | 12/1990 | Bays et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao |
| 5,053,046 A | 10/1991 | Janese |
| 5,059,193 A | 10/1991 | Kuslich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,682 A | 1/1993 | Chow |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,203,787 A | 4/1993 | Noblitt et al. |
| 5,204,106 A | 4/1993 | Schepers et al. |
| 5,207,695 A | 5/1993 | Trout |
| 5,222,962 A | 6/1993 | Burkhart |
| 5,222,974 A | 6/1993 | Kensey et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,269,809 A | 12/1993 | Hayhurst et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,662 A | 12/1994 | Stone et al. |
| 5,370,697 A | 12/1994 | Baumgartner |
| 5,374,268 A | 12/1994 | Sander |
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,359 A | 4/1995 | Pierce |
| 5,405,360 A | 4/1995 | Tovey |
| 5,411,523 A | 5/1995 | Goble |
| 5,417,691 A | 5/1995 | Hayhurst |
| 5,417,699 A | 5/1995 | Klein et al. |
| 5,425,772 A | 6/1995 | Brantigan |
| 5,425,773 A | 6/1995 | Boyd et al. |
| 5,429,598 A | 7/1995 | Waxman et al. |
| 5,437,631 A | 8/1995 | Janzen |
| 5,437,680 A | 8/1995 | Yoon |
| 5,439,464 A | 8/1995 | Shapiro |
| 5,441,502 A | 8/1995 | Bartlett |
| 5,456,720 A | 10/1995 | Schultz et al. |
| 5,464,407 A | 11/1995 | McGuire |
| 5,464,425 A | 11/1995 | Skiba |
| 5,470,337 A | 11/1995 | Moss |
| 5,489,307 A | 2/1996 | Kuslich et al. |
| 5,492,697 A | 2/1996 | Boyan et al. |
| 5,496,348 A | 3/1996 | Bonutti |
| 5,500,000 A | 3/1996 | Feagin et al. |
| 5,507,754 A | 4/1996 | Green et al. |
| 5,507,755 A | 4/1996 | Gresl et al. |
| 5,514,180 A | 5/1996 | Heggeness et al. |
| 5,520,696 A | 5/1996 | Wenstrom, Jr. |
| 5,520,700 A | 5/1996 | Beyar et al. |
| 5,527,342 A | 6/1996 | Pietrzak et al. |
| 5,527,343 A | 6/1996 | Bonutti |
| 5,531,678 A | 7/1996 | Tomba et al. |
| 5,531,759 A | 7/1996 | Kensey et al. |
| 5,534,012 A | 7/1996 | Bonutti |

| Patent Number | Date | Inventor(s) | | Patent Number | Date | Inventor(s) |
|---|---|---|---|---|---|---|
| 5,534,028 A | 7/1996 | Bao et al. | | 5,733,307 A | 3/1998 | Dinsdale |
| 5,534,030 A | 7/1996 | Navarro et al. | | 5,733,337 A | 3/1998 | Carr, Jr. et al. |
| 5,540,704 A | 7/1996 | Gordon et al. | | 5,735,875 A | 4/1998 | Bonutti |
| 5,540,715 A | 7/1996 | Katsaros et al. | | 5,736,746 A | 4/1998 | Furutoh |
| 5,545,178 A | 8/1996 | Kensey et al. | | 5,743,917 A | 4/1998 | Saxon |
| 5,545,229 A | 8/1996 | Parsons et al. | | 5,746,755 A | 5/1998 | Wood et al. |
| 5,549,617 A | 8/1996 | Green et al. | | 5,752,964 A | 5/1998 | Mericle |
| 5,549,679 A | 8/1996 | Kuslich | | 5,755,797 A | 5/1998 | Baumgartner |
| 5,556,428 A | 9/1996 | Shah | | 5,759,189 A | 6/1998 | Ferragamo et al. |
| 5,556,429 A | 9/1996 | Felt | | 5,766,246 A | 6/1998 | Mulhauser et al. |
| 5,562,684 A | 10/1996 | Kammerer | | 5,769,864 A | 6/1998 | Kugel |
| 5,562,689 A | 10/1996 | Green et al. | | 5,769,893 A | 6/1998 | Shah |
| 5,562,736 A | 10/1996 | Ray et al. | | 5,772,661 A | 6/1998 | Michelson |
| 5,562,738 A | 10/1996 | Boyd et al. | | 5,776,183 A | 7/1998 | Kanesaka et al. |
| 5,569,242 A | 10/1996 | Lax et al. | | 5,782,844 A | 7/1998 | Yoon et al. |
| 5,569,252 A | 10/1996 | Justin et al. | | 5,782,860 A | 7/1998 | Epstein et al. |
| 5,569,303 A | 10/1996 | Johnson | | 5,782,864 A | 7/1998 | Lizardi |
| 5,569,306 A | 10/1996 | Thal | | 5,785,705 A | 7/1998 | Baker |
| 5,571,189 A | 11/1996 | Kuslich | | 5,786,217 A | 7/1998 | Tubo et al. |
| 5,573,286 A | 11/1996 | Rogozinski | | 5,788,625 A | 8/1998 | Plouhar et al. |
| 5,573,548 A | 11/1996 | Nazre et al. | | 5,792,152 A | 8/1998 | Klein et al. |
| 5,578,057 A | 11/1996 | Wenstrom, Jr. | | 5,797,929 A | 8/1998 | Andreas et al. |
| 5,582,616 A | 12/1996 | Bolduc et al. | | 5,800,549 A | 9/1998 | Bao et al. |
| 5,584,862 A | 12/1996 | Bonutti | | 5,800,550 A | 9/1998 | Sertich |
| 5,591,177 A | 1/1997 | Lehrer | | 5,810,848 A | 9/1998 | Hayhurst |
| 5,591,223 A | 1/1997 | Lock et al. | | 5,810,851 A | 9/1998 | Yoon |
| 5,593,425 A | 1/1997 | Bonutti et al. | | 5,814,051 A | 9/1998 | Wenstrom, Jr. |
| 5,599,279 A | 2/1997 | Slotman et al. | | 5,823,994 A | 10/1998 | Sharkey et al. |
| 5,601,557 A | 2/1997 | Hayhurst | | 5,824,008 A | 10/1998 | Bolduc et al. |
| 5,613,974 A | 3/1997 | Andreas et al. | | 5,824,011 A | 10/1998 | Stone et al. |
| 5,618,314 A | 4/1997 | Harwin et al. | | 5,824,082 A | 10/1998 | Brown |
| 5,620,012 A | 4/1997 | Benderev et al. | | 5,824,093 A | 10/1998 | Ray et al. |
| 5,624,463 A | 4/1997 | Stone et al. | | 5,824,094 A | 10/1998 | Serhan et al. |
| 5,626,612 A | 5/1997 | Bartlett et al. | | 5,827,298 A | 10/1998 | Hart et al. |
| 5,626,613 A | 5/1997 | Schmieding | | 5,827,325 A | 10/1998 | Landgrebe et al. |
| 5,626,614 A | 5/1997 | Hart | | 5,827,328 A | 10/1998 | Buttermann |
| 5,634,931 A | 6/1997 | Kugel | | 5,836,315 A | 11/1998 | Benderev et al. |
| 5,634,944 A | 6/1997 | Magram | | 5,842,477 A | 12/1998 | Naughton et al. |
| 5,643,319 A | 7/1997 | Green et al. | | 5,843,084 A | 12/1998 | Hart et al. |
| 5,643,320 A | 7/1997 | Lower et al. | | 5,846,261 A | 12/1998 | Kotula et al. |
| 5,645,084 A | 7/1997 | McKay | | 5,849,331 A | 12/1998 | Ducheyne et al. |
| 5,645,597 A | 7/1997 | Krapiva | | 5,851,219 A | 12/1998 | Goble et al. |
| 5,649,945 A | 7/1997 | Ray et al. | | 5,853,422 A | 12/1998 | Huebsch et al. |
| 5,658,343 A | 8/1997 | Hauselmann et al. | | 5,855,614 A | 1/1999 | Stevens et al. |
| 5,662,658 A | 9/1997 | Wenstrom, Jr. | | 5,860,425 A | 1/1999 | Benderev et al. |
| 5,662,681 A | 9/1997 | Nash et al. | | 5,860,977 A | 1/1999 | Zucherman et al. |
| 5,662,683 A | 9/1997 | Kay | | 5,865,845 A | 2/1999 | Thalgott |
| 5,669,935 A | 9/1997 | Rosenman et al. | | 5,865,846 A | 2/1999 | Bryan et al. |
| 5,674,294 A | 10/1997 | Bainville et al. | | 5,868,762 A | 2/1999 | Cragg et al. |
| 5,674,296 A | 10/1997 | Bryan et al. | | 5,879,366 A | 3/1999 | Shaw et al. |
| 5,676,698 A | 10/1997 | Janzen et al. | | 5,888,220 A | 3/1999 | Felt et al. |
| 5,676,701 A | 10/1997 | Yuan et al. | | 5,888,222 A | 3/1999 | Coates |
| 5,681,310 A | 10/1997 | Yuan et al. | | 5,888,226 A | 3/1999 | Rogozinski |
| 5,681,351 A | 10/1997 | Jamiolkowski et al. | | 5,891,146 A | 4/1999 | Simon et al. |
| 5,683,417 A | 11/1997 | Cooper | | 5,893,592 A | 4/1999 | Schulze et al. |
| 5,683,418 A | 11/1997 | Luscombe et al. | | 5,893,889 A | 4/1999 | Harrington |
| 5,683,419 A | 11/1997 | Thal | | 5,895,426 A | 4/1999 | Scarborough et al. |
| 5,683,465 A | 11/1997 | Shinn et al. | | 5,899,920 A | 5/1999 | DeSatnick et al. |
| 5,690,677 A | 11/1997 | Schmieding et al. | | 5,904,703 A | 5/1999 | Gilson |
| 5,695,525 A | 12/1997 | Mulhauser et al. | | 5,916,225 A | 6/1999 | Kugel |
| 5,697,950 A | 12/1997 | Fucci et al. | | 5,919,235 A | 7/1999 | Husson et al. |
| 5,702,449 A | 12/1997 | McKay | | 5,922,026 A | 7/1999 | Chin |
| 5,702,450 A | 12/1997 | Bisserie | | 5,922,028 A | 7/1999 | Plouhar et al. |
| 5,702,451 A | 12/1997 | Biedermann et al. | | 5,928,284 A | 7/1999 | Mehdizadeh |
| 5,702,454 A | 12/1997 | Baumgartner | | 5,935,147 A | 8/1999 | Kensey et al. |
| 5,702,462 A | 12/1997 | Oberlander | | 5,941,439 A | 8/1999 | Kammerer et al. |
| 5,704,943 A | 1/1998 | Yoon et al. | | 5,944,738 A | 8/1999 | Amplatz et al. |
| 5,709,708 A | 1/1998 | Thal | | 5,948,001 A | 9/1999 | Larsen |
| 5,716,404 A | 2/1998 | Vacanti et al. | | 5,948,002 A | 9/1999 | Bonutti |
| 5,716,408 A | 2/1998 | Eldridge et al. | | 5,954,716 A | 9/1999 | Sharkey et al. |
| 5,716,409 A | 2/1998 | Debbas | | 5,954,767 A | 9/1999 | Pajotin et al. |
| 5,716,413 A | 2/1998 | Walter et al. | | 5,957,939 A | 9/1999 | Heaven et al. |
| 5,716,416 A | 2/1998 | Lin | | 5,961,538 A | 10/1999 | Pedlick et al. |
| 5,718,717 A | 2/1998 | Bonutti | | 5,964,783 A | 10/1999 | Grafton et al. |
| 5,725,552 A | 3/1998 | Kotula et al. | | 5,964,807 A | 10/1999 | Gan et al. |
| 5,725,577 A | 3/1998 | Saxon | | 5,972,000 A | 10/1999 | Beyar et al. |
| 5,728,109 A | 3/1998 | Schulze et al. | | 5,972,007 A | 10/1999 | Sheffield et al. |
| 5,728,150 A | 3/1998 | McDonald et al. | | 5,972,022 A | 10/1999 | Huxel |
| 5,730,744 A | 3/1998 | Justin et al. | | 5,976,174 A | 11/1999 | Ruiz |

| | | | |
|---|---|---|---|
| 5,976,186 A | 11/1999 | Bao et al. |
| 5,980,504 A | 11/1999 | Sharkey et al. |
| 5,980,558 A | 11/1999 | Wiley |
| 5,984,948 A | 11/1999 | Hasson |
| 6,001,130 A | 12/1999 | Bryan et al. |
| 6,007,567 A | 12/1999 | Bonutti |
| 6,007,570 A | 12/1999 | Sharkey et al. |
| 6,007,575 A | 12/1999 | Samuels |
| 6,010,525 A | 1/2000 | Bonutti et al. |
| 6,019,792 A | 2/2000 | Cauthen |
| 6,019,793 A | 2/2000 | Perren et al. |
| 6,024,096 A | 2/2000 | Buckberg |
| 6,024,754 A | 2/2000 | Engelson |
| 6,024,758 A | 2/2000 | Thal |
| 6,027,523 A | 2/2000 | Schmieding |
| 6,027,527 A | 2/2000 | Asano et al. |
| 6,036,699 A | 3/2000 | Andreas et al. |
| 6,039,761 A | 3/2000 | Li et al. |
| 6,039,762 A | 3/2000 | McKay |
| 6,045,561 A | 4/2000 | Marshall et al. |
| 6,045,573 A | 4/2000 | Wenstrom, Jr. et al. |
| 6,053,909 A | 4/2000 | Shadduck |
| 6,063,378 A | 5/2000 | Nohara et al. |
| 6,066,146 A | 5/2000 | Carroll et al. |
| 6,066,776 A | 5/2000 | Goodwin et al. |
| 6,068,648 A | 5/2000 | Cole et al. |
| 6,073,051 A | 6/2000 | Sharkey et al. |
| 6,080,182 A | 6/2000 | Shaw et al. |
| 6,093,205 A | 7/2000 | McLeod et al. |
| 6,095,149 A | 8/2000 | Sharkey et al. |
| 6,099,514 A | 8/2000 | Sharkey et al. |
| 6,102,934 A | 8/2000 | Li |
| 6,106,545 A | 8/2000 | Egan |
| 6,113,609 A | 9/2000 | Adams |
| 6,113,623 A | 9/2000 | Sgro |
| 6,113,639 A | 9/2000 | Ray et al. |
| 6,117,162 A | 9/2000 | Schmieding et al. |
| 6,123,715 A | 9/2000 | Amplatz |
| 6,126,682 A | 10/2000 | Sharkey et al. |
| 6,139,565 A | 10/2000 | Stone et al. |
| 6,140,452 A | 10/2000 | Felt et al. |
| 6,143,006 A | 11/2000 | Chan et al. |
| 6,143,017 A | 11/2000 | Thal |
| 6,146,380 A | 11/2000 | Racz et al. |
| 6,146,406 A | 11/2000 | Shluzas et al. |
| 6,146,422 A | 11/2000 | Lawson |
| 6,162,203 A | 12/2000 | Haago |
| 6,168,598 B1 | 1/2001 | Martello |
| 6,171,317 B1 | 1/2001 | Jackson et al. |
| 6,171,318 B1 | 1/2001 | Kugel et al. |
| 6,171,329 B1 | 1/2001 | Shaw et al. |
| 6,174,322 B1 | 1/2001 | Schneidt |
| 6,176,863 B1 | 1/2001 | Kugel et al. |
| 6,179,874 B1 | 1/2001 | Cauthen |
| 6,179,879 B1 | 1/2001 | Robinson et al. |
| 6,183,479 B1 | 2/2001 | Tormala et al. |
| 6,183,518 B1 | 2/2001 | Ross et al. |
| 6,187,048 B1 | 2/2001 | Milner et al. |
| 6,190,401 B1 | 2/2001 | Green et al. |
| 6,200,329 B1 | 3/2001 | Fung et al. |
| 6,203,554 B1 | 3/2001 | Roberts |
| 6,203,565 B1 | 3/2001 | Bonutti |
| 6,206,895 B1 | 3/2001 | Levinson |
| 6,206,921 B1 | 3/2001 | Guagliano et al. |
| 6,221,092 B1 | 4/2001 | Koike et al. |
| 6,221,109 B1 | 4/2001 | Geistlich et al. |
| 6,224,630 B1 | 5/2001 | Bao et al. |
| 6,231,615 B1 | 5/2001 | Preissman |
| 6,241,768 B1 | 6/2001 | Agarwal et al. |
| 6,245,080 B1 | 6/2001 | Levinson |
| 6,245,107 B1 | 6/2001 | Ferree |
| 6,248,106 B1 | 6/2001 | Ferree |
| 6,248,131 B1 | 6/2001 | Felt et al. |
| 6,258,094 B1 | 7/2001 | Nicholson et al. |
| 6,264,677 B1 | 7/2001 | Simon et al. |
| 6,267,772 B1 | 7/2001 | Mulhauser et al. |
| 6,280,453 B1 | 8/2001 | Kugel et al. |
| 6,287,324 B1 | 9/2001 | Yarnitsky et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,306,177 B1 | 10/2001 | Felt et al. |
| 6,312,448 B1 | 11/2001 | Bonutti |
| 6,319,263 B1 | 11/2001 | Levinson |
| 6,332,894 B1 | 12/2001 | Stalcup |
| 6,340,369 B1 | 1/2002 | Ferree |
| 6,342,064 B1 | 1/2002 | Koike et al. |
| 6,344,057 B1 | 2/2002 | Rabbe et al. |
| 6,344,058 B1 | 2/2002 | Ferree |
| 6,352,557 B1 | 3/2002 | Ferree |
| 6,355,052 B1 | 3/2002 | Neuss |
| 6,364,897 B1 | 4/2002 | Bonutti |
| 6,371,984 B1 | 4/2002 | Van Dyke et al. |
| 6,371,990 B1 | 4/2002 | Ferree |
| 6,391,060 B1 | 5/2002 | Ory et al. |
| 6,402,750 B1 | 6/2002 | Atkinson et al. |
| 6,402,784 B1 | 6/2002 | Wardlaw |
| 6,402,785 B1 | 6/2002 | Zdeblick |
| 6,409,739 B1 | 6/2002 | Nobles et al. |
| 6,419,676 B1 | 7/2002 | Zucherman et al. |
| 6,419,702 B1 | 7/2002 | Ferree |
| 6,419,703 B1 | 7/2002 | Fallin et al. |
| 6,419,704 B1 | 7/2002 | Ferree |
| 6,419,706 B1 | 7/2002 | Graf |
| 6,423,065 B2 | 7/2002 | Ferree |
| 6,425,919 B1 | 7/2002 | Lambrecht |
| 6,425,924 B1 | 7/2002 | Rousseau |
| 6,428,562 B2 | 8/2002 | Bonutti |
| 6,428,576 B1 | 8/2002 | Haldimann |
| 6,432,107 B1 | 8/2002 | Ferree |
| 6,432,123 B2 | 8/2002 | Schwartz et al. |
| 6,436,098 B1 | 8/2002 | Michelson |
| 6,436,143 B1 | 8/2002 | Ross et al. |
| 6,443,988 B2 | 9/2002 | Felt et al. |
| 6,447,531 B1 | 9/2002 | Amplatz |
| 6,452,924 B1 | 9/2002 | Golden et al. |
| 6,454,804 B1 | 9/2002 | Ferree |
| 6,464,712 B1 | 10/2002 | Epstein |
| 6,482,235 B1 | 11/2002 | Lambrecht et al. |
| 6,488,691 B1 | 12/2002 | Carroll et al. |
| 6,491,724 B1 | 12/2002 | Ferree |
| 6,494,883 B1 | 12/2002 | Ferree |
| 6,500,132 B1 | 12/2002 | Li |
| 6,500,184 B1 | 12/2002 | Chan et al. |
| 6,508,828 B1 | 1/2003 | Akerfeldt et al. |
| 6,508,839 B1 | 1/2003 | Lambrecht et al. |
| 6,511,488 B1 | 1/2003 | Marshall et al. |
| 6,511,498 B1 | 1/2003 | Fumex |
| 6,511,958 B1 | 1/2003 | Atkinson et al. |
| 6,514,255 B1 | 2/2003 | Ferree |
| 6,514,514 B1 | 2/2003 | Atkinson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,530,933 B1 | 3/2003 | Yeung et al. |
| 6,533,799 B1 | 3/2003 | Bouchier |
| 6,533,817 B1 | 3/2003 | Norton et al. |
| 6,547,800 B2 | 4/2003 | Foerster et al. |
| 6,547,806 B1 | 4/2003 | Ding |
| 6,558,386 B1 | 5/2003 | Cragg |
| 6,558,390 B1 | 5/2003 | Cragg |
| 6,562,052 B2 | 5/2003 | Nobles et al. |
| 6,569,187 B1 | 5/2003 | Bonutti et al. |
| 6,569,442 B2 | 5/2003 | Gan et al. |
| 6,572,635 B1 | 6/2003 | Bonutti |
| 6,572,653 B1 | 6/2003 | Simonson |
| 6,575,979 B1 | 6/2003 | Cragg |
| 6,576,017 B2 | 6/2003 | Foley et al. |
| 6,579,291 B1 | 6/2003 | Keith et al. |
| 6,582,453 B1 | 6/2003 | Tran et al. |
| 6,592,608 B1 | 7/2003 | Fisher et al. |
| 6,592,609 B1 | 7/2003 | Bonutti |
| 6,592,625 B2 | 7/2003 | Cauthen |
| 6,596,012 B2 | 7/2003 | Akerfeldt et al. |
| 6,602,291 B1 | 8/2003 | Ray et al. |
| 6,605,096 B1 | 8/2003 | Ritchart |
| 6,607,541 B1 | 8/2003 | Gardiner et al. |
| 6,610,006 B1 | 8/2003 | Amid et al. |

| | | | | | | |
|---|---|---|---|---|---|---|
| 6,610,071 B1 | 8/2003 | Cohn et al. | | 6,835,208 B2 | 12/2004 | Marchosky |
| 6,610,079 B1 | 8/2003 | Li et al. | | 6,841,150 B2 | 1/2005 | Halvorsen et al. |
| 6,610,091 B1 | 8/2003 | Reiley | | 6,843,799 B2 | 1/2005 | Bartlett |
| 6,610,666 B1 | 8/2003 | Akerblom | | 6,852,128 B2 | 2/2005 | Lange |
| 6,613,044 B2 | 9/2003 | Carl | | 6,860,895 B1 | 3/2005 | Akerfeldt et al. |
| 6,620,185 B1 | 9/2003 | Harvie et al. | | 6,878,155 B2 | 4/2005 | Sharkey et al. |
| 6,620,196 B1 | 9/2003 | Trieu | | 6,878,167 B2 | 4/2005 | Ferree |
| 6,623,492 B1 | 9/2003 | Berube et al. | | 6,883,520 B2 | 4/2005 | Lambrecht et al. |
| 6,623,508 B2 | 9/2003 | Shaw et al. | | 6,893,462 B2 | 5/2005 | Buskirk et al. |
| 6,626,899 B2 | 9/2003 | Houser et al. | | 6,896,675 B2 | 5/2005 | Leung et al. |
| 6,626,916 B1 | 9/2003 | Yeung et al. | | 6,913,622 B2 | 7/2005 | Gjunter |
| 6,635,073 B2 | 10/2003 | Bonutti et al. | | 6,923,823 B1 | 8/2005 | Bartlett et al. |
| 6,645,227 B2 | 11/2003 | Fallin et al. | | 6,932,833 B1 | 8/2005 | Sandoval et al. |
| 6,645,247 B2 | 11/2003 | Ferree | | 6,936,070 B1 | 8/2005 | Muhanna |
| 6,648,892 B2 | 11/2003 | Martello | | 6,936,072 B2 | 8/2005 | Lambrecht et al. |
| 6,648,918 B2 | 11/2003 | Ferree | | 6,960,215 B2 | 11/2005 | Olson, Jr. et al. |
| 6,648,919 B2 | 11/2003 | Ferree | | 6,964,674 B1 | 11/2005 | Matsuura et al. |
| 6,648,920 B2 | 11/2003 | Ferree | | 6,966,910 B2 | 11/2005 | Ritland |
| 6,652,561 B1 | 11/2003 | Tran | | 6,966,931 B2 | 11/2005 | Huang |
| 6,652,585 B2 | 11/2003 | Lange | | 6,969,404 B2 | 11/2005 | Ferree |
| 6,656,182 B1 | 12/2003 | Hayhurst | | 6,972,027 B2 | 12/2005 | Fallin et al. |
| 6,669,687 B1 | 12/2003 | Saadat | | 6,974,479 B2 | 12/2005 | Trieu |
| 6,669,707 B1 | 12/2003 | Swanstrom et al. | | 6,980,862 B2 | 12/2005 | Fredricks et al. |
| 6,669,729 B2 | 12/2003 | Chin | | 6,984,247 B2 | 1/2006 | Cauthen |
| 6,673,088 B1 | 1/2004 | Vargas et al. | | 6,997,956 B2 | 2/2006 | Cauthen |
| 6,676,665 B2 | 1/2004 | Foley et al. | | 7,001,431 B2 | 2/2006 | Bao et al. |
| 6,679,887 B2 | 1/2004 | Nicholson et al. | | 7,004,970 B2 | 2/2006 | Cauthen |
| 6,679,914 B1 | 1/2004 | Gabbay | | 7,033,393 B2 | 4/2006 | Gainor et al. |
| 6,684,886 B1 | 2/2004 | Alleyne | | 7,033,395 B2 | 4/2006 | Cauthen |
| 6,685,695 B2 | 2/2004 | Ferree | | 7,037,334 B2 | 5/2006 | Hlavka et al. |
| 6,685,728 B2 | 2/2004 | Sinnott et al. | | 7,052,516 B2 | 5/2006 | Cauthen, III et al. |
| 6,689,125 B1 | 2/2004 | Keith et al. | | 7,094,258 B2 | 8/2006 | Lambrecht et al. |
| 6,692,506 B1 | 2/2004 | Ory et al. | | 7,189,235 B2 | 3/2007 | Cauthen |
| 6,695,858 B1 | 2/2004 | Dubrul et al. | | 7,217,279 B2 | 5/2007 | Reese |
| 6,696,073 B2 | 2/2004 | Boyce | | 7,223,289 B2 | 5/2007 | Trieu et al. |
| 6,699,263 B2 | 3/2004 | Cope | | 7,309,337 B2 | 12/2007 | Colleran et al. |
| 6,706,068 B2 | 3/2004 | Ferree | | 7,318,840 B2 | 1/2008 | McKay |
| 6,712,836 B1 | 3/2004 | Berg et al. | | 7,320,701 B2 | 1/2008 | Haut et al. |
| 6,712,837 B2 | 3/2004 | Akerfeldt et al. | | 7,322,978 B2 | 1/2008 | West, Jr. |
| 6,712,853 B2 | 3/2004 | Kuslich | | 7,329,272 B2 | 2/2008 | Burkhart et al. |
| 6,716,216 B1 | 4/2004 | Boucher et al. | | 7,331,982 B1 | 2/2008 | Kaiser et al. |
| 6,719,761 B1 | 4/2004 | Reiley et al. | | 7,371,253 B2 | 5/2008 | Leung et al. |
| 6,719,773 B1 | 4/2004 | Boucher et al. | | 7,390,332 B2 | 6/2008 | Selvitelli et al. |
| 6,719,797 B1 | 4/2004 | Ferree | | 2002/0032483 A1 | 3/2002 | Nicholson et al. |
| 6,723,058 B2 | 4/2004 | Li | | 2002/0077701 A1 | 6/2002 | Kuslich |
| 6,723,095 B2 | 4/2004 | Hammerslag | | 2002/0082698 A1 | 6/2002 | Parenteau et al. |
| 6,723,097 B2 | 4/2004 | Fraser et al. | | 2002/0111688 A1 | 8/2002 | Cauthen |
| 6,723,107 B2 | 4/2004 | Skiba et al. | | 2002/0123807 A1 | 9/2002 | Cauthen, III |
| 6,723,133 B1 | 4/2004 | Pajotin | | 2002/0147461 A1 | 10/2002 | Aldrich |
| 6,723,335 B1 | 4/2004 | Moehlenbruck et al. | | 2002/0151979 A1 | 10/2002 | Lambrecht et al. |
| 6,726,721 B2 | 4/2004 | Stoy et al. | | 2002/0173851 A1 | 11/2002 | McKay |
| 6,730,112 B2 | 5/2004 | Levinson | | 2003/0074075 A1 | 4/2003 | Thomas |
| 6,733,531 B1 | 5/2004 | Trieu | | 2003/0125807 A1 | 7/2003 | Lambrecht et al. |
| 6,733,534 B2 | 5/2004 | Sherman | | 2003/0153976 A1 | 8/2003 | Cauthen, III et al. |
| 6,736,815 B2 | 5/2004 | Ginn | | 2003/0158604 A1 | 8/2003 | Cauthen |
| 6,740,093 B2 | 5/2004 | Hochschuler et al. | | 2003/0181983 A1 | 9/2003 | Cauthen |
| 6,743,255 B2 | 6/2004 | Ferree | | 2003/0195514 A1 | 10/2003 | Trieu et al. |
| 6,752,831 B2 | 6/2004 | Sybert et al. | | 2003/0195628 A1 | 10/2003 | Bao et al. |
| 6,758,863 B2 | 7/2004 | Estes | | 2003/0220649 A1 | 11/2003 | Bao et al. |
| 6,761,720 B1 | 7/2004 | Senegas | | 2003/0220690 A1 | 11/2003 | Cauthen, III |
| 6,764,514 B1 | 7/2004 | Li et al. | | 2003/0220693 A1 | 11/2003 | Cauthen, III |
| 6,767,037 B2 | 7/2004 | Wenstrom | | 2003/0220694 A1 | 11/2003 | Cauthen, III |
| 6,770,076 B2 | 8/2004 | Foerster | | 2004/0039392 A1 | 2/2004 | Trieu |
| 6,773,436 B2 | 8/2004 | Donnelly et al. | | 2004/0054414 A1 | 3/2004 | Trieu |
| 6,773,699 B1 | 8/2004 | Soltz et al. | | 2004/0097980 A1 | 5/2004 | Ferree |
| 6,780,198 B1 | 8/2004 | Gregoire et al. | | 2004/0260397 A1 | 12/2004 | Lambrecht et al. |
| 6,783,546 B2 | 8/2004 | Zucherman et al. | | 2005/0033363 A1 | 2/2005 | Bojarski et al. |
| 6,805,695 B2 | 10/2004 | Keith et al. | | 2005/0033440 A1 | 2/2005 | Lambrecht et al. |
| 6,805,697 B1 | 10/2004 | Helm et al. | | 2005/0038519 A1 | 2/2005 | Lambrecht et al. |
| 6,805,715 B2 | 10/2004 | Reuter et al. | | 2005/0049592 A1 | 3/2005 | Keith et al. |
| 6,812,211 B2 | 11/2004 | Slivka et al. | | 2005/0049704 A1 | 3/2005 | Jackson |
| 6,821,276 B2 | 11/2004 | Lambrecht et al. | | 2005/0049708 A1 | 3/2005 | Atkinson et al. |
| 6,824,562 B2 | 11/2004 | Mathis et al. | | 2005/0149197 A1 | 7/2005 | Cauthen |
| 6,827,716 B2 | 12/2004 | Ryan et al. | | 2005/0256582 A1 | 11/2005 | Ferree |
| 6,827,743 B2 | 12/2004 | Eisermann et al. | | 2005/0283246 A1 | 12/2005 | Cauthen, III et al. |
| 6,830,570 B1 | 12/2004 | Frey et al. | | 2006/0060038 A1 | 3/2006 | Sammartin |
| 6,833,006 B2 | 12/2004 | Foley et al. | | 2006/0084994 A1 | 4/2006 | Atkinson et al. |
| 6,835,205 B2 | 12/2004 | Atkinson et al. | | 2006/0100711 A1 | 5/2006 | Cauthen |
| 6,835,207 B2 | 12/2004 | Zacouto et al. | | 2006/0129156 A1 | 6/2006 | Cauthen, III et al. |

| | | | |
|---|---|---|---|
| 2006/0129245 A1 | 6/2006 | Cauthen | |
| 2006/0142864 A1 | 6/2006 | Cauthen | |
| 2006/0161258 A1 | 7/2006 | Cauthen | |
| 2006/0167553 A1 | 7/2006 | Cauthen | |
| 2006/0173545 A1 | 8/2006 | Cauthen | |
| 2006/0190085 A1 | 8/2006 | Cauthen | |
| 2006/0241773 A1 | 10/2006 | Cauthen | |
| 2006/0253152 A1 | 11/2006 | Evans et al. | |
| 2006/0287731 A1 | 12/2006 | Cauthen, III et al. | |
| 2007/0061012 A1 | 3/2007 | Cauthen, III | |
| 2007/0061013 A1 | 3/2007 | Cauthen, III et al. | |
| 2007/0073407 A1 | 3/2007 | Cauthen et al. | |
| 2007/0088438 A1 | 4/2007 | Cauthen, III et al. | |
| 2007/0100348 A1 | 5/2007 | Cauthen, III et al. | |
| 2007/0100354 A1 | 5/2007 | Cauthen, III et al. | |
| 2007/0118226 A1 | 5/2007 | Lambrecht et al. | |
| 2007/0156244 A1 | 7/2007 | Cauthen | |
| 2007/0156245 A1 | 7/2007 | Cauthen, III et al. | |
| 2007/0185497 A1 | 8/2007 | Cauthen et al. | |
| 2007/0198021 A1 | 8/2007 | Wales | |
| 2007/0225814 A1 | 9/2007 | Atkinson et al. | |
| 2007/0225815 A1 | 9/2007 | Keith et al. | |
| 2007/0225816 A1 | 9/2007 | Keith et al. | |
| 2007/0233257 A1 | 10/2007 | Keith et al. | |
| 2007/0239280 A1 | 10/2007 | Keith et al. | |
| 2007/0288041 A1 | 12/2007 | Cauthen | |
| 2008/0033561 A1 | 2/2008 | Cauthen | |
| 2009/0024165 A1 | 1/2009 | Ferree | |

FOREIGN PATENT DOCUMENTS

| | | |
|---|---|---|
| EP | 0 025 706 | 3/1981 |
| EP | 0 042 953 | 1/1982 |
| EP | 0 049 978 | 4/1982 |
| EP | 0 076 409 | 4/1983 |
| EP | 0 110 316 | 6/1984 |
| EP | 0 122 902 | 10/1984 |
| EP | 0 126 570 | 11/1984 |
| EP | 0 145 577 | 6/1985 |
| EP | 0 193 784 | 9/1986 |
| EP | 1 797 827 | 6/2007 |
| EP | 1 857 055 | 11/2007 |
| GB | 2 054 383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 4/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/26570 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |

OTHER PUBLICATIONS

International Search Report and Written Opinion issued in PCT/US2009/060425, mailed Feb. 15, 2010, 16 pages.
U.S. Appl. No. 60/378,132, filed May 15, 2002, (claimed for purposes of priority in U.S. Appl. No. 6,878,167), publicly available as of at least Apr. 12, 2005.
U.S. Appl. No. 60/375,185, filed Apr. 24, 2002, (claimed for purposes of priority in U.S. Appl. No. 6,878,167), publicly available as of at least Apr. 12, 2005.
U.S. Appl. No. 60/590,942, filed Jul. 23, 2004, (claimed for purposes of priority in U.S. Publication 2005/0256582), publicly available as of at least Nov. 17, 2005.
U.S. Appl. No. 60/149,490, filed Aug. 18, 1999, (claimed for purposes of priority in U.S. Publication 2003/0125807), publicly available as of at least Jul. 3, 2003.
Ahlgren, B.D., MD, et al., "Anular Incision Technique on the Strength and Multidirectional Flexibility of the Healing Intervertebral Disc," Spine 19(8):948-954 (1994).
Ahlgren, B.D., MD., et al., Effect of Anular Repair on the Healing Strength of the Intervertebral Disc: Spine 25(17):2165-2170 (2000).
Cauthen, Joseph, Draft Abstract entitled "Microsurgical Annular Reconstruction (Annuloplasty) Following Lumbar Microdiscectomy: Preliminary Report of a New Technique" from abstracts@neurosurgery.org Sep. 4, 1998.
Cauthen, Joseph C., MD., "Microsurgical Annular Reconstruction (Annuloplasty) Following Lumbar Microdiscectomy: Preliminary Report of a New Technique," Abstract for Poster Presentation. AANS/CNS Section on Disorders of the Spine and Peripheral Nerves Annual Meeting (1999).
Cauthen, Joseph C., "Annulotomy Study, Preliminary Results: Updated Feb. 1999 for all procedures with at least one year follow-up" (Table). Feb. 8, 1999.
Lehmann, Thomas R., M.D., et al., "Refinements in technique for Open Lumbar Discectomy," International Society for the Study of the Lumbar Spine (1997).
Mineiro, J., et al., "Dynamic Neutralization With Dynesys Review of 113 Cases with More than 1 Year Follow-Up," Spineweek 2004, Porto, Portugal May 30 to Jun. 5, 2004, Abstract B19, p. 181.
Ordway, N.R., et al., "Failure Properties of a Hydrogel Nucleus the Intervertebral Disc," North American Spine Society, pp. 168-169 (1997).
Osti, O.L., et al., "Annular Tears and Disc Degeneration in the Lumbar Spine," The Journal of Bone and Joint Surgery 74-8(5);678-82 (1992).
Panjabi, Manohar, PhD., et al., "Intrinsic Disc Pressure as a Measure of Integrity of the Lumbar Spine," Spine 13(8):913-17 (1988).
Ray, Charles D., "Prosthetic Disc Nucleus Implants: Update," North American Spine Society 13th Annual Meeting, p. 252 (1998).
Yasargil, M.G., "Microsurgical Operation of Herniated Lumbar Disc," Lumbar Disc Adult Hydrocephelus, p. 81 (1977).

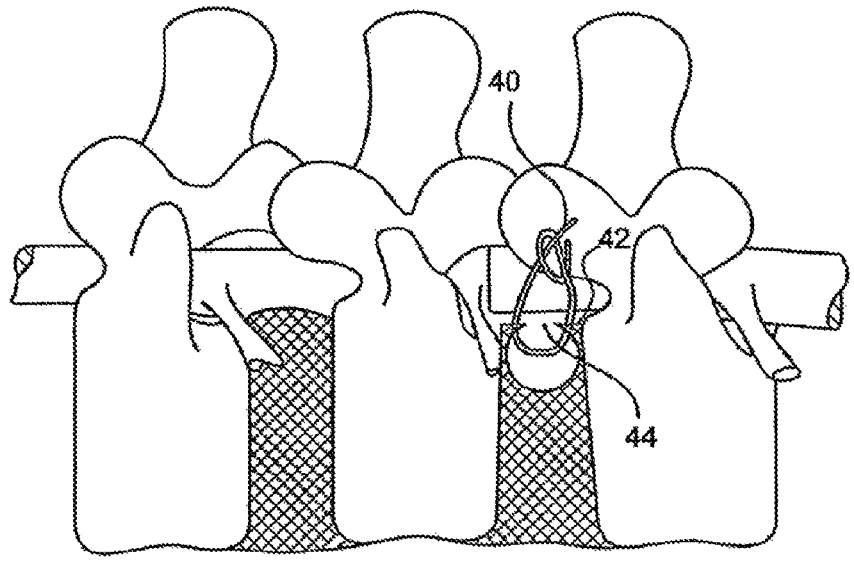
FIG. 1
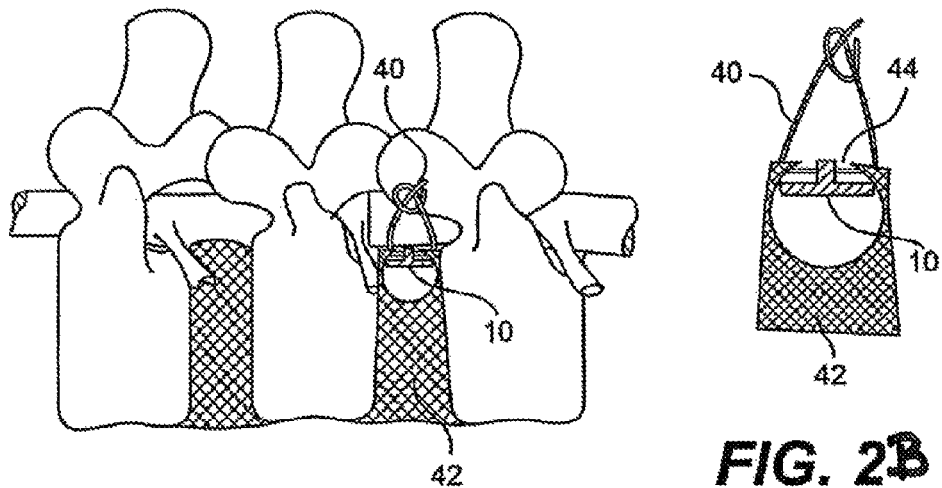
FIG. 2A
FIG. 2B

HERNIATED DISC

DISC, POST-DISCECTOMY

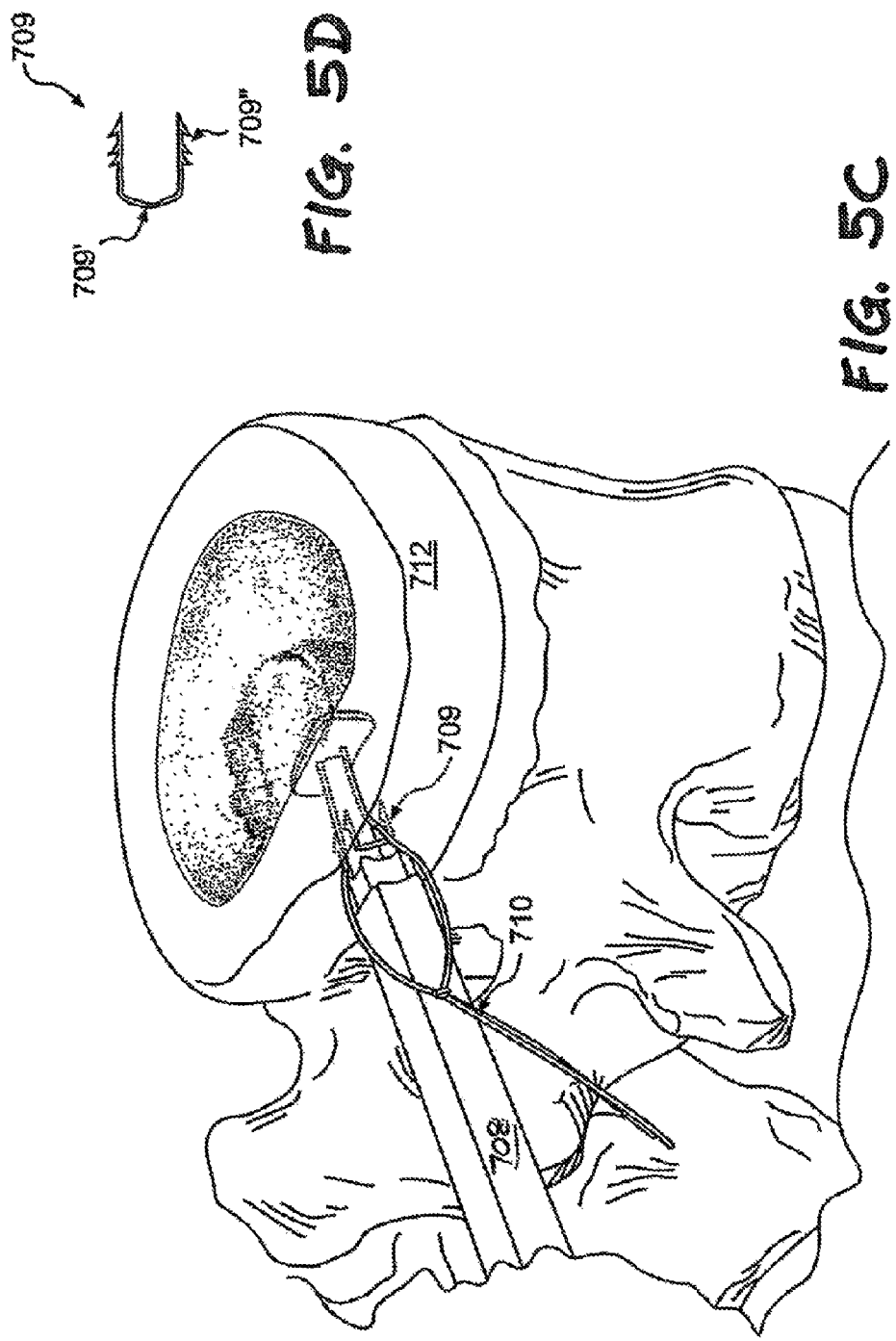

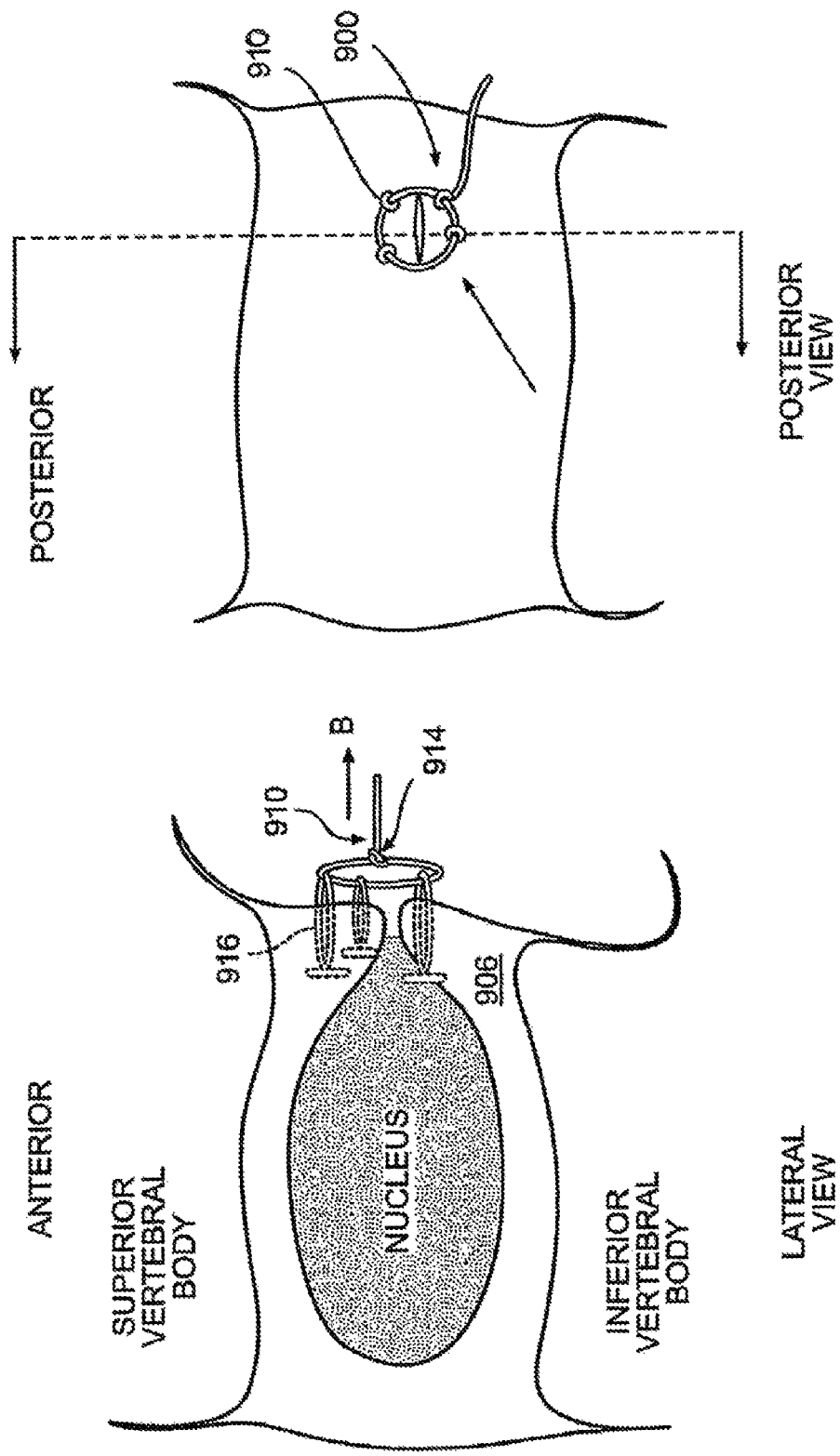

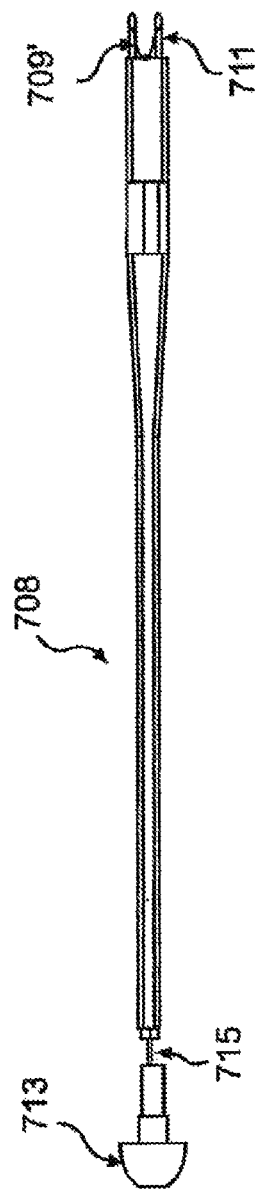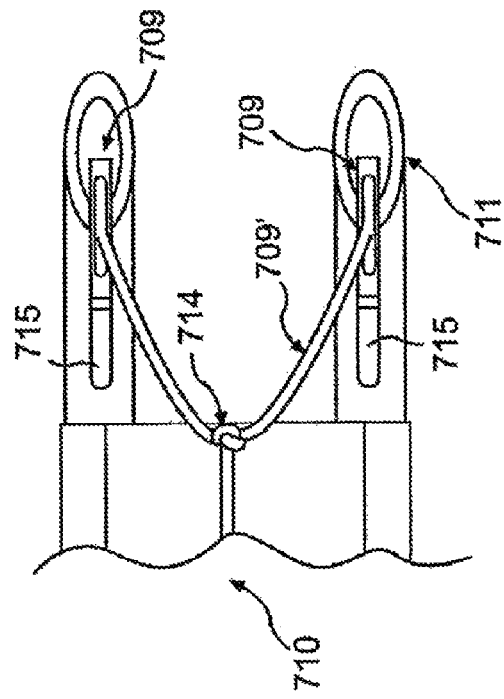

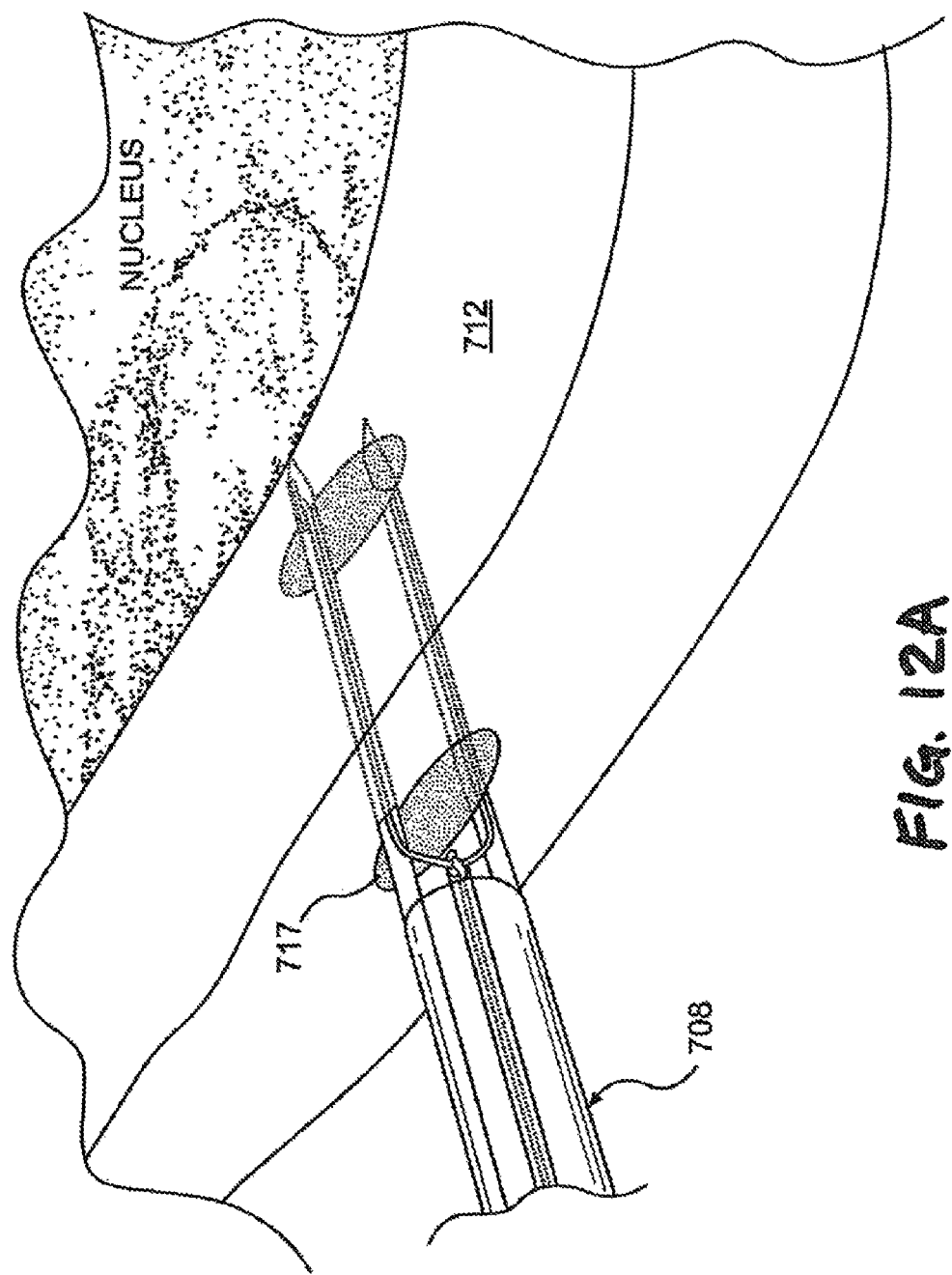

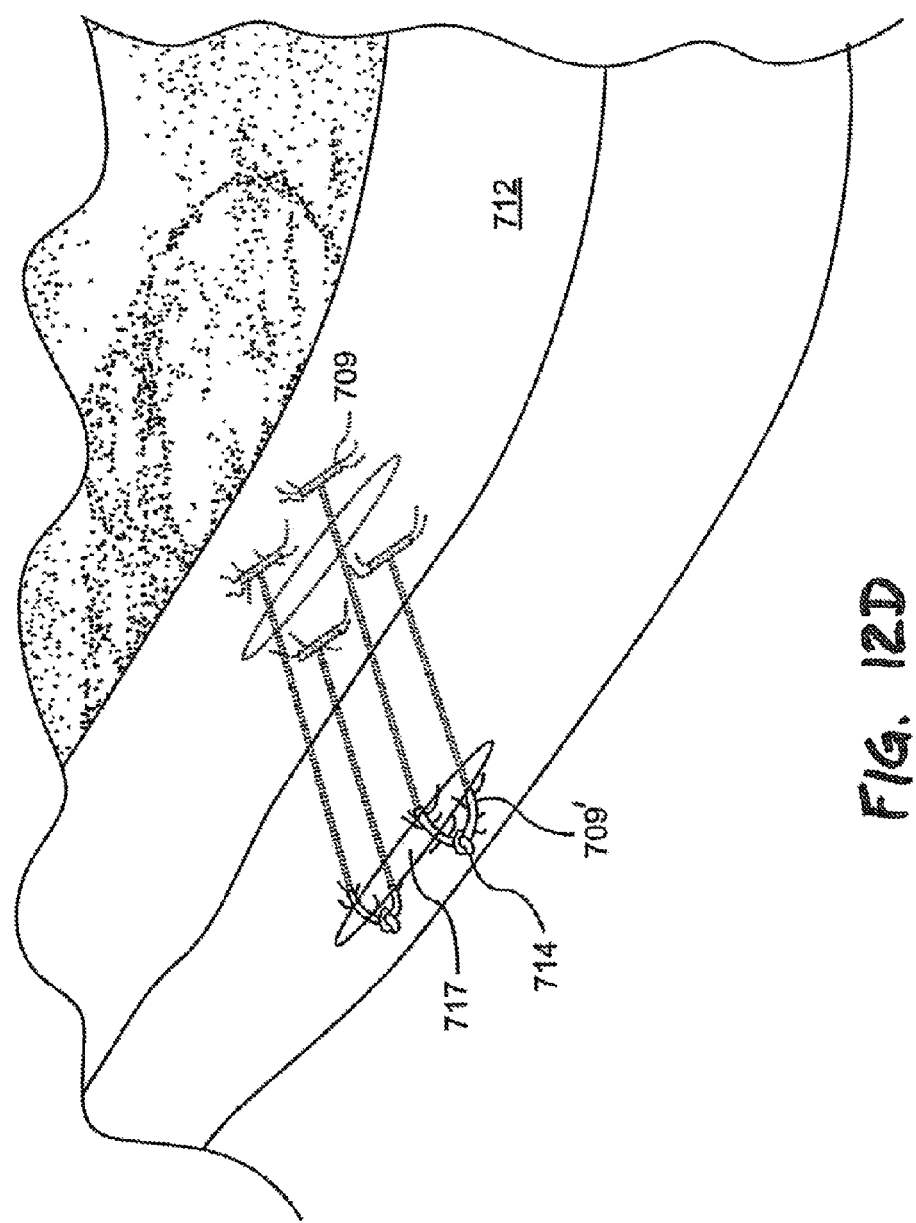

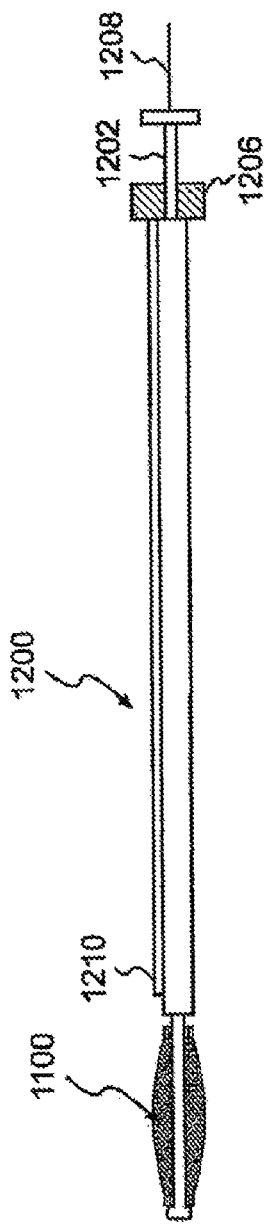
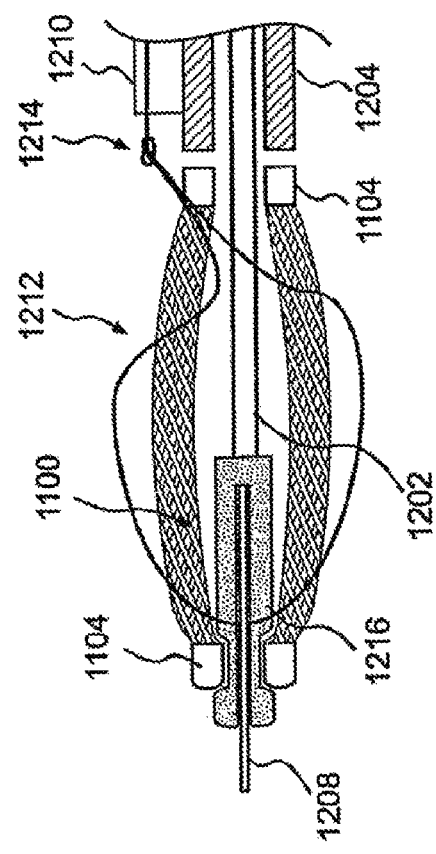
FIG. 15
FIG. 16

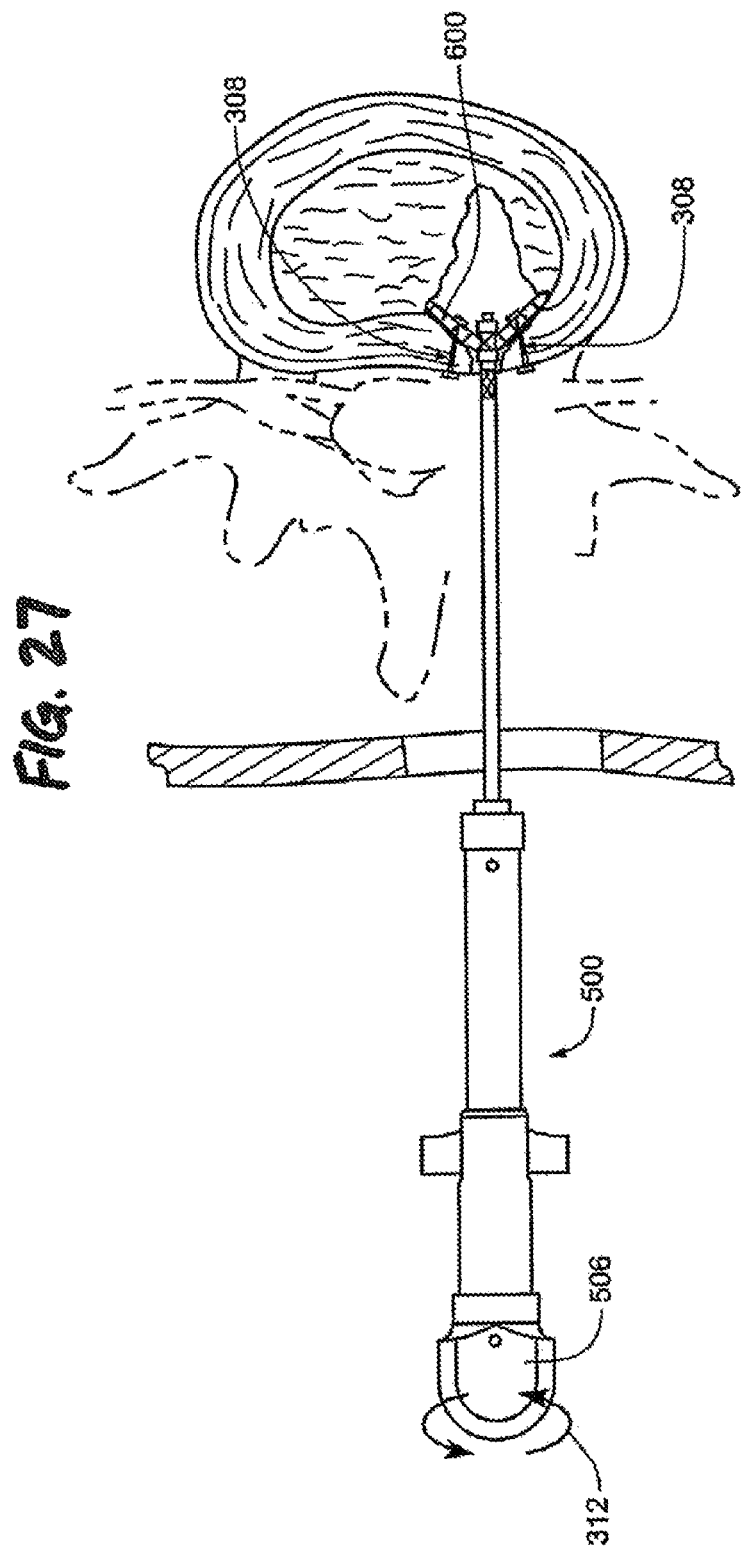

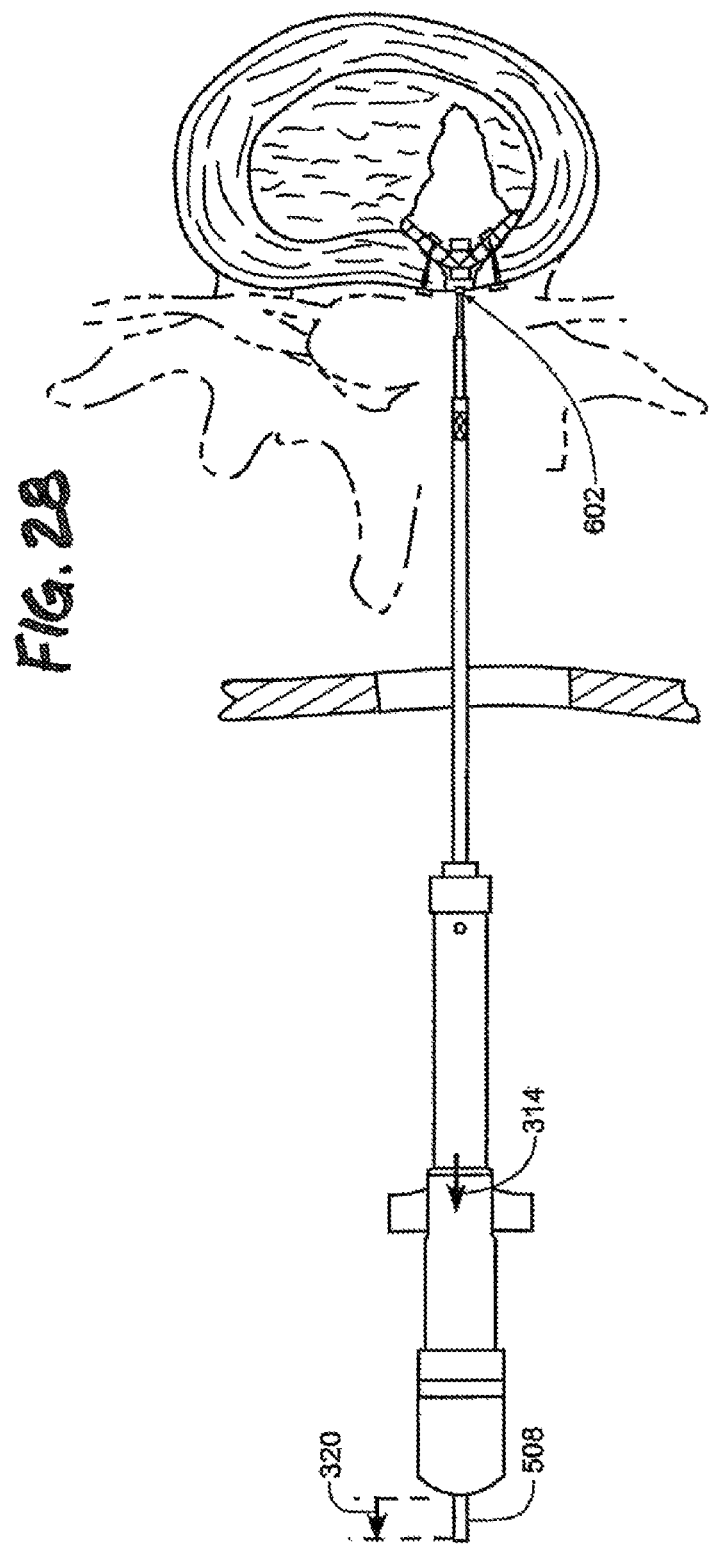

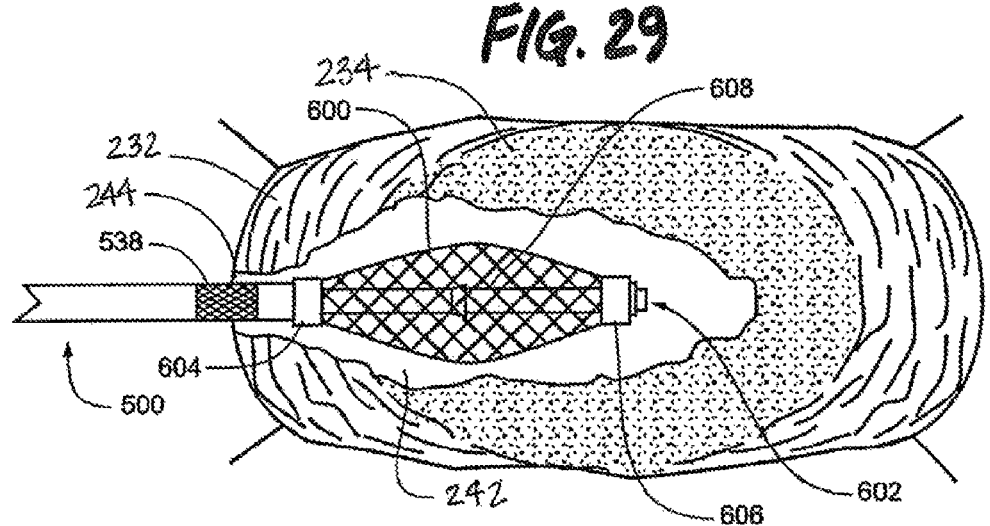
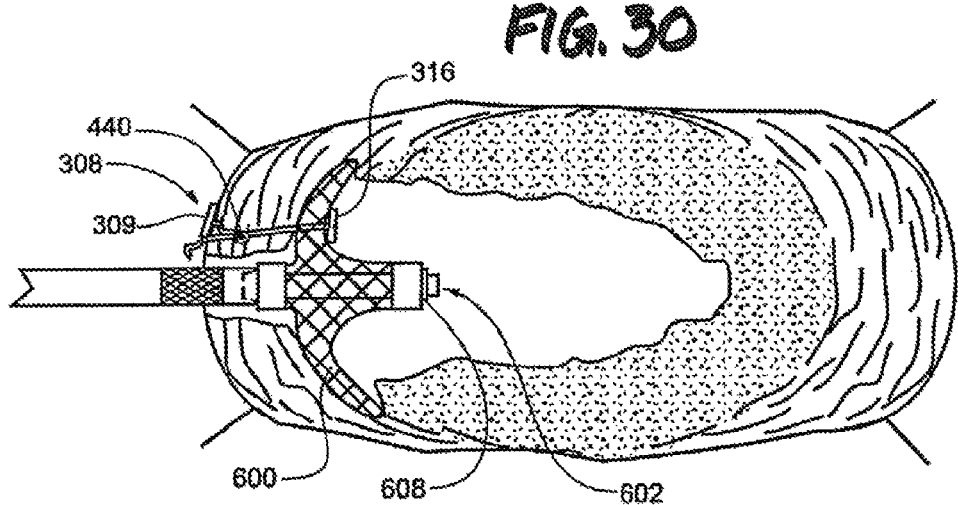

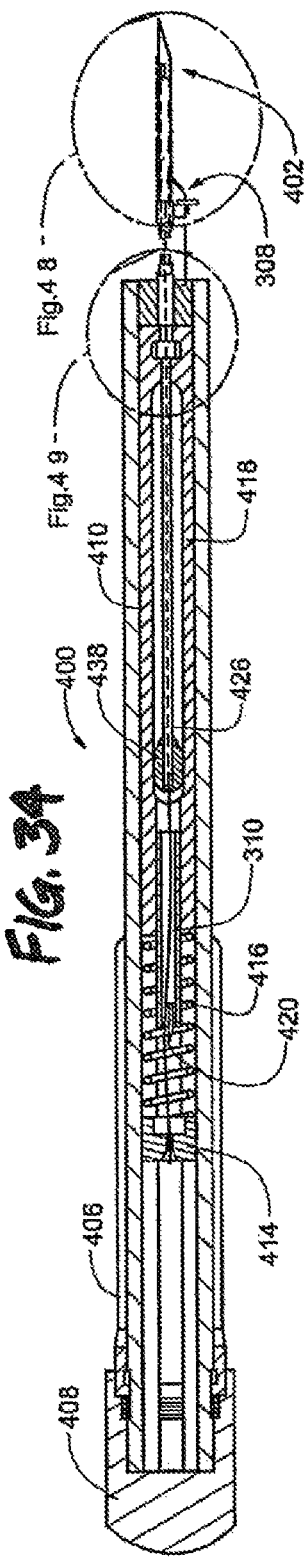
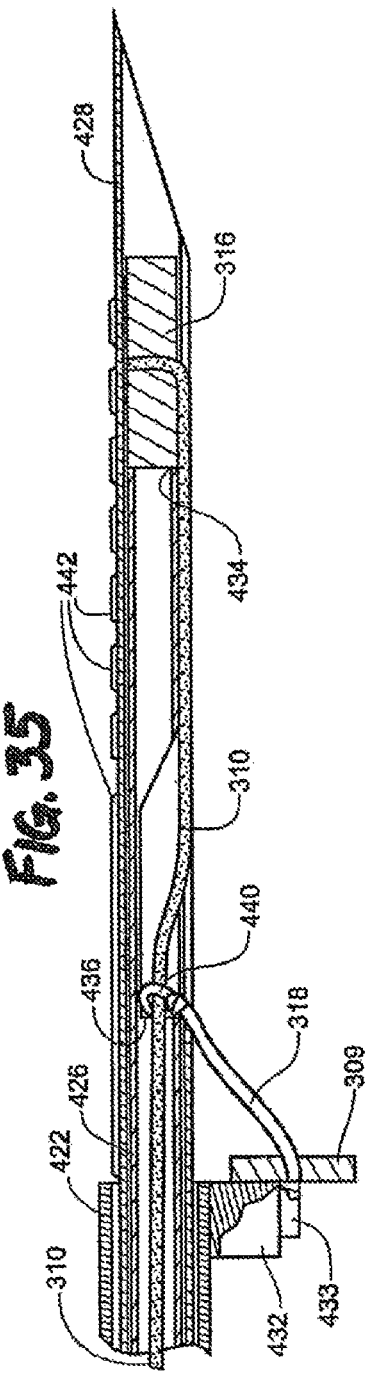

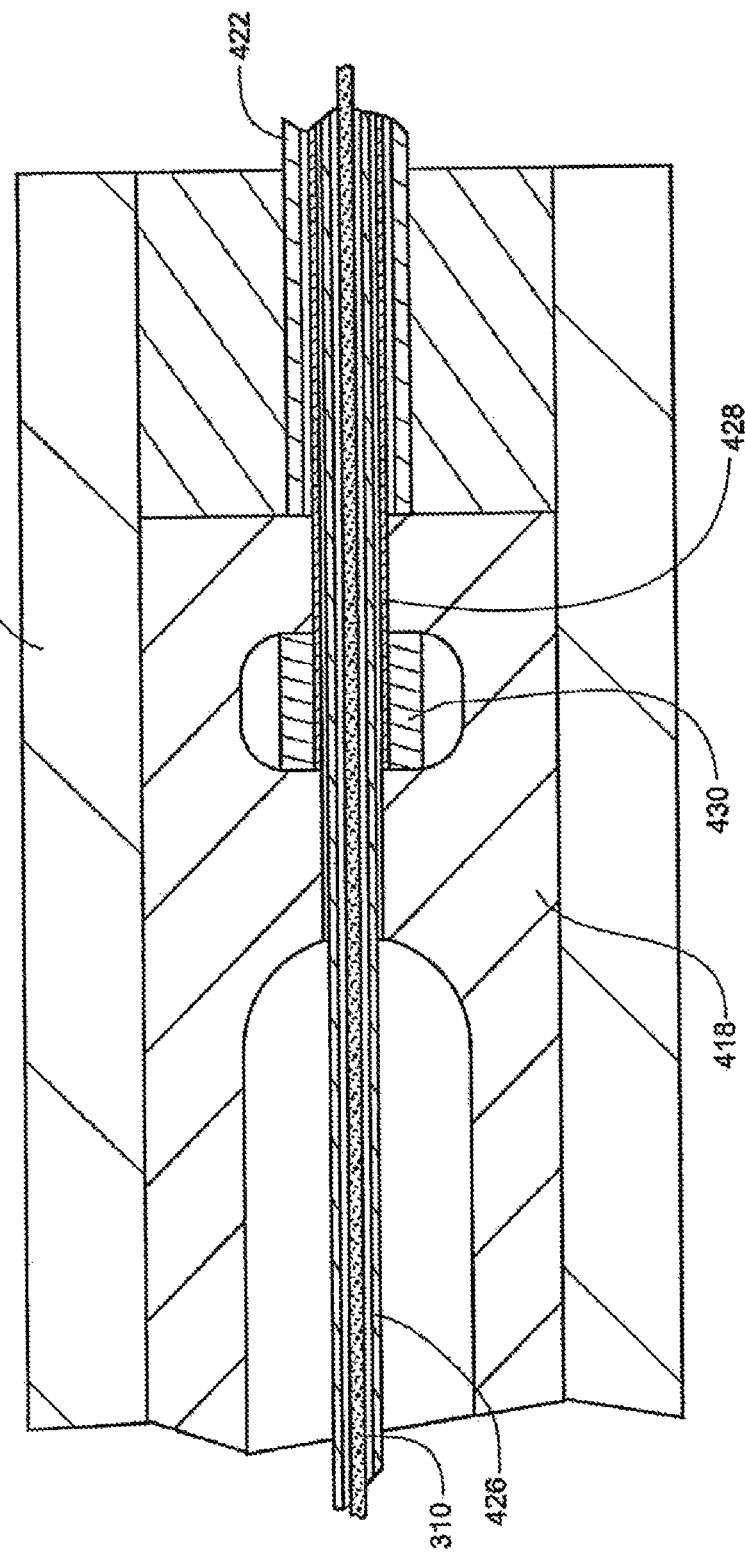

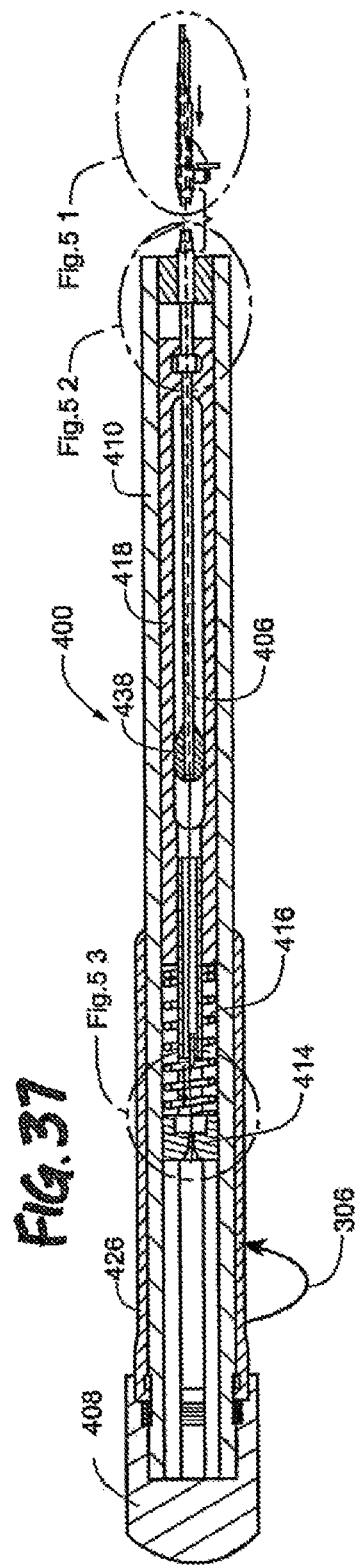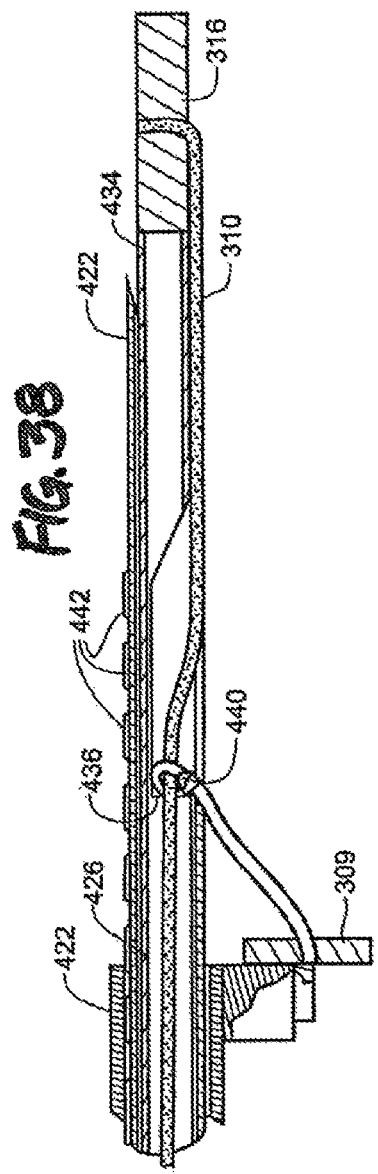

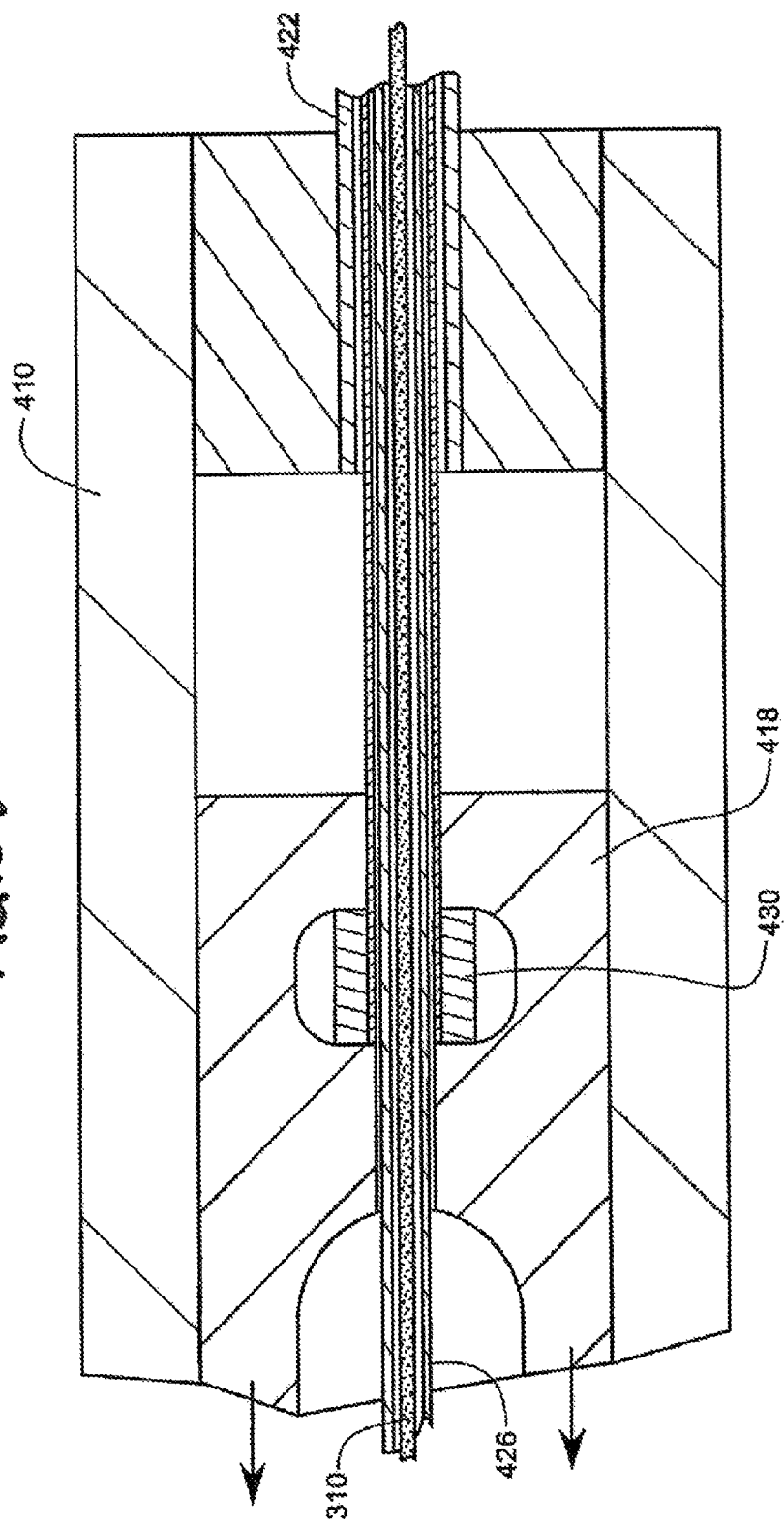

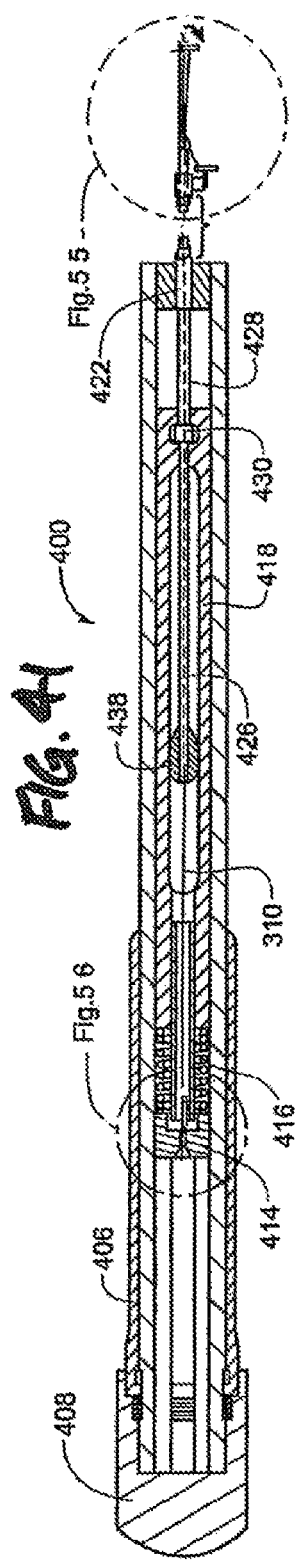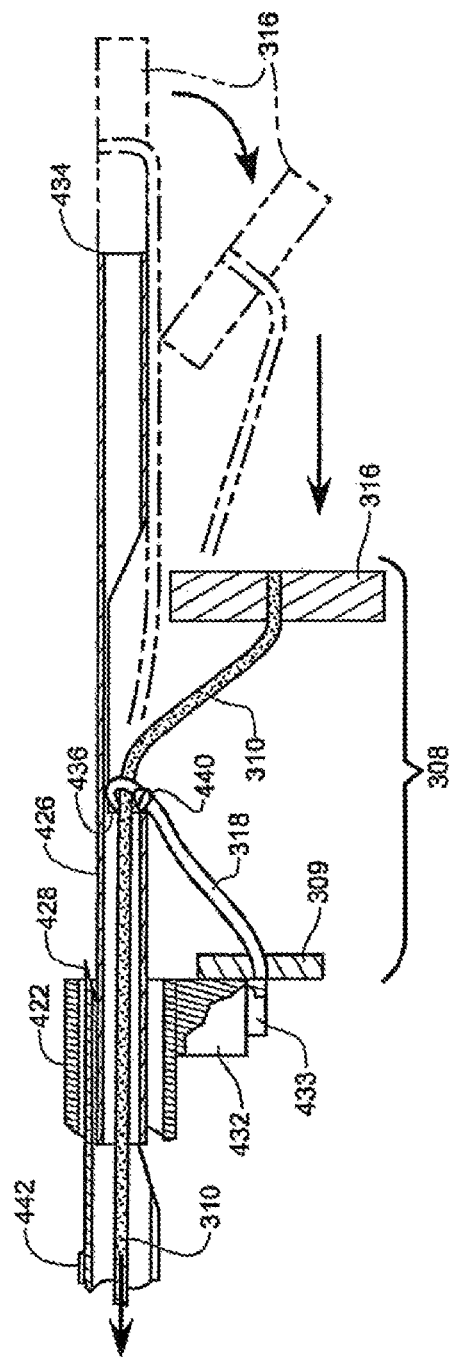

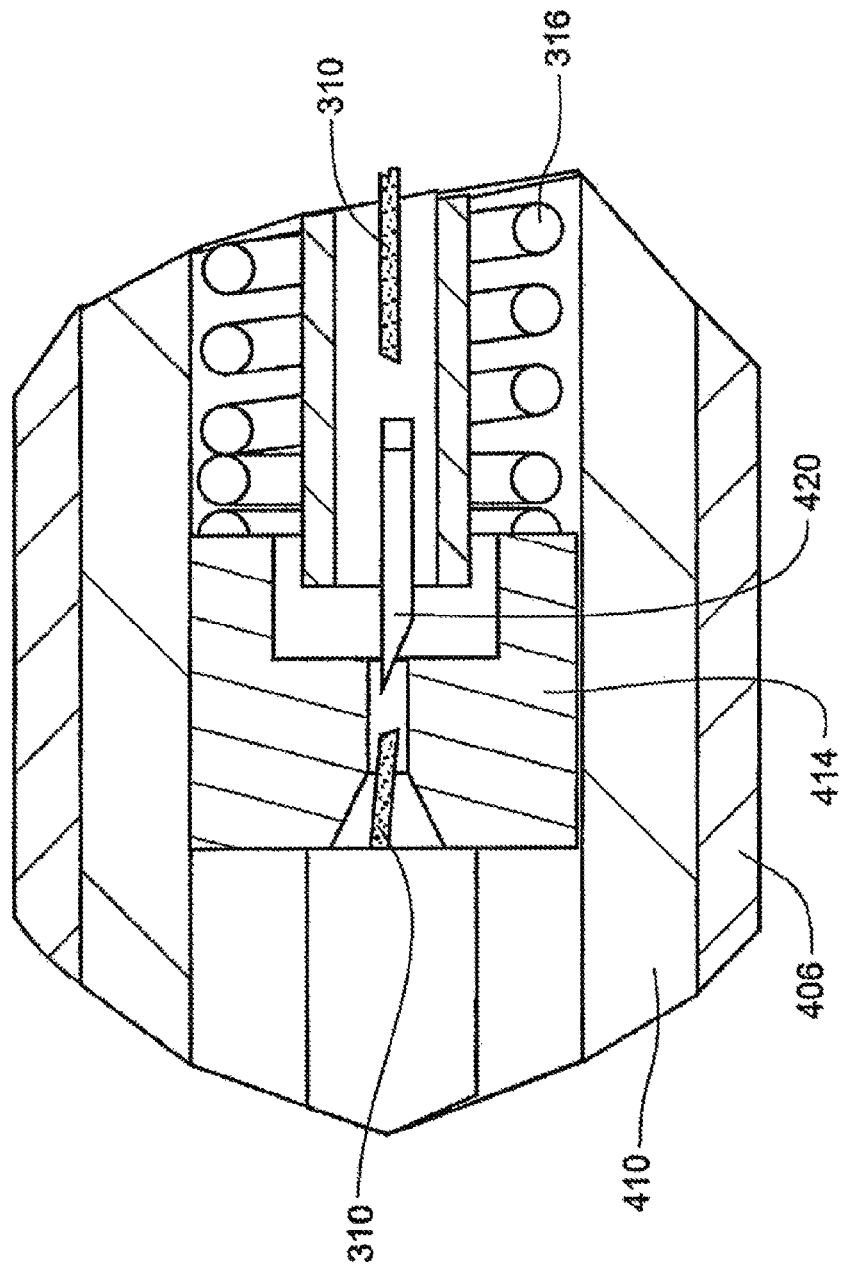

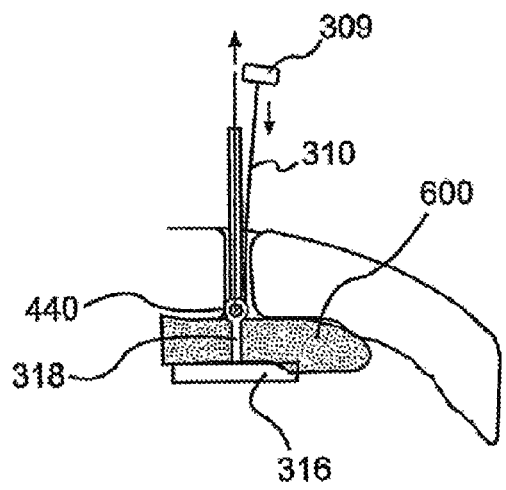
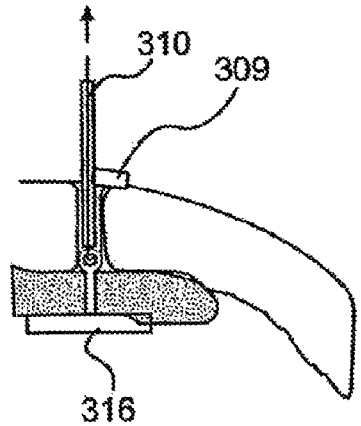
FIG. 46A      FIG. 46B
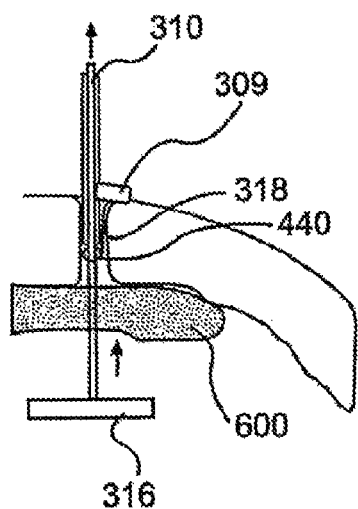
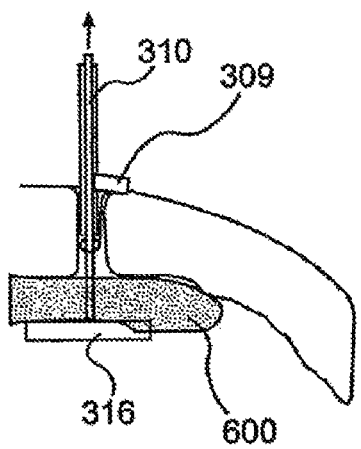
FIG. 47A      FIG. 47B

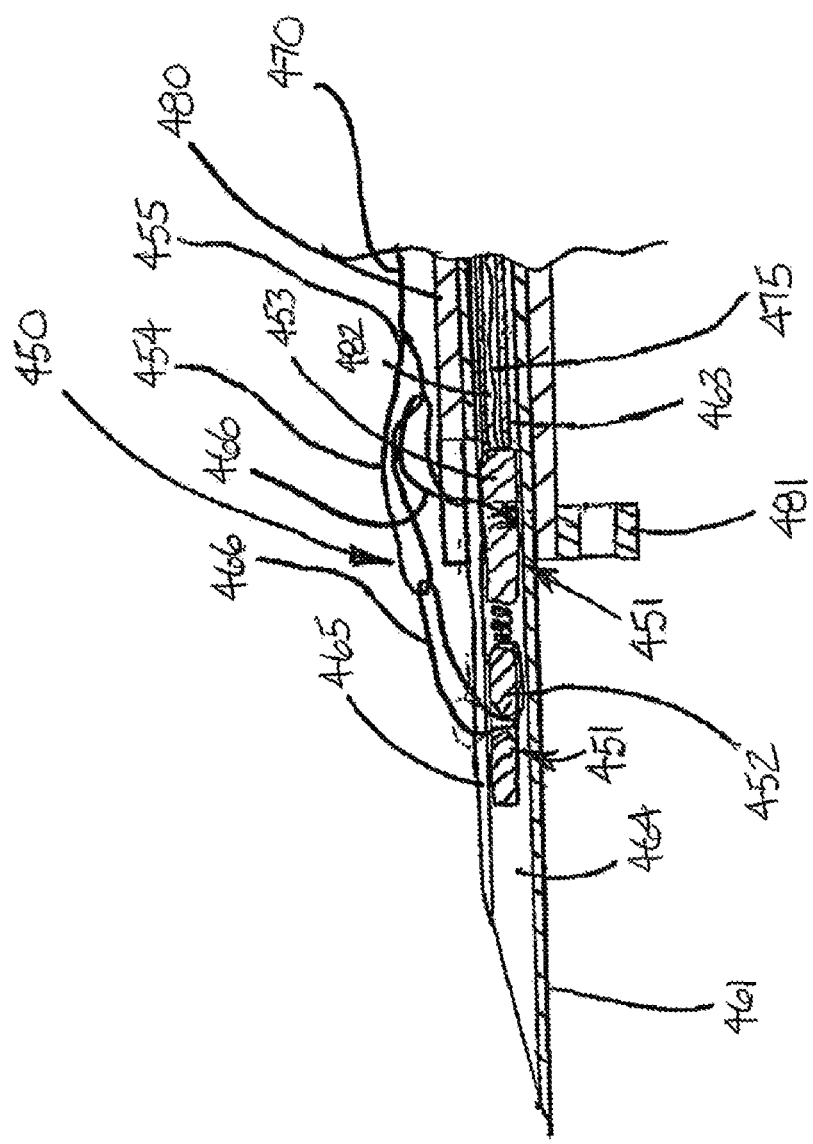

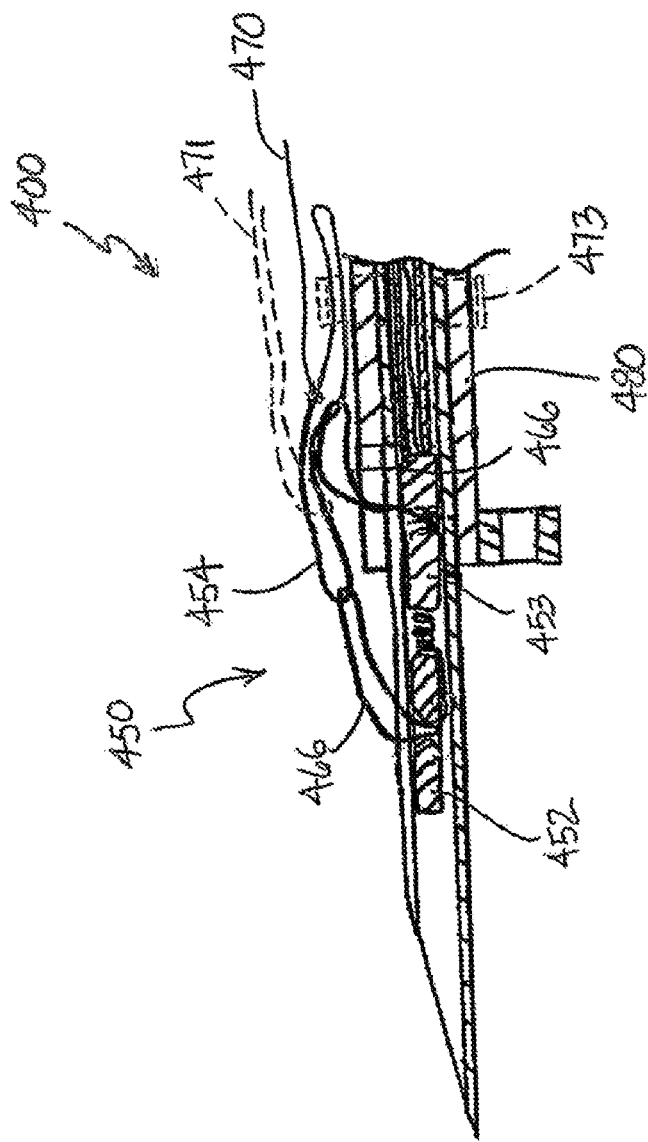

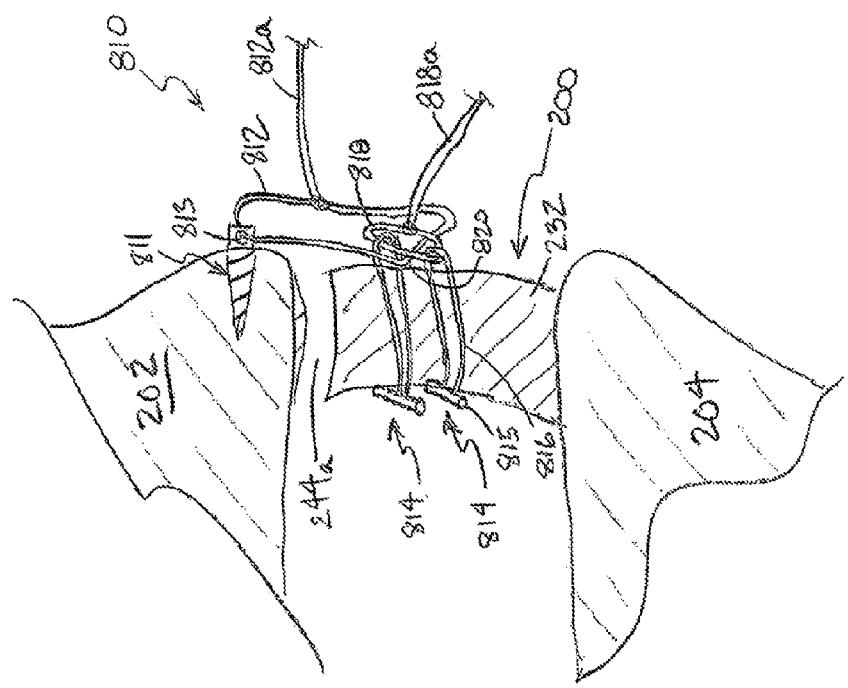
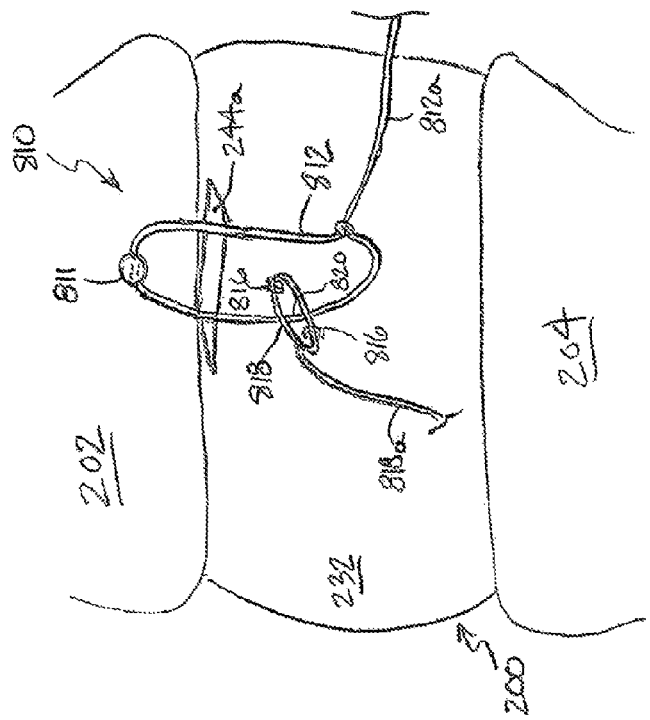

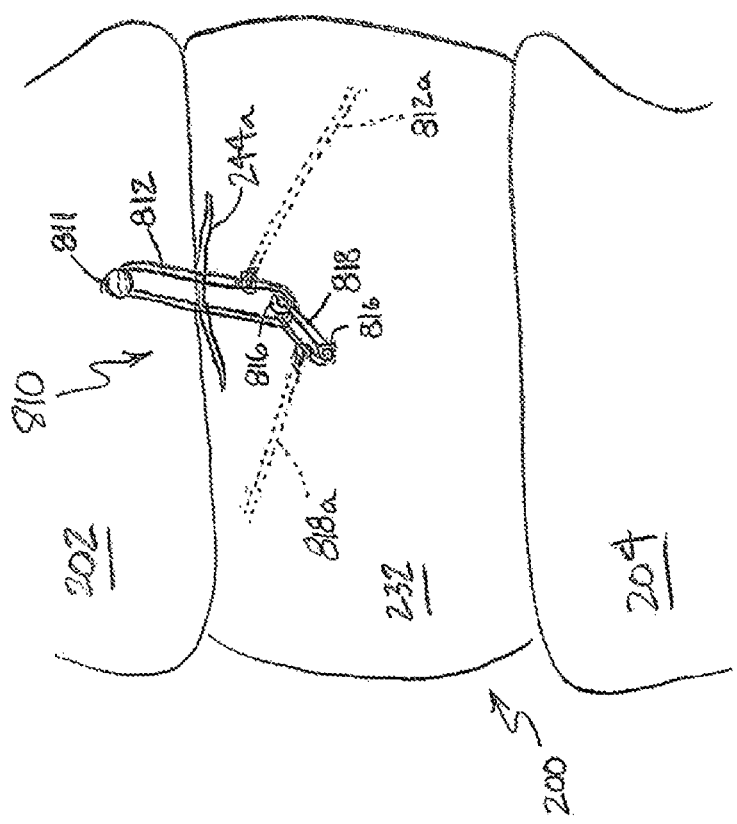

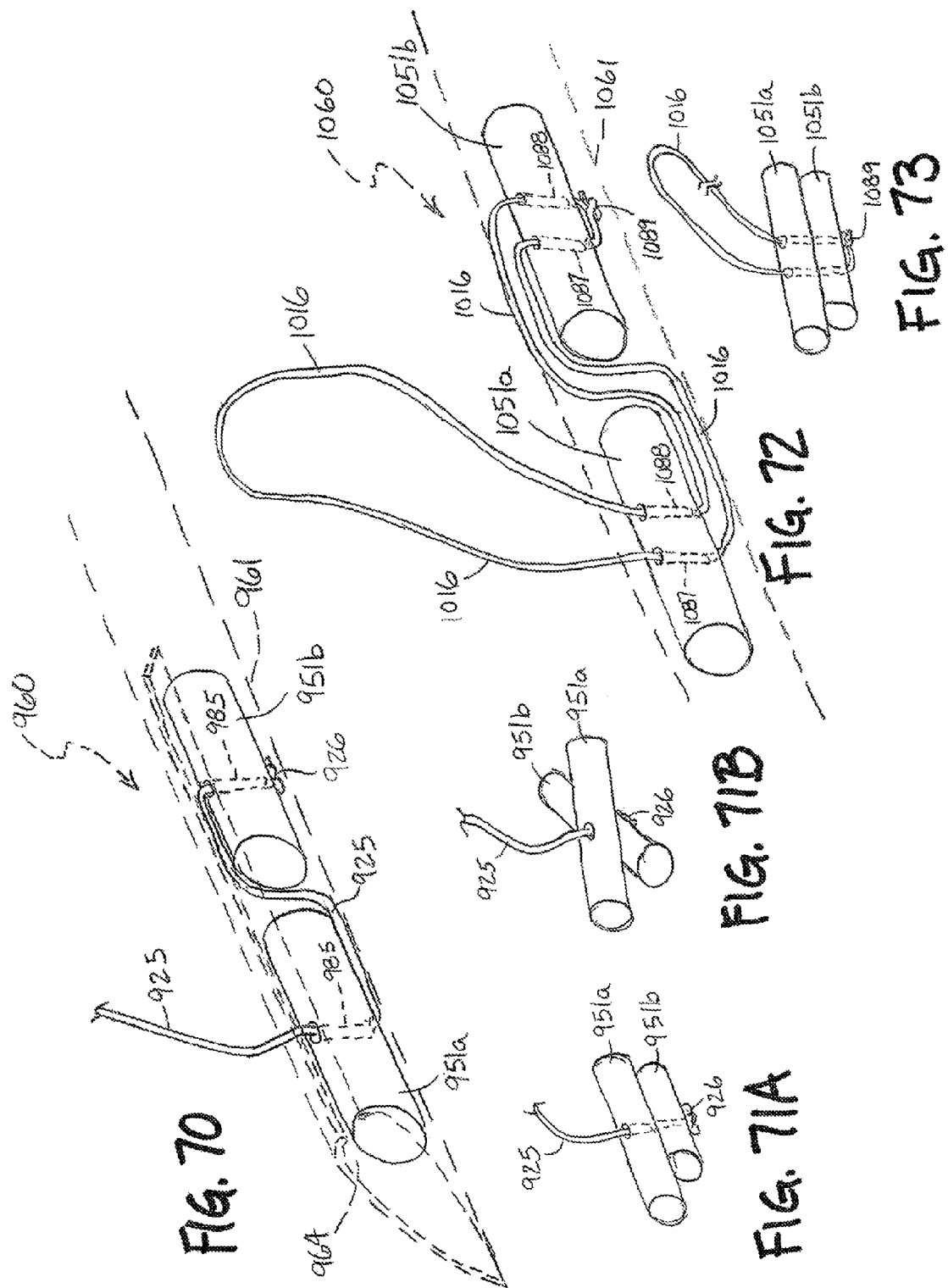

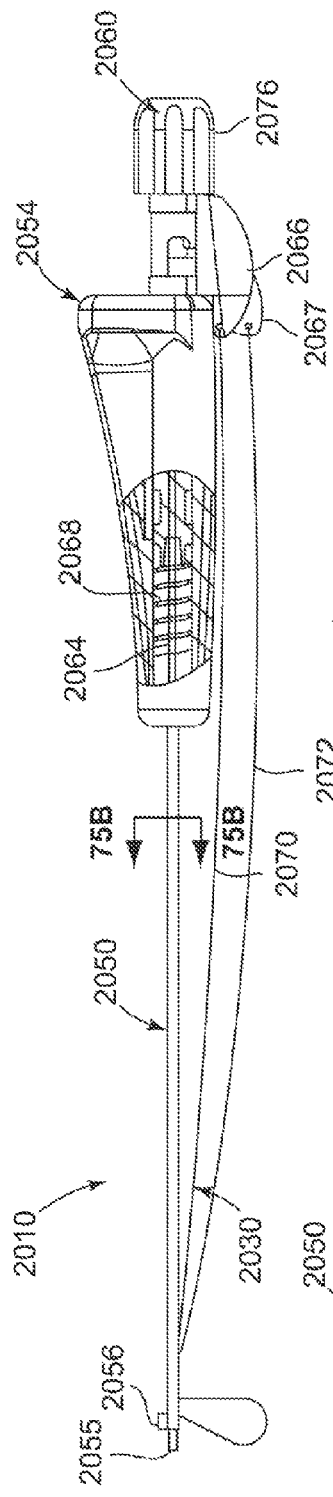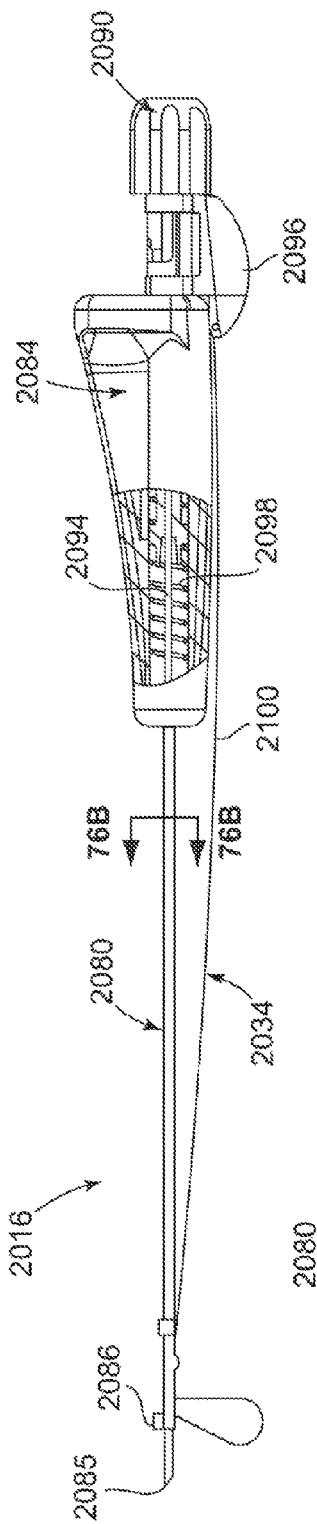

METHOD AND APPARATUS FOR THE TREATMENT OF TISSUE

CROSS-REFERENCE TO RELATED APPLICATION

This application is a continuation of U.S. application Ser. No. 12/553,583, filed Sep. 3, 2009, now U.S. Pat. No. 8,163,022, which is a continuation-in-part of U.S. application Ser. No. 12/251,295, filed Oct. 14, 2008, now U.S. Pat. No. 8,128,698, which are herein incorporated by reference in their entirety.

TECHNICAL HELD

The invention generally relates to methods and devices for the closure, sealing, repair and/or reconstruction of an intervertebral disc annulus, and accompanying delivery devices and tools, and their methods of use.

BACKGROUND

The spinal column is formed from a number of bony vertebrae, which in their normal state are separated from each other by intervertebral discs. These discs are comprised of the annulus fibrosus, and the nucleus pulposus, both of which are soft tissue. The intervertebral disc acts in the spine as a crucial stabilizer, and as a mechanism for force distribution between adjacent vertebral bodies. Without a competent disc, collapse of the intervertebral disc may occur, contributing to abnormal joint mechanics and premature development of degenerative and/or arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. Fissures in the annulus fibrosus can occur due to various causes, including disease or other pathological conditions, or the natural aging process. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

The present inventors have found, advantageously and contrary to accepted practice, that the annulus tissue may be repaired or otherwise treated and that annular healing may be facilitated by reapproximation, reinforcement, and/or support of annular tissue. Methods and devices for carrying out annular repair and/or reconstruction are a subject of the present invention.

SUMMARY

The present invention, in one embodiment, is a system for at least partially closing an aperture in an annulus fibrosus of an intervertebral disc adjacent to a vertebral body of a patient. The system comprises a first fixation delivery apparatus, a first fixation apparatus, a second fixation delivery apparatus, and a second fixation apparatus. The first fixation delivery apparatus has a tubular shaft and a proximal handle. The first fixation apparatus is releasably coupled to the first fixation delivery apparatus and includes a bone anchor configured to be deployed at least partially into and attached to a vertebral body, and an adjustable flexible connecting element connected to the bone anchor. At least a portion of the bone anchor and a portion of the adjustable connecting element are disposed within the tubular shaft of the first fixation delivery apparatus prior to deployment of the first fixation apparatus, and the flexible connecting element can be manipulated by a user to adjust a length of thereof. The second fixation delivery apparatus includes a tubular shaft having a sharpened tissue-piercing distal tip, a proximal handle coupled to the tubular shaft, a releasable tab coupled to the handle, an ejection rod slidably disposed within the tubular shaft, and an actuator slidably coupled to the handle and operatively coupled to the ejection rod. The second fixation apparatus is releasably coupled to the second fixation delivery apparatus and includes a pair of tissue anchors and an adjustable flexible connecting element connecting the tissue anchors. The tissue anchors and a first portion of the flexible connecting element of the second fixation apparatus are disposed within the tubular shaft of the second fixation delivery apparatus, and a second portion of the flexible connecting element is coupled to the releasable tab of the second fixation delivery apparatus prior to deployment. Additionally, the bone anchor is configured to be attached to the vertebral body, the tissue anchors are configured to be attached to the annulus fibrosus with the aperture located between the bone anchor and the tissue anchors, and the flexible connecting elements of the first fixation apparatus and the second fixation apparatus are configured to be interconnected and placed in tension to at least partially dose the aperture in the annulus fibrosus.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 shows a primary closure of an opening in the disc annulus.

FIGS. 2A-2B show a primary closure with a stent.

FIGS. 5A-5G show a still further illustrative embodiment of an introduced and expanded annulus stent/patch being fixated and the aperture reapproximated.

FIG. 10 shows a delivered configuration of fixation means that may result from the use of a single, or multiple, devices to deliver multiple barbs, anchor, or T-anchors sequentially or simultaneously.

FIGS. 11A-11B show an illustrative configuration of an anchor band delivery device.

FIGS. 12A-12D show an anchor band delivery device comprising two devices, each with at least one T-anchor and band with pre-tied knot and optional knot pusher according to illustrative embodiments of the invention.

FIG. 15 shows a lateral view of the exemplary embodiment of FIG. 27A in a collapsed configuration mounted on an illustrative delivery device.

FIG. 16 shows a lateral cutaway view of the exemplary embodiment of FIG. 27A in a collapsed configuration.

FIG. 27 shows a transverse view of an additional fixation element locked in place on the opposite side of the treatment device.

FIG. 28 shows a transverse view of the removal of the treatment device delivery tool.

FIG. 29 shows an transverse view of an illustrative embodiment of a treatment device mounted on a delivery tool in an unexpanded configuration in the subannular cavity.

FIG. 30 shows a transverse view after affixing a fixation element to the treatment device of FIG. 29.

FIG. 34 is a view of the anchor band delivery tool pre-deployment in cross section.

FIG. 35 shows a detail of the distal end of the anchor band (fixation element) delivery tool in cross section.

FIG. 36 shows a detail of the slide body and cannula anchor of an exemplary fixation element delivery tool in cross section.

FIG. 37 is a view of the anchor band delivery tool in cross section during a deployment cycle.

FIG. 38 is a detail of the distal end of the anchor band delivery tool depicted in FIG. 37.

FIG. 39 shows a detail of the slide body and cannula anchor of an exemplary fixation element delivery tool in cross section during a deployment cycle.

FIG. 41 is a view of the anchor band delivery tool in cross section during the cutting of the suture tether and release of the anchor band.

FIG. 42 shows a detail of the distal end of the anchor band delivery tool during release of the anchor band.

FIG. 43 shows a detail of the shows a detail of the suture retention block and blade assembly of the anchor band delivery tool during the cutting of the tether.

FIGS. 46A-463 show alternative illustrative mechanisms of drawing together locking elements/anchors.

FIGS. 47A-47B show alternative illustrative attachment mechanisms where a pledget element that initially resides on outer annular surface.

FIGS. 48A-48E illustrate a fixation delivery apparatus and fixation apparatus in accordance with aspects of the present invention.

FIGS. 49-57B shows an exemplary treatment apparatus comprising an annulus fibrosus tissue anchor assembly coupled to a bone anchor via a shortenable elongate element, and the assembly and activation thereof.

FIGS. 70-71B illustrate an exemplary T-anchor type anchor construct comprising a dual T-anchor implant, with two T-anchors shown ready for insertion in series (FIG. 70) and those two anchors implanted and activated in vivo (FIGS. 71A-71B).

FIGS. 72-73 show an alternative exemplary T-anchor type anchor construct comprising a dual T-anchor implant, with two T-anchors shown ready for insertion in series (FIG. 72) and those two anchors implanted and activated in vivo (FIG. 73).

FIG. 75A is a partial cutaway illustration of a first fixation delivery tool and a first fixation device of the system of FIG. 73 according to one embodiment of the present invention.

FIG. 75B is a cross-sectional view of a portion of the delivery tool of FIG. 75A taken along the line 75B-75B.

FIG. 76A is a partial cutaway illustration of a second fixation delivery tool and a second fixation device of the system of FIG. 73 according to one embodiment of the present invention.

FIG. 76B is a cross-sectional view of a portion of the delivery tool of FIG. 76A taken along the line 76B-76B.

Figure 2C:
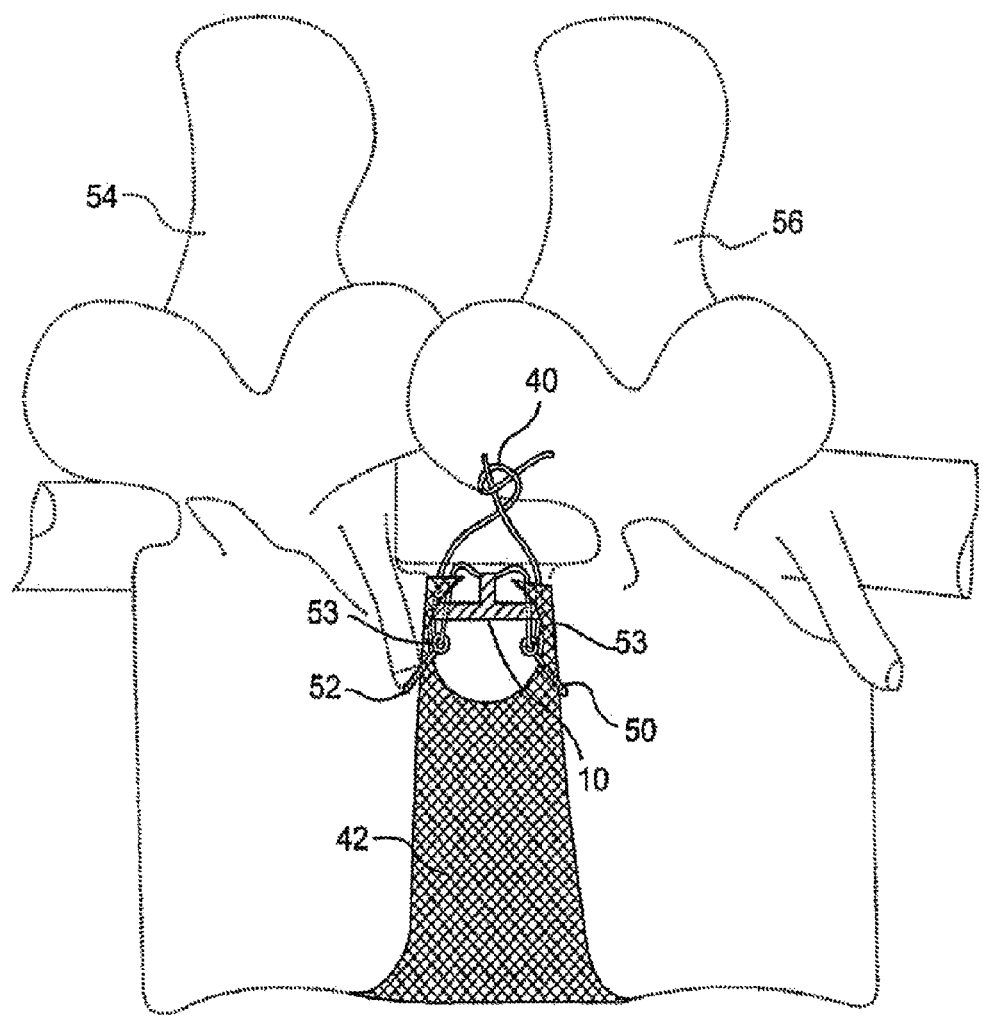
FIG. 2C shows a method of affixing an annulus stent into the disc annulus utilizing fixation points on vertebral bodies.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claim.

DETAILED DESCRIPTION

In the surgical repair of an aperture in the annulus, as shown in FIG. 1 and as described in related commonly-assigned U.S. Pat. No. 6,592,625 to Cauthen, a damaged annulus 42 is repaired by use of surgical sutures 40. One or more surgical sutures 40 are placed at about equal distances along the sides of a pathologic aperture 44 in the annulus 42. Reapproximation or closure of the aperture 44 is accomplished by tying the sutures 40 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 40 are biodegradable, but permanent non-biodegradable may be utilized. In all embodiments where biodegradable materials are indicated, suitable biodegradable materials may include, but are not limited to, biodegradable polyglycolic acid, swine submucosal intestine, collagen, or polylactic acid. Other suitable suturing (and band) materials include, e.g., polymeric materials such as polyethylene teraphthalate (PET), polyester (e.g., Dacron®), polypropylene, polyethylene, polycarbonate urethane or metallic material include, e.g., titanium, nickel titanium alloy, stainless steel, surgical steels or any combinations thereof.

Additionally, to repair a weakened or thinned wall of a disc annulus 42, a surgical incision or dissection can be made along the weakened or thinned region of the annulus 42 and one or more surgical sutures 40 can be placed at about equal distances laterally from the incision. Reapproximation or closure of the incision is accomplished by tying the sutures 40 so that the sides of the incision are drawn together. The reapproximation or closure, of the incision/dissection enhances the natural healing and subsequent reconstruction by the natural tissue crossing the now surgically narrowed gap in the annulus 42. Preferably, the surgical sutures 40 are biodegradable, but permanent non-biodegradable materials may be utilized.

Where necessary or desirable, the method can be augmented by placing a patch in and across the aperture 44. The patch acts as a bridge in and across the aperture 44, providing a platform for traverse of fibroblasts or other normal cells of repair existing in and around the various layers of the disc annulus 42, prior to closure of the aperture 44. FIGS. 2A-B, for example, show a biocompatible device employed as an annulus stent 10, being placed in and across the aperture 44. The annulus stent 10 acts as a bridge in and across the aperture 44, providing a platform for a traverse of fibroblasts or other normal cells of repair existing in and around the various layers of the disc annulus 42, prior to closure of the aperture 44. In some embodiments the device, stent or patch can act as a scaffold to assist in tissue growth that healingly scars the annulus.

In an illustrative embodiment, the annulus stent 10 is a solid unit, formed from one or more of the flexible resilient biocompatible or bioresorbable materials well know in the art. The selection of appropriate stent materials may be partially predicated on specific stent construction and the relative properties of the material such that, after fixed placement of the stent, the repair may act to enhance the healing process at the aperture by relatively stabilizing the tissue and reducing movement of the tissue surrounding the aperture.

For example, the annulus stent 10 may be made from:

A porous matrix or mesh of biocompatible and bioresorbable fibers acting as a scaffold to regenerate disc tissue and replace annulus fibrosus as disclosed in, for example, U.S. Pat. Nos. 5,108,438 (Stone) and 5,258,043 (Stone), a strong network of inert fibers intermingled with a bioresorbable (or bioabsorbable) material which attracts tissue ingrowth as disclosed in, for example, U.S. Pat. No. 4,904,260 (Ray et al.).

a biodegradable substrate as disclosed in, for example, U.S. Pat. No. 5,964,807 (Gan at al); or an expandable polytetrafluoroethylene (ePTFE), as used for conventional vascular grafts, such as those sold by W.L. Gore and Associates, Inc. under the trademarks GORE-TEX and PRECLUDE, or by Impra, Inc. under the trademark IMPRA.

Furthermore, the annulus, stent 10, may contain hygroscopic material for a controlled limited expansion of the annulus stent 10 to fill the evacuated disc space cavity.

Additionally, the annulus stent 10 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

Many of the materials disclosed and described above represent embodiments where the device actively promotes the healing process. It is also possible that the selection of alternative materials or treatments may modulate the role in the healing process, and thus promote or prevent healing as may be required. It is also contemplated that these modulating factors could be applied to material substrates of the device as a coating, or similar covering, to evoke a different tissue response than the substrate without the coating.

Materials of the patch could include a metallic material (e.g., NiTi alloy, Stainless steel, Titanium), or a polymeric material (e.g., polypropylene, polyethylene, polyurethane, polycarbonate urethane, polyetheretherketone (PEEK), polyester, PET, poly olefin copolymer, polypropylene, polyethylene), or a biodegradable or bioresorbable material (e.g., collagen, cellulose, polysaccharide, polyglycolic acid (PGA), a polylevolactic acid (PPLA), a polydioxanone (PDA) or for example a racemic polylactic acid (PDLLA), or a combination of these materials.

In an alternative method of securing the annulus stent 10 in the aperture 44, as shown in FIG. 2C, a first surgical screw 50 and second surgical screw 52, with eyeholes 53 located at the top of the screws 50 and 52, are inserted into the vertebral bodies, illustratively depicted as adjacent vertebrae 54 and 56. After insertion of the annulus stent 10 into the aperture 44, an affixation element 40 is passed through the disc annulus 42, adjacent to the aperture 44, through the eye hole 53 on the first screw 50 then back up through the disc annulus 42 and through the orifice 18 on the annulus stent 10. This is repeated for the second screw 52, after which the affixation element 40 is secured. One or more elements 40 are placed at about equal distances along the sides of the aperture 44 in the disc annulus 42. Reapproximation or closure of the aperture 44 is accomplished by tensioning elements 40 in such a fashion that the sides of the aperture 44 are drawn, partially or wholly, together. The reapproximation or closure of the aperture 44 enhances the natural healing and subsequent reconstruction by the natural tissue crossing the now surgically narrowed gap in the annulus 42. Preferably, the elements 40, such as surgical sutures, are biodegradable but permanent non-biodegradable forms may be utilized. This method should decrease the strain on the disc annulus 42 adjacent to the aperture 44, precluding the tearing of the elements through the disc annulus 42.

Figure 3A:
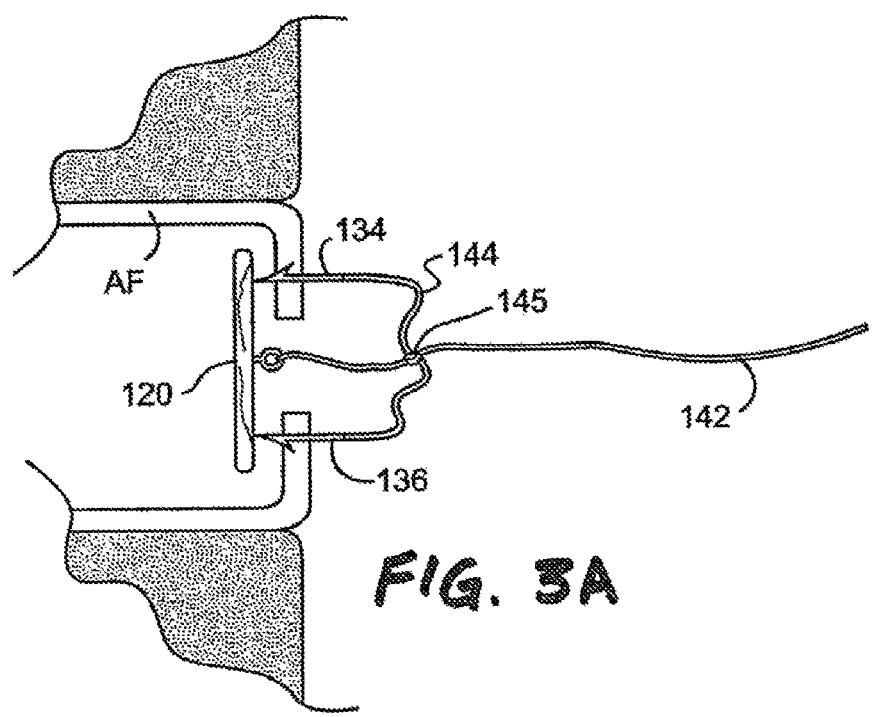
FIGS. 3A-3B show a still further illustrative embodiment of an annulus stent employing secondary barbed fixation devices.

FIG. 3A shows an alternative fixation strategy where a pair of barbs 134 and 136 are plunged into the annulus fibrosus from the exterior of the annulus while the device 120 is retained in the sub-annular space by means of a tether 142. Although there are a wide variety of fixation devices in this particular example, a tether 142 may be knotted 145 with the band 144 holding the barbs 134 and 136 together to fix the device in the sub-annular space. The knot is shown in an uncinched position to clarify the relationship between the tether 142 and the bands 144. Using this approach, the device can be maintained in a subannular position by the barbed bands while the tether knot is cinched, advantageously simultaneously reapproximating the annulus to close the aperture while drawing the device into sealing, bridging engagement with the subannular wall of the annulus fibrosus.

Figure 3B:
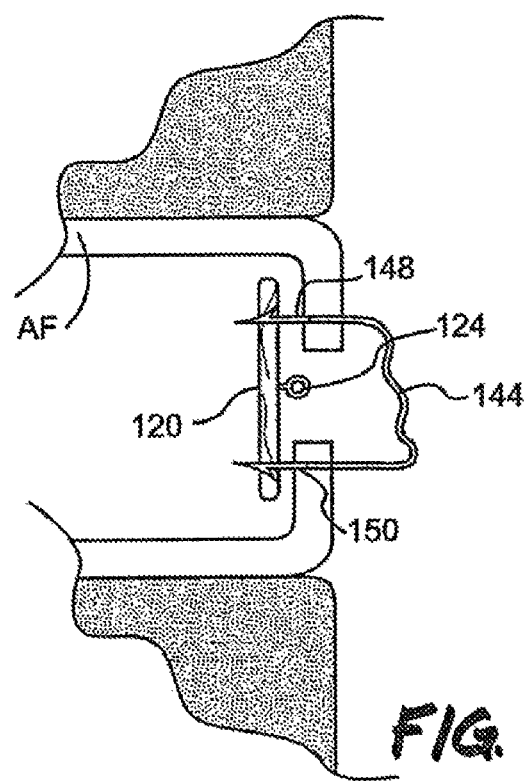

FIG. 3B shows an alternative fixation strategy where the barbs 148 and 150 are sufficiently long that they can pierce the body of the device 120 and extend all the way through the annulus fibrosus into the device 120. In this configuration, the band 144 connecting the barbs 148 and 150 may be tightened to gently restrain and position the device 120 in the sub-annular space, or tightened with greater force to reapproximate the aperture or rent.

Another fixation means includes the passing of "anchoring bands" into the wall of the annulus, vertebral bodies (superior, inferior, or both), of the Sharpey's Fibers (collagenous fibers between the junction of the annular fibers and vertebral bodies). In the following example of anchors, the barbs or bands are affixed to the annulus/vertebral bodies/Sharpey's fibers. Another element, for example a suture, cinch line, or a staple is utilized to attach the anchor bands to the patch, and thus hold the patch in proximity to the inner wall of the annulus. In addition, these bands may re-approximate the tissues at the aperture.

Revisiting one example of using barbs to anchor the device is shown in FIG. 2C, described hereinabove. Barbs or bone anchor screws 50 and 52 are passed into the superior and inferior vertebral bodies 54 and 56, respectively. Superiorly, affixation element 40 is passed through the outer wall of the annulus, to the sub-annular space. The element is then passed through the eyelet 53 of bone anchor 52 and then passed through the wall of the annulus from the sub-annular space to the outer wall of the annulus. The inferior end of the affixation element is similarly passed through the annulus, eyelet of the bone anchor, and back through the wall of the annulus. Both ends of element 40 are tightened and tied or otherwise secured. The advantage of this concept is that it allows for affixation of the stent device to a surface that is known to be present in all discectomy procedures—the vertebral bodies. Whereas, it is possible, depending on the location and size of a natural rent that there may not be sufficient annulus accessible to affix the patch directly to the annulus. In addition to providing a location for affixing, anchoring into the vertebral bodies may provide a more stable anchor surface.

Figure 14A:
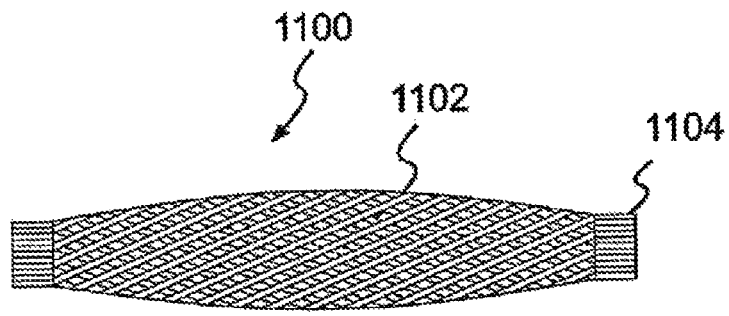
FIGS. 14A-14B show, respectively, a lateral view of a still further exemplary embodiment of the present invention having a braided arrangement in a collapsed configuration and an axial view of the exemplary embodiment in an expanded configuration.

Patches can be folded and expanded in a single plane or in three dimensions. Collapsing the patch can be accomplished laterally, whether the device is a single material or composite. Others can collapse in three dimensions, such as those shown in FIGS. 14, 17 and 21. Devices which expand in three dimensions can optionally be packaged in a restraining sheath, jacket, gelatin shell or "gelcap", or a mesh of biosorbable or dissolvable material, that would allow for facile placement and subsequent expansion.

It is understood that there can be a variety of device designs of patches/stents/meshes/devices/treatment devices to accomplish the expansion of a device from a first configuration, to a second configuration to occupy at least a portion of the sub-annular space and reduce re-extrusion of the nucleus, or otherwise facilitate maintaining other intradiscal materials within the disc space. These devices can be constructed of single components or multiple components, with a variety of different materials, whether synthetic, naturally occurring, recombinated (genetically engineered) to achieve various objectives in the delivery, deployment and fixation of a device to repair or reconstruct the annulus. The following device concepts are further discussed for additional embodiments of a device and/or system for the repair of an intervertebral disc annulus. The following descriptions will illustratively depict and describe methods, devices, and tools to deliver a treatment to an intervertebral disc after a, lumbar discectomy procedure; although, it is anticipated that these methods, devices, and tools may be similarly used in a variety of applications. As an example, the embodiments described herein may also advantageously maintain materials within the disc space other than natural disc tissue (nucleus, annulus, cartilage, etc.), such as implants and materials that may be used to replace and/or augment the nucleus pulposus or other parts of disc's tissues. These procedures may be performed to treat, for example, degenerative disc disease. Whether these materials are intended to replace the natural functioning of the nucleus pulposus (i.e., implantable prosthetics or injectable, in-situ curable polymer protein, or the like) or provide a fusion between vertebral bodies (i.e., implantable bony or synthetic prosthetics with materials to facilitate fusion, such as growth factors like bone morphogenic proteins) one skilled in the art would realize that variations to the embodiments described herein may be employed to better address characteristic differences in the various materials and/or implants that could be placed within the subannular space, and that these variations would be within the scope of the invention.

Furthermore, it should be noted that surgeons differ in their techniques and methods in performing an intervention on a spinal disc, and the inventive descriptions and depictions of methods, devices and delivery tools to repair annular tissue could be employed with a variety of surgical techniques; such as, but not limited to: open surgical, microsurgical discectomy (using a magnifying scope or loupes), minimally invasive surgical (through, for example, a METRx.® system available from Medtronic, Inc.), and percutaneous access. Surgeons may also employ a variety of techniques for intra-operative assessment and/or visualization of the procedure, which may include: intra-operative probing, radiography (e.g., C-arm, flat plate), and endoscopy. It is contemplated that the inventive embodiments described are not limited by the various techniques that may be employed by the surgeon.

In addition, the surgical approach to the intervertebral disc throughout the figures and descriptions depict a common approach, with related structures, to a lumbar discectomy; although, it is possible that surgeons may prefer alternative approaches to the intervertebral disc for various applications (for example, different intervertebral disc levels such as the cervical or thoracic region, or for nucleus augmentation), which may include, but is not limited to: posterior-lateral, anterior, anterior-lateral, transforaminal, extra-foraminal, extra-pedicular, axial (i.e., through the vertebral bodies), retroperitoneal, trans psoas (through the Psoas muscle), contralateral. The approach to the intervertebral disc space should not be interpreted to limit the use of the invention for the repair or reconstruction of the an aperture, weakened or thin portion of the annulus, as described herein.

It is also important to note that the boundary in the intervertebral disc space between the annulus fibrosus and the nucleus pulposus as depicted herein may be demarked or otherwise highlighted; however, it is important to recognize that these tissues are not as precisely demarked in human tissues, and may be even less so as the patient ages or evinces degeneration of the intervertebral disc. This demarcation may be especially difficult to discern during an operative procedure, using for example; available surgical tools (i.e., probes), fluoroscopic guidance (x-ray), or visual (endoscope) guidance. However, in general, the layers of the annulus have more structural integrity (and strength) than the nucleus, and this integrity varies from the outer most layers of the annulus being of higher structural integrity than the inner most layers of the annulus.

Moreover, the drawings and descriptions herein are necessarily simplified to depict the operation of the devices and illustrate various steps in the method. In use, the tissues may be manipulated by, and are frequently in contact with, the various tools and devices; however, for clarity of construction and operation, the figures may not show intimate contact between the tissues the tools and the devices.

Figure 4A:
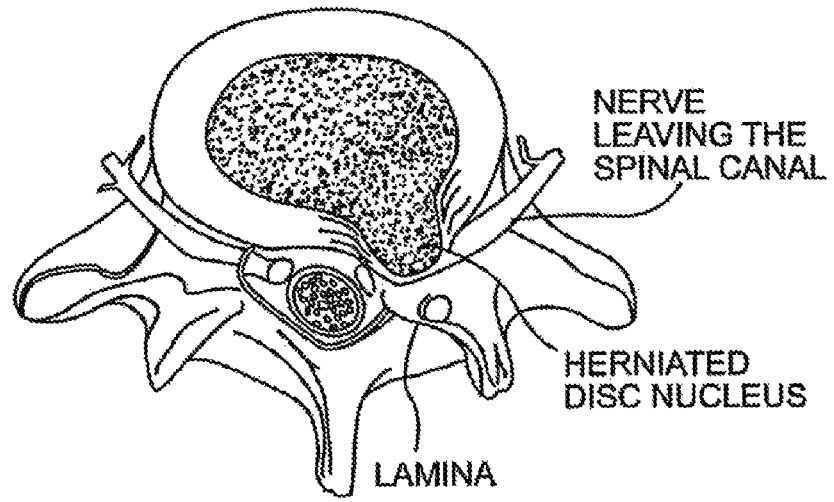
FIG. 4A shows a herniated disc in perspective view.
Figure 4B:
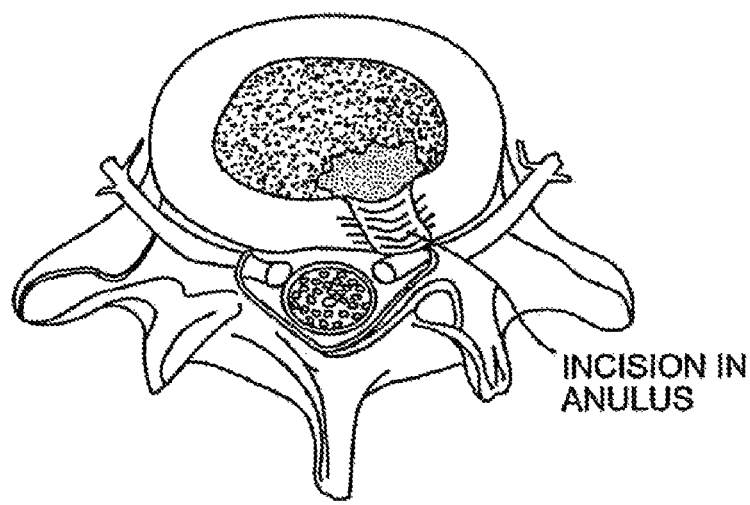
FIG. 4B shows the same disc after discectomy.

As depicted in FIG. 4A, a herniated disc occurs when disc nucleus material emerges from the subannular region and outside of the disc. Herniated disc nucleus material then impinges on nerve tissue, causing pain. A discectomy attempts to relieve pressure on the nerve tissue through surgical removal of disc material, the result usually being an aperture in the disc annulus wall, and usually a void in the subannular space where disc nucleus was removed, as shown in FIG. 4B. FIG. 4B typifies a disc after the discectomy procedure has been performed, as do most of the drawings and descriptions contained herein. However, it should be understood that in order to perform a discectomy procedure, there are a variety of instruments and tools readily available to the surgeon during spine surgery, or other surgical procedures, to obtain the outcome as shown in FIG. 4, or other outcomes intended by the surgeon and the surgical procedure. These tools and instruments may be used to: incise, resect, dissect, remove, manipulate, elevate, retract, probe, cut, curette, measure or otherwise effect a surgical outcome. Tools and instruments that may be used to perform these functions may include: scalpels, Cobb elevators, Kerrison punch, various elevators (straight, angled, for example a Penfield), nerve probe hook, nerve retractor, curettes (angled, straight, ringed), rongeurs (straight or angulated, for example a Peapod), forceps, needle holders, nerve root retractors, scissors. This list is illustrative, but is not intended to be exhaustive or interpreted as limiting. It is anticipated that some of these tools and/or instruments could be used before, during, or after the use of the inventive methods, devices and tools described herein in order to access, probe (e.g., Penfield elevator), prepare (e.g., angled or ringed curette, rongeur, forceps), and/or generally assess (e.g., angled probe) treatment site or facilitate the manipulation (e.g., forceps, needle holder), introduction (e.g., forceps, needle holder, angled probe), or deployment (e.g., forceps, needle holder, angled probe) of the treatment device and/or it's components.

The are a variety of ways to affix a device to the sub-annular wall of the annulus. The following exemplary embodiments are introduced here to provide inventive illustrations of the types of techniques that can be employed to reduce the time and skill required to affix the patch to the annulus, versus suturing and tying a knot. Sutures, staples and other fixation devices can be used to affix the patch to the annulus. In a simple example, a patch/stent could be compressed, passed through a guide tube and expanded within the sub-annular space.

Another fixation means includes the passing of "tissue anchoring elements" into the wall of the annulus, vertebral bodies (superior, inferior, or both), or the Sharpey's Fibers (collagenous fibers between the junction of the annular fibers and vertebral bodies). In the following example of anchoring elements, the barbs or bands may be affixed to the annulus/vertebral bodies/Sharpey's fibers. Another element, for example a suture, band, filament, cinch line, or a staple may be utilized to attach the anchor elements to the patch, and thus hold the patch in proximity to the inner wall of the annulus. In addition, these bands may also re-approximate the tissues of an aperture, weakened, delaminated, or thinned portion of the disc.

Figure 5A:
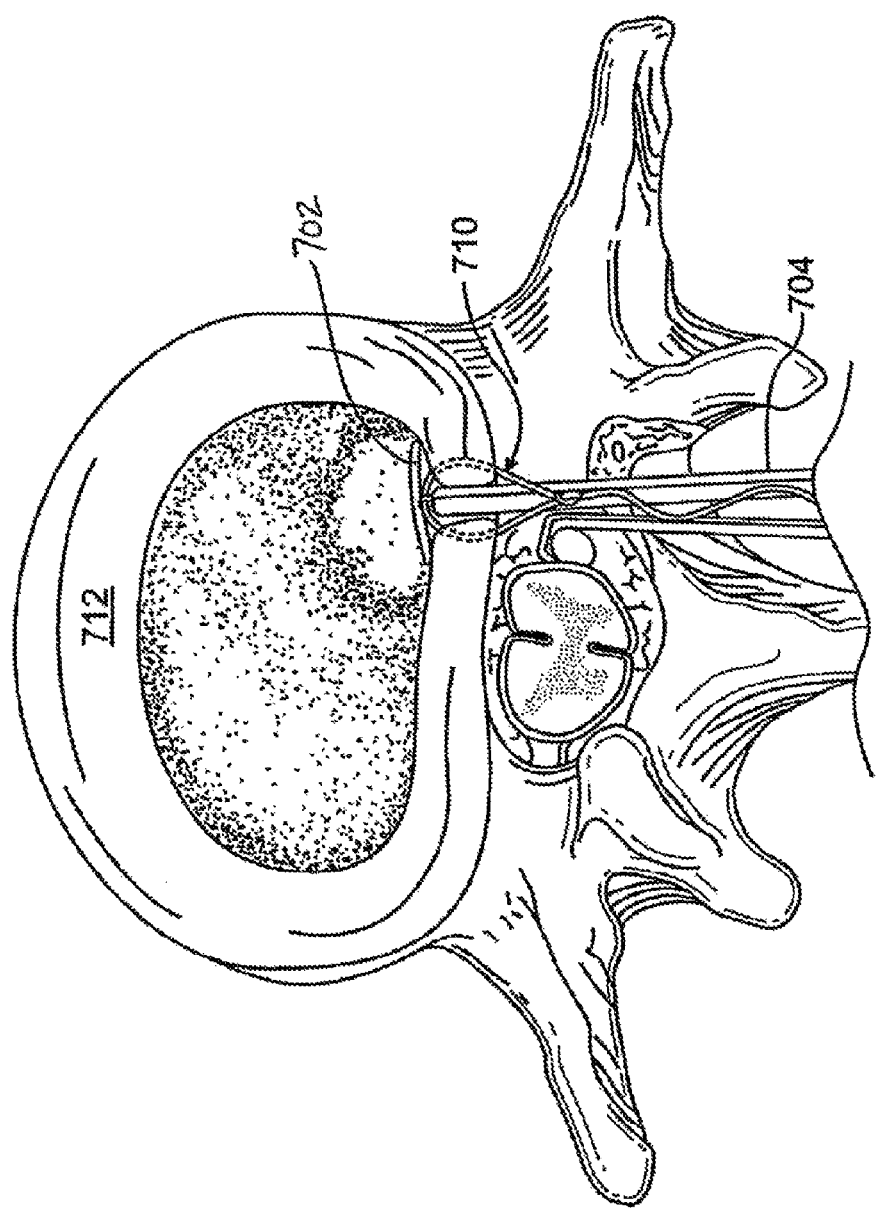
Figure 5B:
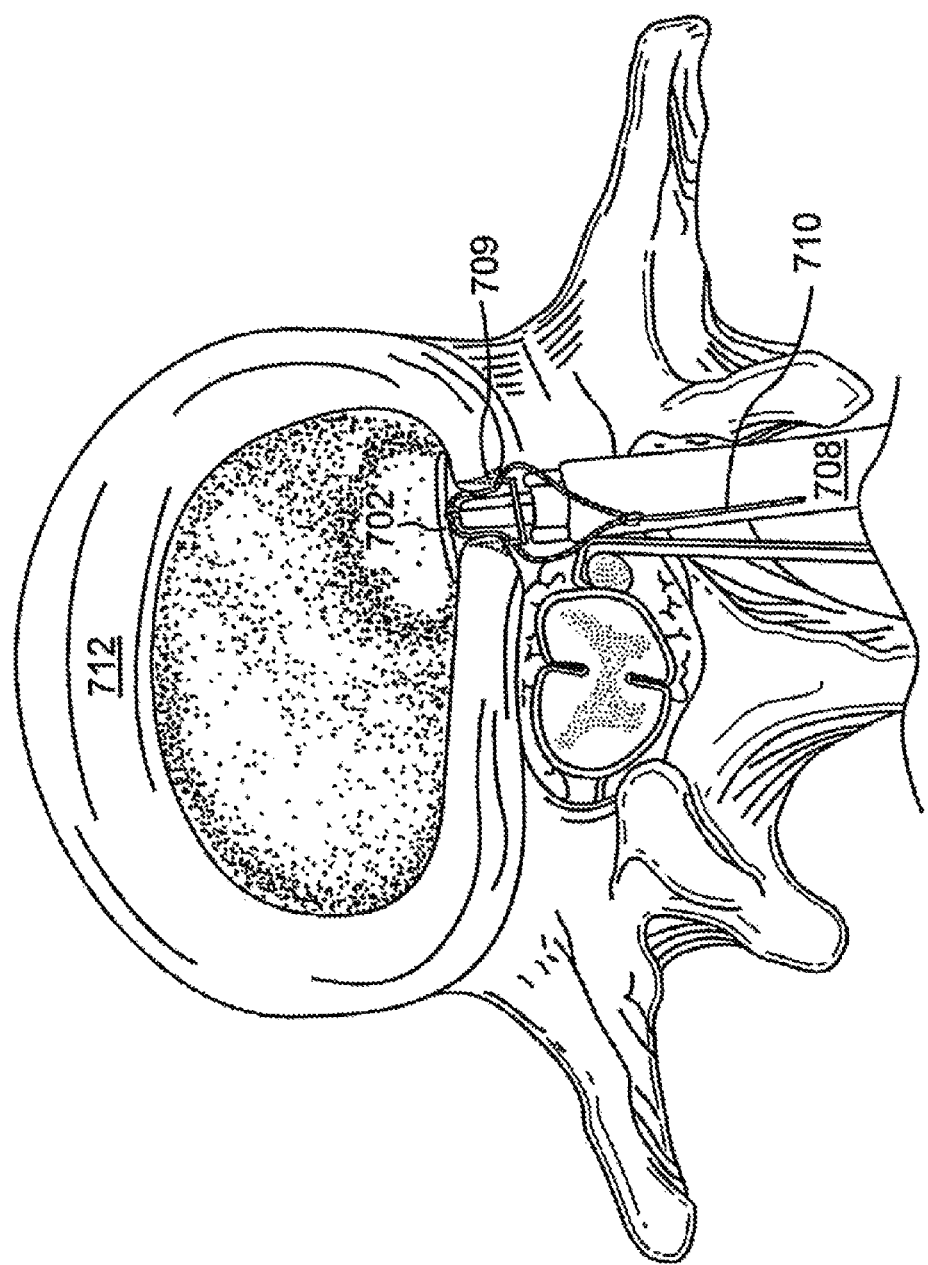

Another example of fixating the device to inner wall of the annulus is further illustrated by FIGS. 5A-5G. FIG. 5A shows a patch 702 that has been folded and passed through a guide tube of a delivery too into the sub-annular space and then expanded. The patch is held by a delivery tool 704. Also shown is a anchor band or staple 709 and an anchor band delivery device 708. Within the guide tube, or within the delivery tool, there is a suture line or cinch line 710 that is attached to the center of the patch 702. In FIG. 5A, the guide tube has been removed. The guide tube is retracted after the patch 702 has been expanded and deployed. Next, as shown in FIG. 5B, an anchor band delivery tool 708 is used to deliver one or more "bands" 709 onto the outer surface of the annulus. These are intended to be anchored into the wall of the annulus with barb shapes that do not allow for the barbs to be pulled back through the annulus. The anchor bands resemble a construction of a "staple". The bands could actually be constructed by connecting two barbed elements with, for example, a suture between the two barbed elements.

The barbs and the connection band between the barbs could be constructed of the same material or of different materials. For example, the barbed part of the anchor band could be a biodegradable/bioabsorbable material (such as, for example, collagen, cellulose, polysaccharides, carbohydrates, polyglycolic acid, polylevolactic acid, polydioxanone, racemic polylactic acid) or could be constructed of a metallic or polymeric biocompatible material (e.g., titanium, NiTi alloy, stainless steel, platinum, gold, polyurethane, polycarbonate urethane, polyimide, polyamide, polypropylene, polyethylene, polypropylene, polyester, PET, PEEK). The anchors could also be constructed of a combination of these materials. In addition, the band that connects these barbs can be constructed of materials that are similar to the barbs, or different materials. For example, the connection band could be a biodegradable/bioabsorbable suture, such as Vicryl, or a biocompatible material such as polypropylene, polyethylene, silk, stainless steel, PET. In addition, it is possible that these elements are constructed from multiple materials to accomplish the objective of anchoring into the annulus and providing for a fixation site to draw the tissues together.

Figure 5E:
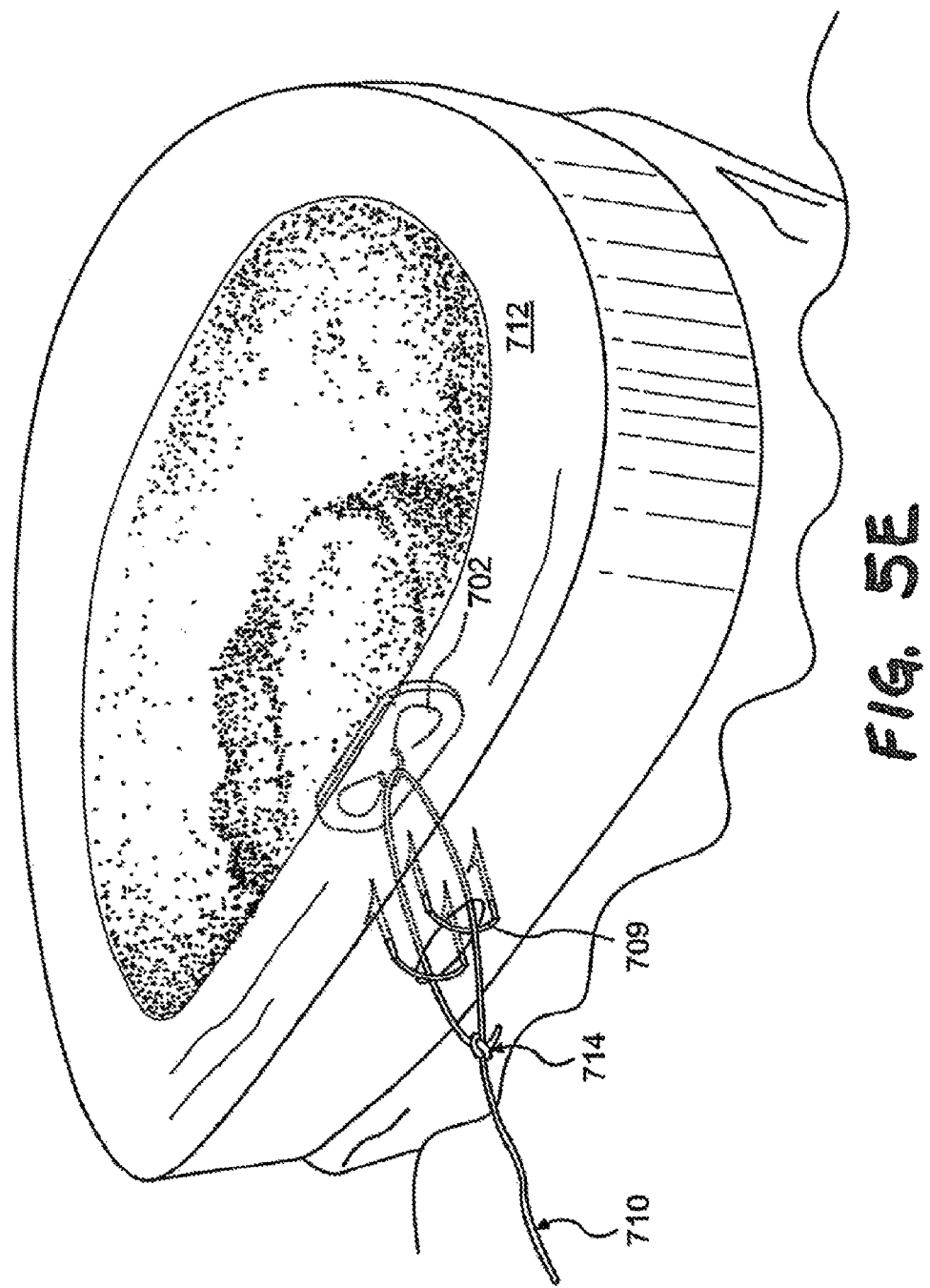
Figure 5F:
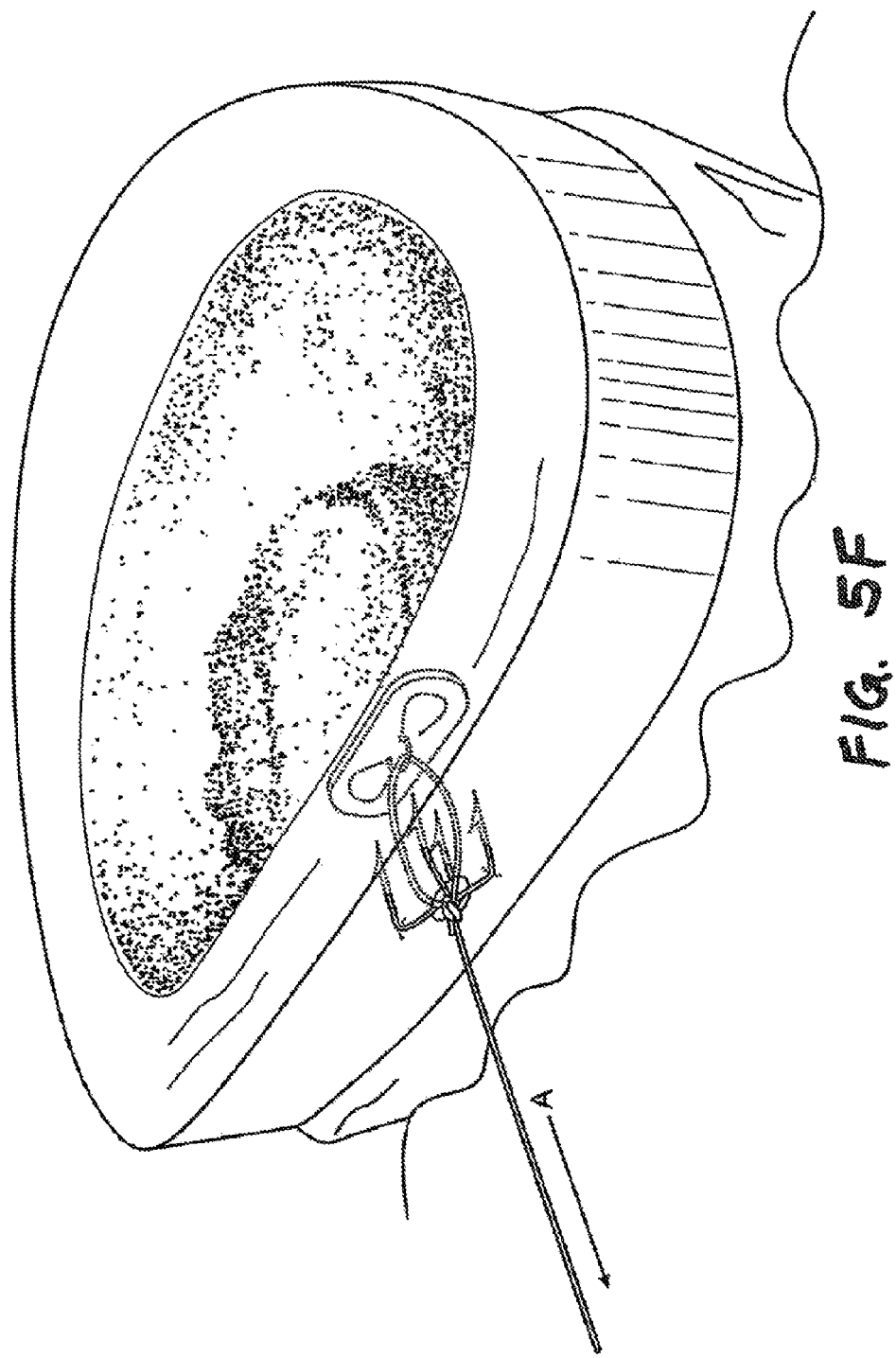
Figure 5G:
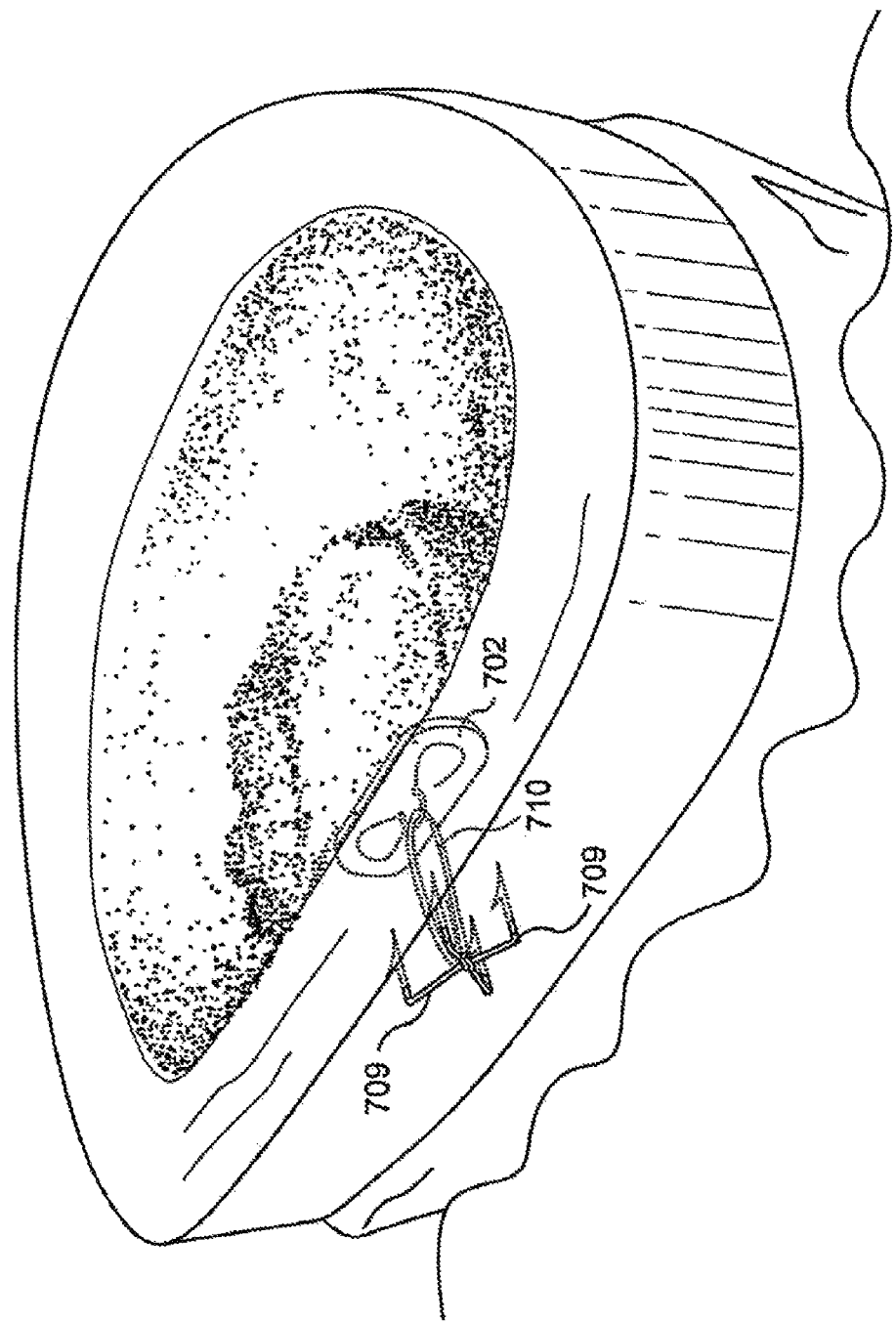

FIGS. 5B and 5C show the placement of the anchor bands 709 into the annulus 712 with the anchor band delivery tool 708. FIG. 5D depicts a representative anchor band 709, having a pair of stainless steel barbs 709" connected by a suture 709. FIG. 5E shows the patch 702, anchor bands 709, and cinch line or suture 710 with the delivery tools removed, prior to drawing the patch and the tissues of the annulus together. In this embodiment there is a pre-fabricated slip knot 714 on the cinch line, although other locking elements or knots are possible. Suture loops can connect to the barbs directly, as in FIG. 5, or loop to surgical staples, or are placed directly into the annulus. The presence of a pre-fabricated knot on the cinch line makes the process of repairing quicker since there is no need to tie a knot. It also facilitates drawing the tissues together. The use of the cinch line and a pre-fabricated knot can be placed by, for example, an external tube such as a knot pusher. FIG. 5E is similar to FIG. 3 described hereinabove prior to "tying" the knot 714. FIG. 5F shows the drawing of the patch and the annular tissues together by puffing on the suture in the direction "A" indicated by the arrow. In this case, the Knot Pusher has been removed from the cinch line 710. The suture 710 is drawn proximally to draw the patch 702 into engagement with the inner wall of the annulus to seal the aperture from within, as well as draw the walls of the annulus together to reapproximate the annular aperture. FIG. 5G shows the cinch line suture 710 tied and drawing the annular tissues together, after the excess suture line has been cut. It is also apparent from this device, fixation and delivery system that the outer surfaces of the aperture may be drawn together for re-approximation.

The cinching of the anchor bands and the patch also allows for taking-up the slack that allows for the accommodation of varying sizes. For example, the thickness of the annular wall surrounding the aperture can vary from 1 mm up to 10 mm. Therefore, if the anchor bands have a set length, this design with a cinch line accommodates different dimensions of the thickness of the wall of the annulus by drawing the "slack" of the bands together within the aperture.

Figure 7A:
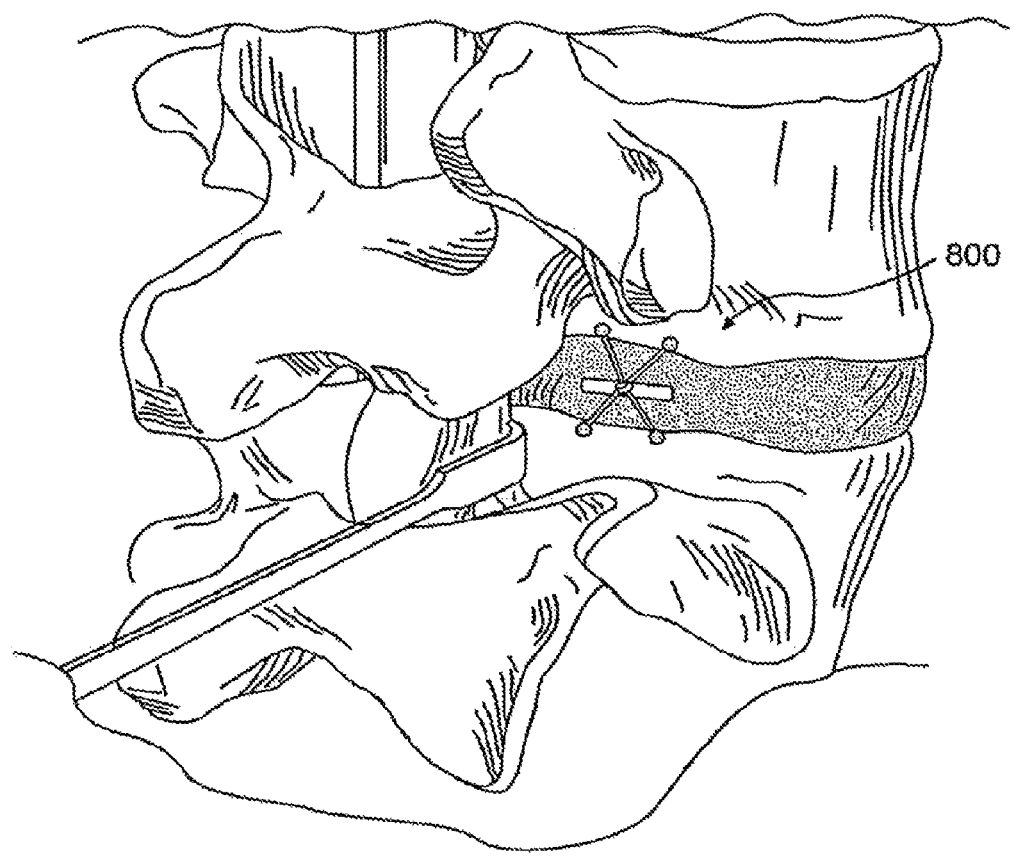
FIGS. 7A-7B depict a still further illustrative embodiment where fixation means are placed into the vertebral body or the Sharpey fibers.
Figure 7B:
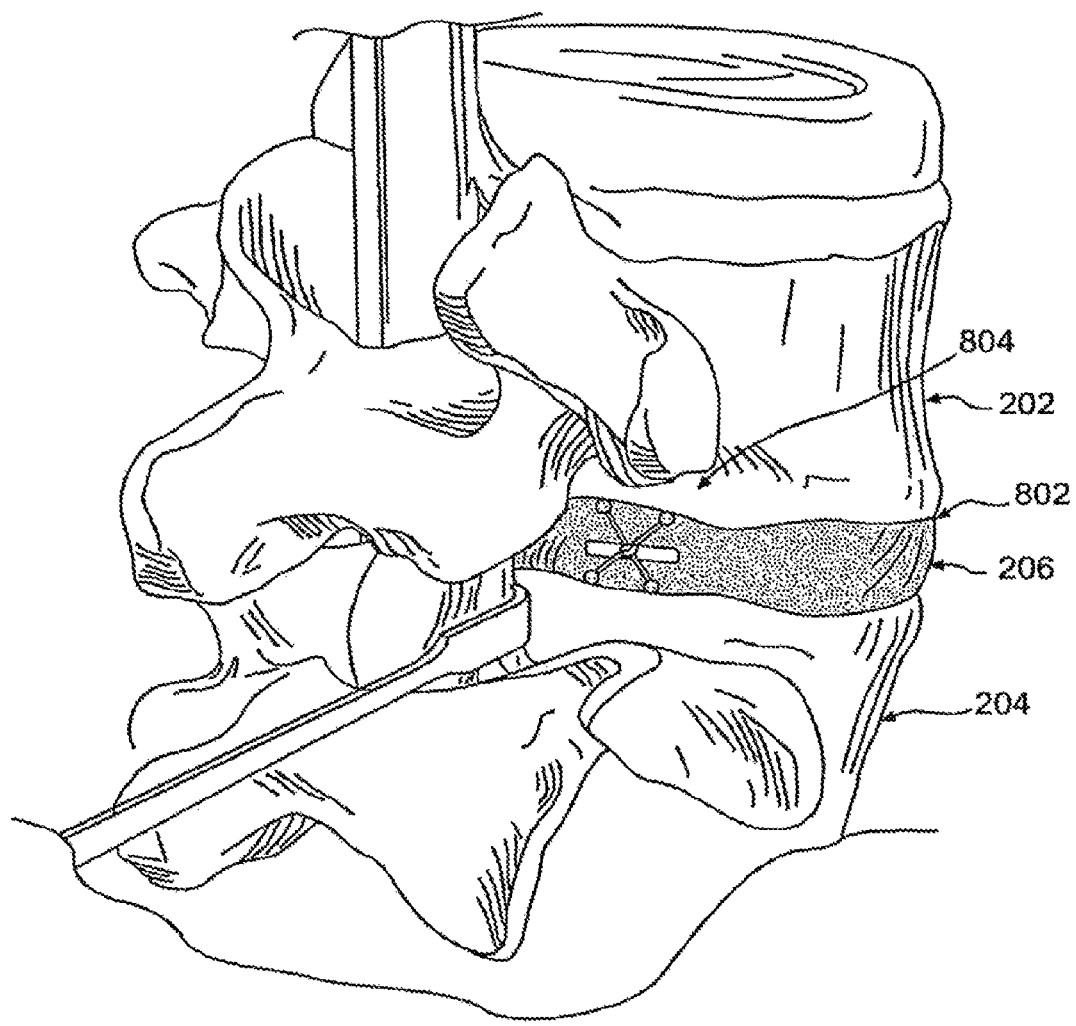

Although it has been described here as patch placement that involves two lateral anchor bands or anchoring elements with a fixation element to draw the patch, bands and tissues together, one or two or more bands could be used and two bands is only an example. Furthermore, the anchor bands were placed with the barbs in a superior-inferior fashion. One skilled in the art would recognize that these could be placed at different locations surrounding the aperture. Moreover, although it was described that the anchoring elements are placed into the annulus, these anchoring elements could also be placed in the vertebral bodies as shown in FIG. 7A generally at 800, or the Sharpey's Fibers 802, as shown in FIG. 7B generally at 804.

Although the patch depicted in the example above does not have barbs attached to the patch, it is also possible to provide barbs on or attached to the patch to further promote the fixation of the patch to the inner wall of the annulus.

Figure 6:
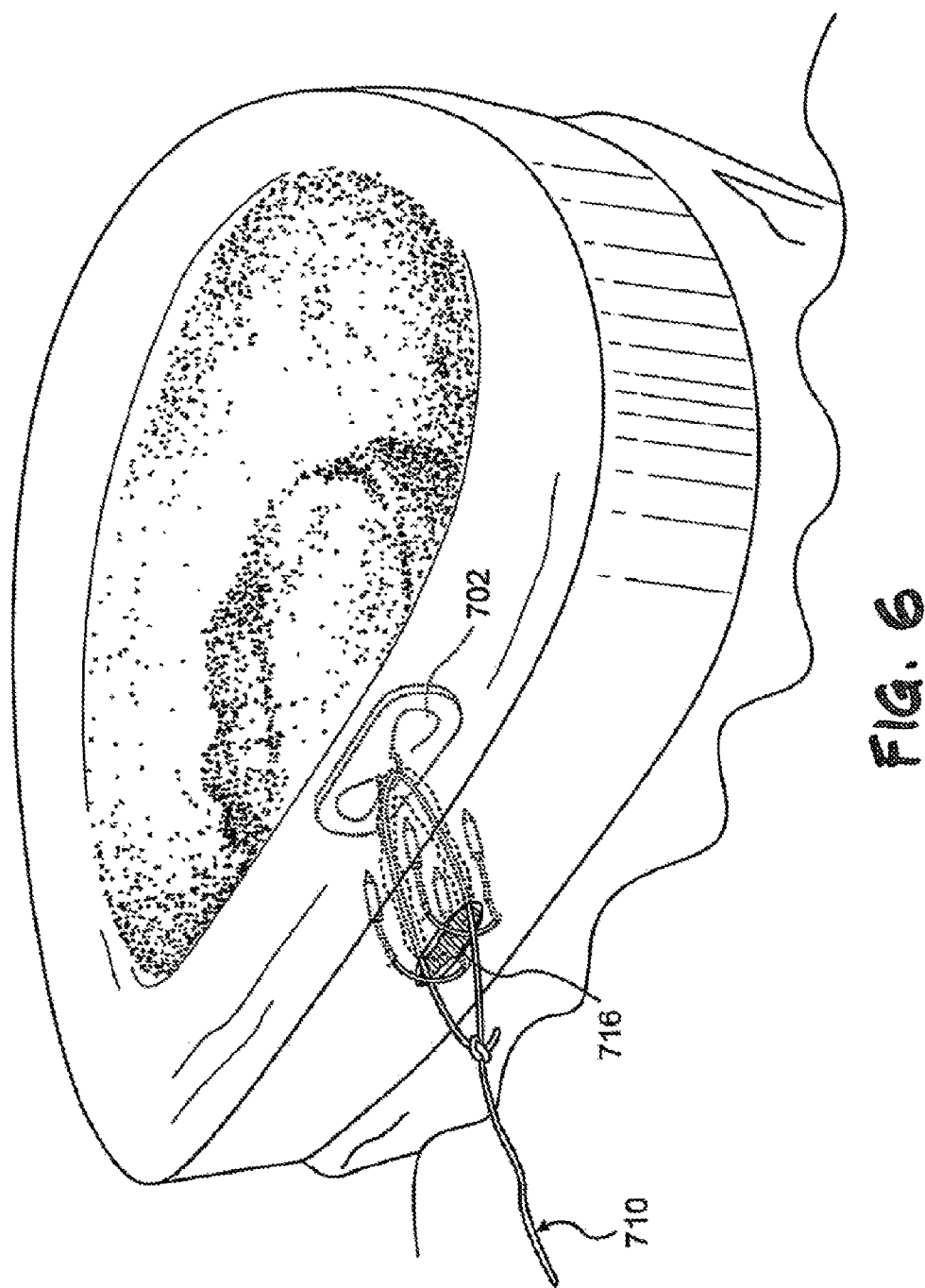
FIG. 6 depicts an exemplary use of filler material within the aperture during placement of a patch/stent tethered by a cinch line.

Finally, although the drawings depict an aperture that lends itself to re-approximating the tissues, it is conceivable that some apertures, whether natural or surgically made, may be relatively large and therefore might require the placement of additional material within the aperture to act as a scaffold for tissue in growth, between the patch on the inner wall of the annulus and the anchor bands located on the outer wall. An example of material to fill the aperture might include autograft para-spinal fascial tissue, xenograft, allograft, or other natural collagenous materials. The filler material could also be of a biocompatible material such as a Dacron (polyester, or PET), polypropylene, polyethylene material. FIG. 6 shows the illustrative filling of an aperture with implant material 716 prior to cinching the suture 710.

As an alternative embodiment of the present invention, the anchor bands 709 as described previously (anchor bands into annulus) could be sufficiently long enough to pass through the annulus and then through the patch. The barbs or anchoring elements in this embodiment have an engaging involvement with the patch. This concept was previously discussed hereinabove in connection with FIG. 3. Passing the barbs through the patch, in this embodiment, provides additional security and safety by reducing the possibility that the anchoring elements may migrate after implantation. In this application of the invention, the suture cinch line may or may not be used in addition to the anchor bands to draw the tissues together and reduce tissue movement surrounding the aperture.

In addition, although the bands shown in FIG. 5 take the form of a "barb", they could as easily take a form of a simple T-barb 720, or a C-type element wherein the object is to have irrevocable engagement with the patch device 702 after the penetration through the patch. A T-type attachment, when aligned longitudinally with the suture, passes through the patch. The T section then rotates to prevent the suture anchor from being pulled back through the patch. In another embodiment a "C" retainer made of a superelastic material may be attached to the end of the suture band. The C retainer is loaded into a needle wherein it is held straight. The needle is used to pass the C retainer and suture through the patch and deploy the retainer hi a second configuration in the shape of a "C".

It is also foreseen within the scope of the invention that there may be patch designs which will accommodate the placement and securement of the anchor to the fabric that covers the frame of the patch. For example, a frame for a patch that is made out of metal such as Nitinol can provide for "windows". The device, covered with a mesh fabric, for example silicone or Dacron, would therefore allow the anchoring barbs to be passed through the "windows" in the frame of the patch. In this case, the barb can be secured to the patch in the fabric covering the frame.

Alternatively, the patch can be secured by passing barbs that engage the lattice of the patch frame. These embodiments of the invention illustrate designs in which the barbs engage with the vertical, horizontal or criss-crossed structures/members of the frame. In this case, the barbs would pass through the mesh or lattice of the frame and they would be unable to pass back out of the structure.

Although this discussion refers to "anchor bands" that are shown to be two anchors connected by a suture, it is also contemplated that single barbs with sutures could be placed and the sutures' ends, at the outer surface of the annulus, are tied after placement through the patch. It is also possible that these "single anchors" could be retained by a suture "pledget" on the outer wall of the annulus to better hold the outer surface, or could include a suture (or band) locking device.

Alternatively, the locking mechanism can be as shown in FIG. 8, although in this case the engagement of the locking element 914 takes part on the anchor. Pulling the tether 910 in the direction of arrow B will tighten and lockingly hold in tension to aid in securement and tissue approximation. The adjustable length band between the two anchors allows slack to be taken up between the anchors 916. Two T-type anchors are illustratively shown in this example, but multiple anchors of differing configurations could be used. The locking features can be included on the feature band, as depicted here, and allow for substantially one-way locking engagement with the anchor members. This adjustability advantageously promotes for the accommodation of varying thickness of the annulus from patient to patient. The suture/band slack in this embodiment may be taken up to close the defect in the annulus and/or to shorten the band between anchors for a secondary cinching of multiple tensioned suture bands as described herein.

Figure 9A:
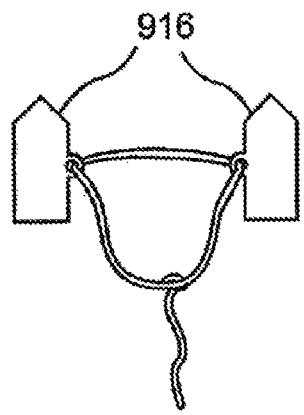
FIGS. 9A-9C show still further embodiments of the invention having fixation anchors.
Figure 9B:
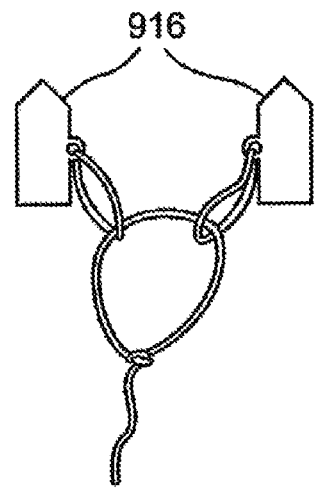
Figure 9C:
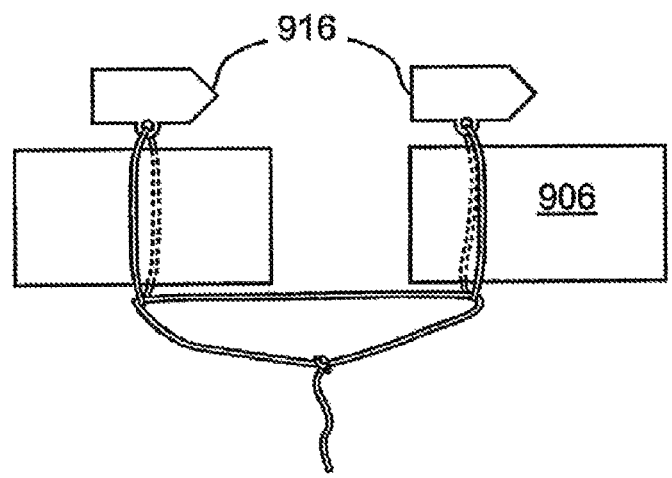

FIG. 9 shows alternative embodiments for tightening "anchoring barbs" with different configurations of sutures and cinch lines. For example in FIG. 9B each independent barb has a looped suture attached to it. Through each of these loops is passed a cinch line, which contains a knot. After placement of the barbs within the annulus, and possibly through the patch, the cinch line draws the loops of the barbs together. The advantage of this embodiment is that it allows for the independent placement of multiple barbs and the ability to draw all of them together.

Although cinch ones have been described as using a knot to "lock" the length of the suture, other mechanisms could also lock the length, as shown in FIG. 8. The locking of the suture length is accomplished through a mechanical element located on the barb which engages with three dimensional elements attached to the suture line which mechanically press fit through the engagement element on the barb, thus locking the length of the suture line into place.

Although the embodiments of FIG. 8 and FIG. 9 depict the use of a single locking mechanism (e.g., knot on cinch line), it is conceivable that various designs could use more than one locking element to achieve the re-approximation and drawing together the tissue surrounding an aperture.

Similarly, an alternative embodiment to cause tension within the device and draw the tissues together after placement of the anchor bands might include an elastic band or band with a spring with one end attached to the anchor bands and the other end attached to the patch. Alternatively, the anchor bands, in and of themselves may be made of an elastic band between the barbs, or may contain a spring element between the barbs. Such an embodiment can be made to resemble a so-called "Bobber Spring." Again, it is contemplated that the elastic or resilient element could be made from a wide variety of metals, polymeric, or biodegradable/bioabsorbable material.

As previously mentioned, the present invention also encompasses delivery devices or tools of the following description. The delivery devices of the present invention are configured to deliver at least one device, or a portion thereof, into (or through) the annulus or other surface or tissue, such as vertebral bodies 202, 204 or Sharpey's Fibers 802, as shown in FIG. 7. The delivery tools (or devices) will typically comprise devices or shafts having proximal and distal ends. As referred to herein, the proximal portion of a device or tool or component will generally refer to the portion of the device/tool/component that is located furthest away from the patient (and closest to the surgeon); whereas, the distal portion will generally refer to the portion that is within (in use) or closest to the patient (and therefore furthest away from the surgeon). Although some of the device descriptions may refer to some fixation element embodiments as being "fixation" or "anchor/anchor band/barb", this is done for clarity reasons and should not be misconstrued to suggest that the device is not capable of also performing a treatment and/or a repair.

In addition, the following descriptions of delivery devices/tools are generally intended to be single-use and disposable; however, it is clear that these tools could as easily be constructed to be partially, or wholly, re-usable and re-sterilizable.

Figure 12B:
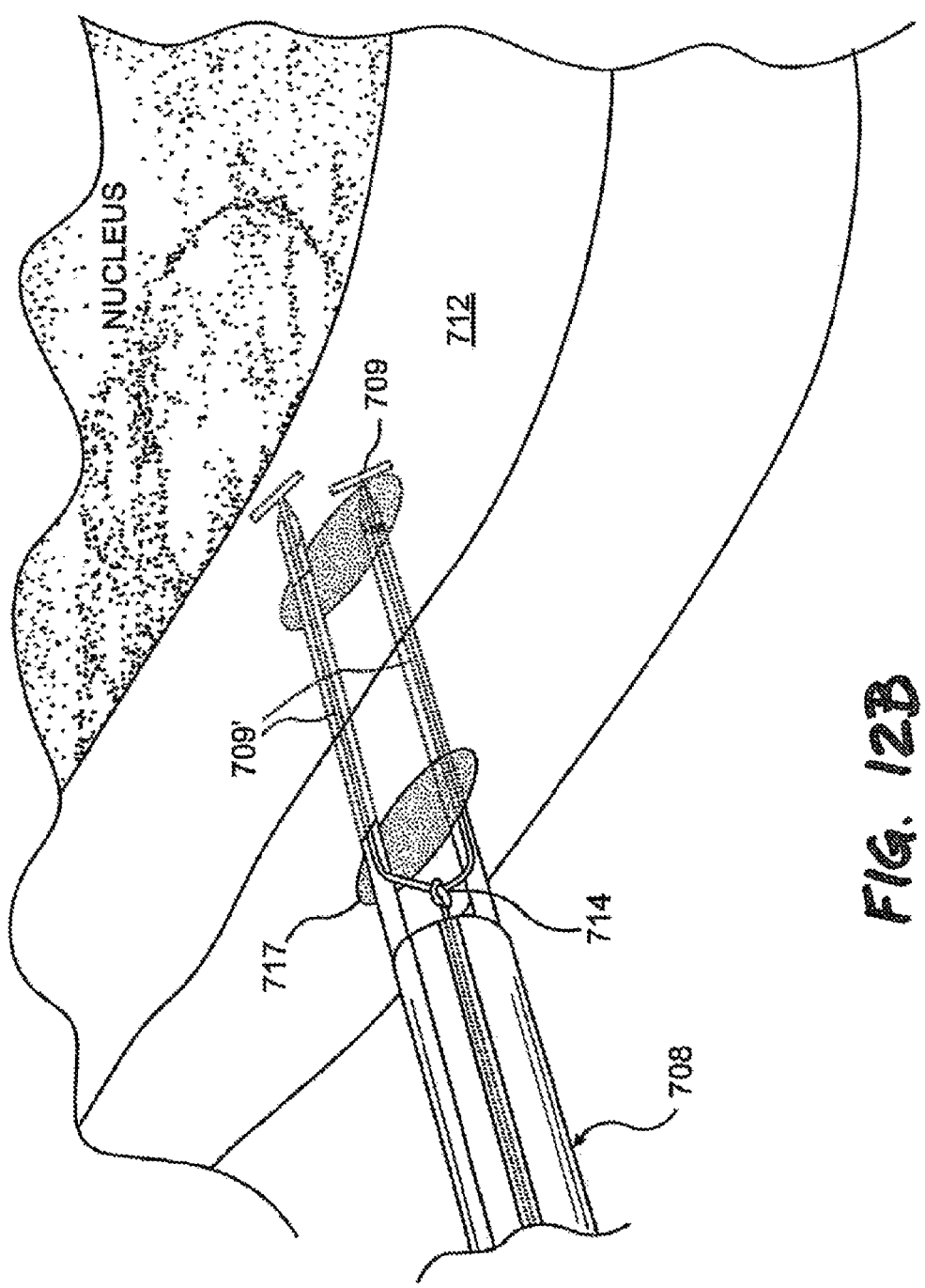
Figure 12C:
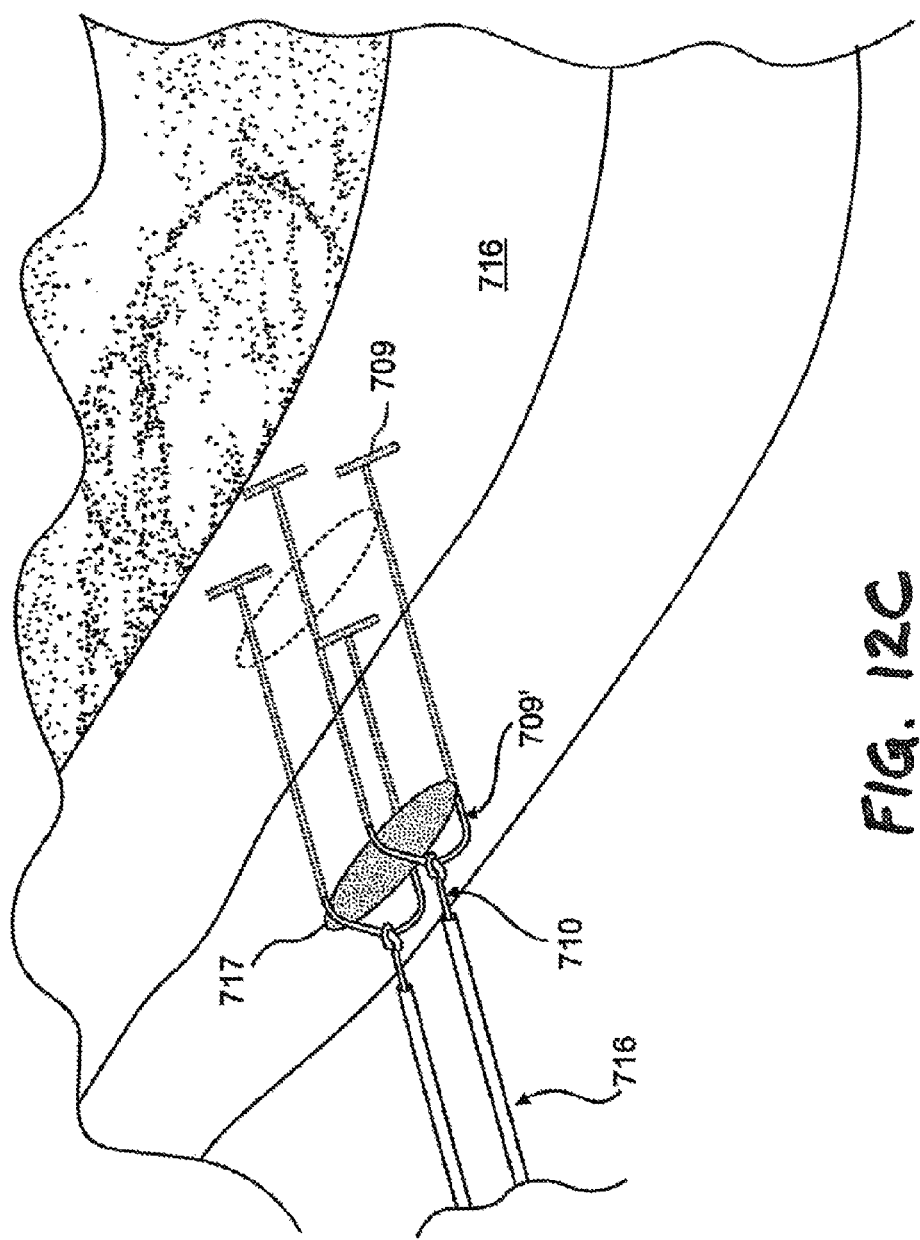
Figure 13:
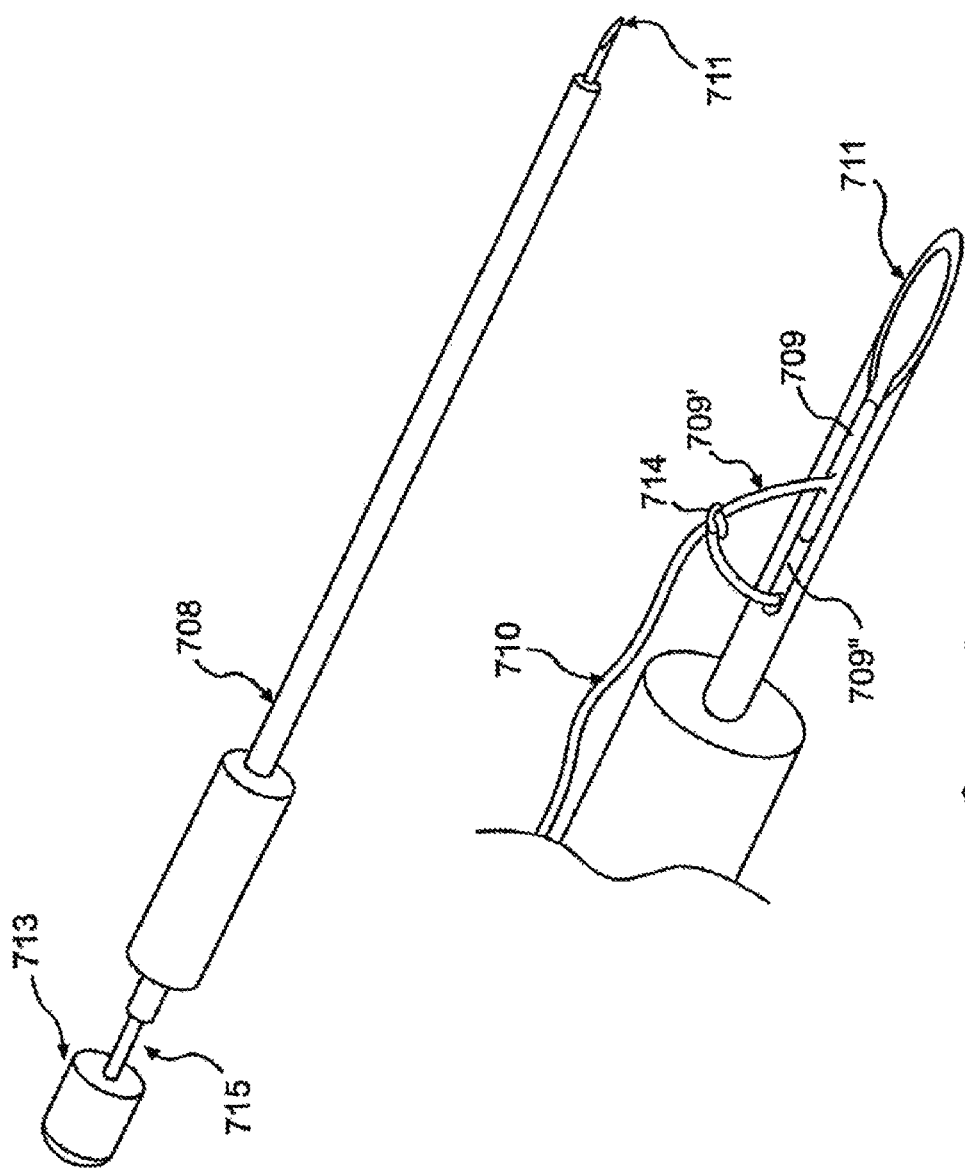
FIG. 13 shows an anchor and band delivery device according to one embodiment of the invention.

An illustrative delivery device, as depicted in FIGS. 11-13, may be configured to accommodate and deploy at least one fixation device, such as a barb or T-anchor with one or more associated bands. Advantageously, the distal end of the delivery device will comprise a hollow needle or cannula 711, having a circular, elliptical, triangular, hexagonal or other inner cross sectional area, suitable to accommodate the cross-sectional shape of the fixation device within. The distal point of the cannula 711 is advantageously sharpened, as a needle, to accommodate insertion. The cannula 711 is advantageously cut obliquely as shown in FIG. 13 to form a sharp leading surface or point for ease of insertion. The cannula 711 may contain a cut or groove 718 along its side to accommodate one or more anchors 709 as shown (or barbs, not shown), e.g., in FIG. 11B or 13. In one embodiment, the at least one fixation device (including band and barb or T-anchor), or portion thereof, is disposed within the cannula 711 as shown in FIGS. 11A, 11B and/or 13. Alternatively, the T-anchor 709 (or barb, not shown), or other fixation device may be hollow and disposed in a manner surrounding a portion of the delivery device (not shown).

The delivery device 708 may also advantageously contain within it an ejection rod 715. The proximal end of the ejection rod 715 may contain an end portion 713 to function as a stopper, e.g., having a diameter larger than the remaining portion of the rod, such as is shown in FIG. 11A. The diameter of the remaining portion of the ejection rod 715 will be small enough for insertion within the shaft of the device 708. Upon insertion of the cannula 711 into the location of choice, the ejection rod is pushed to deliver the fixation device. The delivery device is then removed.

Advantageously, the ejection rod 715 and delivery device may be configured to deliver multiple fixation devices, sequentially or simultaneously. Thus, if multiple fixation devices are contained within the device, the ejection rod 715 and delivery device may be configured such that the rod 715 be pushed a first distance, sufficient to deliver a first fixation device. The device is then removed from the first insertion point and inserted into a second insertion point, where the ejection rod is then pushed a second distance for delivery of a second fixation device, and so-on as desired. For simultaneous delivery of multiple fixation devices, multiple delivery devices may be arranged in parallel (or substantially parallel).

The distance between (or among) the delivery devices may be fixed or adjustable, as desired.

The distance the ejection rod 715 is pushed to define a first, second, and subsequent distances may be regulated by feel. Alternatively, the distance can be regulated by the architecture of the device. For example, the shaft and ejection rod may be fitted with a notch-and-groove configuration, respectively. In such configuration, the notch in the outer surface of the ejection rod may be aligned with a groove in the inner surface of the device. The length of the groove defines a first distance. The ejection rod 715 would be then turned or rotated within the device, aligning the notch within the device to a second groove defining a second distance, and so-on. In an alternative embodiment, the ejection rod and anchor portion of the fixation device (e.g., barb or T-anchor) may surround the shaft of the device, as a sleeve surrounds an arm. In such a configuration, the delivery tool would comprise a solid shaft and the ejection rod and fixation device would be at least partially hollow and disposed over the distal portion of the delivery device. Pushing the ejection rod in a proximal to distal direction would deploy the anchor portion of the fixation device.

FIGS. 11A and 11B describe one embodiment of an anchor band delivery device 708 and fixation means. FIG. 11A shows a general drawing of a delivery device. FIG. 11B further depicts the distal end of the delivery device. Anchor band delivery device 708 contains two pointed needles or cannulas 711. Each cannula 711 contains an anchoring T-type anchor 709 (or barb) positioned within the distal end of the cannula 711. A band 709' links the two anchors 709 (or barbs) together and a cinch knot 714 secures the anchors (or barbs). Cinch line 710 is pulled to decrease the length of the band 709' that attaches the anchors 709.

Referring to FIG. 12A, anchor band delivery device 708 is inserted into the annulus 712 sufficiently to engage the inner layers of the annulus 712, and preferably located at the inner wall of the annulus 712. The anchors 709 are ejected from the delivery device by pressing the ejection rod 715 in a fashion to expel the T-anchors 709 (or barbs, not shown) from the device. For example, pressing on the proximal end of ejection rod 715 as shown in FIG. 11A drives the ejection rod 715 in a distal direction, thus expelling the anchor from the device. FIG. 12B shows the anchors 709 (or barbs) after being ejected. FIG. 12C shows a knot pusher 716 attached to the delivery tool 708 that can be used to tighten the knot 714 once the fixation device is secured into the annular tissue. FIG. 12C shows the placement of two pairs of anchors 709, or fixation devices (anchors and bands), after they have been delivered to the annulus and before the bands 709' have been tightened. The knot pushers 716 of both devices are still in contact with the knots and the delivery needles have been pulled back, away from the annulus. FIG. 12D shows the final placement of the two anchor bands after drawing together the tissues surrounding the aperture 717, the inner wall of the annulus 712, and/or the outer wall of the annulus; and, after tightening and cutting the knot 714 located on each anchor band 709'. Although FIG. 12 shows the passage of the bands superior and inferior to the aperture, these bands could also be placed in a multitude of locations to effect desired or equivalent outcomes.

In addition, as previously described, one could use barbs having a multitude of configurations. One could also configure delivery devices to deliver one (as in FIG. 13), two (as in FIG. 11A), or more barbs simultaneously, and according to predetermined or variable distances or patterns. The delivery devices may also be configured to eject one, two, or more barbs sequentially. Further, the barbs could be delivered by a delivery device that does not require a cannula to cover the barb. In such a configuration, the barb may be disposed on the tip or outside of the delivery device's shaft, and removed therefrom upon injection into the desired location of the annulus or other tissue. Bands and knots may be pre-tied to accommodate each configuration, as previously discussed.

For example, although FIGS. 11 and 12A-B depict a device that places two anchors 709 banded together with one device, one could accomplish an equivalent or other desired result with a single device that delivers multiple barbs at the same time.

FIG. 13 shows an alternative delivery device that delivers two or more anchors (or barbs) from a single cannula 711. In this embodiment, a first single anchor 709 is ejected from the cannula 711 by pushing the ejection rod 715 a first distance sufficient to eject the first anchor 709, but insufficient to eject a second anchor 709". Then the delivery device is removed from the first site and passed into another annular location. The second anchor 709" (or barb) connected to the first anchor 709 (or barb) by band 709', is ejected out of the cannula 711 by pushing the ejection rod 715 an additional distance sufficient to eject the second anchor 709 (or barb) into a second fixation point in the annulus.

Although much of this description has described placement of the anchors into the annulus (or soft tissue) of the disc, one could perform anchoring into other tissues surrounding the aperture, including the bone or Sharpey fibers, it is also contemplated that, given the delivery device construction, a bone drill or similar device may facilitate the placement of the delivery device through the bony or similar tissue. Alternatively, the device delivery tool and/or the anchoring element may be of an architectural structure so as to enable the passage of the anchoring element into and/or through bony or similar tissue. For example, the device delivery tool may be of sufficient integrity so as to allow a physician to apply a force to the delivery tool with, or without, a mallet. Alternatively, the delivery tool distal end and/or anchoring elements may contain a serrated surface to facilitate placement, as an example.

The band 709' connecting the thus implanted anchors (or barbs) advantageously contains a moveable knot 714 between the anchors. Suitable knots include, but are not limited to, the Roeder knot and its functional equivalents, and are advantageously, but not necessarily, pre-tied. After insertion of both anchors 709 (or barbs), the band 709' is advantageously tightened by hand or by pushing on the knot with a knot-pusher or similar device. Although not shown in FIG. 13, the knot pusher may be integral to the delivery device. After drawing together the tissues surrounding the aperture, inner wall, and outer wall of the annulus, the excess suture line can be cut. It is also possible to use a cutting device integral to the delivery device to cut the band after cinching. Although the device shown in FIG. 13 depicts two anchors being delivered from a single device, multiple anchors or barbs could be delivered from the same or a similar type of device. Additionally, a delivered configuration of fixation means may result from the use of a single device to deliver multiple anchors sequentially.

The shaft of the device may be of any convenient length, typically from, e.g., 1 inch to 10 inches. Materials of which to make the delivery device include, but are not limited to: metals, such as stainless steel, nickel, titanium alloy, and titanium; plastics, such as PTFE, polypropylene, PEEK, polyethylene, and polyurethane, acrylic, polycarbonate, engineering plastics; and/or composites.

Advantageously, the shaft of the device will have a cross-sectional shape suitable to accommodate an ejection rod and at least one fixation element, or portion thereof. In one embodiment, at least a portion of the shaft of the device may be hollow, having a circular, elliptical, triangular, trapezoidal or other suitable cross-sectional area sufficient to accommodate an ejection rod.

The delivery device may also contain a handle or raised surface configured to accommodate the shape of surgeon's hands or fingers for easier handling. Such raised or configured portion may be made of the same or different material as the tube or shaft. Suitable materials known in the art include, among others, polymers, such as acrylic polymers, polyurethane, polycarbonate, engineering plastics; and metals, such as stainless steel and titanium.

Much of the previous discussion relates to the use of a patch (or stent) for annular repair and/or reconstruction. In some clinical instances, the method of the invention may be accomplished without the use of a patch, however. For example, a patch may be unnecessary to repair small apertures or apertures of certain shapes, or certain weakened or thin portion(s) of an annulus. The invention therefore also encompasses methods for repairing or reconstructing annular tissue that do not necessarily involve the use of a patch, and to fixation devices and tools useful in carrying out these methods, as exemplified in FIG. 12. Accordingly, an additional embodiment of the invention also provides fixation devices that may be used to reapproximate and hold annular tissue. Such fixation devices, as described herein, may contain an anchor portion and a band portion. The anchor portion serves to fix the fixation device relative to tissue. The band portion, attached to the anchor portion, serves to draw together annular tissue when tightened and secured. At least one fixation device is placed into, or through, the wall of an annulus surrounding an aperture, weakened, or thin portion of the annulus. The device is then drawn in tension to pull together, wholly or partially, the surrounding annular tissue.

The band and the barbs may be separate elements or comprise one continuous element. Bands and barbs may be made of the same or different materials.

The bands may be string-like, made from suture or similar material, or of any construction or dimension that is amenable to the delivery and engagement of the fixation device. For example, the band may have a width greater than, in some embodiments far greater than, its thickness. The band material may in some embodiments have a width:height ratio of 1.25:1. In some embodiments, bands may be constructed, wholly or partially, of a mesh tube. Moreover, different segments along the length of the band may have different dimensions and constructions. For example, the band may be constructed of thin material, such as nickel titanium ahoy or stainless steel wire, dose to the anchor barbs, while the middle portion that spans the aperture may comprise a much wider band made of optionally softer material.

Figure 8A:
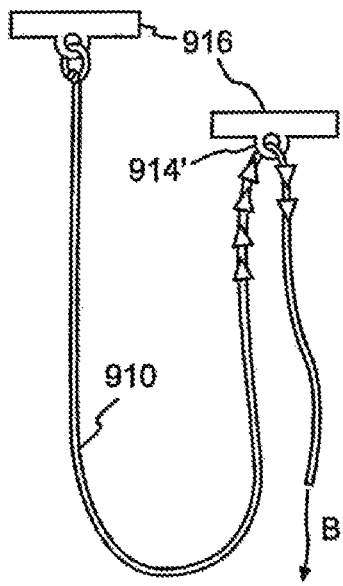
FIGS. 8A-8C show still further embodiments of the invention having fixation anchors.
Figure 8B:
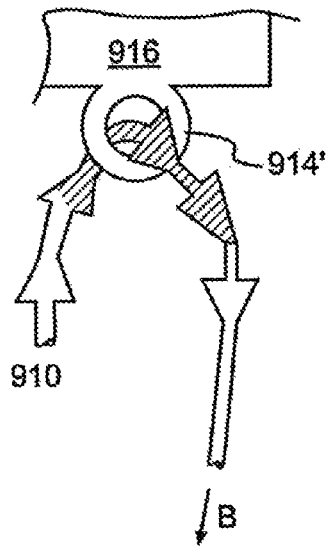
Figure 8C:
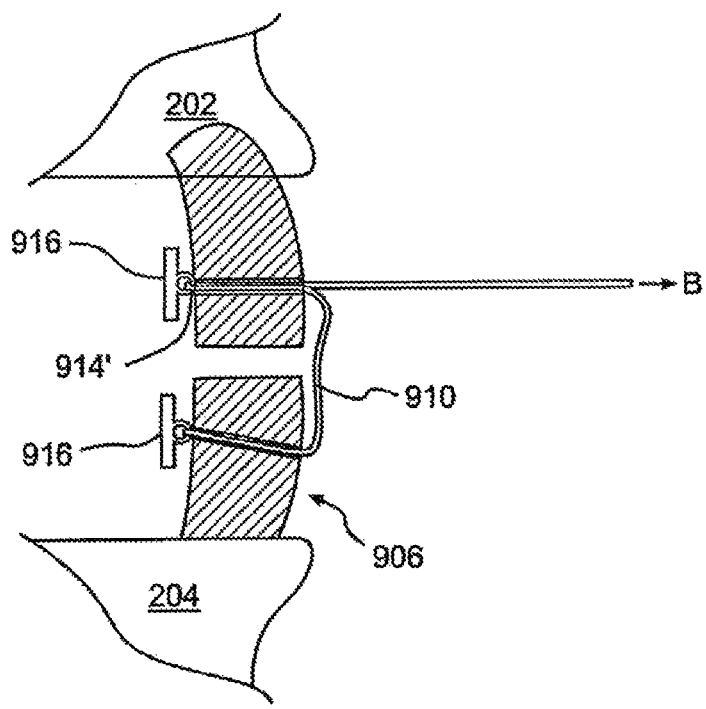

FIGS. 8, 9 and 10 show additional examples of embodiments of the invention for repair or reconstruction of the annulus that could be utilized without the additional use of a patch. For instance, in FIGS. 8A-8C, in lieu of (or optionally in addition to) a patch, two anchors are shown having passed through the annulus to the subannular space. By drawing on band 910, the inner and outer walls of the annulus may be drawn together in tension, and may also reapproximate the tissue surrounding the aperture. FIG. 8C shows a single anchor band being placed along an incision or tear in the annulus.

The fixation devices of the invention could be delivered as a pair of barbs attached by a single band, or each barb could be delivered individually Alternatively, multiple barbs (anchors) may be pre-attached to a single or multiple bands for ease and speed of delivery. For example, FIG. 10 shows a fixation device that has multiple anchors 916 (or barbs, not shown) connected together in a configuration similar to FIGS. 9B and 90, with each anchor 916 being delivered individually into, or through the nucleus or annulus. The anchors, if present, may be shown as in FIG. 10. By drawing on the cinch line, the tissues surrounding the aperture and/or the inner wall of the annulus and/or the outer wall of the annulus are drawn together. Although a knot 914 is shown to affix the suture lines together, other means to lock, fasten clip, retain, or secure the sutures together may also be used.

Figure 44A:
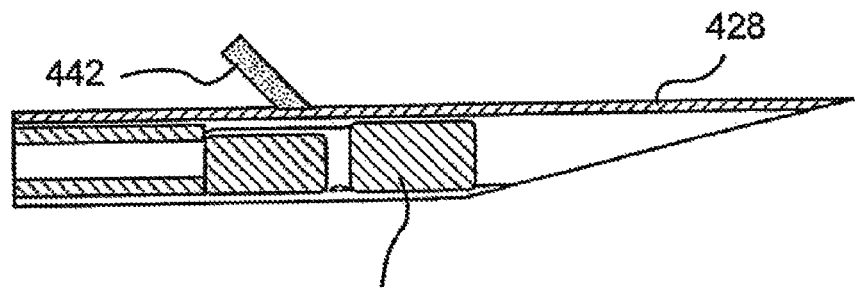
FIGS. 44A-44C illustratively show means that may be attached to the anchor band or anchor band delivery tool for providing perceptible feedback.
Figure 44B:
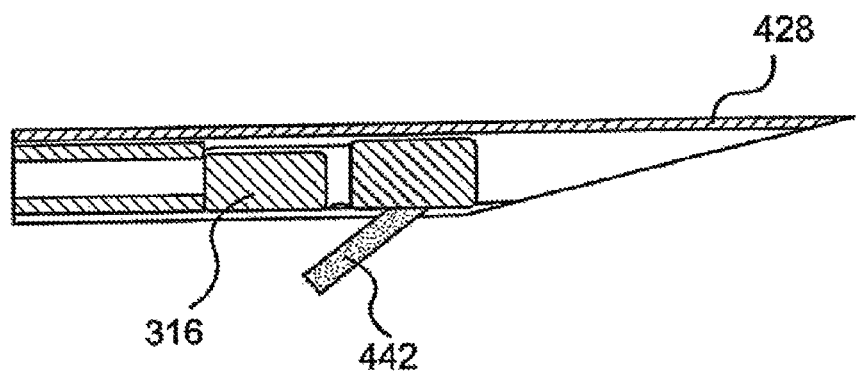
Figure 44C:
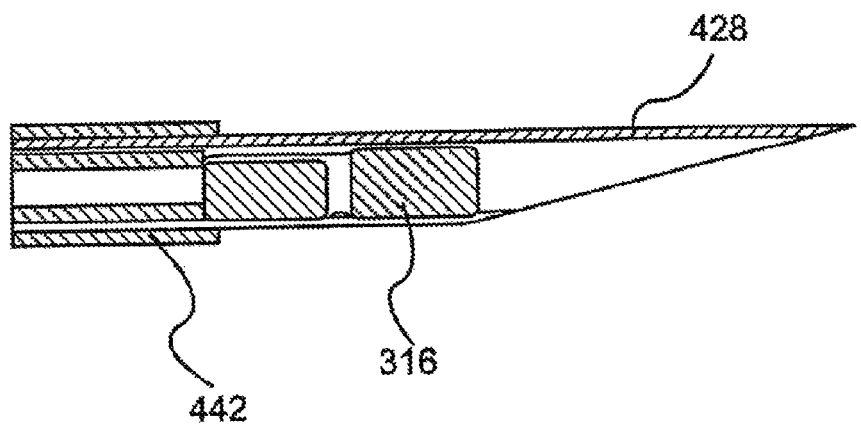
Figure 45A:
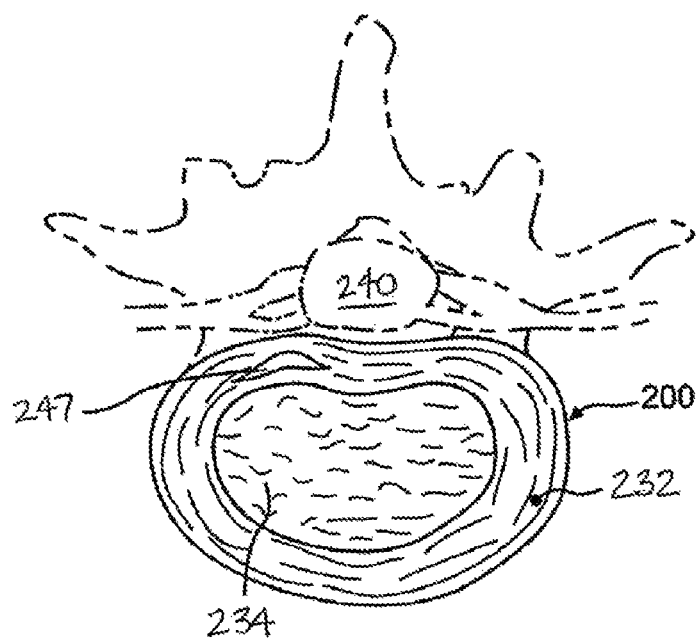
FIGS. 45A-45B depicts an anchor band assembly used to repair a circumferential tear in the annulus.
Figure 45B:
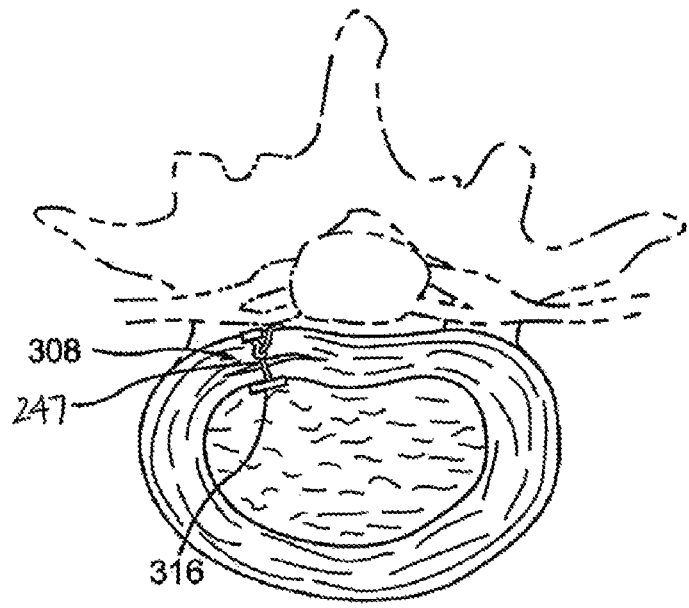

An additional exemplary depiction of fixation devices that may be used to reapproximate and hold annular tissue as previously described in FIGS. 8-10 can be seen, for example, in FIG. 45. In FIG. 45, an anchor band assembly 308 and its complementary delivery tool 400, as exemplarily depicted in FIG. 25 and FIGS. 34-44 and FIG. 48, are used to repair a damaged, degenerated, weakened, or thin portion in an intervertebral disc annulus 232 having, for example, a circumferential tear 247 compromising the integrity of the annulus. Anchor band assembly 308 may draw in tension the annular tissue surrounding the tear 247 or delamination of the annular laminae, helping to fortify, reconstruct, augment, repair, or otherwise reinforce the annular tissue.

A further exemplary embodiment of the invention in the form of a braided patch 1100 such as depicted in FIGS. 14-19, is a further illustrative embodiment of the present invention that can be deployed into the subannular space to act as a barrier to the extrusion of the nucleus pulposus, or other intradiscal material.

The "patch" 1100 is constructed from a braided tube of filaments 1102. The ends 1104 of the braided tube are heat-sealed to keep the braid from unraveling and the seals also provide structural integrity to the patch when deployed. Although the devices described herein principally utilize heat sealing for forming the ends of the device, there may be a variety of ways to fixate, secure or otherwise form the ends of the device through the addition of other materials to add structure to the filaments, to include, but not limited to, the addition of collars or sleeves, dipping the ends in a material to fixate (i.e., heated polymer, adhesive). These added materials could be metallic or polymeric.

The braided patch 1100 is woven on a braiding machine with multiple filaments 1102 to create the structure. For example, the patch can be woven with 72 polyester filaments in order to create the construct that readily deploys into the annular defect, promotes tissue or matrix ingrowth into the device, and retains an anchor after it has been placed through the wall of the annulus and through the patch. Changing the number of filaments 1102 in the patch, the material of the filaments, the dimension of the filaments (e.g., diameter), as well as the configuration of the filaments (e.g., cross-sectional area), or changing the braid pattern, can create differences in the characteristics of the patch. The braided patch can be made on a standard Steeger braider, or similar type braiding machine, that can handle braiding from anywhere from 16 filaments at a time, to up to 196 filaments. Preferably the patch is braided with between 32 to 144 filaments. In one exemplary embodiment of the present invention, the device is braided with 72 filaments of polyester filaments, with every other braid filament being approximately 0.012" diameter, alternating with yarn (e.g., approximately 64 microfilaments, each approximately 17 microns in diameter, bundled) or alternating with a polyester braid monofilament approximately 0.004° in diameter.

In addition, much of the description herein depicts devices that generally have a tubular form, although it is also anticipated that these devices could be woven on the braider (i.e., by changing the configuration of the braiding mandrel), or re-formed in processing (i.e., heat forming) to obtain a patch construct that deviates from a "circular" cross section, in order to obtain different characteristics of the patch pre, during or post deployment to accommodate anatomical, physical, and biological considerations of the patient or the delivery of the implant. These device configurations may include square, rectangular, oblong, symmetrical, non-symmetrical, triangular, "clover leaf", or other cross-sectional constructions that may be partially (i.e., only in a portion of the device body, and/or only in a portion of the device ends), or completely present throughout the device.

The filaments 1102 of the patch can be made of different materials or dimensions, or all of the filaments in a patch can be of like material and dimensions. The filaments can be biocompatible metallic material, such as a stainless steel, a nickel titanium alloy, or other metallic materials. The patch 1100 can also be made from biocompatible polymeric material such as polyethyleneteraphthalate (PET), polyester, polyethylene, polycarbonate urethane, polymethylmethacrylate, or polypropylene, for example. It is also conceivable that the patch can be braided from biodegradable materials, such as polyglycolic add (PGA), polylactic add (PLA), collagen (or its derivatives), fibrin (or its derivatives), cellulose (or its derivatives), polysaccharides (or its derivatives) or other biocompatible material that may degrade and/or be re-absorbed by the body over time.

It is also possible to braid the patch 1100 with multiple materials and/or multiple dimensions of the filaments. For example, the patch can be braided with 32 filaments of a polymeric PET material and 32 filaments of polyester yarn material to create a patch that may be optimal for sealing an annulus. The combination of different filament materials, sizes, cross-sectional configuration, number of filaments, and braiding pattern can be used to construct a braided patch that can be delivered into the sub-annular space, while acting as a scaffold to induce healing of the aperture.

The braided patch has advantages in that it can be placed through an aperture in the wall of the annulus that is relatively small, but then expand to a dimension that is substantially greater than the aperture. For example, it is possible to construct the braided tube to be less than 5 mm in diameter, whereas in its fully deployed state it could be greater than, for example, 20 mm. This is exemplary and is not intended to be construed as limiting in the actual dimensions of the device pre and post deployment.

Figure 14B:
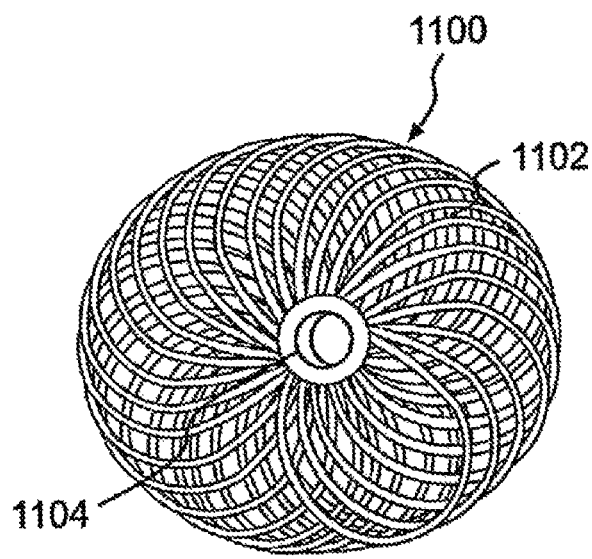
Figure 17:
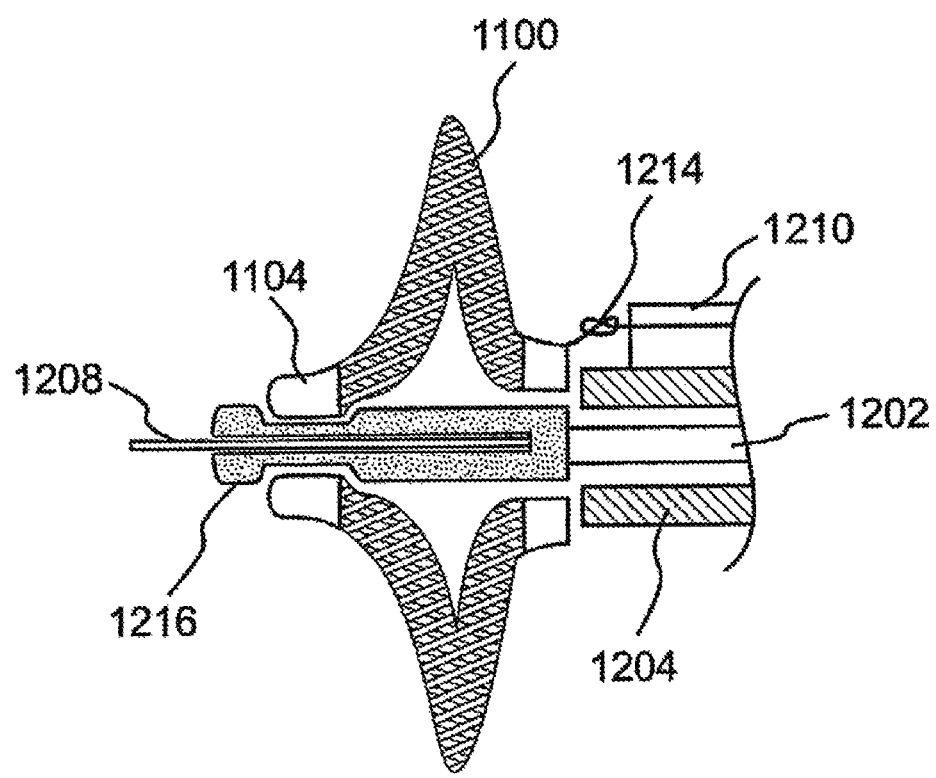
FIG. 17 shows a lateral cutaway view of the exemplary embodiment of FIG. 27B in an expanded configuration.
Figure 18:
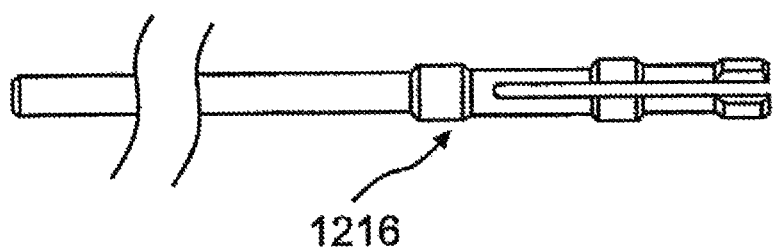
FIG. 18 shows a lateral view of an illustrative delivery member as shown in the exemplary embodiment of FIGS. 16 and 17.

Referring to FIG. 15, the non-deployed braided patch 1100 is affixed on the distal end of the patch delivery tool 1200. It is situated in a fashion that is co-axial 1208 with the delivery tool's delivery members, which include inner delivery member 1202. A finger grip 1206 can be formed onto the proximal end of the delivery tool body to assist in manipulation. Further detail of the deployment mechanism can be seen in FIG. 16. The braided patch 1100 is placed on the distal end of the inner delivery member 1202. The heat-set distal cuff 1104 of the patch is situated within a depressed region on the distal region of the inner delivery member 1216. The distal portion of the delivery member 1216 is slotted as shown in FIG. 18, and, in the non-deployed state, contains a co-axial retention member 1208 that acts to press the slotted potions of the inner delivery member apart, and thus securing the distal cuff of the patch 1104 on the distal region of the inner delivery member 1202. The proximal portion of the patch abuts and is in contact with an outer pusher member 1204. In the non-deployed state, the delivery device is passed into the aperture of the annulus. Once inside the annular aperture, the outer pusher member 1204 of the delivery device 1200 is pushed toward the distal end of the device, while the inner delivery member 1202 is pulled proximally. This action of moving these members in such a fashion results in the braided patch expanding perpendicular to tube's axis, as shown in FIGS. 14B and 17.

Once the patch 1100 has been expanded to its fully expanded state, a cinch line 1212 that is connected to the distal and proximal ends of the patch can be tightened and a knot, such as a Roeder knot, can be used to hold the braided patch in its expanded configuration. Although, the device is shown with a cinch knot 1214, it is possible that a locking element may not be needed, depending on the means used to fixate the patch into the annulus. It is possible that no locking means is necessary. It is also possible that alternative locking means can be contemplated to keep the braided patch in its expanded form. A knot pusher 1210 can also be employed to manipulate the knot locking device 1214.

Once the device patch has been expanded into its final configuration in the aperture and subannular space, the retention member 1208 can be removed from the distal portion of the inner member by slidably pulling the proximal end of the retention member in a proximal direction. Removing the retention member relieves the stress holding the distal cuff of the patch in place and allows the patch to be slidably removed from the distal end of the delivery device, and thus deployed into the subannular space.

Figure 19:
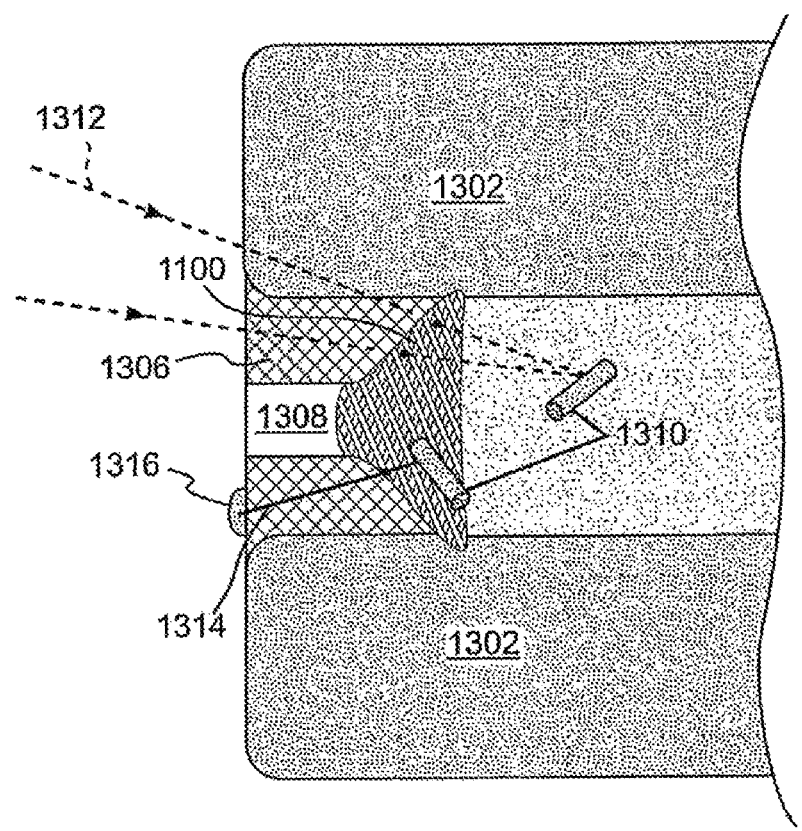
FIG. 19 shows a lateral view of an exemplary embodiment of the invention in an expanded configuration subannularly.

As depicted in FIG. 19, the patch 1100 can be affixed to the inner surface either before or after the deployment of the patch from the delivery device. It is also contemplated that this patch can be affixed to the inner surface of the annulus by the various fixation means described in other parts of this application. For example, anchor bands as shown in FIG. 19 could be used to penetrate the annulus 1306, shown between vertebrae 1302, and the patch to anchor the patch into the sub-annular space. It is also conceivable that single T-anchors 1310 with a band 1314 (e.g., suture) could be delivered through the annulus 1306 and patch 1100 with the portion of the suture on the outer surface of the annulus locked to the outer surface with a knot, pledget, or other locking device 1316. Path 1312 illustrates another possible suture path through the bone of the vertebra to penetrate and hold a T-anchor member 1310 in the patch.

It is also conceivable that the patch could be affixed to the inner surface of the annulus through the use of adhesives, such as cyanoacrylate, fibrin glue, polymer protein, polyurethane, compounds that mimic mussel she adhesive proteins (manufactured by Nerites Corp.), adhesive materials that may be used as adhesives for dural or dermal wound repairs/ sealing, or other material used to cure, or adhesively affix the patch in the subannular space in situ. The delivery of these adhesive fixation materials could be delivered through the patch delivery tool, or through the anchor band delivery tool, or both. It is also contemplated that if an adhesive were used to affix the patch to the annulus that an additional membrane material may be added to the patch device to further help restrict fluidic extravasation of the material out of the disc during adhesive delivery, if required. Conversely, the patch construction may be altered to reduce the patch porosity in order to accomplish a similar objective. Furthermore, it is anticipated that materials maybe added to, or changed, on portions the delivery tools to reduce the possibility of the tools being adhesively bonded to the instruments during delivery. For example, a cannula or other portions of a device used for adhesive delivery may be coated with, or be constructed of, PTFE, FEP, polypropylene, polyethylene or other lubriocious materials or coatings.

The advantages of the braided design, given the right selection of filament dimension, configuration, material, braid pattern, and number of filaments is that it can be easily delivered to the annular repair site, have the flexibility to take the shape of the annular defect while maintaining the mechanical integrity needed to remain within the disc space upon loading. Another advantage, again with the appropriate selection of material, filament configuration, braiding, dimensional considerations, and multiple filament weaves, is that one can construct a patch that is conducive, in its deployed state, for incorporation of fibrosis and the fibrotic healing of the annular defect. Finally, the patch can be designed so that when it is in its delivered state, it can easily receive one or more anchor bands through the braided filaments while retaining the T-anchor or other similar type fixation device, after passing the fixation device through the patch.

FIGS. 20-28 depict an illustrative method for the deployment of a treatment device into the intervertebral disc 200. As described previously, there are a variety of applications, approaches, techniques, tools, and methods for accessing and performing spinal disc surgery which may be dependent on physician preferences and could be arbitrary. Therefore, the following description and depiction of the method should be considered illustrative and not limiting. In the illustrative scenario which is used in the following descriptions, and with reference to FIG. 20, the disc 200, which is comprised of the annulus fibrosus 232 and the nucleus pulposus 234, is shown in a transverse cross section. The disc 200, as described above, is disposed anatomically between caudal and cephalad vertebral bodies, which a portion of a vertebral body (spinous process 236) seen in FIG. 20. The disc 200 may be accessed for treatment via a surgical incision 238 made in the paramedian region lateral of the spinal canal 240. A microdiscectomy procedure may precede the placement of a treatment device in order to remove disc fragments and to provide a subannular cavity 242. The subannular cavity 242, however, may be preexisting or may be created for the purpose of performing a nuclear augmentation An aperture 244 in the annulus provides a path for the mesh or treatment device delivery tool 500 to place treatment device 600. The treatment device 600 can take the form as described in the embodiments disclosed herein, or as additionally described in commonly-assigned copending U.S. patent application Ser. No. 10/352,981, filed on Jan. 29, 2003 and incorporated herein by reference, or any other appropriate form. Likewise, the anchor band delivery device 400 can take the form as described in the embodiments disclosed herein (e.g., with reference to FIGS. 34-44 and 48), as described in commonly-assigned copending U.S. patent application Ser. No, 10/327,106, filed on Dec. 24, 2002 and incorporated herein by reference, or any other appropriate form.

Figure 20:
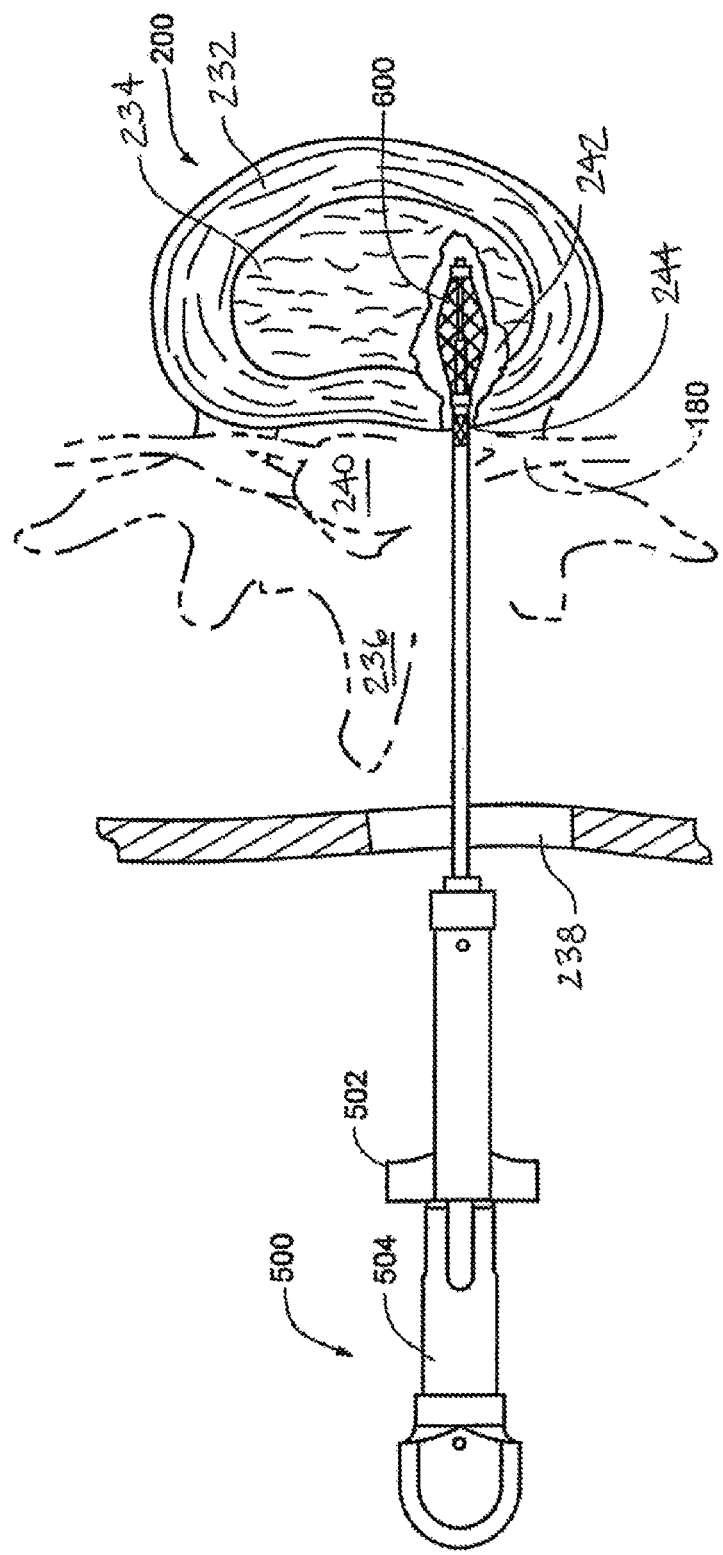
FIG. 20 shows a transverse view of a treatment device mounted on a delivery tool in an unexpanded configuration in the subannular cavity.
Figure 21:
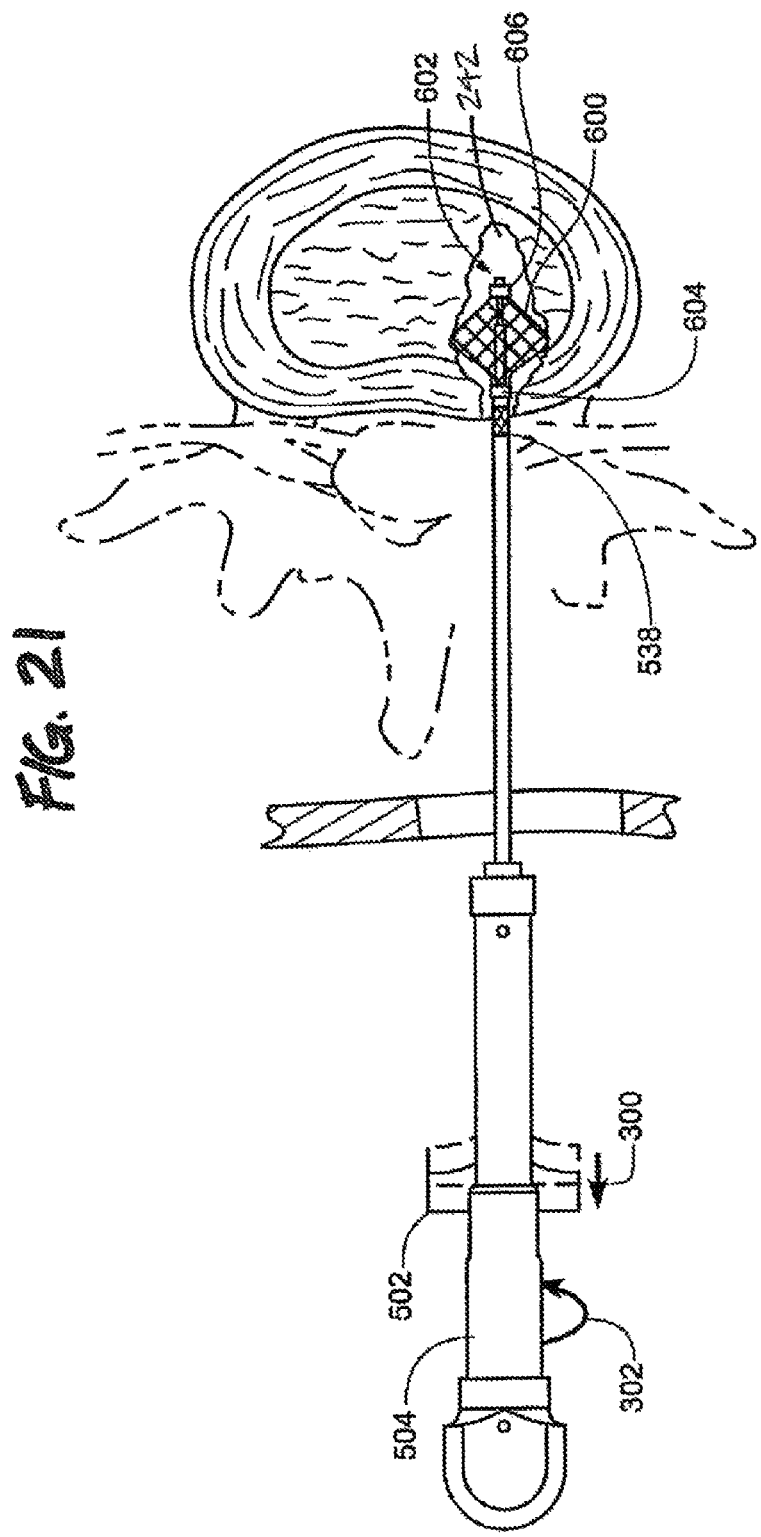
FIG. 21 shows a transverse view of the treatment device being deployed into an expanded configuration in the subannular cavity.

As shown in FIG. 20, a delivery device 500 is introduced through surgical incision 238 to traverse aperture 244 and position treatment device 600 in subannular cavity 242. As depicted, treatment device 600 is in a first configuration sized to permit its passage to the subannular cavity 242. FIG. 21 shows a detail, sagittal view of mesh device 600 mounted on the distal portion 602 of delivery tool 500, introduced to the cavity. Also shown are sections of intervertebral disc tissues. As illustrated, treatment device 600 may have element 608 (FIGS. 29 and 30) to latch the mesh device once deployed into its final deployed configuration. If required, there may be a variety of ways to latch, lock or otherwise secure the device in its final configuration.

As depicted in FIG. 21, the treatment device delivery tool 500 can be manipulated by, for example, pulling a finger grip 502 in the direction of arrow 300 to deploy treatment device 600 in the subannular cavity 242. As illustrated here, this deployment involves a longitudinal shortening of the treatment device, drawing end 606 toward end 604, resulting in a lateral expansion of the treatment device 600. The pulling of the finger grip 502 may be preceded by the release of a safety lock 504 preventing deployment of the treatment device until intended by the surgeon. As illustrated here, the lock is released through rotation of handle member 504 in the direction of arrow 302. Also shown is a marking 538 on the delivery tool 500 that may visually assist the surgeon in assessing the degree to which the device has been placed in subannular space.

Figure 22:
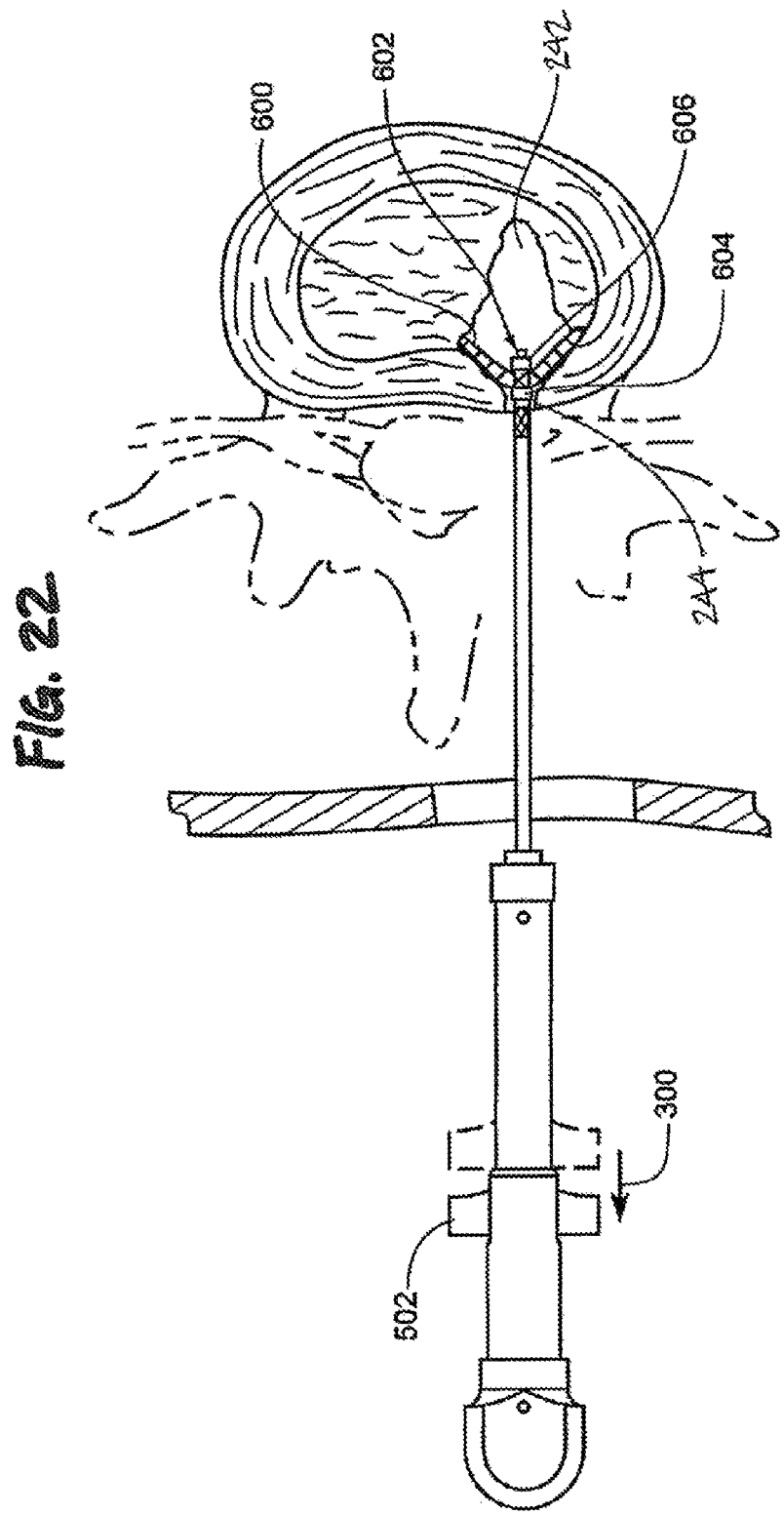
FIG. 22 shows a transverse view of the treatment device fully deployed and adjacent the annular wall.

FIG. 22 shows the finger grip 502 reaching its intended limit, and the concomitant full intended deployment of treatment device 600, where end 606 reaches its intended design position for the deployed configuration of the device 600. In this illustrative depiction, end 606 is pulled adjacent to end 604, and device 600 has reached its maximum intended lateral expansion. As shown, the deployed device 600 may be pulled to internally engage and at least partially conform to the cavity 242. Naturally, the full travel of the finger grip 502 can be determined by the design of the delivery device, or informed by the judgment of the surgeon through visualization, tactile realization, or the like. Once the intended limit has been achieved and the device fully deployed, the delivery device 500 can lock finger pull 502 in place so as to maintain the treatment device 600 in the deployed configuration. It may also be advantageous for the delivery tool 500 to have a perceptible (i.e., audible, tactile, visual) indication that the treatment device has been fully deployed. The mesh/patch delivery tool 500 may be of the type described hereinabove, or as additionally described in other sections of this disclosure.

Figure 23:
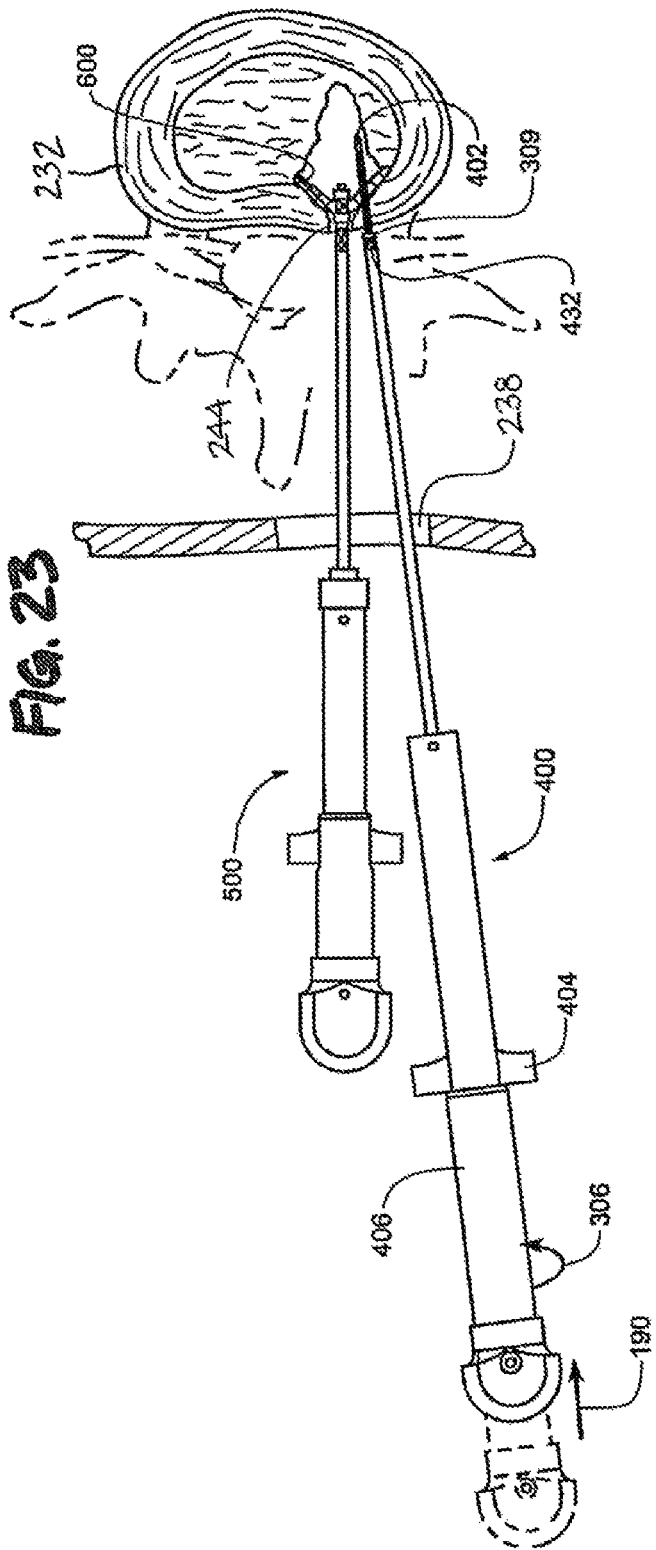
FIG. 23 shows a transverse view of the placement of a fixation element delivery device into the deployed treatment device.
Figure 31:
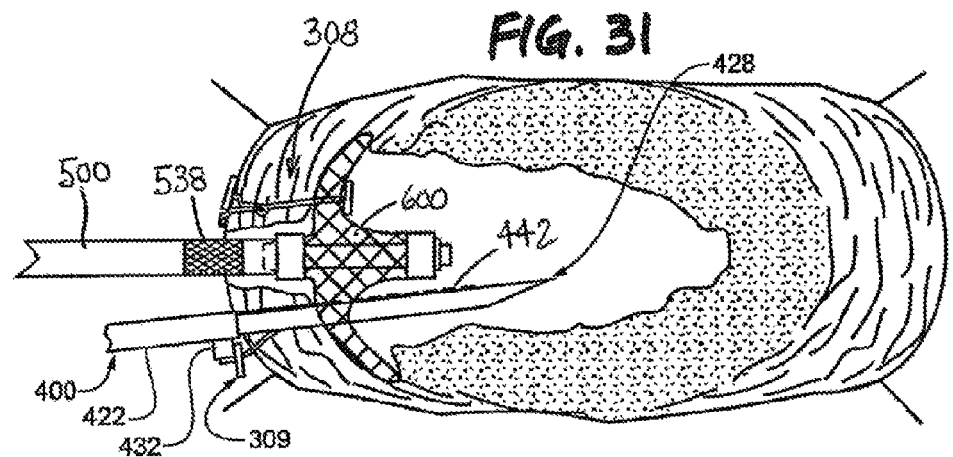
FIG. 31 shows a transverse view of the placement of a fixation element delivery tool through the treatment device and the annular wall.

FIG. 23 next depicts a fixation element or anchor band delivery device 400 introduced through surgical incision 238, where the distal end 402 is passed through the annulus fibrosus 232 adjacent to the aperture 244, and subsequently through treatment device 600, as illustrated by arrow 190. Fixation element delivery tool 400 may have features to provide tactile feedback once the delivery tool has been introduced into tissue to an acceptable extent, for example a feature like tissue-stop 432. As illustrated, delivery device 400 is passed distally until stop 432 and pledget member 309 of the fixation device 308 come in contact with the outer surface of the annulus. Alternatively, and without tissue stop 432 use, pledget member 309 could be of construction to similarly resist, or otherwise visually or tactilely indicate ceasing the passage of delivery device 400 through annular tissue. FIG. 31 shows a detail, sagittal view of a distal end of a fixation element delivery tool 400 introduced into disc tissue and through treatment patch 600. As shown in FIG. 31, one fixation element has been deployed and fixated. FIG. 31 also depicts an exemplary treatment device detection feature 442 on the outer surface of needle cannula 428, as more clearly illustrated in FIG. 35. The patch detection feature 442 on the distal end of needle cannula 428 may advantageously provide perceptible feedback (tactile and/or audible) to the surgeon that the anchor band delivery tool has accessed and penetrated the patch and it is therefore acceptable to deliver the band. Feature 442 is discussed in more detail below. In operation as illustrated in FIG. 23 and in FIG. 24, the delivery device 400 can be manipulated similarly to the treatment device delivery tool. For example, moving finger grip 404 in the direction of arrow 304 will withdraw a portion (for example, the slotted needle cannula 428) of distal end 402 of the device 400 and deploy a fixation element 308 in the subannular cavity 242 to secure the treatment device 600. The pulling of the finger grip 404 may be preceded by the release of a safety lock 406 preventing deployment of the fixation element until intended by the surgeon. As illustrated here, the safety 406 is released through rotation of safety 406 in the direction of arrow 306. The fixation element delivery tool 400 may be of the type described hereinabove, or as additionally described in, e.g., FIG. 34-44 or 48 below, or in other areas of this disclosure.

Figure 24:
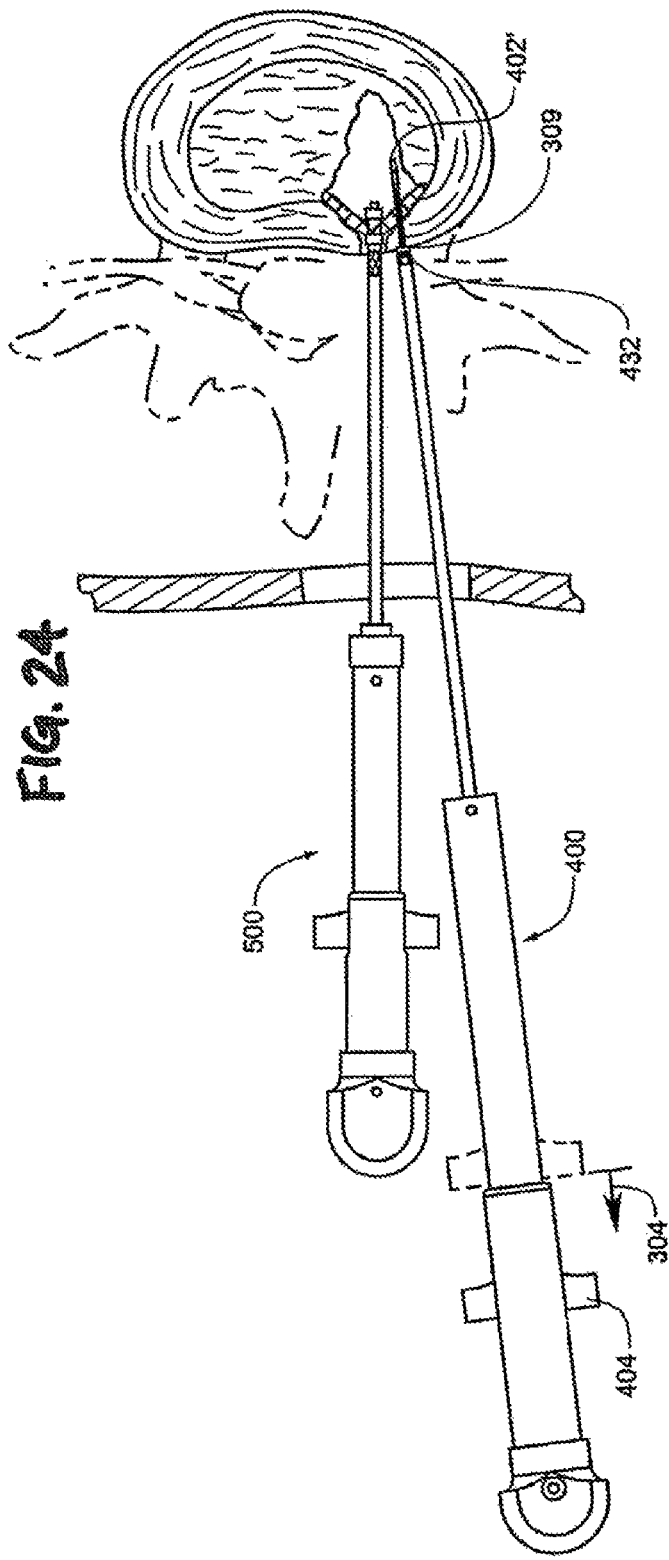
FIG. 24 shows a transverse view of the placement of a fixation element through the treatment device and the annular wall.
Figure 32:
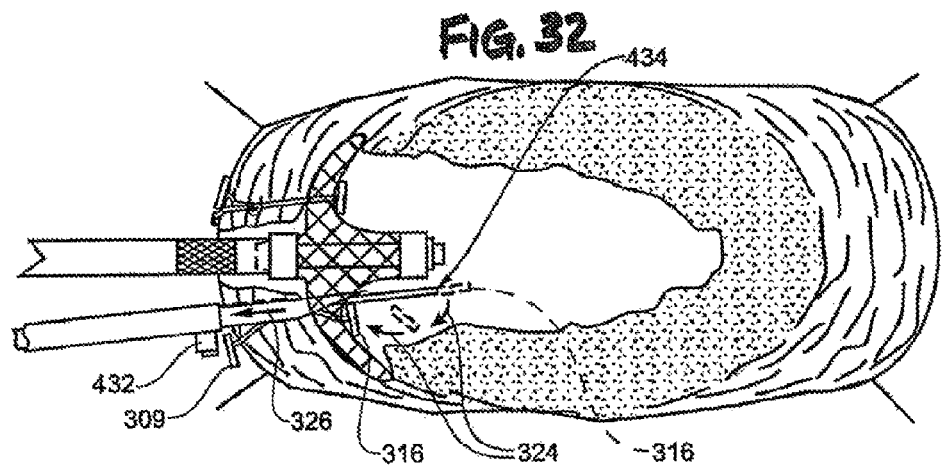
FIG. 32 shows a transverse view of the placement of an additional fixation element through the treatment device and the annular wall.

FIG. 24 depicts the deployment of a fixation element, 308 into disc tissue following the deployment of FIG. 23. The fixation device may be as described herein, for instance a T-anchor, suture, tether, knot, pledget or barb. As illustrated here, the fixation element 308 is a T-anchor with suture bodies, knot, and pledget as more fully described herein. During the pulling of finger grip 404 and retraction of slotted needle cannula 428, a knot pusher end 406 of inner cannula 426 is shown holding a proximal portion of the fixation device's 308 slip knot 440, while T-anchor 316 is drawn in tension proximally by tether or suture line 310, to adjust the length of the fixation element 308 to provide the proper tension to securely hold the treatment device 600 in situ. A proximal end of the fixation element, such as a pledget 309, is held or urged into engagement with a bearing surface on the exterior of the annulus. The proximal end of the fixation device can also include a T-anchor or knot or similar tissue locking element. FIG. 35 is a cross sectional view of the distal end of delivery tool 400 as it may be introduced in disc tissue. FIG. 42 shows the distal end of the delivery tool 400 after retraction of the slotted needle cannula 428 and tensioning and drawing T-anchor 316 proximally to a potential final state. The proximal drawing of T-anchor 316 is also illustrated in a detail, sagittal view in FIG. 32, with arrows 324 illustrating motion of the T-anchor. The construction of the locking element 316 is exemplary and is not intended to be limiting of alternative constructions of 316, such as one or more pledgets, knots, barbs or other forms to effect the same function.

Figure 25:
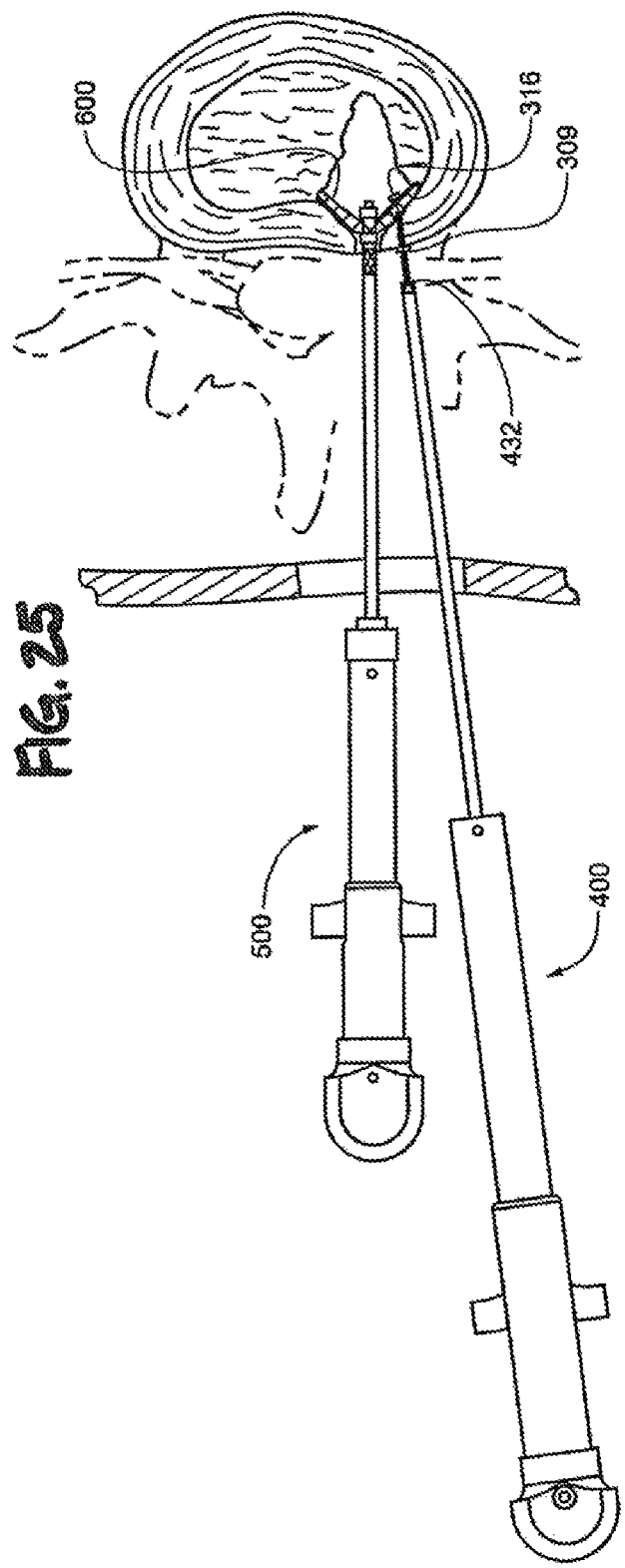
FIG. 25 shows a transverse view after affixing a fixation element delivered in FIG. 24 and partial removal of the fixation element delivery device.
Figure 26:
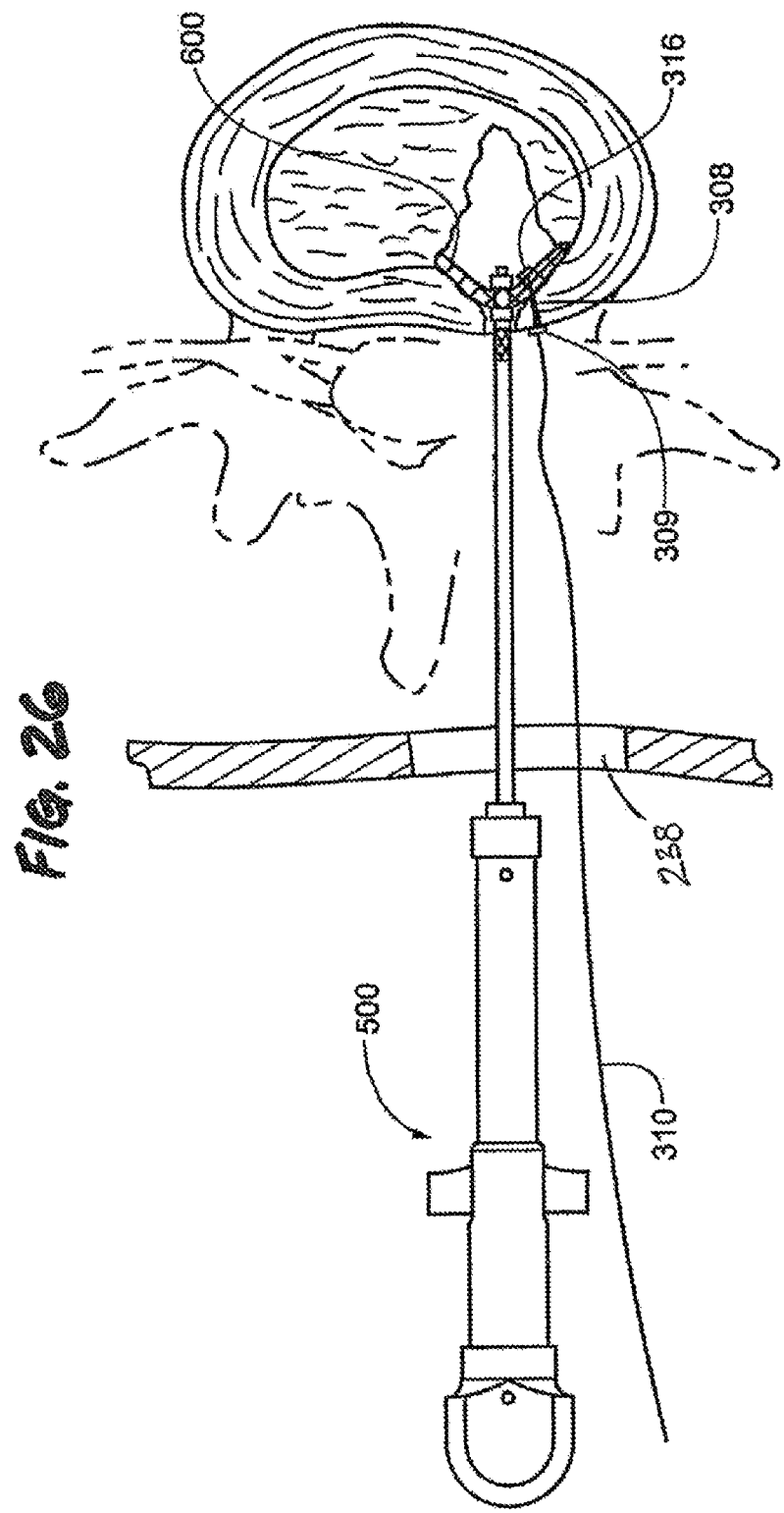
FIG. 26 shows a transverse view of the fixation element after removal of the fixation element delivery tool.
Figure 33:
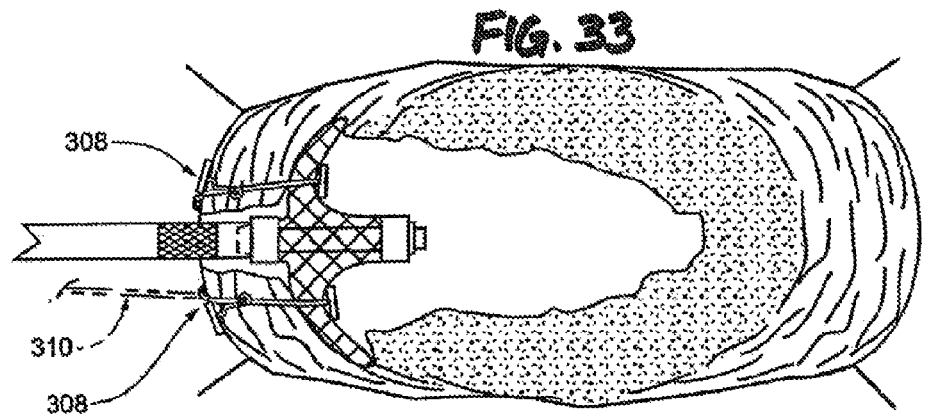
FIG. 33 shows a transverse view after the removal of the fixation element delivery tool.

FIG. 25 shows the partial withdrawal of the fixation element delivery device once the fixation element has been deployed. In the illustrations shown, the final step during the pulling of finger grip 404 proximally results in the release of the fixation element in situ. The release may be accompanied by visual or tactile or auditory confirmation, such as a click. Once released, the fixation element delivery tool can be completely withdrawn as shown in FIG. 26, leaving the suture body 310 of a fixation element extending through the surgical incision 238. The proximal portion of suture body 310 may be cut to a suitable length with readily available surgical tools such as a scalpel or surgical scissors and removed from the surgical site. FIG. 30 shows a detail, sagittal view of a single deployed anchor band assembly 308 with T-anchor 316, pledget 309, slip knot 440 and associated tether components 318 and 310 (after it has been cut in the epi-annular space). Also shown are portions or sections of intervertebral disc tissues. As shown, fixation element 308 is fixedly engaged with the disc tissue and the patch 600. FIG. 27 depicts the treatment device 600 after placement of two fixation devices 308, as does FIG. 33 shown in a detail, sagittal view. Of course, any number of fixation devices appropriate to secure the treatment device 600 can be used. It is also anticipated that device 600 may be of a construction and design, as described herein, that does not necessitate anchor bands to effect securement of device 600 within the disc space and therefore, illustrations using fixation elements are to be exemplary, and not limiting. Once secured, the treatment device 600 is released from the delivery tool 500. As illustrated here, this is accomplished in a two-step process. First the release mechanism is enabled by rotating knob 506 in the direction of arrows 312. An indicator may then be activated as shown by arrow 320 of indicator 508 in FIG. 28, such as spring-loaded release indicator 508 to notify the surgeon that the treatment device has been released from the delivery tool 500. Accompanying the deployment of indicator 508 is the uncoupling of the treatment device 600 at the distal end 602. The delivery tool 500 can then be withdrawn as depicted in the transverse view of FIG. 28, leaving treatment device 600 in situ.

FIGS. 34-44 depict illustrative embodiments of an fixation element delivery tool (or FEDT) as discussed herein, which may be referred to alternatively as an anchor band delivery tool (or ABDT). The fixation element 308 is depicted as loaded in the distal end 402 of the ABDT, which will be discussed in greater detail with reference to FIG. 35. The ABDT 400 is comprised of a main body member 410 which may be fixedly attached distally to outer cannula 422, and also to inner cannula 426 at inner cannula anchor 438. Distally, inner cannula 426, as better illustrated in detail in FIG. 35, may comprise a knot pusher (or other means to effect securement of suture tethers 310 and 318 with locking element 440) and T-anchor stand-off 434. Proximally, main body 410 has disposed safety member 406 with an outside diameter telescopically and rotatably received in the inner diameter of a knob 408. Knob 408 and main body member 410 are rigidly attached to one another Slidably disposed within the lumen of the main body member 410 is suture retention block 414, depicted with suture body 310 threaded through its center hole. A spring 316 is also slidably disposed within the lumen of the main body member and can abut either suture retention block 414 or slider member 418. Slider member 418 can be integral with finger grip 404 (not shown) as depicted in FIGS. 23-25. Attached to the proximal end of slider member 418 is a suture cutting blade assembly 420. The blade assembly, as will be discussed in greater detail below, serves to sever the suture body after deployment of the fixation elements as described herein. A slot in the slider member 418 allows the slider member 418 to slide past the outer cannula anchor 426 and, as described previously, 426 may be stationary with respect to main body 410. A slotted needle cannula 428, slidably disposed in the lumen of the outer cannula 422, is secured the distal end of slider member 418 by needle cannula anchor 430, such that the translation of the slider member 418 within main body member 410 concomitantly translates the slotted hypotube 428 within the outer cannula 422.

FIG. 35 is a detailed view of the distal end 402 of the ABDT 400. As described above, the slotted hypotube 428 is slidably received in the outer cannula 422. A tether, consisting of a suture line 318 and a pledget body 309 is located in proximity to an optional tissue stop 432 on the outer cannula 422. It is also possible for pledget 309 to be held by an optional outer cannula pledget holder 433 until release of the anchor band. The suture line 318 is slidably knotted to suture body 310. The distal end of suture body 310 is attached to T-anchor 316, which is held by T-anchor stand-off 434. As described above. T-anchor stand-off 434 and knot pusher 436 may be components of inner cannula 426. In the initial configuration, needle hypotube 428 extends distally of outer cannula 422 and allows the point of slotted hypotube 428 to extend distally of the T-anchor holder 434.

FIGS. 34 and 35 depict the ABDT in its initial delivery configuration. The ABDT is locked in this configuration by the distal end of safety 406 engaging the finger grip 404 (not shown) as depicted in FIGS. 23-25. Turning now to FIG. 23, the rotation of handle member 406 in the direction of arrow 306 allows the finger grip 404 (not shown) to engage a slot on safety 406, and permits the surgeon to pull finger grip 404 proximally toward the proximal knob 408. Doing so results in the translation of the slider member 418 proximally; and concomitantly, the proximal translation of the slotted needle cannula 426 (as a result of slotted needle cannula anchor 430) in the direction of arrow 326 (illustrated in FIG. 32). The result, as discussed above, is the unsheathing by the needle 428 of T-anchor 316 held by T-anchor holder 434. The translation of the slide body 418 proximally also urges the spring 416 and suture retention block 414 proximally. The suture retention block 414 is attached to suture body 310, and therefore tension is leveraged onto the suture body 310 to hold it taught and, when appropriate, draw T-anchor 316 from within the delivery tool to a position proximally.

Figure 40:
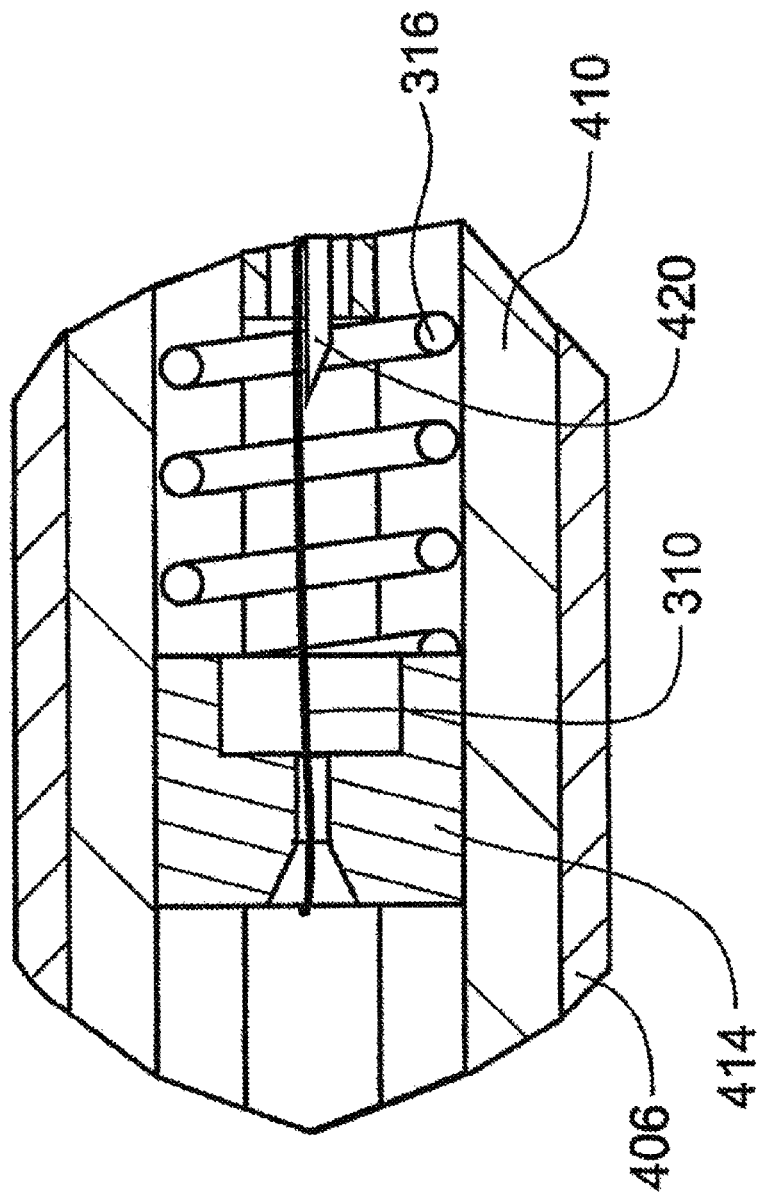
FIG. 40 shows a detail of the suture retention block and blade assembly of the anchor band delivery tool.

FIGS. 37 and 38 illustrate the partial deployment of anchor band assembly from ABDT, wherein slotted needle cannula 428 has been partially retracted to expose T-anchor 316. FIG. 36 is a detail, cross sectional view of the distal end of the handle of ABDT 400, illustratively showing the inter-relationships of delivery, tool components in the initial configuration and FIG. 39 is a similar detail, cross sectional view showing the inter-relationships after at least a partial deployment of device 400. FIG. 40 is a detail of the suture retention body 414, suture body 310, spring 316 and cutting assembly blade 420, during partial deployment of delivery tool 400, as discussed above. As depicted in FIG. 41 and detail drawings of FIGS. 42 and 43, as slider body 418 continues to slide proximally, in addition to continuing to draw T-anchor as shown in FIG. 42 with arrows, the tether retention block 414 reaches the limit of it's proximal translation (discussed further below), and the slider member engages and compresses spring 316. As the spring is compressed, the blade assembly 420, which is aligned with the hole of suture retention body 414 through which suture body 310 passes, comes into engagement with the suture body 310. FIG. 43 is a detail view of the blade 420 severing the suture body 310. Up to the limit of travel of the suture block 414 and the severing of tether 310, the suture body 310 continues to apply tension to the T-anchor, as shown in greater detail in FIG. 42. With knot pusher holding knot 440, pledget 309, and suture 318 in apposition, and in distally exerted fashion, to the tensioning of suture body 310, anchor band assembly 308 is advantageously cinched into a fixing and/or compressive relationship between ends 309 and 316, as well as any structures (e.g., nucleus, annulus, treatment device) between elements 309 and 316. After severing suture body 310, suture body 310 is still attached, to the anchor band, but has at this point been severed proximally. The suture body 310 will therefore be unthreaded from the interior of the ABDT as the ABDT is withdrawn. As discussed above the suture line 310 may be further cut to length with readily available surgical scissors. Alternatively, a severing mechanism similar to those described herein in the distal portion of tool 400 may be employed to avoid an additional step of trimming the end of body 310.

FIG. 40 is a detail of the suture retention body 414, suture body 310, spring 316 and cutting assembly blade 420, during partial deployment of delivery tool 400, as discussed above.

Additionally inventive of the anchor band device (and its delivery and deployment tools) is the unique inter-relationship of the slide body, spring, and the tension delivered to the T-anchor and tissue during deployment. For example, T-anchor assembly can be designed to pass through softer, or otherwise more pliable tissues (e.g., nucleus pulposus, softer annular layers) while resisting, under the same tension, passage through tougher tissues and/or substrates (e.g., outer annular layers, treatment device construct). In further illustrative description, tension delivered to the suture line 310 can be limited by the interface between the slide body member 318 and the suture retention block 414, through spring 316 such that tension is exerted on T-anchor body 316 which may sufficiently allow movement of T-anchor 316 through softer tissue, but alternatively requires a greater force to pull T-anchor body through other materials or substrates such as the treatment device 600 or outer layers of the annulus 232. Spring 316 can be designed to sufficiently draw tissues and/or the patch together, while not overloading suture line 310 when the fixation has been effected. Spring 318 may also be advantageously designed to allow blade assembly 420, upon reaching an appropriate loading to effect the delivery, to sever the suture line 310. As illustrative example, but not intended to be limiting, T-anchor body and suture line may be constructed to require approximately 5 pounds of force to draw the T-anchor assembly through nuclear tissue, but substantially greater bad to draw T-anchor through annular tissue and/or patch device. Spring may be designed to exert approximately 5 pounds, sufficiently pulling anchor through nuclear tissue, and in proximity to treatment device, as intended. Once sufficient bad has been applied to move T-anchor to engage patch, the loading on the suture line is not allowed to substantially increase. Advantageously, additional loading would cause the final compression of spring between suture retention block and blade assembly to sever suture line. Preferably, the severing and the design of the tether elements are such that the ultimate strength of the suture line is greater than the bad required to draw T-anchor through soft tissue, or the like, and less than the bad inflicted to cause the severing by blade assembly. The description herein is intended to be illustrative and not limiting, in that other device and delivery tools could be derived to employ the inventive embodiments.

Figure 46D:
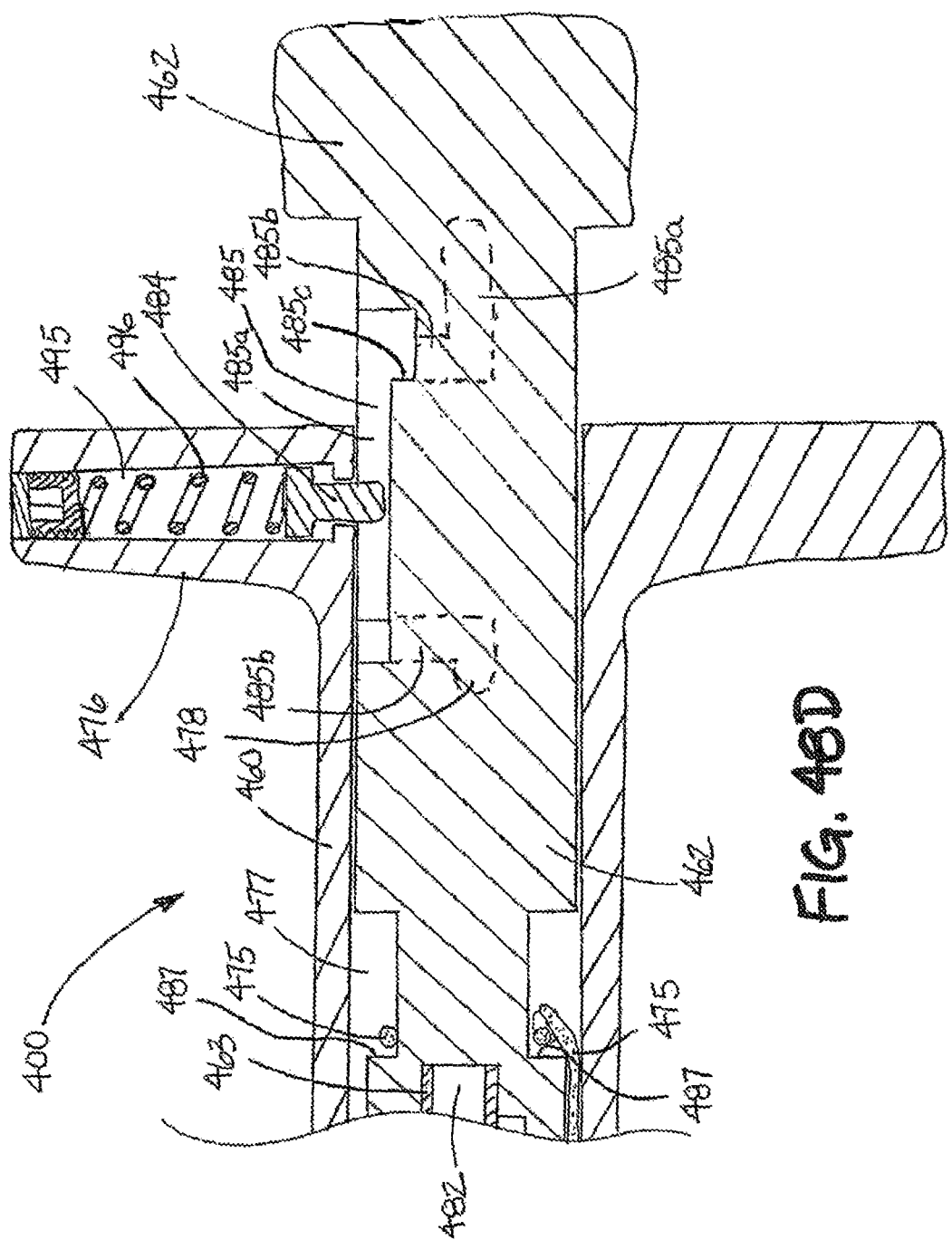
Figure 52:
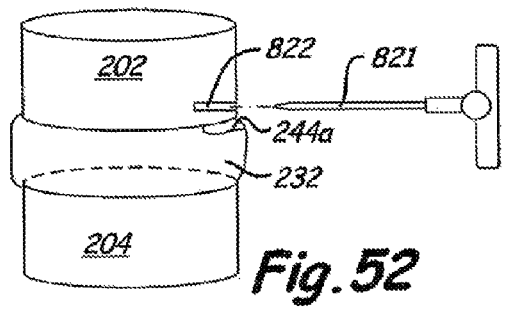

With regards to introduction, delivery, deployment and/or fixation of fixation element 308 as described previously and in particular, with regards to FIGS. 34-44, for example, anchor band assembly 308 and its associated delivery tool 400 may be described as effecting a fixation as shown in FIGS. 47A and 47B. FIG. 47A shows a pledget element 309 that, initially, may be placed on outer annular surface. As depicted, tether 318 is attached to pledget 309, and pledget and tether are secured to suture line 310 via a slip knot 440, for example. During deployment, T-anchor is drawn toward, and engaged with, treatment device 600 as illustrated in FIG. 47B. There may be alternative methods and mechanisms of drawing together locking elements/anchors 309 and 316, as exemplified in FIGS. 46A and 46B. FIGS. 46A and 46B illustrate a T-anchor member 316 that may be positioned, initially, in proximity of patch 600. As depicted, tether 318 is attached to T-anchor, and T-anchor and tether are secured to suture line 310 via a slip knot 440, for example. During deployment, pledget 309 may be drawn to, and engage with, the surface of outer annulus tissue, as illustrated in FIG. 46B. The description of methods of drawing members together and effecting a fixation of an fixation element with its fixation element delivery tools are intended to be illustrative, and not limiting in the scope of the invention.

Since the surgeon's visualization of during discectomy procedures is typically limited to the epi-annular space and the aperture at the outside surface of the annulus, any tactile, visual or audible signals to assist, or otherwise enhance, the surgeon's ability to reliably deliver and deploy treatment devices and/or anchor bands may be advantageous. The anchor band delivery tool 400, may have a patch detection feature 442 on the distal end of slotted needle cannula 428 which may provide perceptible feedback (tactile and/or audible) to the surgeon that the anchor band delivery tool has accessed and penetrated the patch and it is therefore acceptable to deliver the band. As shown, detection feature 442 is composed of multiple bands or ribs although the outer surface of needle 428. The movement of the ribs of 442 against the patch structure (e.g., the filaments of treatment device 600) may produce a clicking sound and feel, and the interface of the components of the devices and tools may be optimally designed to enhance such feedback features. One, or multiple, ribs or tabs may be utilized to achieve the perceptible features. The feed back may be perceived on or with the patch and/or patch delivery tool or through the anchor band and/or anchor band delivery tool, or both. FIGS. 44A-44C illustratively shows additional means that may be attached to the anchor band or anchor band delivery tool which might also provide perceptible feedback. These depictions are meant to be illustrative and not limiting in scope of the invention. FIG. 44A shows a tab 442 attached to needle cannula 428 which may be laser cut from the distal end of needle 428. Detection tab 442 may be designed to readily pass through soft tissue and the patch 600 without causing significant disruption, but may be capable due to its design construction to produce tactile and/or audible sensation as it engages the patch lattice or structure. Lateral extent of tab 442 of FIG. 44A may advantageously deflect, or otherwise deform or bend toward the distal end of needle cannula upon removal of the delivery tool so as not to be restricted by the lattice or structure of treatment device 600 upon its removal. Alternatively, detection tab 442 of FIG. 44B is affixed to, or integral with, T-anchor 316. Similarly, detection tab 442 may be designed to readily pass through soft tissue and treatment device 600 without causing significant disruption, but may be capable of producing tactile and/or audible sensation as it engages the patch lattice or structure. In this embodiment, tab 442 advantageously remains with T-anchor 316 after removal of delivery tool 400. Moreover, it is possible to have a detection feature 442 as depicted in FIG. 44C wherein the feature is wholly, or partially, coaxial disposed on the delivery tool and feature 442 may be of a construction that does not readily pass through patch 600, but it is capable of passing through soft tissue of the disc and produce a tactile and/or audible sensation as it engages the patch lattice or structure. Although some of the embodiments illustrate a single tab or rib, it is possible to use more than a single element. Detection features described herein may be of a variety of shapes and affixed to the devices or delivery tools (for example, welding ribs onto the surface of the delivery tool, affixing a flexible filament member to the T-anchor) or be incorporated as an integral component thereof (for example, laser cutting or stamping tabs out of a portion of needle 428, injection molding tabs as part of t-anchor 316). Exemplary materials that could be used to construct the various detection features include, but are not limited to: biocompatible polymeric materials (polyester, polypropylene, polyethylene, polyimides and derivatives thereof (e.g., polyetherimide), polyamide and derivatives thereof (e.g., polyphthalamide), polyketones and derivatives thereof (e.g., PEEK, PAEK, PEKK), PET, polycarbonate, acrylic, polyurethane, polycarbonate urethane, acetates and derivatives thereof (e.g., acetal copolymer), Polysulfones and derivatives thereof (e.g., polyphenylsulfone), or biocompatible metallic materials (stainless steel, nickel titanium, titanium, cobalt chromium, platinum and its alloys, gold and it alloys).

Although much of the description of the expandable braided treatment device has illustrated the use of the braided construct as a patching-type element, the expandable braided element 1100, of for example, FIGS. 14-18, could also be used to facilitate anchoring of treatment devices depicted in, for example: FIG. 10 as anchor 916; FIG. 1 as anchoring element 709; and/or AG, 19 as anchoring element 1310. In this use, the braided element may be delivered in an unexpanded state, and upon deployment and delivery obtain an expanded, anchored state. Two or more of these braided anchor elements could be tethered to one another to effect the repair as previously described in, for example, FIGS. 10, 12 and 19. A braided expandable anchoring element could also facilitate anchoring into soft tissues of ligaments or annulus, or other tissues; such as, vertebral bodies 202, 204 or Sharpey's Fibers 802 of FIG. 7.

As generally illustrated in FIGS. 48A to 48D, alternative embodiments of present inventions include various additional fixation delivery apparatus described previously as, for example, tool device or apparatus 400. Fixation delivery apparatus in accordance with the present inventions may permit the placement of a fixation apparatus described previously as for example, 308 will now be further described by 450 in FIGS. 48A to 48D and within an intervertebral disc of a patient. Typically, the fixation delivery apparatus may be configured to deliver one or more anchors as described previously, and now will be further described by anchor 451 in FIGS. 48A to 48D of a fixation apparatus 450 into and/or through an intervertebral disc, which may include the annulus fibrosus, the nucleus pulposus, vertebral bodies and surrounding connective tissues. The fixation delivery apparatus 450 may be configured to deliver multiple anchors 451, for example, a first anchor 452 to a first location on an intervertebral disc and a second anchor 453 to a second location on the intervertebral disc. The anchors 451 are typically interconnected by one or more elongate members as described previously and now will be further described by 454 in FIGS. 48A to 48D, such as bands, sutures, wires, and cables for example, which may be cinched, tightened, reduced, or otherwise shortened so as to reduce the length of the connection between at least a first anchor 452 and a second anchor 453. Two or more elongate members 454 may include retention devices and/or knots 455 as described previously to interconnect the members and to permit the cinching of the elongate members 454. The cinching of the elongate members 454 may reconstruct, retain, stabilize, re-approximate and/or draw together tissues surrounding a defect, tear, cut or delamination in the tissues of an intervertebral disc of a patient.

As generally illustrated throughout the FIGS. 48A to 48D, fixation delivery apparatus 400 generally includes a delivery apparatus body 460, one or more shafts 461, actuators 462, and displacement rods 463. The delivery apparatus body 460 is typically secured to one or more shafts 461 to allow a surgeon to position the distal end of the shaft 461 within an intervertebral disc of a patient. Each shaft 461 may define a lumen 464 and/or slot 465 which may removably receive at least a portion of at least one anchor 451 and or connecting band or loop 466. A displacement rod 463 may be positioned through at least a portion of the lumen 464 and/or slot 465. A displacement rod 463 may be axially slidable along at least a portion of the lumen 464 and/or slot 465 of a shaft 461. A displacement rod 463 may communicate with anchor 451 and/or fixation apparatus 450 to displace an anchor 451 from the lumen 464 and/or slot 465 of a shaft 461. An actuator 462 may be movable by a user relative to a delivery apparatus body 460. The actuator 462 may be in communication with a displacement rod 463 to confer movement of the displacement rod 463 within the lumen 464 and/or slot 465 of a shaft 461 such that at least one anchor 451 may be expelled from the lumen 464 and/or slot 465 of the shaft 461 while the distal portion of the shaft 461 is positioned proximate and/or within an intervertebral disc of a patient and the delivery apparatus body 460 and actuator 462 may be positioned at least partially external to the patient to allow actuation by a surgeon.

In one aspect, a fixation delivery apparatus 400 may include a single shaft 461. The shaft 461 may define a lumen 464 and/or slot 465 to serially receive two or more anchors

451. The tissue anchors 451 may be sequentially dispensed from the distal end of the shaft 461 at one or more locations within an intervertebral disc. In this embodiment, the distally positioned anchor 451 may be particularly referred to as the first anchor 452 and the proximally positioned anchor 451 may be particularly referred to as the second anchor 453. The anchors 451 are displaced from the lumen 464 and/or slot 465 of the shaft 461 by a displacement rod 463. A displacement rod 463 may communicate with an actuator 462 so that a user may advance a displacement rod 463 within the lumen 464 and/or slot 465 to dispense anchors 451 from the lumen 464 and/or slot 465 of the shaft 461. The first anchor 452 may be sized to be frictionally held within the lumen 464 and/or slot 465, may be retained in the lumen 464 and/or slot 465 by one or more detents formed within the lumen 464 and/or slot 465, may be retained in the lumen 464 and/or slot 465 by an elongated member 454 or other interconnecting members between anchors 451 and/or tethers 470, or may be otherwise temporarily secured to the lumen 464 and/or slot 465 of shaft 461. The second anchor 453 may be similarly secured to shaft 461 in a manner similar to a first anchor 452 or, alternatively, may be tethered by a tether 475 to retain a second anchor 453 secured to lumen 464 and/or slot 465 during and/or after displacement of the first anchor 452 into the intervertebral disc of a patient. In one aspect, the tether 475 may be secured to the displacement rod 463 or the actuator 462. Before, or upon, or after placement of the second anchor 453, the tether 475 may be severed, broken, cut or otherwise released from an actuator 462, displacement rod 463, and/or the delivery apparatus body 460 or shaft 461 to permit the release of the second anchor 453 from the structure to which the tether 475 is secured. In this exemplary embodiment, the first anchor 452 can be displaced from the shaft 461 by movement of the displacement rod 463 a first distance sufficient to displace the first anchor 452. This first distance may be insufficient to displace the second anchor 453. Then, the shaft 461 of the fixation delivery apparatus 400 may be moved from the first location where the first anchor 452 was dispensed and repositioned at a second location on or in the intervertebral disc to dispense the second anchor 453. The second anchor 453 may be connected to the first anchor 452 by one or more bops 466 and/or elongate members 454.

In another aspect, a fixation delivery apparatus 400 may include two or more shafts 461. In an exemplary embodiment, wherein there are two shafts, (similar to, for example, FIG. 11), one shaft may be particularly referred to as the first shaft and the other shaft may be particularly referred to as the second shaft. The first shaft and the second shaft may be adjacent one another and could be parallel to one another over at least a portion of their length (such as the cannulas 711 illustrated in FIG. 11). Each shaft may define a lumen and/or slot to receive one or more anchors. In various configurations, the anchors may be simultaneously or sequentially dispensed at one or more locations within an intervertebral disc from the distal end of the respective shaft in which the anchors are positioned. In this embodiment, the anchor positioned in the first shaft may be particularly referred to as the first anchor and the anchor positioned in the second shaft may be particularly referred to as the second anchor. In this embodiment, a first anchor can be displaced from the first shaft by movement of a first displacement rod a distance sufficient to displace the first anchor from the lumen and/or slot of the first shaft. A second anchor may be displaced from the second shaft by movement of a second displacement rod a distance sufficient to displace the second anchor from the lumen and/or slot of the second shaft. The first displacement rod and second displacement rod may communicate with one or more actuators to simultaneously or sequentially dispense the first anchor and the second anchor from the respective lumen and/or slot in which they are secured. The second anchor is typically connected to the first anchor by one or more loops and/or elongate members. The first anchor and the second anchor may be sized to be frictionally held within the respective lumen and/or slot of first shaft and second shaft, may be retained in the respective lumen and/or slot by one or more detents within the lumen and/or slot or may be otherwise temporarily secured within the lumen and/or slot as described previously.

The delivery apparatus body 460 may be generally configured to provide a user with a structure to manipulate the distal portion of the shaft 461 within a patient. The delivery apparatus body 460 may have an elongated form and define a longitudinal aspect. In one aspect the proximal portion of the shaft 461 may be secured to a distal portion of the delivery apparatus body 460. When the shaft 460 is secured to the delivery apparatus body 460, the longitudinal axis of the shaft 460 may be coaxial with the longitudinal axis of the delivery apparatus body 460. In one aspect, the delivery apparatus body 460 may include a handle 476 integral with the body, or secured to the delivery apparatus body 460. When secured to the delivery apparatus body 460, the handle 476 may be secured to the outer surface of the delivery apparatus body 460. The handle 460 is typically positioned to facilitate the manipulation of the fixation delivery apparatus 400 by a surgeon and may be particularly configured to assist the surgeon in the positioning and/or dispensing of a fixation apparatus 450 within a patient. In another aspect, the delivery apparatus body 460 may include a raised textured surface for increased friction between a user's hands and the fixation delivery apparatus 400. The delivery apparatus body 460 may further cooperate with the actuator 461 to control the movement of the displacement rod 463 within a lumen 464 and/or slot 465 of shaft 461. In another aspect, the delivery apparatus body 460 may define a body cavity 477 to movably receive the actuator 462. The delivery apparatus body 460 may also comprise a tether access portal 478 (FIG. 48C) as a primary, or secondary structure to access and/or sever the tether 475 to facilitate the release of the fixation apparatus 450.

The delivery apparatus body 460 may be formed from a metal, polymeric material or other material that will be recognized by those skilled in the art upon review of the present disclosure. Some exemplary suitable materials recognized by those skilled in the art, include among others, polymers, such as acrylic polymers polyurethane, polycarbonate, engineered plastics; and metals, such as stainless steel and titanium.

The shaft 461 may be an elongate member that could be secured to and distally extend from the delivery apparatus body 460. Although the various embodiments described and illustrated herein typically define a delivery device 400 configuration that extends along a longitudinal axis, it is contemplated that the shaft and/or device components could extend along different projections so as to provide better visualization of the distal portions of the instruments within the surgical site. For example, it is possible that the handle and/or the proximal portion of shaft 461 define a longitudinal axis that is at a different angle than, for example, the distal portion of shaft 461. With this configuration, the handle, in use, may extend from the surgical site at a lateral position from the access incision and provide better visualization of the distal portion of shaft 461 within the surgical site. The shaft 461 may define a lumen 464 and/or slot 465 in at least a distal portion of the shaft 461. The lumen 464 and/or slot 465 may be configured to releasably secure one or more anchors 451, or portions thereof. The lumen 464 and/or slot 465 may be particularly sized and shaped to receive anchors 451 and the associated connecting loops 466 and/or elongate members 454, or portions thereof. The slots 465 may permit various components of the anchors 451 and/or elongate members 454 (including components of anchors 451, bops 466 or elongated members 454 such as retention devices and/or knots 455 or retention members, for example) to extend from the shaft 461 at a distal portion of the shaft 461. In one aspect, the lumen 464 and/or slot 465 may extend from the proximal end to the distal end of the shaft 461. In this configuration, the lumen 464 and/or slot 465 may communicate with the body cavity 477 of the delivery apparatus body 460 at a proximal portion of the shaft 461. In one aspect, the lumen 464 and/or slot 465 may be configured to slidably receive a filament 475. The lumen 464 and/or slot 465 may extend distally to about the distal portion of shaft 461 and may extend to the distal tip of the shaft 461. The lumen 464 and/or slot 465 of the shaft 461 may have a circular, elliptical, hexagonal, pentagonal square, diamond, rectangular, triangular, or other cross sectional shape and may be configured to releasably receive at least a portion of an anchor 451. In one aspect, the cross sectional shape of the lumen 464 and/or slot 465 may correspond to the cross-sectional shape of the anchor 451. In one aspect, the lumen 464 and/or slot 465 of shaft 461 may have a cross-sectional shape suitable to accommodate a displacement rod 463 and at least one anchor 451, or portion thereof. The lumen 464 and/or slot 465 may have the same or a varying configuration along their length.

The distal tip of the shaft 461 may be generally configured to permit the shaft 461 to penetrate the surface of an intervertebral disc or vertebral body using a force exerted by a surgeon on the delivery apparatus. In one aspect, the distal tip of the shaft 461 may include a sharpened tip. In another aspect, the distal tip of the shaft 461 may be chamfered to provide a point which may be sharpened to accommodate insertion through at least a portion of the annulus fibrosus of an intervertebral disc. In one embodiment, the distal tip of the shaft 461 may be cut obliquely to form a sharp leading surface or point for ease of insertion. In one embodiment, the device delivery tool and/or the anchoring element may be of an architectural structure so as to enable the passage of the anchoring element into and/or through bony issue, such as the vertebral bodies. For example, the delivery apparatus may be of sufficient integrity so as to allow a physician to apply a force to the apparatus (e.g., with, or without, a mallet). Alternatively, the distal end of the apparatus and/or anchoring elements could contain a serrated surface.

A sheath 480 may be provided over at least a portion of the length of the shaft 461. The sheath 480 may function to reinforce the shaft 461. In alternative embodiments, the sheath 480 may provide a change in diameter longitudinally along the shaft 461 such that the penetration of the annulus fibrosus may be inhibited as the leading edge of the sheath 480 contacts the annulus. In another aspect, the shaft 461 may include a tissue stop 481 positioned relative to the distal end of the shaft 461 to inhibit the penetration of the annulus fibrosus. Typically, the tissue stop 481 may inhibit the penetration of the annulus fibrosus by providing a region of the shaft 461 with increased surface area. The tissue stop 461 may be typically sized and shaped to efficiently inhibit the penetration of the shaft 461 through the annulus fibrosus while being relatively a traumatic to the tissues which it may contact.

The distal portion of the shaft 461 may include a tactile indicator similar, as an example, to 442 of FIG. 35 to indicate that the distal tip of the shaft 461 has penetrated the intervertebral disc and/or a patch 600 in the case where a reparative fixation apparatus 450 is used in conjunction with a reparative patch 600. The tactile indicator 442 may be integrally formed from the material of the shaft 461 or may be secured to the shaft 461 to provide a tactile indication of proper penetration. Typically, the tactile indicator 442 is provided on an outer surface of the shaft 461, although it is possible for indicator to be provided on other components of the delivery apparatus, such as the sheath 480 and/or the fixations apparatus, such as the anchors 451, as previously described in FIGS. 44A to 44C. The tactile indicator 442 may comprise a series of ribs on the outer surface of the shaft 461 or may comprise an external arm configured to "click" to an extended position when the shaft 461 enters an area of increased diameter or a region of softer material within a patient.

The shaft 461 is typically from about 1 inch to 10 inches long. However, the length of the shaft 461 may vary considerably depending upon the configuration of the fixation apparatus 450 and the fixation delivery apparatus 400, and may particularly depending upon the configuration of the delivery apparatus body 460 to which the shaft 461 may be secured, as well as the technique used to access the intervertebral disc space. The shaft 461 may be made from a wide range of materials having the desired performance characteristics depending, at least in part, on the overall configuration of the fixation delivery apparatus 400 and may include: metals, such as stainless steel, nickel-titanium alloy, and titanium; plastics, such as PTFE, polypropylene, PEEK, polyethylene, and polyurethane, acrylic, polycarbonate, engineering plastics; and/or composites.

The displacement rod 463 may confer a motive force to anchors 451 to displace one or more of the anchors 451 from the lumen 464 and/or slot 465 of the shaft 461. In some embodiments, the displacement rod may also function to withdraw one or more anchors 451 into the lumen 464 and/or slot 465. A portion of the displacement rod 463 may communicate with anchors 451 which may be least partially positioned within the lumen 464 and/or slot 465 of shaft 461. In one aspect, the displacement rod 463 extends through at least a portion of lumen 464 and/or slot 465. The displacement rod 463 may be slidably received within the lumen 464 and/or slot 465, in one aspect, the displacement rod 463 may be of a size and cross-sectional shape to correspond with the size and/or internal shape of the lumen 464 and/or slot 465 in which at least a portion of the displacement rod 463 may be received. Although the characteristic of the displacement rod 463 may be typically of a unitary structure, a displacement rod 463 in accordance with the present invention may include multiple components which act in conjunction with one another to displace the anchors 451 from the shaft 461.

In one embodiment, the displacement rod 463 may define a displacement rod lumen 482. In one aspect, the displacement rod lumen 482 may extend from a proximal portion to a distal portion of the displacement rod 463. The displacement rod lumen 482 may communicate with the body cavity 477 of the delivery apparatus body 460 at a proximal portion of the displacement rod 463. In one aspect, the displacement rod lumen 482 may be configured to receive a tether one, suture, wire, filament or otherwise elongate member. Tether 475 can be formed of multiple materials and/or components to perform its function. In addition, a tether passage 483 may be defined in the wall along the proximal portion of the displacement rod 463. The tether passage 483 may permit a portion of tether 475 to exit a displacement rod lumen 482 at a proximal location or a location distal to the proximal end of the displacement rod lumen 482. The proximal portion of the displacement rod 463 may communicate with actuator 462 to actuate or regulate the movement of the displacement rod 463. In one embodiment, a proximal portion of the displacement rod 463 may be secured to actuator 462. The distal portion of the displacement rod 463 may typically communicate with at least one anchor 451. In one aspect, the distal end of the displacement rod 463 may communicate with the proximal end of anchor 451 to confer a motive force to the anchor 451.

In one exemplary embodiment, the displacement rod 463 can be advanced distally a first distance, sufficient to dispense a first anchor 452. The shaft 461 of the fixation delivery apparatus 400 may be then removed from the first insertion point in the intervertebral disc and inserted into the intervertebral disc at a second insertion point, where the displacement rod 463 may then be advanced distally a second distance to dispense a second anchor 453, and so-on as may be desired for more than two anchors 451. Alternatively, for simultaneous delivery of multiple anchors 451, multiple shafts 461, each including a displacement rod 463, may be provided on the fixation delivery apparatus 400 and may be arranged adjacent to, parallel or substantially parallel along a portion of their lengths. In such configurations, the distance between the shafts 461 may be fixed or inter-operatively adjustable, as desired. When adjustable, the fixation delivery apparatus 400 may include a mechanism, such as a ratchet or displacement mechanism (not shown), or otherwise, as will be recognized by those skilled in the art upon review of the present disclosure, to adjust the distances between the distal portions of the shafts 461. The multiple shaft embodiment may also be additionally configured for sequential displacement of anchors 451.

An actuator 462 may communicate with one or more displacement rods 463 or components thereof to assist a user in advancing the displacement rods 463 along the respective shafts 461. The actuator 462 may be configured as an enlarged body residing at the proximal portion of displacement rod 463 which may be integral with, or secured to the displacement rod 463 to assist a user in advancing displacement rod 463. In this aspect, the distance the displacement rod 463 is pushed to define a first, second, and subsequent distances may be regulated by feel. Alternatively, the distance can be regulated by the architecture of the device. In this aspect, the actuator 462 may cooperate with the delivery apparatus body 460 to control the advancing and/or retracting of the displacement rod 463 within shaft 461, for example as shown in FIG. 48.

Exemplary cooperation of actuator 462 and body 460 is shown in FIG. 48D, where the actuator 462 and delivery apparatus body 460 may cooperate by having a guide 484, such as a pin or projection for example, on one component that is slidably received in a groove 485 or similar guide receiving apparatus of the other component. In one such configuration, the guide 484 may be formed in, or positioned in, the body and/or the body cavity 477 of the delivery apparatus and a groove 485 may be defined by the outer surface of the actuator 462. The groove 485 may extend longitudinally along and circumferentially (or laterally depending upon the actuator's shape) around the actuator 462. The actuator 462 may be slidably positioned in the body cavity 477 of the delivery apparatus body 460 such that the guide 484 is received within the groove 485. The guide 484 extending from the body cavity 477 may be aligned within a groove 485 in the actuator 462 defined on the surface of actuator 462 such that the guide 484 is slidably received within the groove 485 and tracks the groove 485 as the actuator 462 is moved within the body cavity 477. Thus, when the displacement rod 463 is mechanically secured to actuator 462, wherein the movement of the actuator 462 corresponds one to one with the movement of the displacement rod 463, the movement of the displacement rod 463 will correspond to the configuration of the groove 485 on the actuator 462.

Fixation apparatus 450 as described herein may be various constructs utilized as primary reparative treatment of the soft tissues of the spine wherein re-approximation, reinforcement, stabilization, retention, reconstruction, and/or fixation as it would be otherwise achieve may be necessary for prophylactic or therapeutic repair of a defect, aperture, weakened, thinned or infirmed portion of the disc including the annulus fibrosus. In addition, fixation apparatus 450 described herein may be utilized in combination with other treatment constructs 600 such as patches, membranes, scaffolds, barriers, stents (used interchangeably) wherein fixation devices may additionally enable a treatment device 600 to be affixed to the soft tissue, including the annulus fibrosus, of the spine.

Fixation apparatus 450 may contain two or more anchors 451 and one or more elongate members 454 or may contain one or more anchors 451, one or more pledgets 309 and one or more elongate members 454. Furthermore, it is understood that multiple fixation apparatuses 450 may be used together to perform a repair or other procedure. Anchors 451 may generally be configured to maintain a position within an intervertebral disc as forces are applied to the elongate members 454. The one or more elongate members 454 may typically be connected to a first anchor 452 and a second anchor 453, or an anchor 451 and a pledget 309 and may be configured to apply a force between the first anchor 452 and the second anchor 453 or the anchor 451 and the pledget 309, while allowing the components to be drawn toward one another. One of the elongate members 454 may be elongated and may function as a cinch line 470 that is accessible to a surgeon after implantation of the anchors 451 of the fixation apparatus 450. In operation, the elongate members 454 secured between the anchors 451 may allow drawing together disc tissue, such as the annulus, between the anchors 451 when tightened. Accordingly, the fixation apparatus 450 can be placed in tension applying a force to pull together, wholly or partially, the surrounding tissue of the intervertebral disc. The forces may be applied to reapproximate, reinforce, retain, reconstruct or otherwise fix a tear, defect, incision, rent and/or delamination in the intervertebral disc of a patient.

Anchors 451 are generally configured to substantially maintain a desired position within and/or on an intervertebral disc as tension is applied to a band 454 or multiple elongate members 454 securing two or more anchors 451 together. The anchors 451 are typically configured to permit their positioning within and/or on an intervertebral disc using a fixation delivery apparatus 400 and, once positioned and secured, to resist movement within the intervertebral disc. The anchors 451 may be configured as barbed anchors, T-anchors, coiled anchors, darts, conical, elliptical or other configurations as will be recognized by those skilled in the art upon review of the present disclosure. In an exemplary embodiment, a barbed anchor 451 may include an elongated body having at least one barb extending laterally from its longitudinal axis. One end of the elongated body may be particularly configured to penetrate the tissues of an intervertebral disc when the anchor 451 is directed through tissue in a direction along its longitudinal axis. In an exemplary embodiment, an anchor 451 may be connected to an elongated body, band 454, filament, filament loop or eyelet 466 secured at, near or proximate its midpoint such that, after insertion in a longitudinal orientation, the anchor 451 tends to assume a position perpendicular to a line of force exerted by the loops 466 and/or band 454. Loops or eyelets 466 may be a rigid structure or may be a flexible structure defining a loop through which a band 454 may be positioned. In one aspect, the eyelets 466 are integral with or secured to the anchor 451 and are a rigid structure, in another aspect, the eyelets 466 are secured to the anchors 451 and are a flexible structure such as a wire, filament, line, tether or suture, for example, in an exemplary embodiment of a coned anchor, a anchor 451 may include an elongated body in the form of a coil that is formed from flexible and resilient material such that it may be insertable from a lumen 464 and/or slot 465 in a shaft 461 in a substantially straightened or collapsed position and once dispensed from the shaft may resume its original shape. In an alternative exemplary embodiment of a coiled anchor, an anchor 451 may include an open-wound, helically configured rigid element that may be attachably connected to the distal end of the shaft 461. Rotation of the shaft 461 or displacement rod 463 may, for example, advantageously "screw" the coned anchor into tissue of an intervertebral disc.

The anchors 451 may be elongated in shape. The anchors 451 may be integral with or secured to elongate members 454. The elongate members 454 can be secured to the anchors 451 through loops or eyelets 466 which may be integral with or attached to the anchors 451, can be secured to the anchor 451 through one or more band passages extending into or through the anchors 451. In one aspect, a band passage may extend through the anchor 451 perpendicular to or substantially perpendicular to the longitudinal axis of the anchor 451. In other aspect, a band passage may extend through the anchor 451 at other angles relative to the longitudinal axis of the anchor 451. Typically, the anchors 451 will be configured to permit at least partial placement within a lumen 464 and/or slot 465 of the shaft 461 of a fixation delivery apparatus 400. Alternatively, anchor 451 may have a defined cavity or passage to permit anchor 451 to be positioned at least partially over the distal tip of shaft 461 of a fixation delivery apparatus 400. In this alternative embodiment, anchor 451 may have a surface configured to pierce the soft tissue of the intervertebral disc and allow delivery of the anchor 451, or may even have a surface configured to pierce or otherwise become secured to the bony tissue of a vertebral body.

The anchors 451 are typically formed from a substantially biocompatible material of a metallic or polymeric biocompatible material such as, for example, titanium, NiTi alloy, stainless steel, platinum, gold, polyurethane, polycarbonate urethane, polyimide, polyamide, polypropylene, polyethylene, polypropylene, polyester, PET, or PEEK, or could be constructed from a biodegradable/bioabsorbable material such as, for example, collagen, silk, cellulose, polysaccharides, carbohydrates, polyglycolic acid, polylevolactic acid, polydioxanone, or racemic polylactic acid. In addition, the anchors 451 can be constructed of a combination of these materials.

One or more elongate members 454 may interconnect anchors 451 and/or pledgets 309 of fixation apparatus 450. At a first end or region, the elongate members 454 may secured to one or more anchors 451. The elongate members 454 may be tied to the anchors 451, may be mechanically secured to the anchors, may be integral with the anchors 451 or may be otherwise secured to the anchors as will be recognized by those skilled in the art upon review of the present disclosure. In one aspect, one or more anchors 451 may be slidably secured to the elongate members 454 or may be slidably received over the elongate members 454. Typically, one or more elongate members 454 may be tied to one another with one or more retention devices and/or knots 455 that may permit the cinching (or shortening) of the length of elongate members 454 separating two or more of the anchors 451. The retention devices and/or knots 455 in the band are typically movable along one of the elongate members 454 but may be movable along two or more elongate members 454. The retention devices and/or knots 455 are typically positioned between the anchors 451. One suitable family of retention devices and/or knots 455 include, but are not limited to, the Roeder knot 455 and its functional equivalents. These knots may be pre-tied during the assembly of a fixation apparatus 450. Alternatively, a mechanical element slidably received over a first band 454 and secured to the end of another band 454 which is lockable in a desired position over the first band 454 may also be used. In another aspect, two or more anchors 451 may include loops or eyelets 466 which may be comprised of looped elongate members 454 through which a band 454 in the form of a cinchable loop or "lasso" may be passed. The cinching of the elongate members 454, or a bop in a band 454, allows for taking-up slack and drawing towards one another intervertebral disc tissues so as to reapproximate, retain, reinforce or otherwise repair tissues surrounding a disc tear, incision, defect, rent, infirmation or delamination.

As noted previously, the elongate members 454 may be formed from a variety of materials. In one aspect, the elongate members 454 may be formed from sutures or suture materials commonly used by surgeons. The elongate members 454 may be configured to have sufficient strength to re-approximate or draw together tissue surrounding tear, rent, incision, defect or delamination in the annulus fibrosus of a patient. In one aspect, the elongate members 454 may be substantially inelastic to, among other things, permit a surgeon to sufficiently retain or draw the tissue of the intervertebral disc together by cinching the elongate members 454. In another aspect, the elongate members 454 may be formed from an elastic material and configured to be in a stretched position upon implantation in a patient to apply a dosing force to a defect in an annulus fibrosus of a patient. The elasticity of the elongate members 454 may also be selected to substantially correspond to that of the intervertebral disc of the patient. The elongate members 454 may be string-like filaments having a construction and dimension, as disclosed herein and as will be understood by those skilled in the art upon review of the present disclosure, that are amenable to the delivery to and repair of the intervertebral disc, as well as engagement with the fixation apparatus 450. For example, an elongate member 454 may have a width greater than, in some embodiments far greater than, its thickness. When the elongate member 454 is formed from a suture or similar filamentous material, the elongate member 454 may, in some embodiments, have a width:height ratio of 1.25:1. In some embodiments, elongate members 454 may be constructed, wholly or partially, of a mesh tube. Moreover, different segments along the length of the band may have different dimensions and constructions. For example, the elongate member 454 may be constructed of thin material, such as nickel titanium alloy or stainless steel wire, close to the anchor, while the middle portion that may span the aperture may comprise a much wider band made of optionally softer material and/or a material that has a surface texture or porosity conducive to fibrotic ingrowth and repair or may be otherwise configured as disclosed elsewhere in the present disclosure and/or as will be understood by those skilled in the art upon review of the present disclosure.

In another embodiment, elongate members 454 and/or cinch line 470 may incorporate a retaining element (not shown) so as to temporarily retain or otherwise constrain 454 and/or 470 along the delivery apparatus so as to facilitate the management of the members by the physician prior to the physician's intent to delivery and/or deploy the treatment construct 450. These retaining elements could act as collets in the proximal region and/or the distal region of the delivery apparatus.

As noted herein, a patch-like device 600 in the form of a patch, membrane, scaffold, barrier, stent, sealing device, reinforcement, plug, occlusion device, or otherwise, may be provided for repair, reconstruction, reinforcement, re-approximation, or otherwise treatment of apertures, weakened, thinned or otherwise infirmed tissue such as tears, rents, defects, delaminations and/or incisions within an intervertebral disc. In one embodiment, an apparatus 600 may used in combination with other reparative apparatuses, such as fixation apparatus 450, for the re-approximating, reinforcing, or otherwise repairing tissues. Particularly, it is conceivable that some natural and surgically made defects may be relatively large and accordingly, reapproximation of tissues surrounding an aperture is not actually or practically possible without the introduction of additional material, A device 600 in accordance with the present inventions may provide the material for positioning in and around a defect to bridge some; all or a portion of the defect to facilitate a medically appropriate stabilization of the tissues. The patch 600 may function to reinforce the portion of an intervertebral disc through which a fixation apparatus 450 is implanted. And, patch 600 may be used to bridge tissues of a defect and may also act as a scaffold for tissue ingrowth.

The patch 600 may be configured as a membrane, webbing, mesh, scaffolding, barrier or otherwise as will be recognized by those skilled in the art upon review of the present disclosure. The patch 600 may be of a rigid construction, may be flaccid, or may of an intermediate rigidity. The patch may also have configurations that include multiple rigidities associated with different portions of the patch as may be necessary to address alternative defect pathologies and/or delivery and deployment considerations. The patch 600 may be of a solid material, webbing or otherwise, or may comprise one or more mounting cavities within the patch. In one aspect, the mounting cavities or receptacles may cooperate with a patch insertion tool 500 to assist in the placement of the patch 600. In one aspect, the patch 600 defines a single patch mounting cavity extending along its length and, accordingly, may be configured as a sleeve or a sock. In alternative embodiments, the patch 600 may define a plurality of mounting cavities which are configured to receive one or more projections, brackets, arms or otherwise mounting or retaining elements 504 or 506 of the patch insertion tool 500.

Patches 600 can be formed from a variety of materials or combinations of materials known to those skilled in the art. These materials are typically biocompatible. The patch 600 may be configured from natural or synthetic materials including, but not limited to, various polymers, metals and biological tissues, for example, in one aspect, the patch 600 may be formed from autograft para-spinal fascial tissue, xenograft, allograft, or other natural or processed collagenous materials. The material could also be polymeric such as a Dacron (polyester, or PET), polypropylene, polyethylene, polymethylmethacrylate, PTFE, CPTFE, Surlyn, or PEBAX material, for example. In some exemplary embodiments, the patch 600 could comprise biocompatible metal, such as NiTi alloy, chromium cobalt alloy, titanium, stainless steel or the like. Webbing materials could also be woven or non-woven, or braided. Patches may also be partially or wholly constructed from biodegradeable or bioabsorbable materials, it is also possible for the patches to be constructed, partially or wholly, from previously herein described materials, as well as to comprise of one or more of these materials, as may be generally understood by those skilled in the art. Patches may also comprise bioactive materials and may also be for mechanical, biochemical and medicinal purposes. The patch 600 may also be drug eluting, as known in the medical implant arts. Furthermore, in one exemplary embodiment, the material of the patch 600 may contain a structure sufficient to readily permit the passage of the distal portion of a shaft 461 of a fixation delivery apparatus 400 with little or no resistance while providing resistance to the dislodging of an anchor 451 dispensed within or through patch 600.

Patch delivery tools 500 in accordance with the present inventions are generally configured to position one or more patches 200 at positions in proximity, adjacent or within an intervertebral disk 200 of a patient. Typically, patch delivery tools 500 are configured to releasably secure devices 600 on or about the distal portions of delivery tools 500 such that, after a surgeon has secured at least a portion of the patch 600 to the intervertebral disk 200 of a patient, the patch 600 may be released from the patch delivery tool 500 and the patch delivery tool 500 may be removed from the patient.

FIGS. 48A-48D illustrate exemplary embodiments of a fixation delivery apparatus 400 in accordance with aspects of the present inventions. As particularly illustrated in FIGS. 48A-48D, the fixation delivery apparatus 400 may include a delivery apparatus body 460, shaft 461, actuator 462, and a displacement rod 463. The illustrated fixation delivery apparatus 400 may be configured to accommodate and sequentially deploy two or more anchors 451 of one or more fixation apparatuses 450. The illustrated fixation delivery apparatus may include a mechanism for regulating the advancing of displacement rod 463 for release of the two or more anchors 451 of a fixation apparatus 450 from the shaft 461. The embodiments of the fixation delivery apparatus 400 illustrated in FIGS. 48A-48D are for exemplary purposes only. Any description of these particular figures not written in the permissive form is merely to explain the nature and relationship of the particular components of the illustrated embodiments and is in no way intended to limit the disclosure to the particularly illustrated components.

The delivery apparatus body 460 may include a body cavity 477 within at least a portion of the delivery apparatus body 460. The delivery apparatus body 460 may be elongated and include a handle 476 at the proximal portion of the delivery apparatus body 460. The shaft 461 may be secured to the distal portion of the delivery apparatus body 460. A guide, pin, or projection 484 may extend into the body cavity 477 and may be received by slot or groove 485 of actuator 462 (see FIG. 48O).

The shaft 461 extends from delivery apparatus body 460 and may include a sheath 480. The shaft 461 may comprise a lumen 464 which may extend from the proximal portion to the distal portion of shaft 461. The lumen 464 is illustrated with a circular cross-sectional shape that may be suitable to accommodate the circular cross-sectional shape of the illustrated anchors 451 and to slidably receive displacement rod 463, although, alternative cross-sectional configurations could be employed to accomplish the same function. The lumen 464 of the shaft 461 may be in communication with body cavity 477 of the delivery apparatus body 460 and may permit the at least one displacement rod 463 and/or its components to be slidably received within shaft 461. As illustrated, the distal tip of the shaft 461 may be cut obliquely to form a sharp leading surface or point for ease of insertion into an intervertebral disc. The shaft 461 may include a slot 465 along its side to accommodate portions of fixation apparatus 450, such as elongate members 454, 466 and anchors 451, and knots 455 that may not reside completely within lumen 464.

The actuator 462 and/or the displacement rod 463 may be movably received within a portion of body cavity 477. As illustrated, the actuator 462 may function as a handle to interface with a user and extends proximally from the proximal end of the delivery apparatus body 460. A distal portion of the actuator 462 may be secured to a proximal portion of displacement rod 463. The displacement rod 463 is particularly shown as secured to the distal portion of the actuator 462. The actuator 462 may configured to advance displacement rod 463 in a 1 to 1 ratio. A displacement spring 486 may be positioned within the body cavity 477 between the distal portion of body cavity 477 and the distal portion of actuator 462, in the example shown. The displacement spring 486 may bias the illustrated actuator 462 and displacement rod 463 in a proximal direction. A groove 485 on actuator 462 may be configured to cooperate with the projection 484 of the delivery apparatus body 460. Those skilled in the art would realize this is an exemplary configuration and, for example, groove 485 could as easily be located on the apparatus body 460 and the pin 484 could reside on the actuator 462.

The displacement rod 463 may generally be configured to apply a motive force to dispense T-anchors 451 from the distal end of the lumen 464 and/or slot 465. The displacement rod, as shown, is an elongated structure having a substantially circular cross-sectional shape and may comprise a displacement rod lumen 482 extending along at least a portion of the length of the displacement rod 463. At least a distal portion of the displacement rod 463 may be slidably received within the lumen 464 of the shaft 461. The movement of the displacement rod 463 within lumen 464 may be modulated by actuator 462. As particularly illustrated, the actuator 462 is configured to advance the displacement rod 463 in a 1 to 1 ratio. A tether passage 483 may be defined in a proximal portion of the displacement rod 463. The tether passage 483 may permit a portion of tether 475 to extend from the displacement rod lumen 482 to be positioned within body cavity 477 of the delivery apparatus body 460. Although tether 475 here is used as a general term, those skilled in the art would recognize that tether 475 could be a wire, string, suture band or other elongate member to satisfy the same purpose.

The tether 475 may be provided to secure an anchor 451 prior to deployment. The proximal portion of tether 475 may be secured to the actuator 462, displacement rod 463, and/or delivery apparatus body 460. As illustrated, the tether 475 is secured to a portion of the actuator 462. More particularly, the distal portion of the actuator 462 defines a flange 487 about which tether 475 is looped around the flange 487 to secure the proximal end of the tether to the actuator 462. Advantageously, the distal end of the actuator 462 may have a tether severing cavity 488 which includes a lip 489. In addition, a tether severing element 490 may be provided in the distal portion of the body cavity 477. The tether severing element 490 may include a cutting edge 491. The tether severing cavity 488 and the tether severing element 490 may cooperate to sever the tether 475 and thus allow anchor 451 to be released from lumen 464 and/or slot 465. As illustrated, the tether 475 is cut by positioning the actuator 462 distally with the passage 483 and the hp 489 of tether severing cavity 488 overlapping the longitudinal axis of the cutting edge 491 of the tether severing element 490 to press the tether 475 against the cutting edge 491. Alternatively, if an automated cutting feature is not used, a tether access portal 478 may be provided through the delivery apparatus body 460 to permit access to the tether 475 with other cutting devices such as scissors or scalpels for example. Although tether 475 is drawn as a single element residing within lumen 464 and connected to anchor 451, an alternative embodiment may include tether 475 as a "looped" element wherein an end of the tether is passed through a receiving portion of anchor 451 and when, for example, a single filament of the tether 475 is cut the filament passes distally, through the anchor 451, and is removed with the delivery apparatus 400. This alternative embodiment may allow the physician to practice the repair with one less step (i.e., the excising of the trailing tether line 475 attached to anchor 451).

A sheath 480 may be secured about the outer surface of shaft 461. The sheath 480 may extend from the delivery apparatus body 460 to a location proximal to the distal end of shaft 461. A tissue stop 481 may be secured to the distal portion of shaft 461. As illustrated, the tissue stop 481 may also be particularly secured on sheath 480. The shaft 461 may further define a slot 465. Slot 465 may be configured to slidably receive components of fixation apparatus 450 as the components slide along the longitudinal axis of the shaft 461. As illustrated in FIG. 48B, eyelets 466 comprised of looped elongate members 454 or filaments extend from the slot 465 and bops 110 are interconnected by an adjustable elongate member 454, such as a cinch line 470 as shown.

Figure 48A:
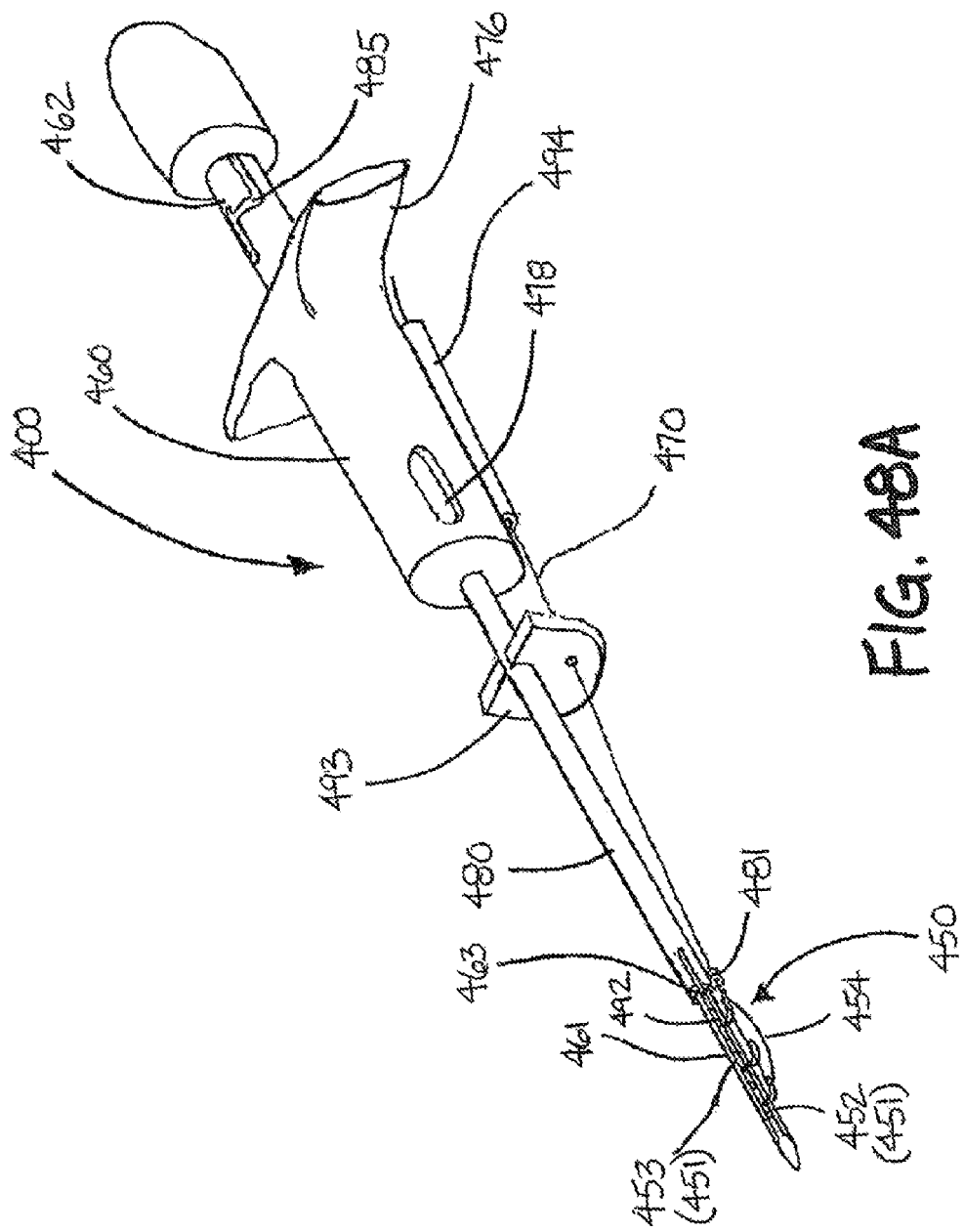

The illustrated fixation apparatus 450 include three anchors 451 in FIG. 48A and two anchors 451 in FIG. 48B. The anchors 451 are sequentially at least partially positioned in a lumen 464 of shaft 461. As illustrated, the anchors 451 are configured as T-anchors, although those skilled in the art would recognize other anchor configurations are possible to achieve the same effect. Each anchor 451 defines a transverse passage which receives a portion of a connecting member 454. As illustrated, elongate connecting member 454 comprises a filament bop or eyelet 466. As illustrated, filament bops or eyelets 466 are flexible lines formed into loops which are secured within the transverse passages of the anchors by enlarged knotted portions. The filament bops 466 extend through the slot 465 from first anchor 452, the second anchor 453, and, when present, the third anchor 492, and are interconnected by an additional elongate band 454 formed into a loop which passes through the passages defined by each of the eyelets 466. The band 454 connecting the implanted anchors 451 with their eyelets 466 includes a moveable knot 455 which permits foreshortening of band 454. With foreshortening of band 454, a trailing end of cinch line 470 may become longer as slack is removed from the loop of band 454. A portion of band 454 may have sufficient length to extend outside the patient and form a cinch line 470 which is accessible by a surgeon after implantation. A tab 493 may be secured to the cinch line 470 to more easily facilitate the locating and/or manipulating of the cinch line 470. The tab 493 may be removably securable to the shaft 461, as illustrated, or the delivery apparatus body 460. Tab 493 may also be advantageously coupled (not shown) to body 460, displacement rod 463, and/or actuator 462 so as to limit the ability to slideable dispense anchors 451 until and/or when the surgeon desires; at which time, removal of tab 493 may allow dispensing of one or more anchors 451. In addition, a cinch line holder 494 may be provided on the delivery apparatus body 460, tab 493, shaft 461, or a combination of components of apparatus 400 so as to allow for line management during the delivery and deployment of fixation apparatus 450. Holder 494 may include features that resistively allow controlled dispensing of line 470 during anchor deployment to assist in the management of the cinch line 470 during a surgical procedure. Resistance on line 470 could be accomplished by the selective sizing of holder 494 with respect to line 470. Alternatively, knotted elements (not shown) along line 470 could be received within holder 494 that comprises mechanical interlocking components (not shown) so as to resistively impede and provide controlled dispensing of line 470. Alternatively, a collet-type arrangement could be applied to the distal portion of apparatus 400 so as to allow for resistive-like action in the management of the delivery of fixation apparatus 450. These are intended to be illustrative examples of causing resistance and control of line 470 elongate members 454 and apparatus 450, and should not be interpreted as being limiting as those skilled in the art would recognize a variety of ways to accomplish a similar effect.

As illustrated in FIG. 48D, a mechanism for regulating movement of displacement rod 463 may generally include a guide 484 extending into body cavity 477 and a groove 485 defined on the surface of the actuator 462. The guide 484 on the delivery apparatus body 460 cooperates with the groove 485 on the actuator 462 and may regulate at least the axial movement of the displacement rod 463.

The guide, pin or projection 484 may be slidably received in groove 485 of the actuator 462. The guide 484 may be secured to or within the body cavity 477 of the delivery apparatus body 460. As illustrated, in FIG. 48D, guide 484 is positioned within a guide cavity 495 and includes a guide spring 496 biasing the guide 484 outward into the body cavity 477. The illustrated guide 484 includes a flange which abuts a cavity flange on a portion of the guide cavity 495 to prevent the guide 484 from being displaced from the guide cavity 495. Note that guide 484, spring 496, body 460 and their cooperative relationship with groove 485 may also advantageously allow for tactile and/or auditory feedback to the surgeon during delivery of anchors as guide 484 passes along groove 485. In alternative embodiments, the guide 484 could be otherwise rigidly or movably secured within the body cavity 477 without departing from the scope of this aspect of the present inventions.

As illustrated in FIG. 48D, the groove 485 may extend along the outer surface of the actuator 462. The groove 485 may include longitudinally extending portions 485*a* and radial extending portions 485*b*. The longitudinally extending portions 485*a* may allow for longitudinal advancing the actuator 462 and associated displacement rod 463. The radially extending portions 485*b* may function to stop the longitudinal advancing of the actuator 462 and associated displacement rod 463. The groove 485 may also include a step 485*c* wherein the depth of the groove 485 increases. When the guide 484 is biased within the groove 485 for example, the step 485*c* could prevent, for example, further proximal withdrawal of the actuator 462 and/or the displacement rod 463 from the body cavity 477 beyond the point where the guide 484 contacts the step 485*c*.

Figure 48C:
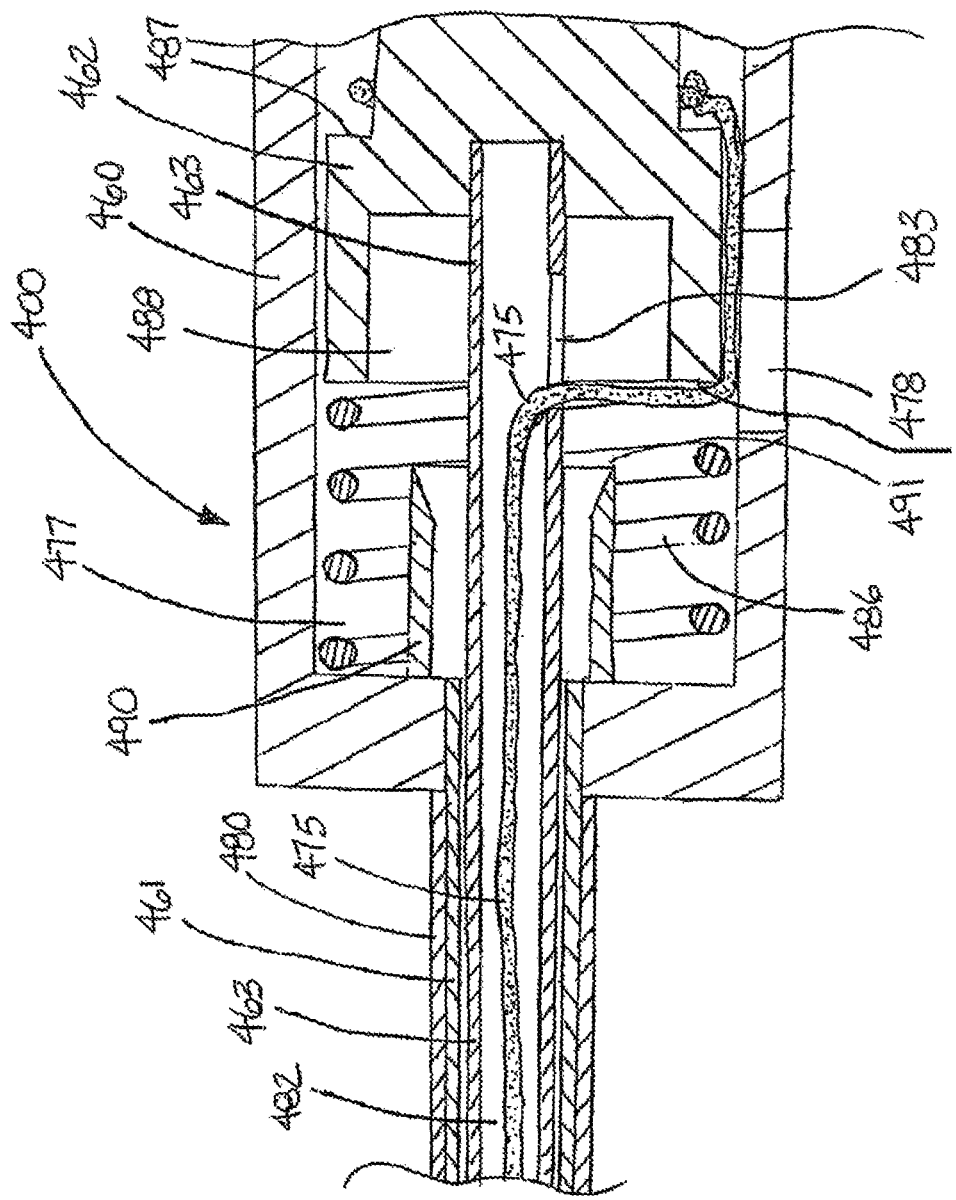

In operation, the guide 484 may be initially positioned within a safety lock position 498 where the displacement rod 463 may be in a most proximal position with respect to shaft 461 and wherein the actuator 462 may be biased in a proximal position with respect to shaft 461 and/or by the displacement spring 486, as seen in FIG. 48C. The tip of the shaft 461 of the fixation delivery apparatus 400 may be positioned adjacent to a first location for insertion of the first anchor 452. The tip of the shaft 461 is inserted at the first location and the shaft 461 is advanced into the intervertebral disc. In the illustrated embodiment, the motive force is typically applied to the delivery apparatus body 460 by the surgeon. The shaft 461 may be advanced until the distal aspect of the tissue stop 481 contacts an outer surface of the intervertebral disc or the tip of the shaft 461 has otherwise been determined to be at the desired location within the intervertebral disc. The surgeon may note that the shaft 461 has been properly advanced by the resistance to further movement resulting from the stop 481 or sheath 480 contacting the outer surface of the intervertebral disc. Once properly positioned, the displacement rod 463 may be advanced relative to the delivery apparatus body 460 by the surgeon to displace the first anchor 452 from the tip of the shaft 461 into the intervertebral disc. To do this, the surgeon may distally displace the actuator 462 relative to the body cavity 477 to release the guide 484 from the safety lock position 498. The actuator may then be rotated approximately 90 degrees sliding the guide 484 through a first radially extending portion 485*b* of the groove 485. The surgeon may then advance the actuator 462 distally within the cavity 477 which may slide the guide 484 through the first longitudinal extending portion 485*a* of groove 485. This movement of the actuator may displace the first anchor 452 from the lumen 464 and/or slot 465 of shaft 461 by distally advancing the displacement rod 463 a first distance. The first distance is selected to be sufficient to displace the first anchor 452, but to be insufficient to eject the second anchor 453. As the guide 484 reaches the proximal portion of the first longitudinal extending portion 485*a* of groove 485, the guide 484 may pass over step 485*c* and extend further into groove 485 due to forces exerted on the guide 484 by guide spring 52. As seen in FIG. 48D, the first longitudinal extending portion 485*a* of groove 485 may extend proximally beyond the second radially extending portion 485*b* of groove 485 to assure proper displacement of the first anchor 452 from shaft 461. A surgeon would have to apply sufficient force to the actuator 462 to slide the guide 484 to the most proximal portion of the first longitudinal extending portion 485*a* of groove 485. Once the surgeon removes the distally extending force on the actuator, the actuator is forced in a proximal direction by the displacement spring 486 until guide 484 contacts the step 485*c* preventing further proximal movement of the actuator 462 relative to delivery apparatus body 460. This proximal motion of the actuator 462 may function to draw the tethered second anchor 453 proximally in lumen 464 and/or slot 465 of shaft 461 dispensing the first anchor 452 from lumen 464. After the first anchor 452 has been positioned at the first location within the intervertebral disc, the shaft 461 of the fixation delivery apparatus 400 may be withdrawn from the first location. The first anchor 452 is left secured within the intervertebral disc.

The second anchor 453 and fixation delivery apparatus 400 may remain secured to the first anchor 452 connecting bands 454 such as 454, 466 and/or trailing cinch line 470 of elongate bands, as shown in FIG. 48B. A loop in elongate member 454 may be configured to be at least long enough to extend from a first anchor location to a second anchor location prior to cinching band 454. The tip of shaft 461 of the fixation delivery apparatus 400 may be then repositioned adjacent to a second location on the intervertebral disc for insertion of the second anchor 453. The tip of the shaft 461 is inserted at the second location and the shaft 461 is again advanced into the intervertebral disc. The shaft 461 may again be advanced until the distal aspect of the tissue stop 481 or sheath 480 contacts an outer surface of the intervertebral disc or the tip of the shaft 461 has otherwise been determined to be at the desired location within the intervertebral disc. Once properly positioned, the displacement rod 463 may be advanced relative to the delivery apparatus body 460 by the surgeon to displace the second anchor 453 from the tip of the shaft 461 into the intervertebral disc. To do this, the surgeon may rotate the actuator approximately 90 degrees by sliding the guide 484 through a second radially extending portion 485*b* of the groove 485. The surgeon may then advance the actuator 462 distally within cavity 477 which may slide the guide 484 through the second longitudinal extending portion 485*a* of groove 485. The movement of the actuator may displace the second anchor 453 from the distal portion of shaft 461 by distally advancing the displacement rod 463 a second distance. The second distance being selected to be sufficient to displace the second anchor 453 from the lumen 464 and/or slot 465 of the shaft 461 into the intervertebral disc. The surgeon then removes the shaft 461 from the intervertebral disc leaving the second anchor 453 at the second anchor location within the intervertebral disc.

After insertion of at least the first anchor 452 and the second anchor 453, the loop of elongate member 454 is shortened by hand or by pushing on, for example, a slip knot 455 with a knot-pusher or similar device to apply a force to the knot to slide the knot along the band 454 and reduce the size of the loop which tends to draw towards one another the anchors 451 and adjacent tissues surrounding an annular defect. Typically, the tightening is managed using a cinch line 470 that can be manipulated by the surgeon. Once tightened, the excess cinch line 470 can be cut.

When inserting the first anchor 452 and second anchor 453 in series, the elongate member 454 may have a tendency to lie across or along the surface of the annulus fibrosus during the anchor insertion process. For instance, after the first anchor 452 has been inserted, since the elongate member 454 is connected to the first anchor 452 via its respective filament loop 466, a portion of the elongate member 454 may be drawn toward and along the surface of the annulus fibrosus. The elongate member 454 may thus interfere with movement of the tool 400 and/or the ease of desired placement of the second anchor 453 therefrom. Accordingly, it may be desirable to provide a means for releasably restraining the elongate member 454 from release from the tool 400 until after or during the process of insertion of the second anchor 453.

FIG. 48 illustrates two additional exemplary means for management and/or retention of the elongate member 454. In one embodiment, a tether 471 (shown in phantom in FIG. 48E) is looped about the elongate member 454, between its respective connections to the filament loops 466 of the first anchor 452 and the second anchor 453. The tether 471 is either secured to the tool 400 or retained in some other manner by the tool operator to prevent complete release of the elongate member 454 from the tool 400, until at least during or after the insertion of the second anchor 453. Alternatively, one or more portions of the elongate member may be releasably secured to the tool 400 by an elastic band 473 (shown in phantom in FIG. 48E) or some other suitable releasable means. In this instance, the band retains one or more portions of the elongate member 454 on the tool 400 (such as against the sheath 480 thereof. While the band 473 has sufficient retaining power to hold the elongate member 454 onto the tool 400, it also is constructed so as to allow the elongate member to slip therefrom during or after insertion of the second anchor 453. The band 473 may be formed, in whole or in part, from an elastic material that stretches to permit release of the elongate member 454 from the tool 400. These examples are intended to illustrate additional exemplary devices and methods to achieve management of the elongate member 454 during deployment and insertion of its associated tissue anchors 451, and should not be interpreted as being limiting embodiments, as those skilled in the art would recognize a variety of ways to accomplish a similar effect.

It is contemplated that one or more fixation apparatuses 450 (and their respective delivery apparatuses 400) as illustratively described and shown in FIGS. 48A-48E could be used to effect annular repairs, but without the use of patch-like device 600 (and its respective delivery tool 500). It is possible that some annular defects may be readily repaired without the use of a patch-like device 600 and could advantageously be mended or otherwise repaired, partially or wholly, through tissue approximation. Exemplary of a re-approximation without a patch-like device could be performed with one or more repair apparatuses 450 comprising anchors 451, loops 466, bands 454, retainers 455 and tethers 470, for example. In this alternative embodiment, tissues surrounding an annular defect may be advantageously drawn towards one another to effect a repair, as previously described with respect to, for example, FIGS. 7-13. One, two or more fixation apparatuses 450 may be used to accomplish the repair. These apparatuses may be positioned along an annular aperture or may be conveniently placed in a non-lineal fashion, such as a cruciate across the annular rent. It is also possible, given alternative presentations of annular defects, that a re-approximation could also be performed that is similar to that of FIG. 6 wherein fixation apparatuses 450 may be used in conjunction with a filler material 716 and without patch 600 present. In this alternative embodiment, fill material 716 may be directly affixed, or otherwise secured, to portions of one or more fixation devices 450 so as to retain filler material 716 in proximity of the annular defect.

Furthermore, it is conceivable that, in order to repair an intervertebral disc annulus that is damaged, degenerated or otherwise infirmed with defects of a circumferential and/or delaminated physiology, one might employ one or more fixation devices 450 so as to draw together or otherwise radially stabilize or retain tissues in a reparative fashion. In this alternative embodiment (which may be additional or further described in co-pending application Ser. No. 11/120,750) there may not be an annular aperture readily apparent in the intervertebral disc, but rather the degenerative pathology may be recognized as high intensity zones under radiological examination, such as for example MRI and CT scans. It is also possible, given this type of repair, that the anchors 451 of apparatus 450 may be placed at spatially far greater distances apart (prior to foreshortening band 454) than may be needed for repair of annular apertures. For example, it is conceivable to repair some large posterior protrusions and/or delaminations of an annulus that anchors 451 could be deployed as far apart as the total posterior, or more, of the annulus so as to reparatively restore or otherwise stabilize the incompetent annular tissue.

Figure 57A:
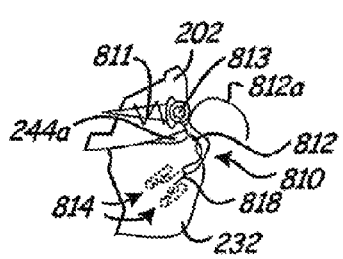
Figure 57B:
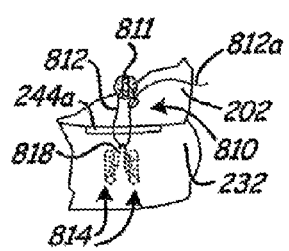
Figure 58:
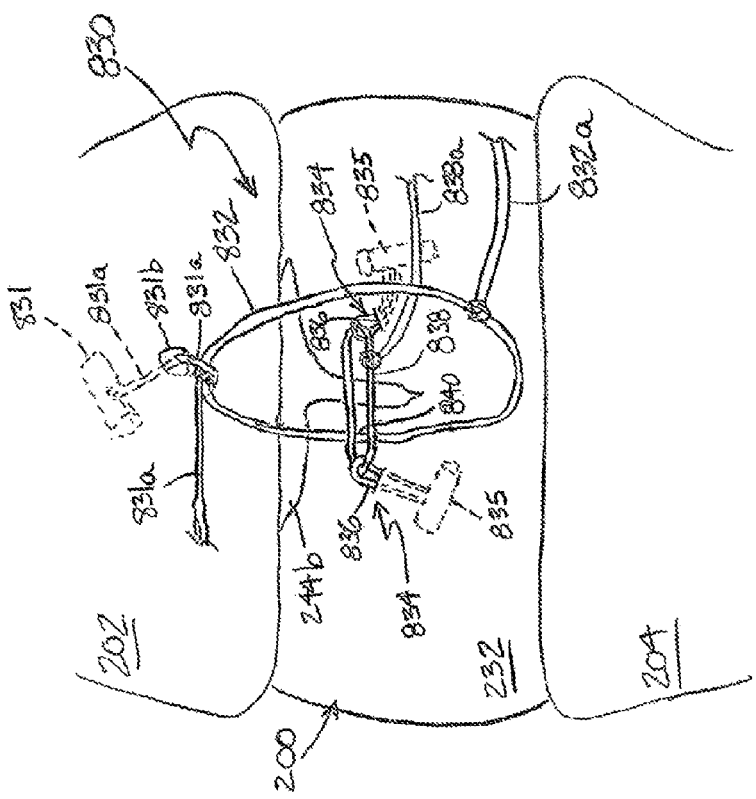
Figure 60:
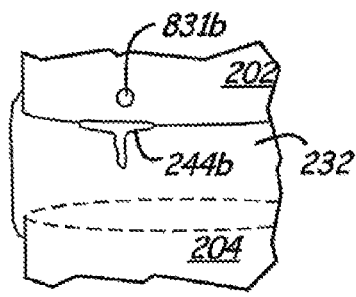

As noted herein, the anchors for annulus fibrosus tissue fixation apparatus may be disposed in annulus fibrosus tissue of a disc, in the disc cavity for the nucleus polposus of the disc, through the entire disc itself, or in or through Sharpey's Fibers or in a vertebral body. A fixation apparatus may include one or more anchors in any one or more of any of these locations to facilitate the repair of a defect in the wall of the annulus fibrosus of a disc. Several exemplary embodiments of fixation apparatus for making such a repair are illustrated in FIGS. 49-69. These fixation apparatus embodiments described and illustrated may be particularly useful when the defect is in proximity of a vertebra (as seen in FIG. 49) or when a portion of the defect is in proximity of a vertebra (as seen in FIG. 58), although, they may be also useful even when the defect is not adjacent to a vertebra, and therefor the description should not be construed as to limit their use. In these embodiments, at least one anchor is disposed in a vertebra, and this, in some cases may provide a beneficial and stable fixation for the repair being made.

FIG. 49 is a lateral view, and FIG. 50 is a posterior view, both showing a superior vertebral body 202, inferior vertebral body 204 and an intervertebral disc 200 therebetween. The disc 200 has a defect or aperture 244a in its annulus fibrosus 232. In this instance, the aperture 244a is in proximity of the vertebral body 202, and may or may not be within the Sharpey's Fibers between the annulus fibrosus 232 and vertebral body 202. A fixation apparatus 810 is shown in FIG. 49 to aid in closing the aperture 244a. The fixation apparatus 810 includes at least one anchor in the vertebral body 202 which, in cooperation with a fixation device having a connection between one or more anchors in the annular fibrosus 232, can serve to draw annular fibrosus tissue toward the vertebral body 202 in order to, partially or wholly, close the aperture 244a.

FIGS. 49 and 50 illustrate the fixation apparatus 810 as affixed in place on the vertebral body 202 and annulus fibrosus 232, prior to repair of the aperture 244a. The fixation apparatus 810 includes a suitable bone anchor 811, illustrated in FIGS. 49 and 50 as a bone screw. A shortenable elongate member 812 is slidably connected to the bone anchor 811, as through eyelet 813 thereon. In one embodiment, a length of the elongate member 812 is shortenable by means a moveable knot such as a Roeder knot or its functional equivalent. The length of the elongate member 812 can be shortened by puffing on its associated tether 812a to, for example, shorten the loop defined by the elongate member 812. Together, the bone anchor 811 and elongate member 812 define a bone anchor assembly (although the bone anchor assembly is shown with only one bone anchor connected to the elongate member, additional bone anchors and/or elongate members may be provided as an assembly).

As shown, one or more soft tissue anchors 814 may be affixed into or through the annulus fibrosus 232. In the illustrated embodiment, each soft tissue anchor 814 has a T-anchor 815 with an elongate element 816 attached thereto. A link, connecting element or coupling 818 slidably connects the elongate elements 816 of each anchor 814. In one embodiment, a length of the connecting element 818 is shortenable by means of a moveable knot such as a Roeder knot, or its functional equivalent. The length of the connecting element 818 can be shortened by pulling on its associated tether 818a to, for example, shorten the loop defined by connecting element 818. Together, the soft tissue anchors 814 and connecting element 818 define a soft tissue anchor assembly (although the soft tissue anchor assembly is shown with two anchors connected to the connecting element, additional soft tissue anchors and/or connecting elements may be provided as an assembly).

In FIGS. 49 and 50, the fixation apparatus 810 is shown assembled but not yet activated for repair of the aperture 244a. In this assembled configuration, the connecting element 818 is disposed over a portion of the elongate member 812 at 820. Accordingly, once the fixation apparatus 810 is assembled as illustrated, the portion 820 of the elongate member 812 is slidably restrained by the soft tissue anchor assembly (incorporating, 815, 816, and 818).

FIG. 51 illustrates activation of the fixation apparatus 810 to facilitate defect repair. The connecting element 818 has been shortened by pulling on its associated tether 818a (which is shown in dotted lines after having been cut away). Elongate member 812 has likewise been shortened by pulling on its associated tether 812a (which is also shown in dotted lines to illustrate it being cut away). The soft tissue anchors 814 and their associated connecting element 818 provide an effective anchor assembly for the affixing elongate member 812 in the annulus fibrosus 232. Since the elongate member 812 is also anchored by the bone anchor 811, the shortening of the length of the elongate member 812 may be utilized to draw tissue of the annulus fibrosus 232 toward, at least partially, the vertebral body 202, thereby facilitating repair of aperture 244a in the annulus fibrosus 232.

Figure 53:
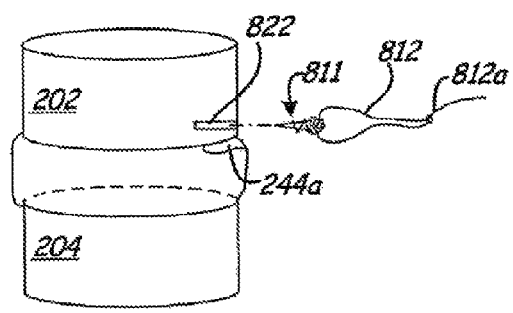
Figure 53A:
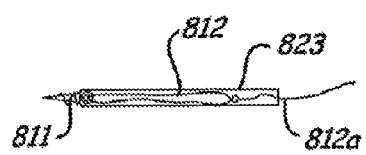

FIGS. 52-57B illustrate, in one embodiment, the placement and activation of fixation apparatus 810 proximate a defect in the wall of a disc's annulus fibrosus. A bone drill 821 may be used to form a bore 822 in the superior vertebral body 202, after which (if needed), the bone anchor 811 is inserted into the bore 822, as illustrated in FIG. 53. FIG. 53A illustrates one means for introducing the bone anchor 811 into the bore 822, such as an elongate element that is formed from a hollow tube or shaft 823 rotatably coupled to the bone anchor 811 (e.g., a bone screw). The shortenable elongate member 812 and its associated tether 812a are received within the tube 823, or captured within or alongside the tube 823, to prevent tangling thereof.

Figure 54:
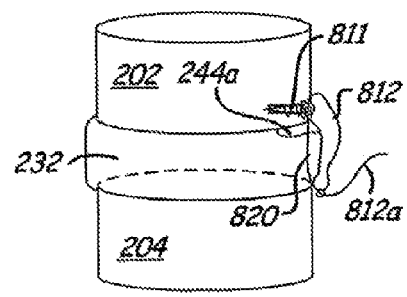

FIG. 54 illustrates the aligning of at least a portion 820 of the shortenable elongate element 812 along the annulus fibrosus 232, in proximity of a portion of the annulus to be repaired.

Figure 55:
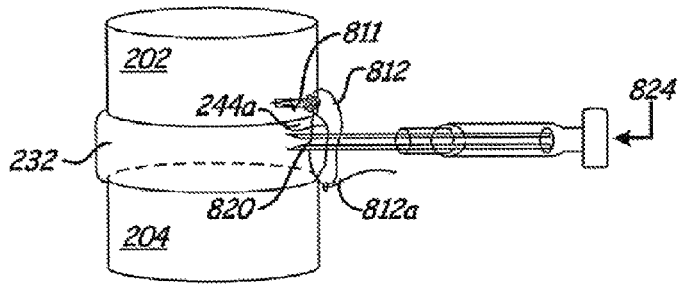
Figure 55A:
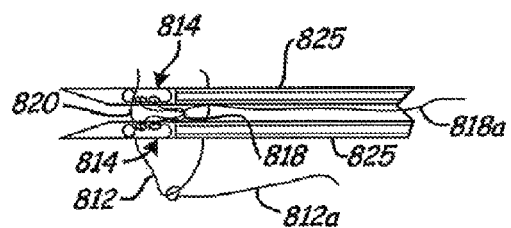

FIG. 55 illustrates one means for introducing soft tissue anchors 814 into the annulus fibrosus 232. In the embodiment illustrated (in FIGS. 55 and 55A) a tissue anchor delivery device 824 has a hollow needle or cannula 825 for slidably receiving each one of the tissue anchors 814 therein. The device 824 may be similar in form and function to the delivery tool 708 illustrated in FIG. 11, and otherwise disclosed herein. It is also contemplated that the anchor delivery tool can deliver the anchors 814 in series to the desired locations into and/or through the annulus fibrosus 232. One means for achieving retention of the elongate element 812 relative to the connecting element 818 is to dispose one soft tissue anchor 814 on one side of the portion 820 of the shortenable elongate member 812, while disposing the other soft tissue anchor 814 on the other side thereof. This configuration is illustrated by the association of elements during tissue anchor delivery shown in FIG. 55A. As such, the connecting element 818 between soft tissue anchors 814 extends across, or spans, the portion 820 of the elongate member 812.

Figure 56:
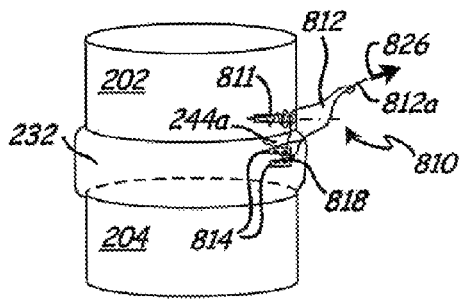

FIG. 56 illustrates the fixation apparatus 810 as being delivered to the soft tissue of the disc and vertebral body 202, with the tether 812a of the shortenable elongate member 812 being pulled in direction of arrow 826 (in FIG. 56, the associated tether 818a of the link or coupling or connecting element 818 has already been pulled to shorten the length of connecting element 818, and cut away). Once the length of the shortenable elongate member 812 has been shortened to an extent sufficient to cause the connecting element 818 for the soft tissue anchors 814 to be drawn in tension (pulling the tissue anchors 814 toward one another), this may serve to pull, wholly or partially, annulus fibrosus tissue together. In addition, shortening the elongate member 812 pulls the connecting element 818 (and its associated soft tissue anchors 814) toward the bone screw 811, which may also serve to pull, wholly or partially, annulus fibrosus tissue toward the bone screw 811 in the vertebral body 202. In doing so, the aperture 244a is closed, repaired, or otherwise drawn to a smaller configuration. An exemplary orientation and configuration for the activated fixation apparatus 810, with the lengths of both the connecting element 818 and elongate member 812 shortened, is illustrated in FIG. 57, which shows fixation apparatus 810 in both a lateral view (FIG. 57A) and a posterior view (FIG. 57B).

An alternative embodiment of a fixation apparatus having at least one bone anchor is illustrated in FIGS. 58-64. In this instance, the disc 200 has a defect or aperture 244b in its annulus fibrosus 232. In this instance, a portion of the aperture 244b is also in proximity the vertebral body 20 (and may or may not be within the Sharpey's Fibers between the annulus fibrosus 232 and vertebral body 202), and another portion of the aperture 244b is spaced from the vertebral body 202. Although the description and illustrations depict repairs of defects in proximity to vertebrae, this is illustrative and is not intended to be limiting the use of these devices. A fixation apparatus 830 is shown in FIG. 58 to aid in repair of defect 244h. The fixation apparatus 830 includes at least one anchor in the vertebral body 202 which, in cooperation with a fixation device having a connection between one or more anchors in the annulus fibrosus 232, can serve to draw annulus fibrosus tissue toward the vertebral body 202 in order to repair defect 244b.

FIG. 58 illustrates a fixation apparatus 830 as affixed in place to vertebral body 202 and annulus fibrosus 232, prior to closure of the aperture 244b. The fixation apparatus 830 includes a suitable bone anchor 831, illustrated in FIG. 58 as a T-anchor. The bone anchor 831 has a tether 831a connected thereto, and the bone anchor 831 and a portion of the tether 831a are inserted in the vertebral body 202. Bone anchor 831 may be delivered by pre-drilling a bone anchor bore 831b, if required. A shortenable elongate member 832 is slidably connected to the tether 831a. In one embodiment, a length of the elongate member 832 is shortenable by means of a moveable knot such as a Roeder knot, or its equivalent. The length of the elongate member 832 can be shortened by pulling on its associated tether 832a to, for example, shorten the loop defined by the elongate member 832. Together, the bone anchor 831 and elongate member 832 define a bone anchor assembly (although the bone anchor assembly is shown with only one bone anchor connected to the elongate member, additional bone anchors and/or tethers and/or elongate members 832 may be provided on the assembly).

In an alternative embodiment (not shown), tether 831a may also include a slidable and locking element so as to be capable of shortening the distance between the bone anchor 831 and elongate member 832.

As shown, one or more soft tissue anchors 834 may be affixed into or through the annulus fibrosus 232. In the illustrated embodiment, each tissue anchor 834 has a T-anchor 835 with an elongate element 836 attached thereto that extends into and/or through the annulus fibrosus 232. A link, connecting element or coupling 838 slidably connects the elongate elements 836 of each tissue anchor 834. In one embodiment, a length of the coupling or connecting element 838 is shortenable by means of a moveable knot such as a Roeder knot, or its functional equivalent. The length of the connecting element 838 can be shortened by pulling on its associated tether 838a to, for example, shorten the loop defined by coupling 838. Together, the tissue anchors 834 and connecting element 838 define a soft tissue anchor assembly (although the soft tissue anchor assembly is shown with two soft tissue anchors coupled to a connecting element, additional soft tissue anchors and/or connecting elements may be provided on the assembly).

Figure 59:
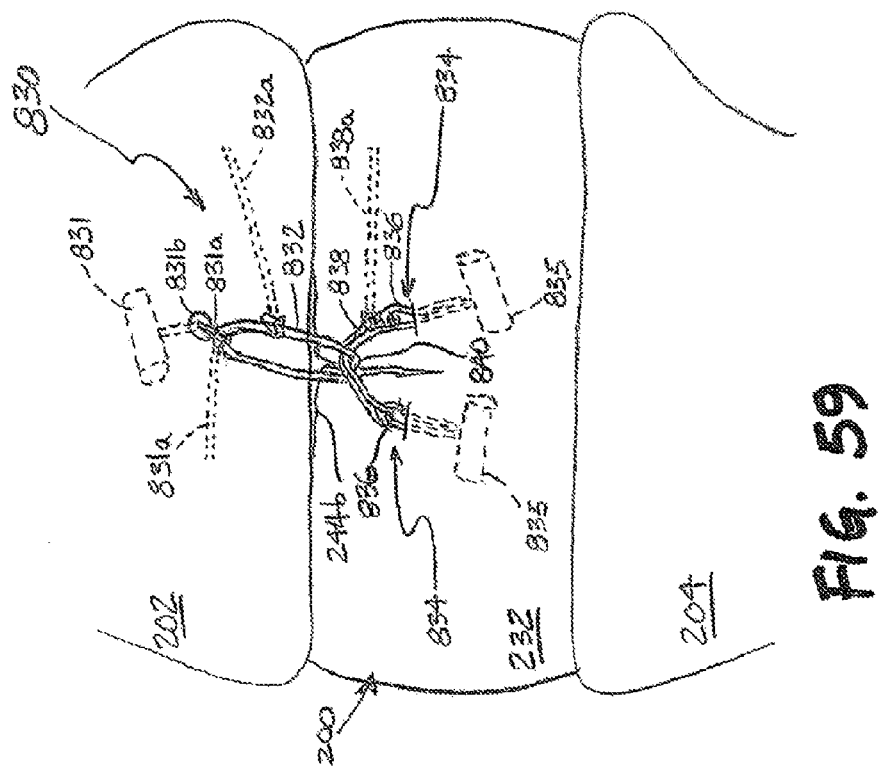
FIGS. 58-64 show an alternative exemplary treatment apparatus comprising an annulus fibrosus tissue anchor assembly connected to a bone anchor via a shortenable elongate element, and the assembly and activation thereof.

In FIG. 58, the fixation apparatus 830 is shown assembled but not yet activated for closure of the aperture 244b in the annulus fibrosus 232. As shown, in this assembled configuration, the connecting element 838 is disposed over a portion 840 of the elongate member 832. Accordingly, once fixation apparatus 830 is assembled as illustrated, the portion 840 of the elongate member 832 may be slidably restrained between the soft tissue anchors 834 and the connecting element 838. FIG. 59 illustrates activation of the fixation apparatus 830 to facilitate defect repair. The elongate member 832 has been pulled to shorten the length thereof between the bone anchor tether 831b and the elongate member 832 by pulling on the free end of the member 832a (which is shown in dotted lines after having been cut away). The connecting element 838 has been shortened by pulling on its associated tether 838a (which is shown in dotted lines after having been cut away). As stated previously, tether 831a may also be capable of being shortened (not shown), to facilitate the defect repair. Soft tissue anchors 834 and theft associated connecting element 838 provide an effective anchor assembly for anchoring to the annulus fibrosus 232. Since the elongate member 832 is also, as illustrated, anchored by the bone anchor 831, the shortening of the length of the elongate member 832 may act to draw tissue of the annulus fibrosus 232 toward the vertebral body 202, thereby urging closure of the aperture 244b. In the embodiment illustrated in FIGS. 58 and 59, since the tissue anchors 834 have also been placed on opposite sides of the portion of the aperture 244b, the shortening of the lengths of the associated connections between the tissue anchors 834 and the bone anchor 831 also serves to urge annulus fibrosus tissue together between the tissue anchors 834, thereby further providing stabilization of tissue surrounding defect 244b in the annulus fibrosus 232.

Figure 61:
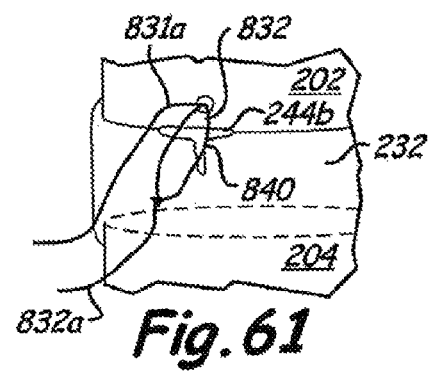

FIGS. 60-64 illustrate, in one embodiment, the placement and activation of fixation apparatus 830 proximate a defect in the wall of a disc's annulus fibrosus. A bone drill may be used to form the bore 831b in the superior vertebral body 202 that is contiguous to the disc 200, adjacent the aperture 244b in the annulus fibrosus 232. The bone anchor 831 is inserted into the bore 831b and suitably manipulated to be secured within the vertebral body 202 with the tether 831a extending through the bore 831b and outwardly therefrom. This arrangement is illustrated in FIG. 61, which also illustrates the aligning of at least a portion 840 of the shortenable elongate element 832 along the annulus fibrosus 232, proximate to the aperture 244b therein.

Figure 62:
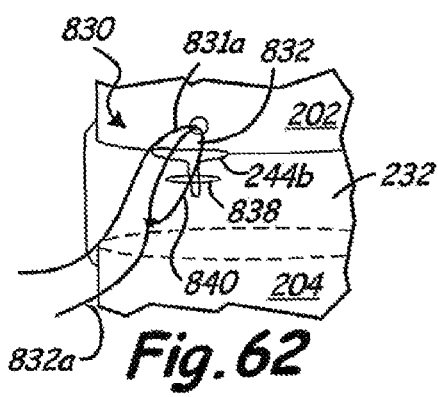

FIG. 62 illustrates a fixation apparatus 830 with tissue anchors 835 (not shown) thereof (and their associated connecting element 838, shown) already introduced into or through the annulus fibrosus 232. The tissue anchors 834 can be introduced by various anchor delivery devices, as disclosed herein, and either in parallel or sequentially. One means for achieving retention of the elongate member 832 relative to the connecting element 838 is to dispose one tissue anchor 834 on one side of the portion 840 of the shortenable elongate member 832, while disposing the other tissue anchor 834 on the other side thereof. As such, the connecting element 838 between tissue anchors 834 extends across or spans the portion 840 of the elongate member 832.

Figure 63:
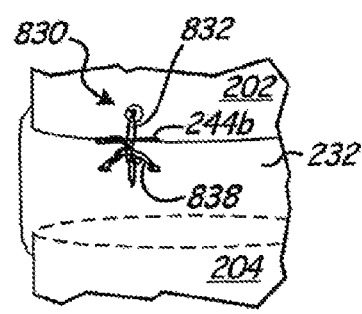
Figure 64:
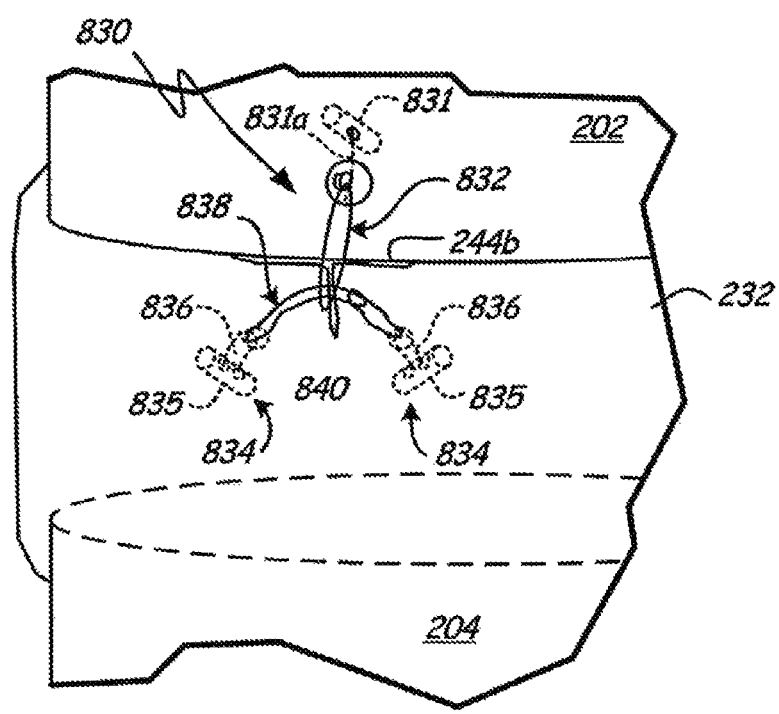

FIG. 62 illustrates the fixation apparatus 830 as now assembled with respect to the annulus fibrosus 232 and vertebral body 202, with tether 832a of the shortenable elongate member 832 ready to be pulled to shorten the length of the elongate member 832. As illustrated, the associated tether 838a of the link or coupling or connecting element 838 has already been pulled to shorten the length of the connecting element 838 (and has been cut away in FIG. 62). Shortening elongate member 832 may be sufficient to cause coupling 838 and tissue anchors 834 to be drawn in tension pulling, wholly or partially, annulus fibrosus tissue together. In addition, shortening the elongate member 832 may additionally draw connecting element 838 toward the bone anchor 831, thus pulling wholly or partially, annulus fibrosus tissue toward the vertebral body 202. In doing so, the defect 244b is closed, repaired, or otherwise stabilized. An exemplary orientation and configuration for activated fixation apparatus 830 is illustrated in FIGS. 63 and 64, which show fixation apparatus 830 with the lengths of both the connecting element 838 and elongate member 832 shortened.

Figure 65:
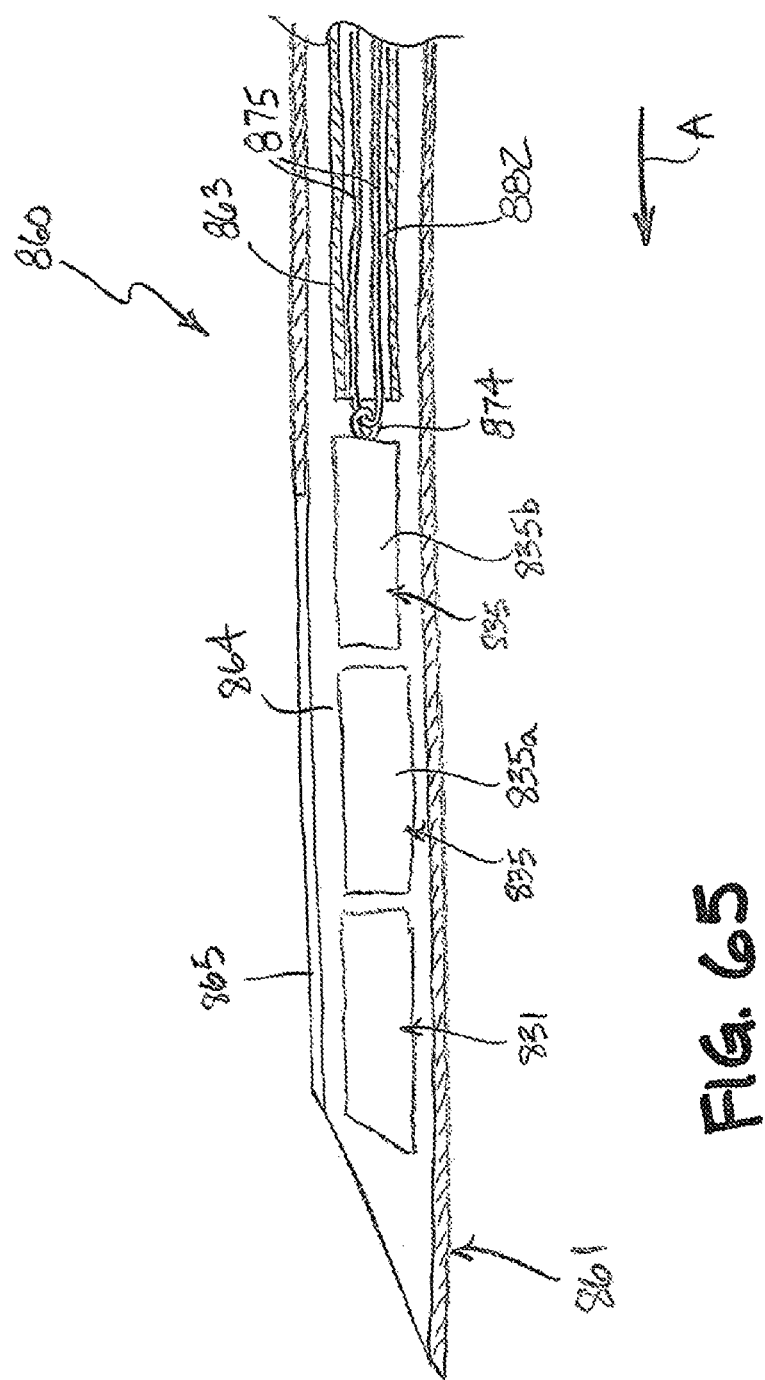
FIG. 65 schematically illustrates a distal end of a hollow shaft on an anchor delivery tool, having three anchors disposed therein for sequential insertion.

As noted above, the tissue anchors 834 may be disposed in the annulus fibrosus 232 at the same time, using a delivery tool such as illustrated in FIGS. 11 and 55. In addition, the bone anchor 831 may also be delivered by such a delivery tool. Alternatively, all of the anchors may be delivered by a single delivery tool, similar to those illustrated in FIGS. 13 and 48. FIG. 65 illustrates schematically the disposition of an anchor 831 capable of being anchored into bone and soft tissue anchors 835 capable of being delivered into soft tissue (e.g., first anchor 835a and second anchor 835b) within a shaft 861 of an anchor delivery tool 860. In this instance, the shaft 861 has a lumen 864 therein adjacent its distal end, and the shaft 861 has a slot 865 associated with the lumen 864 to accommodate the various tethers, connections and/or knots between and among the bone anchor 831 and tissue anchors 835 (tethers, connections and/or knots not shown in FIG. 65). In one embodiment, bone anchor 831 is the first anchor to be disposed within a patient's tissue, and is advanced by manipulation of a displacement rod 863 that is slidably disposed within the lumen 864 of the shaft 861. The form and operation of the displacement rod 863 relative to the shaft 861 and associated anchors therein is accomplished in a similar manner to that illustrated by the device 400 in FIG. 48. Movement of the displacement rod 863 (in direction of arrow A in FIG. 65) dispenses, in sequence, the anchors 831, 835a and 835b out of the shaft 861 of the tool 860. The second soft tissue anchor 835b has an eyelet 874 or other suitable means for slidably engaging a tether 875 therefor. In one embodiment, the tether 875 extends proximally through a displacement rod lumen 882 in the displacement rod 863, and both proximal ends of the tether 865 are affixed to portions of a handle (not shown) of the delivery tool 860. While one proximal end remains affixed to the tool, the other proximal end of the tether 875 is severed by manipulation of the delivery tool 860 once the second tissue anchor 835b has been disposed in a desired location in the annulus fibrosus 232 (see, e.g., tether 475 and tether severing element 490 on tool 400 in FIG. 48C). The tether 875 is thus free to be removed from the second tissue anchor 835b, by slipping it through the eyelet 874 thereon as the delivery device tool 860 is withdrawn. Prior to its being cut, the tether 875 for the second tissue anchor 835b serves the same purpose as the tether 475 for the anchor 453 illustrated in FIG. 48 and explained above. Such an arrangement (to retain the second soft tissue anchor 835b) could also be provided for the first soft tissue anchor 835a. Moreover, it is conceivable to have multiple anchors capable of being anchored to bone as well as multiple soft tissue anchors in one tool, with the order of delivery not expressed as illustrated in FIG. 65, but workable in the opposite order, or in a different fashion.

Figure 66:
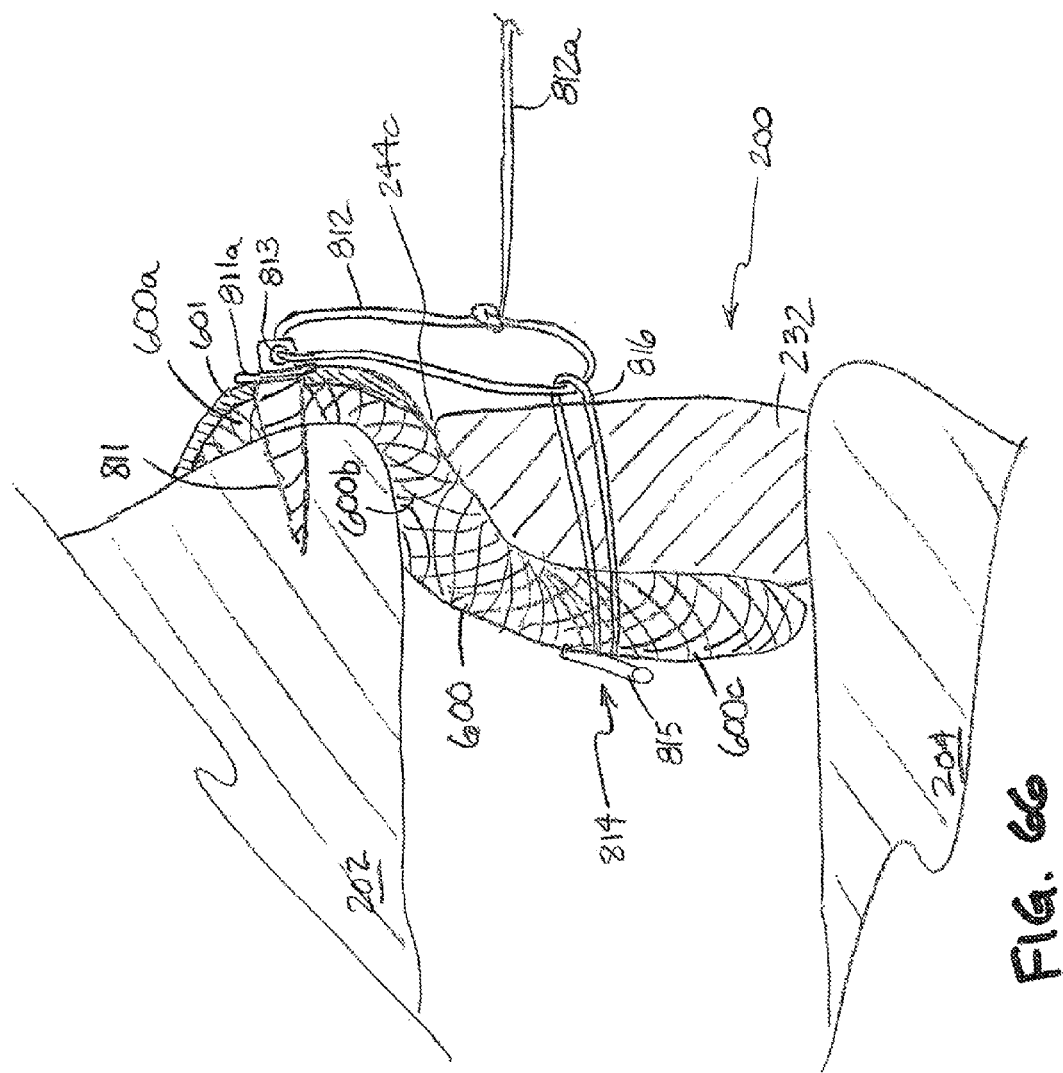
FIG. 66 illustrates an alternative exemplary embodiment of a reparative apparatus comprising at least one anchor assembly in a vertebra, at least one anchor assembly in the annulus fibrosus, and at least one patch member connected to both anchor assemblies with a shortenable elongate member also connecting the anchor assemblies.

FIG. 66 illustrates another embodiment for repair of a defect that is proximate to a vertebral body. In this instance, the fixation apparatus for facilitating closure of the defect further includes a patching, scaffolding, filling-type element. In all of the fixation apparatus embodiments disclosed herein, it may be possible to provide a patch to further aid in the repair, reconstruction or closure of a defect, such as a patch 600 as discussed and illustrated in this disclosure.

In the fixation apparatus embodiment of FIG. 66, patch 600 is retained not only within the nucleus of the disc 200, it also extends through at least a portion of a defect 244c therein and is affixed to a vertebral body, such as superior vertebral body 202. The patch 600 may take any suitable form for a patch, such as disclosed herein. The patch 600 has a first portion 600a to which a bone anchor 811 has been inserted and secured to the vertebral body 202. The first portion 600a of the patch 600 is also covered, on its exposed surfaces, by a non-adhesion material 601, which may be retained thereon in part by the bone anchor 811, which has an enlarged head 811a thereon for that purpose. A second, intermediate portion 600b of the patch 600 extends through at least a portion of the defect 244c in the annulus fibrosus 232. A third portion 600c of the patch 600 extends along an inner face of the wall of the annulus fibrosus 232. One or more tissue anchors 814 are inserted into the annulus fibrosus 232 and through the third portion 600c of the patch 600, to affix the patch 600 to the annulus fibrosus 232, as seen in FIG. 66. An exemplary tissue anchor assembly for this purpose comprises at least one tissue anchor 814 having a T-anchor 815 with an elongate element 816 attached thereto that extends into and/or through the annulus fibrosus 232. A shortenable elongate member 812 is slidably connected to the bone anchor 811, as through an eyelet 813 thereon. In one embodiment, a length of the elongate member 812 is shortenable by means of a moveable knot, such as a Roeder knot, or its functional equivalent. The length of the elongate member 812 can be shortened by pulling on its associated tether 812a to, for example, shorten the loop defined by the elongate member 812. In the manner illustrated in FIG. 66, or using the types of fixation apparatus illustrated herein (such as, for example, those shown in FIGS. 49-64), a patch 600 can be additionally employed to aid in closure of a defect in an annulus fibrosus, particularly where the defect is proximate to a vertebral body. By shortening the length of the elongate member 812, the annulus fibrosus tissue adjacent any tissue anchors 814 therein is drawn toward the bone anchor 811 in the vertebral body 202, thereby urging closed the defect 244c and urging annulus fibrosus tissue against the second portion 600b of the patch 600 in the defect 244c. Although FIG. 66 illustrates the patch-like material being affixed by the bone anchor, it is clear that a similar repair could be performed without directly affixing the patch with the anchor. For example, a tether or other connective element could attach patch 600 to anchor 811. However, patch 600 may merely be affixed to the annulus with anchors.

Figure 67:
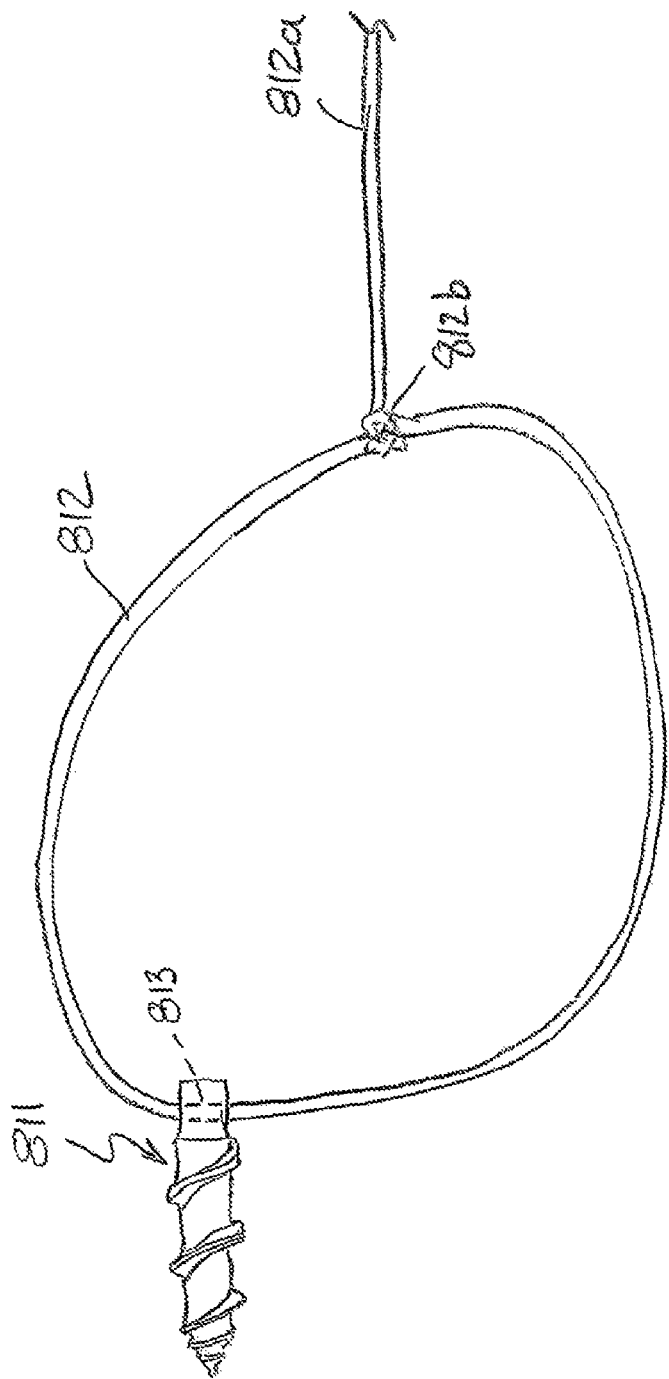
FIGS. 67 and 68 illustrate alternative embodiments of anchor assemblies and associated shortenable elongate elements thereon.
Figure 68:
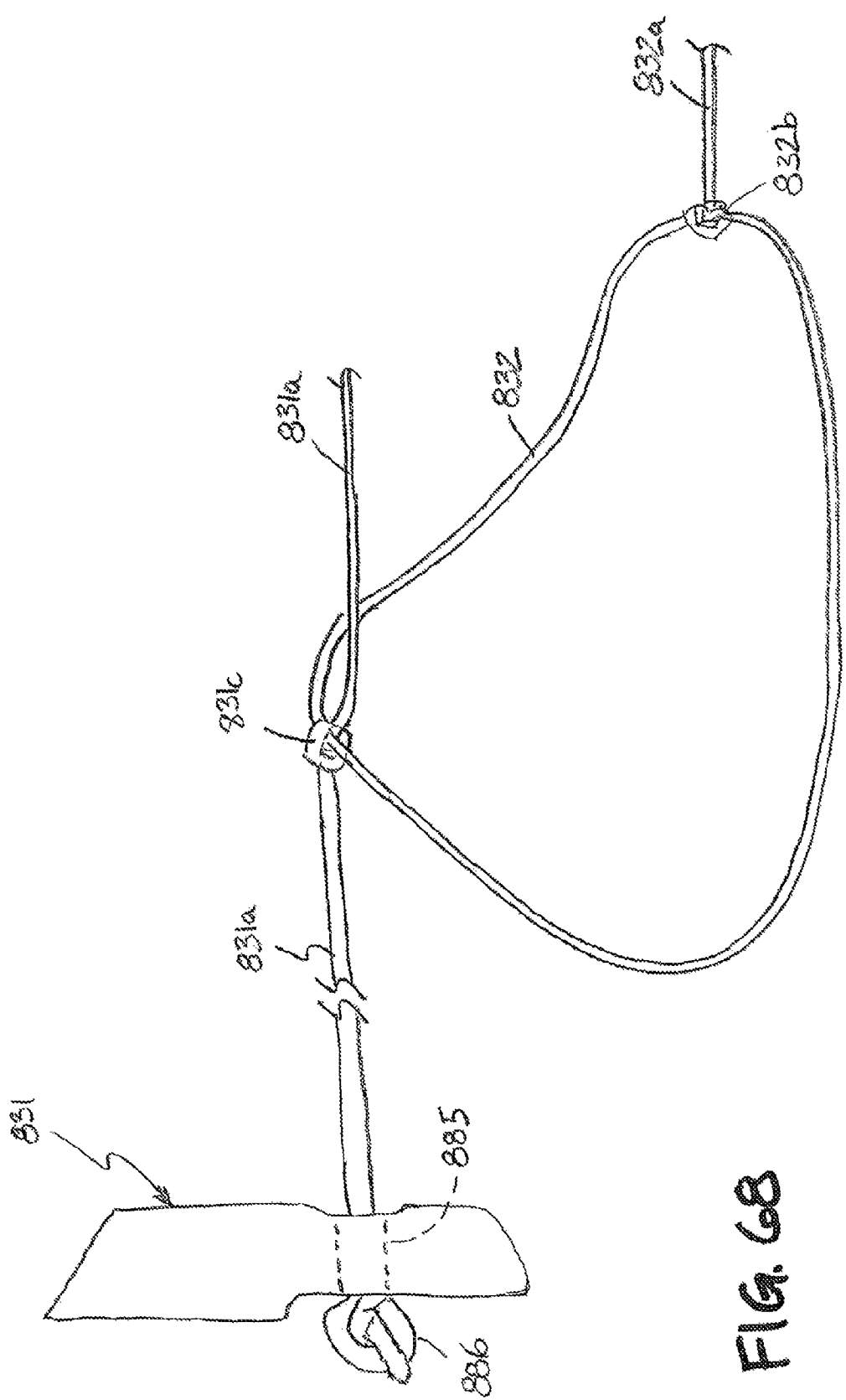

As noted in the illustrative embodiments herein (see, e.g., FIGS. 2C, 7A, 19, 49, 58 and 66), a suitable bone anchor can take a variety of forms, such as a bone screw 811 or T-anchor 831 (or even a bone anchor that extends completely through a bone, such as seen in FIG. 19). The bone screw may be self tapping, or may require a pre-drilled bore in the vertebral body for reception thereof. Likewise, depending upon the delivery tool, a T-anchor type bone anchor 831 may be self penetrating, or may require a pre-drilled bore formed in the vertebral body. A suitable bone anchor may take alternative forms, such as a barb, an expandable element and/or an adhesive element. FIG. 67 illustrates a bone anchor 811 formed as an exemplary bone screw, while FIG. 68 illustrates a bone anchor 831 formed as an exemplary T-anchor. As illustrated in the exemplary embodiments of FIGS. 67 and 68, each bone anchor has a shortenable elongate member 812 connected thereto. The elongate member 812 may comprise a bop (as shown) or a tether or some other suitable shortenable means. The elongate member may comprise a line, wire, filament, band or suture.

An expandable mesh bone anchor may also be used as a holding device inside of a vertebral body. The mesh anchor can have pre-attached tether elements attached thereto (e.g., sutures in the form of a shortenable elongate element) for connecting the bone anchor to its complementary tissue anchor or tissue anchor assembly in the annulus fibrosus. For insertion, an expandable mesh bone anchor has a small diameter. Once inserted into the vertebral body, the bone anchor opens up to a larger diameter and includes some means for locking the bone anchor in its larger diameter deployed shape. For use as an anchor in a vertebral body, an expandable bone mesh anchor is inserted through a pre-drilled hole and then deployed (i.e., expanded) inside the cancellous bone and seated up against the harder cortical bone, which allows for a strong supporting structure. The porous mesh formed by a deployed expandable mesh bone anchor construct also allows for growth in and around the construct. The bone anchor may also take the form of an adhesive or expandable material disposed onto or inserted into a vertebral body, or an adhesive may be used in conjunction with other types of bone anchors, such as a bone screw, T-anchor, barb or expandable element.

FIG. 67 illustrates a bone anchor 811 in the form of a bone screw with a shortenable elongate member 812 slidably connected thereto through an eyelet 813 on the bone anchor 811. A Roeder knot 85B on the elongate member 812 leads to an associated tether 812a. Once the bone screw 811 is anchored, puffing on the tether 812a away from the bone anchor 811 shortens the loop defined by the elongate member 812. FIG. 68 illustrates a bone anchor 831 in the form of a T-anchor. The T-anchor has a bore 885 extending therethrough for a slidable reception of the tether 831a therein. On one side of the T-anchor, the tether 831a is knotted, such as at knot 886. One the other side of the T-anchor, the tether 831a leads to a Roeder knot 831c formed about the shortenable elongate member 832. Once the bone anchor 831 has been affixed in place, pulling on the free end of the tether 831a shortens the length between the knot 831c and the bone anchor 831. As noted above, the elongate member 832 also has a Roeder knot 832b thereon. Once the bone anchor 831 has been affixed in place, puffing on the tether 832a in a direction away from the bone anchor 831 shortens the loop defined by the elongate member 832.

Figure 69:
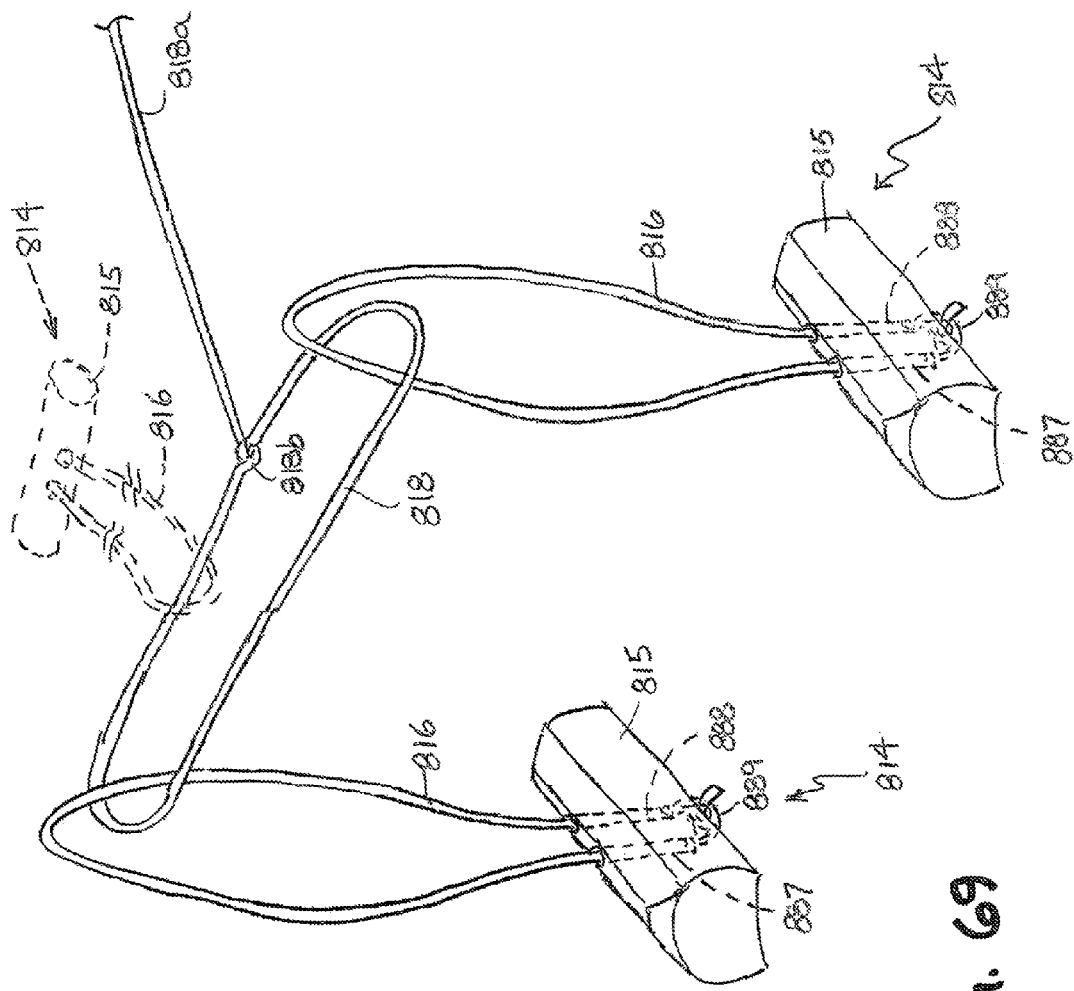
FIG. 69 illustrates an exemplary anchor assembly having a plurality of anchors connected by a shortenable coupling or connection therebetween.

FIG. 69 is an illustration of a tissue anchor assembly, such as that illustratively deployed in the exemplary embodiments of FIGS. 49 and 58. Each tissue anchor 814 has a T-anchor 815 with an elongate element 816 attached thereto. In this embodiment, each T-anchor 815 has a pair of bores 887, 888 therethrough for slidable reception of portions of the elongate element 816. On one side of the T-anchor 815, the elongate element 816 is knotted, such as at knot 889, to affix it to the T-anchor 815. In one embodiment, each elongate element 816 defines a bop. A link or connecting element or coupling 818 slidably connects the loops of the elongate elements 816 of each tissue anchor 814. In one embodiment, the coupling 818 also defines a loop, and the loop of the coupling 818 extends through the loops of the elongate elements 816, as shown in FIG. 69. The connecting element 818 has a Roeder knot 816b thereon. Once the tissue anchors 814 are affixed in place, pulling on the tether 818a of the connecting element 818 in direction away from the tissue anchors 814 shortens the loop defined by the connecting element 818. FIG. 69 illustrates two tissue anchors 814, such as illustrated in the exemplary embodiments of FIGS. 49 and 58. FIG. 69 also illustrates, in phantom, that a third anchor 814 may be provided in slidable connection with the connecting element 818. Additional tissue anchors, as desired for the application at hand, may also be provided. Such a third anchor (or even more tissue anchors, if desired) may be attached to the connecting element 818, and inserted into or through the annulus fibrosus tissue at a location (for each additional anchor) that is spaced from the insertions of the first and second tissue anchors. In one embodiment, the connecting element 818 between anchors is shortenable (such as, for example, by applying tension thereto) to draw those inserted anchors toward one another, and to cause a drawing together of annulus fibrosus tissue proximate to those anchors. In addition, while the connecting element 818 is shown as a loop, it may be possible to also achieve the same result (a shortenable link or coupling or connection) using a tether or some other suitable shortenable means. The coupling may comprise a line, wire, filament, and or suture.

While the fixation apparatus embodiments illustrated in FIGS. 49-69 illustrate tissue anchors formed as T-anchors, it is understood that any suitable tissue anchors such as those disclosed herein will suffice so long as the tissue anchor provides a suitable platform for interconnection with one another (whether or not they are bony tissue or soft tissue anchors) via a shortenable elongate element. For instance, a further suitable anchor that may be used as a tissue anchor (bony or soft) comprises a dual T-anchor implant. In this anchor arrangement (see FIGS. 70-73), two T-anchors are attached together via one or more suture lines. The T-anchors may be of the type having a single bore therethrough (such as the T-anchors illustrated in FIGS. 68 and 70-71) or having two bores therethrough (such as the T-anchors illustrated in FIGS. 69 and 72-73).

FIG. 70 illustrates schematically two T-anchors connected by a single suture line and mounted for insertion in a delivery tool (shown in phantom) to ultimately form a dual T-anchor implant. An anchor delivery tool 960 has a distally slotted shaft 961 with a lumen 964 therein for reception, in series, of a first T-anchor 951a and a second T-anchor 951b. Each T-anchor 951a and 951b has at least one bore 985 therethrough, for slidable reception of a single anchor tether 925 therein. On one side of the second T-anchor 951b, the tether 925 has a knot 926 thereon of size sufficient to prevent passage through the bore 985 of the second T-anchor 951b. The first and second T-anchors 951a and 951b may be inserted into patient tissue in series, as discussed herein. Once inserted, pulling on the tether 925 in a direction away from the first and second anchors 951a and 951b pulls the anchors together as illustrated, for example, in FIGS. 71A and 71B. The first and second anchors 951a and 951b may line up in a generally parallel alignment, as indicated in FIG. 71A, or may be rotationally skewed relative to their respective bores, as illustrated in FIG. 71B. On the one hand, when aligned as seen in FIG. 71A, the second anchor 951B creates a support structure for the first anchor 951a, which in turn makes for a more robust anchor. On the other hand, when aligned as seen in FIG. 71B, an anchor arrangement having greater surface area resting against patient tissue may be provided, which also may be advantageous. While both anchors should be of a size that may be received in the shaft 961 of the tool 960, the first and second anchors 951a and 951b may be of the same length or of different lengths. For example, the second anchor 951b may be shorter than the first anchor 951a.

FIG. 72 illustrates schematically an alternative dual T-anchor implant. In FIG. 72, two anchors are again aligned for sequential insertion within an anchor delivery tool 1060 (shown in phantom) having a shaft 1061. In this arrangement, a first anchor 1051a and a second anchor 1051b are provided. Each anchor has at least two bores therethrough (such as the T-anchors 814 illustrated in FIG. 69), such as bores 1087 and 1088. A single elongate element 1016 slidably is received within each of the bores 1087 and 1088. At some point along the length of the elongate element 1016, it is knotted together (as at knot 1089) to form the elongate element 1016 into a continuous loop. The dual T-anchor implant illustrated in FIG. 72 can be sequentially inserted from the tool 1060, as disclosed herein. Once inserted, pulling on the loop 1060 in a direction away from the first and second anchors 1051a and 1051b pulls the second anchor 1051b into engagement and alignment (generally parallel) under the first anchor 1051a, as illustrated in FIG. 73. This creates a support structure for the first anchor, which in turn makes for a more robust anchor. While both anchors should be of a size that may be received in the shaft 961 of the tool 960, the first and second anchors 1051a and 1051b may be of the same length or of different lengths. For example, the second anchor 1051b may be shorter than the first anchor 1051a. In either exemplary construct illustrated in FIGS. 70-73, the use of a dual T-anchor implant arrangement serves to provide a larger, more robust anchor, without increasing the diameter of the lumen of the shaft of the anchor delivery tool.

Figure 74:
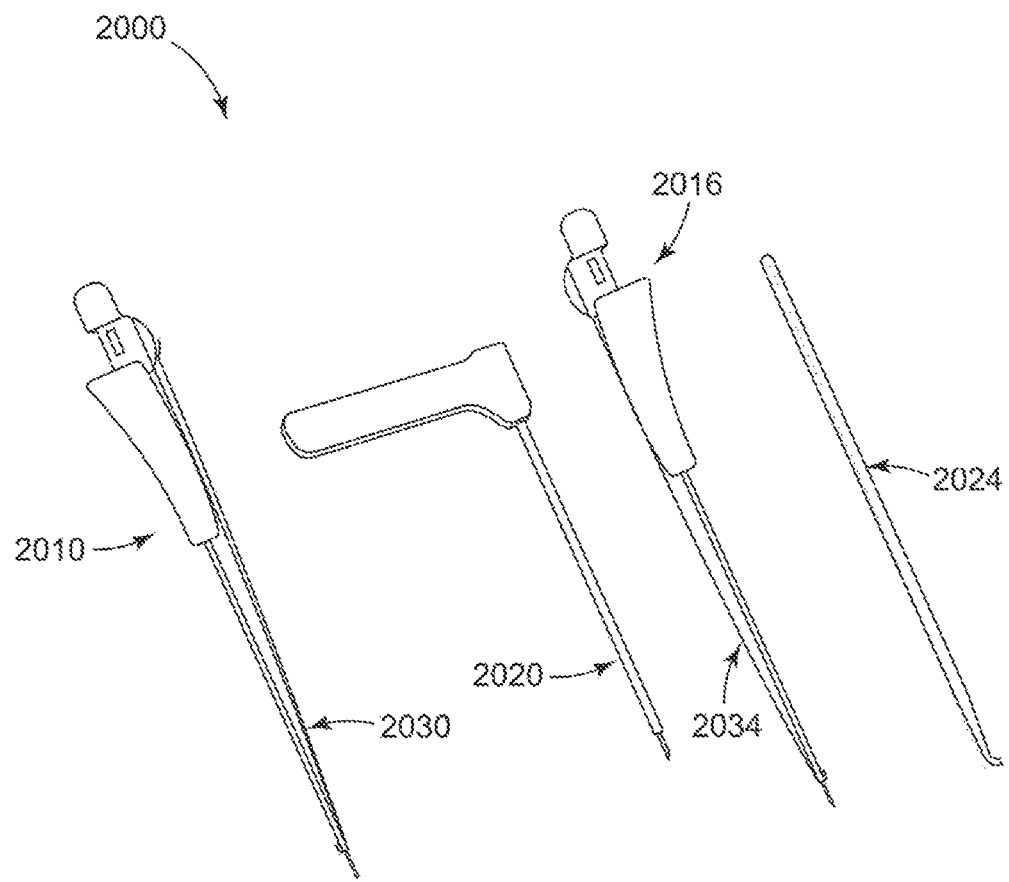
FIG. 74 illustrates a system for repairing an aperture or a defect in an intervertebral disc according to another embodiment of the present invention.

FIG. 74 illustrates a system 2000 for repairing an aperture or a defect in an intervertebral disc according to another embodiment of the present invention. As shown in FIG. 74, the system 2000 includes a pair of fixation delivery apparatus 2010, 2016, a bone awl 2020, and a knot pusher 2024. As shown and as discussed in further detail below, releasably coupled to the fixation delivery apparatus 2010 is a fixation apparatus 2030 configured to be deployed and attached to a vertebral body (e.g., the vertebral bodies 202 or 204 illustrated in FIG. 9 above). Additionally, releasably coupled to the fixation delivery apparatus 2016 is a fixation apparatus 2034 configured to be deployed and attached to vertebral disc tissue. The fixation apparatus 2030 and the fixation apparatus 2034 are configured to form a completed repair system for closing a defect or aperture in the annulus fibrosus as explained in the various embodiments described and illustrated above, for example, in FIGS. 58-64 and/or FIG. 69 above and the corresponding detailed description. In various embodiments, the bone awl 2020 and/or the knot pusher 2024 are optional, and thus may be omitted from the system 2000.

FIG. 75A is a partial cutaway illustration of the fixation delivery apparatus 2010 with the fixation apparatus 2030 coupled thereto, and FIG. 75B is a cross-sectional view of a portion of the fixation delivery apparatus 2010 taken along the line 75B-75B. As shown, the fixation delivery apparatus 2010 includes a tubular shaft 2050 and a proximal handle 2054 coupled thereto. In the illustrated embodiment, the shaft 2050 terminates in a relatively blunt distal tip 2055, and further includes a tissue stop 2056, although these elements are, in various embodiments, optional. The fixation delivery apparatus 2010 further includes an actuator 2060 coupled to an ejection rod 2064, and a pair of tabs 2066, 2067 releasably coupled to a portion of the actuator 2060. As further shown, the delivery apparatus 2010 includes a spring 2068 in the handle 2054 positioned to bias the actuator 2060 axially away from the handle 2054.

The fixation apparatus 2030 is partially disposed within the tubular shaft 2050, with a pair of tethers 2070, 2072 of the fixation apparatus 2030 extending external to the delivery apparatus 2010 and connected to the tabs 2066, 2067, respectively. The fixation apparatus 2030 is, in one embodiment, configured to anchor a suture assembly (including a portion of the tether 2070) to a vertebral body adjacent to an intervertebral disc annulus having an aperture or defect to be repaired. Thus, in one embodiment, the fixation apparatus 2030 can include a bone anchor (not shown) such as the bone anchor 831 of the bone anchor fixation apparatus 830 illustrated in FIGS. 58-64 and described in the corresponding text above. In one embodiment, the fixation apparatus 2030 includes the bone anchor 831 illustrated in FIG. 68 above, and the tethers 2070, 2072 correspond, respectively, to the tethers 832a and 831a illustrated in the construct of FIG. 68. Thus, in the assembled and undeployed state of the fixation delivery apparatus 2010 and fixation apparatus 2030 shown in FIG. 75A, the bone anchor is positioned within the tubular shaft 2050, and is coupled to the tether 2072.

In the illustrated embodiment, the ejection rod 2064 is partially slidably disposed within the tubular shaft 2050, and is configured to eject the bone anchor of the fixation apparatus 2030 from the tubular shaft 2050 into the desired implantation location (e.g., a pre-formed anchor bore in the vertebra 202 or 204 such as shown in FIG. 58 above) by manipulation of the actuator 2060. Thus, the actuator 2060 is slidable relative to the handle 2054 to effectuate axial movement of the ejection rod 2064. As shown, the actuator 2060 includes a knob 2076 for manipulation by the user. In various embodiments, the actuator 2060 and the handle 2054 further include additional features that allow the actuator 2060 and, in turn the ejection rod 2064, to be advanced in discrete steps, e.g., to selectively and sequentially eject multiple bone anchors in series, in much the same manner as described above with respect to the 400 shown in FIGS. 48A-48E and described in the corresponding text.

The tab 2066 is releasably coupled to a portion of the actuator 2060 and, in the undeployed state of FIG. 75A, is positioned so as to prevent spontaneous axial movement of the actuator 2060 and, in turn, the ejection rod 2064. Additionally, the tether 2070 is connected to the tab 2066, which can be manipulated by the user to apply tension to the tether 2070 to adjust the length of the suture assembly connected to the bone anchor (such as shown in FIGS. 58-64 and 68 above). In addition, the tether 2072 is connected to the tab 2067, which can be manipulated by the user to facilitate engagement of the bone anchor with the vertebral body once deployed therein, in various embodiments, connecting the tether 2072 to the tab 2067 further provides an additional means to prevent unintentional deployment of the bone anchor from the shaft 2050 of the fixation delivery apparatus 2010. In other embodiments, only a single tether and single tab may be provided.

FIG. 76A is a partial cutaway illustration of the fixation delivery apparatus 2016 with the fixation apparatus 2034 coupled thereto, and FIG. 76B is a cross-sectional view of a portion of the fixation delivery apparatus 2016 taken along the line 76B-76B. As shown in FIG. 76A, the fixation delivery apparatus 2016 includes a tubular shaft 2080 and a proximal handle 2084 coupled thereto. In the illustrated embodiment, the shaft 2080 terminates in a sharpened, tissue-piercing distal tip 2085 and includes a tissue stop 2086. The fixation delivery apparatus 2016 further includes an actuator 2090 coupled to an ejection rod 2094, and at least one tab 2096 releasably coupled to a portion of the actuator 2090. As further shown, the delivery apparatus 2016 includes a spring 2098 in the handle 2084 positioned to bias the actuator 2090 axially away from the handle 2084.

The fixation apparatus 2034 is partially disposed within the tubular shaft 2080, with at least one tension line 2100 of the fixation apparatus 2034 extending external to the delivery apparatus 2016 and connected to the tab 2096. The fixation apparatus 2034 is, in one embodiment, configured to anchor a suture assembly (including the tension line 2100) to the intervertebral disc annulus having an aperture or defect to be repaired. In various embodiments, the fixation apparatus 2034 is configured in a similar or identical manner as the soft tissue fixation apparatus illustrated in FIGS. 58-64, or the fixation apparatus 450 illustrated in FIGS. 48A-48E and described in the corresponding text. Thus, in one embodiment, the fixation apparatus 2034 can include a pair of tissue anchors (not shown in FIG. 76A) such as the soft tissue anchors 834 illustrated above in FIGS. 58-64, connected by an adjustable connecting element configured to be shortened to place the deployed tissue anchors in tension to facilitate closure of the aperture or defect, again as discussed in connection with the various embodiments illustrated above. In various other embodiments, the fixation apparatus 2034 is configured to be substantially identical to the fixation apparatus 450 shown in FIGS. 48A-48E, and thus includes a pair of tissue anchors 452, 453 connected by an adjustable elongate member 454. Thus, in the assembled and undeployed state of the fixation delivery apparatus 2016 and fixation apparatus 2034 shown in FIG. 76A, the tissue anchors (not shown) are positioned within the tubular shaft 2080.

The fixation delivery apparatus 2016 may, in most respects, have the same general functionality as, for example, the fixation delivery apparatus 400 described above and illustrated in FIGS. 48A-48E. Thus, the ejection rod 2094 is partially slidably disposed within the tubular shaft 2080, and is configured to eject the tissue anchors of the fixation apparatus 2034 from the tubular shaft 2080 into the desired implantation location within the disc annulus by manipulation of the actuator 2090. Thus, the actuator 2090 is slidable relative to the handle 2084 to effectuate axial movement of the ejection rod 2094. As shown, the actuator 2090 includes a knob 2116 for manipulation by the user. In various embodiments, the actuator 2090 and the handle 2084 further include additional features that allow the actuator 2090 and, in turn the ejection rod 2094, to be advanced in discrete steps, e.g., to selectively and sequentially eject multiple bone anchors in series, in much the same manner as described above with respect to the fixation delivery apparatus 400 of FIGS. 48A-48E.

In various embodiments, the fixation delivery apparatus 2016 includes additional features also present in the fixation delivery apparatus 400. For example, the shaft 2080 may, in various embodiments, include a slot to facilitate loading and management of the fixation apparatus 2034. In addition, the fixation delivery apparatus 2016 may also include means for managing the elongate connecting member connecting the tissue anchors of the fixation apparatus 2034, similar or identical to the elastic band 473 shown in FIG. 48E.

Similar to the tab 2066 of the fixation delivery apparatus 2010, the tab 2096 is releasably coupled to a portion of the actuator 2090 and, in the undeployed state of FIG. 76A, is positioned so as to prevent spontaneous axial movement of the actuator 2090 and, in turn, the ejection rod 2094. Additionally, the tension line 2100 is connected to the tab 2096, which can be manipulated by the user to apply tension to the tension line 2100 to facilitate adjustment, i.e., shortening, of the connecting assembly between the tissue anchors, e.g., using the knot pusher 2024 (see FIG. 74).

In use, the physician can use the bone awl 2020 (or other suitable instrument) to form an access bore in the vertebra 202 or 204 (see, e.g., FIG. 52) into which the bone anchor of the fixation apparatus 2030 can be inserted. Next, the distal tip 2055 of the fixation delivery apparatus 2010 is inserted into the access bore up to the tissue stop 2056. The tab 2067 (to which the tether 2072 is connected) is then removed from the actuator 2060 and set aside. The bone anchor of the fixation apparatus 2034 is then deployed into the vertebra 202 or 204 by manipulation of the actuator 2060. Next, the bone anchor is toggled by pulling on the tab 2067, thus applying tension to the tether 2072 (which as discussed above, is also connected to the bone anchor). Thus, by applying tension to the tether 2072, the bone anchor positively engages the vertebra to secure the bone anchor therein. For example, when the bone anchor 831 of FIG. 68 is utilized, toggling the bone anchor 831 by applying tension to the tether 2072 (corresponding to the tether 831a of FIG. 68) causes the relatively sharp end of the bone anchor 831 to engage the vertebral body.

Next, the fixation apparatus 2034 is deployed into the disc annulus fibrosus using the fixation delivery apparatus 2016 to facilitate partial or complete closure of the aperture in the annulus fibrosus. The configurations of the fixation apparatus 2034 during and after deployment are substantially identical or identical to the configurations of the soft tissue anchor assembly shown in FIGS. 58-64 and described in the corresponding text.

Figure 77:
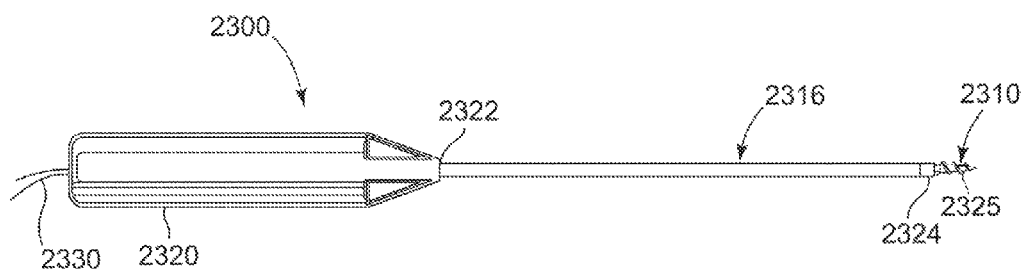
FIG. 77 is an elevation view of an alternative fixation delivery tool and fixation device coupled thereto according to another embodiment of the present invention.

FIG. 77 is an elevation view of a fixation delivery tool 2300 and a fixation apparatus 2310 coupled thereto according to another embodiment of the present invention. In various embodiments, the fixation delivery tool 2300 and the fixation apparatus 2310 can be used in lieu of the bone screw 811 and delivery tool 823 illustrated in FIG. 53A above. Alternatively, in other embodiments, the fixation delivery tool 2300 and the fixation apparatus 2310 can be used in lieu of the fixation delivery apparatus 2010 and the fixation apparatus 2030 discussed above and illustrated in FIGS. 74 and 75 above. Thus, the fixation apparatus 2310 can, in various embodiments, be deployed in conjunction with the fixation apparatus 2034 to facilitate repair of an aperture in an annulus fibrosus of an intervertebral disc.

As shown in FIG. 77, the fixation delivery apparatus 2300 includes a shaft 2316 and a handle 2320. The shaft 2316 includes a proximal end 2322 and a distal end 2324, with the proximal end 2322 connected to the handle 2320. As further shown, the fixation apparatus 2310 includes a bone screw 2325 coupled to the distal end 2324 of the fixation delivery apparatus 2300. The fixation delivery apparatus 2300 is operable by a user to screw the bone screw 2325 into the patient's vertebra adjacent to the disc annulus to be repaired. As will be illustrated and described in greater detail below, the fixation apparatus 2310 further includes a flexible connecting element 2030 shown exiting the handle 2320 of the fixation delivery apparatus 2300 in FIG. 77.

Figure 78:
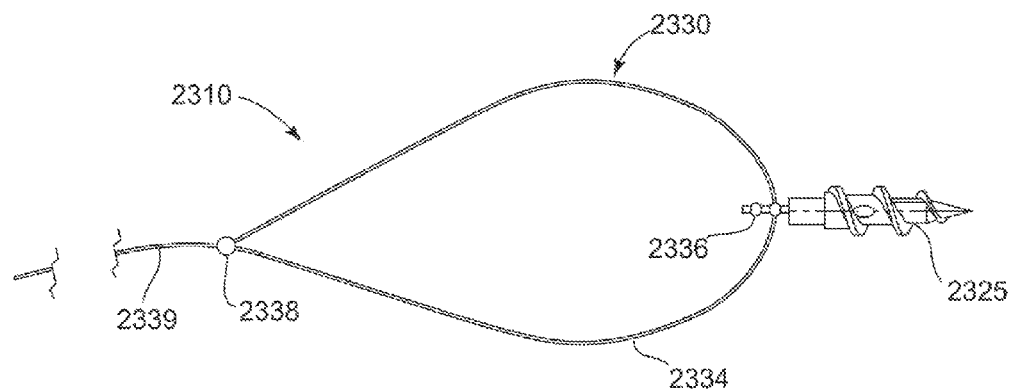
FIG. 78 is a further illustration of the fixation device of FIG. 77.

FIG. 78 is a further illustration of the fixation apparatus 2310. As shown, the fixation apparatus 2310 includes the flexible connecting element 2330, e.g., an adjustable suture assembly, connected to the bone screw 2325. In the illustrated embodiment, the connecting element includes an adjustable loop 2334 and a connecting segment 2336. A locking element 2338, e.g., a slip knot or Roeder knot as illustrated, is formed in the adjustable loop 2334, and a tension line 2339 extends away from the adjustable loop 2334 and can be accessed by the user to adjust the dimensions of the adjustable loop 2334. The connecting segment 2336 is connected to the bone screw 2325, and the adjustable loop 2334 is in turn connected to the connecting segment 2336. In use, the connecting element 2330 can have substantially the same or identical functionality as the elongate member 812 coupled to the bone screw 811 described above in connection with FIGS. 49-57.

Figure 79A:
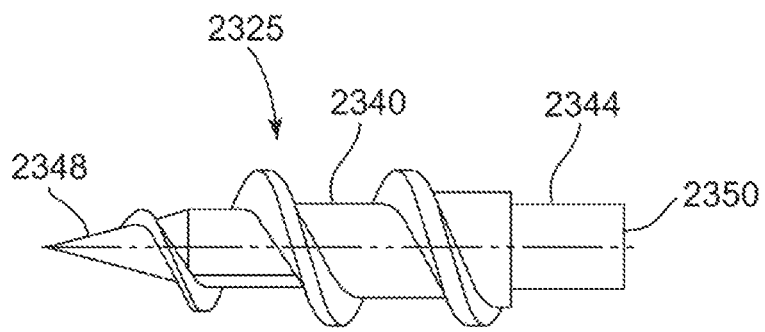
FIG. 79A is a detailed view of a bone screw of the fixation device of FIG. 77.
Figure 79B:
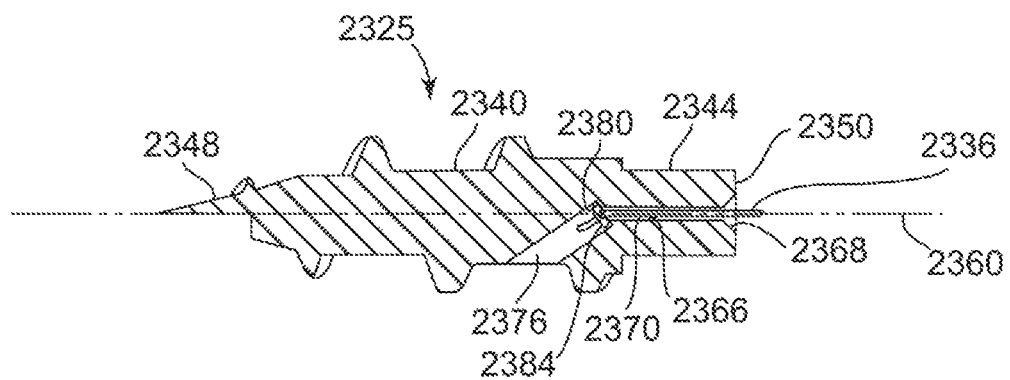
FIG. 79B is a cross-sectional view of the bone screw shown in FIG. 79A.

FIG. 79A is a detailed view of the bone screw 2325, and FIG. 79B is a cross-sectional elevation view of the bone screw 2325. As shown, the bone screw 2325 has a threaded shaft 2340 with a proximal end portion 2344 and a distal tip portion 2348. The proximal end portion 2344 has a proximal end 2350 and is shaped, e.g., with a hexagonal cross-sectional shape, to mate with a complementary shape in the distal end 2324 of the shaft 2316 of the delivery tool 2310 so as to enable torque applied to the delivery tool 2310 to be transferred to the bone screw 2325 to enable the user to screw the bone screw 2325 into the vertebra as desired. In various embodiments, the distal tip portion 2348 has a self-tapping configuration so as to eliminate the need for a pre-formed hole in the vertebra into which the bone screw 2325 is to be implanted.

As can perhaps be best seen in the cross-sectional view of FIG. 79B, the general shape of the bone screw 2325 defines a longitudinal axis 2360, and the bone screw 2325 includes an open lumen 2366 originating at the proximal end 2350. As further shown, the lumen 2366 exits the bone screw 2325 laterally at a location between the proximal end 2350 and the distal tip portion 2348. Additionally, the inner surface of the lumen 2366 includes a chamfered or radiused region 2368 at the proximal end 2350 of the bone screw 2325.

In the illustrated embodiment, the lumen 2366 includes a proximal segment 2370 extending substantially parallel to the longitudinal axis 2360 from the proximal end 2350, and a lateral segment 2376 extending from the proximal segment 2370. As shown, the proximal segment 2370 has a smaller diameter than the lateral segment 2376, thus forming a shoulder 2380 at the junction of the proximal and lateral segments 2370, 2376.

For illustration purposes, the connecting segment 2336 of the connecting element 2330 is shown inserted in the lumen 2366 in FIG. 79B to show the functionality of the lumen 2366. As shown in FIG. 79B, the connecting segment 2336 is fed through the lumen 2366 and exits the open end of the lumen at the proximal end 2350 of the bone screw 2325. Additionally, the connecting segment 2336 includes a stop feature 2384 (e.g., a knot or pledget) having a diameter larger than the diameter of the proximal segment 2370 of the lumen 2366. Accordingly, the stop feature 2384 engages the shoulder 2380 thus preventing the connecting segment 2336 from being pulled axially from the lumen 2366. Additionally, tension applied to the connecting segment 2336, i.e., by puffing on the tension line 2339 of the connecting element 2330, is thus transferred to the bone screw 2325 by the engagement of the stop feature 2384 and the shoulder 2380.

The configuration of the bone screw 2325 advantageously allows the connecting segment 2336 to exit the bone screw 2325 parallel to the longitudinal axis 2360, thus allowing the bone screw 2325 to be threaded into the vertebra with the proximal end 2350 flush or substantially flush with the outer surface of the vertebra. Additionally, the radiused region 2368 of the inner surface of the lumen at the proximal end 2350 provides strain relief and reduces frictional wear on the connecting segment 2336 due to contact against the bone screw 2325.

As explained above, the fixation apparatus 2310 including the bone screw 2325 and the adjustable connecting element 2330 can be used in substantially the same manner as the bone screw 811 and the elongate member 812 described above and illustrated in FIGS. 49-57. Accordingly, the fixation apparatus 2310 can be employed in conjunction with a soft tissue anchoring assembly such as described above and illustrated in FIG. 48A-48E, 49-57, or 58-64, to facilitate closure of an aperture in the intervertebral disc.

It will be appreciated that the particular configurations of the various adjustable elongate members and connecting elements associated with the soft tissue anchors and bone anchors/screws described and illustrated above are exemplary only. Accordingly, other configurations of these adjustable elongate members and connecting elements can be employed within the scope of the various embodiments of the present invention.

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Oucheyne et al.), U.S. Pat. No. 5,122,154 (Rhodes), U.S. Pat. No. 5,204,106 (Schepers at al.), U.S. Pat. No. 5,888,220 (Felt et al.),U.S. Pat. No. 5,376,120 (Sarver et al.) and U.S. Pat. No. 5,976,186 (Bao et al.).

Various materials know to those skilled in the art can be employed in practicing the present invention. By means of example only, the body portions of the stent could be made of NiTi alloy, plastics including polypropylene and polyethylene, polymethylmethacrylate, stainless steel and other biocompatible metals, chromium cobalt ahoy, or collagen. Webbing materials can include silicone, collagen, ePTFE, DACRON, polyester, polypropylene, polyethylene, and other biocompatible materials and can be woven or non-woven. Membranes might be fashioned of silicone, polypropylene, polyester, SURLYN, PEBAX, polyethylene, polyurethane or other biocompatible materials. Inflation fluids for membranes can include gases, liquids, foams, emulsions, and can be or contain bioactive materials and can also be for mechanical, biochemical and medicinal purposes. The stent body, webbing and/or membrane can be drug eluting or bioabsorbable, as known in the medical implant arts.

Further, any of the devices or delivery tools described herein, or portions thereof, could be rendered visible or more visible via fluoroscopy, if desired, through the incorporation of radioopaque materials or markers. Preferably implantable devices are constructed with MRI compatible materials. In particular, devices and/or their components could be wholly or partially radiopaque, as result of, for example: compounding various radiopaque materials (e.g., barium sulphate) into device materials; affixing radiopaque materials to device structures (e.g., bands of platinum, gold, or their derivative alloys); deposition of radiopaque materials onto device structures (e.g., deposition of platinum, gold of their derivative alloys); processing radiopaque materials into device structures (e.g., braiding/weaving platinum or gold wires or its alloy derivatives). One inventive way to achieve radiopacity of a device described herein, for example treatment device 600, is placing one or more radiopaque marker bands onto filaments of braided device 600 before (or possibly after) creating end potions of the device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A system for at least partially closing a defect in soft tissue of a patient, the system comprising:
   a first fixation delivery apparatus having a tubular shaft, and a proximal handle
   a first fixation apparatus releasably coupled to the first fixation delivery apparatus including a bone anchor configured to be deployed at least partially into and attached to a bone structure adjacent to the soft tissue including the defect, and an adjustable flexible connecting element connected to the bone anchor, wherein at least a portion of the bone anchor and a portion of the adjustable connecting element are disposed within the tubular shaft of the first fixation delivery apparatus prior to deployment of the first fixation apparatus, and wherein the flexible connecting element can be manipulated by a user to adjust a length thereof;
   a second fixation delivery apparatus including a tubular shaft having a sharpened tissue-piercing distal tip, a proximal handle coupled to the tubular shaft, an ejection rod slidably disposed within the tubular shaft, and an actuator slidably coupled to the handle and operatively coupled to the ejection rod; and
   a second fixation apparatus releasably coupled to the second fixation delivery apparatus including a pair of soft tissue anchors and an adjustable flexible connecting element connecting the soft tissue anchors, wherein the soft tissue anchors and a first portion of the flexible connecting element are disposed within the tubular shaft and a second portion of the flexible connecting element is releasably coupled to the handle of the second fixation delivery apparatus prior to deployment,
   wherein the bone anchor is configured to be attached to the bone structure, the soft tissue anchors are configured to be deployed within and attached to the soft tissue with the defect located between the bone anchor and the soft tissue anchors, and the flexible connecting elements of the first fixation apparatus and the second fixation apparatus are configured to be interconnected and placed in tension to at least partially close the defect in the soft tissue.

2. The system of claim 1 wherein the first fixation delivery apparatus further includes an actuator slidably coupled to the handle and connected to an ejection rod slidably disposed within the tubular shaft, and a releasable tab coupled to the actuator, and wherein the actuator and the ejection rod are configured to eject the bone anchor from the tubular shaft, and wherein at least a portion of the adjustable connecting element of the first fixation apparatus is connected to the releasable tab, and wherein the tab is positioned to prevent axial movement of the actuator relative to the handle when coupled to the actuator.

3. The system of claim 2 wherein the releasable tab of the first fixation delivery apparatus is further operable by a user to change an orientation of the bone anchor after the bone anchor is ejected from the tubular shaft.

4. The system of claim 3 wherein the releasable tab of the first fixation delivery apparatus is operable by a user to at least partially rotate the bone anchor after the bone anchor is ejected from the tubular shaft of the first fixation delivery apparatus and deployed at least partially within the bone structure.

5. The system of claim 4 wherein the bone anchor is a T-anchor having a relatively sharp end, and wherein in use, the relatively sharp end is configured to engage the bone structure upon manipulation of the releasable tab of the first fixation delivery apparatus by the user.

6. The system of claim 1 wherein the bone anchor is a bone screw.

7. The system of claim 6 wherein the bone screw is a self-tapping bone screw.

8. The system of claim 6 wherein the portion of the adjustable connecting element disposed within the tubular shaft of the first fixation delivery apparatus exits the first fixation delivery apparatus proximate the handle.

9. The system of claim 6 wherein the bone screw has a longitudinal axis, a proximal end, a self-tapping distal tip, a threaded region between the proximal end and the distal tip, and an open lumen originating at the proximal end and exiting the bone screw laterally between the proximal end and the distal tip, and wherein the flexible connecting element of the first fixation apparatus includes a connecting segment partially disposed within the lumen and exiting therefrom at the proximal end of the bone screw.

10. The system of claim 9 wherein the lumen includes a first segment extending longitudinally from the proximal end of the bone screw generally parallel to the longitudinal axis, and a second segment extending at an oblique angle relative to the longitudinal axis.

11. The system of claim 10 wherein the first segment has a first cross-sectional dimension and the second segment has a second cross-sectional dimension larger than the first cross-sectional dimension so as to form a shoulder at an intersection of the first and second segments.

12. The system of claim 11 wherein the connecting member includes a stop feature configured to engage the shoulder to substantially prevent the connecting member from being pulled from the lumen.

13. The system of claim 1 wherein the connecting elements of the first and second fixation apparatus each include a locking element to maintain the respective connecting elements in a shortened configuration under tension.

* * * * *

UNITED STATES PATENT AND TRADEMARK OFFICE
CERTIFICATE OF CORRECTION

PATENT NO. : 8,454,697 B2  
APPLICATION NO. : 13/440838  
DATED : June 4, 2013  
INVENTOR(S) : Ishmael Bentley et al.

Page 1 of 1

It is certified that error appears in the above-identified patent and that said Letters Patent is hereby corrected as shown below:

In the Specification

Column 4, Line 45

Delete "463" and replace it with -- 46B --

Signed and Sealed this
Thirtieth Day of June, 2015

Michelle K. Lee
*Director of the United States Patent and Trademark Office*